(12) United States Patent
Guerette et al.

(10) Patent No.: US 10,899,803 B2
(45) Date of Patent: Jan. 26, 2021

(54) COMPOUNDS AND METHODS FOR THE PRODUCTION OF SUCKERIN AND USES THEREOF

(71) Applicants: Nanyang Technological University, Singapore (SG); Agency for Science, Technology and Research, Connexis (SG)

(72) Inventors: Paul Andre Guerette, Singapore (SG); Ali Gilles Tchenguise Miserez, Singapore (SG); Shawn Hoon, Connexis (SG)

(73) Assignees: Nanyang Technological University, Singapore (SG); Agency for Science, Technology and Researech, Connexis (SG)

( * ) Notice: Subject to any disclaimer, the term of this patent is extended or adjusted under 35 U.S.C. 154(b) by 310 days.

(21) Appl. No.: 14/436,745

(22) PCT Filed: Oct. 17, 2013

(86) PCT No.: PCT/SG2013/000447
§ 371 (c)(1),
(2) Date: Apr. 17, 2015

(87) PCT Pub. No.: WO2014/062134
PCT Pub. Date: Apr. 24, 2014

(65) Prior Publication Data
US 2015/0274789 A1    Oct. 1, 2015

Related U.S. Application Data

(60) Provisional application No. 61/715,068, filed on Oct. 17, 2012.

(51) Int. Cl.
| | | |
|---|---|---|
| *C07K 14/435* | (2006.01) | |
| *B29C 48/00* | (2019.01) | |
| *A61L 27/22* | (2006.01) | |
| *B29C 37/00* | (2006.01) | |
| *C08L 89/00* | (2006.01) | |
| *D01F 4/00* | (2006.01) | |
| *B29K 79/00* | (2006.01) | |
| *B29L 31/00* | (2006.01) | |

(52) U.S. Cl.
CPC ...... *C07K 14/43504* (2013.01); *A61L 27/227* (2013.01); *B29C 37/0003* (2013.01); *B29C 48/022* (2019.02); *C08L 89/00* (2013.01); *D01F 4/00* (2013.01); *B29K 2079/00* (2013.01); *B29L 2031/731* (2013.01); *D10B 2211/01* (2013.01)

(58) Field of Classification Search
None
See application file for complete search history.

(56) References Cited

U.S. PATENT DOCUMENTS

| | | |
|---|---|---|
| 5,252,285 A | 10/1993 | Lock |
| 5,994,099 A | 11/1999 | Lewis et al. |
| 6,268,169 B1 | 7/2001 | Fahnestock |
| 6,608,242 B1 | 8/2003 | Yang |
| 6,965,060 B2 | 11/2005 | Yang |
| 7,057,023 B2 | 6/2006 | Islam et al. |
| 7,157,615 B2 | 1/2007 | Karatzas et al. |
| 7,335,739 B2 | 2/2008 | Mello et al. |
| 7,521,228 B2 | 4/2009 | Lewis et al. |
| 7,674,882 B2 | 3/2010 | Kaplan et al. |
| 7,951,908 B2 | 5/2011 | Scheibel et al. |
| 8,034,897 B1 | 10/2011 | Scheibel et al. |
| 8,097,583 B2 | 1/2012 | Scheibel et al. |
| 8,173,772 B2 | 5/2012 | Johansson et al. |
| 2005/0010035 A1 | 1/2005 | Lewis et al. |
| 2009/0234026 A1 | 9/2009 | Kaplan et al. |

OTHER PUBLICATIONS

Vepari, C., et al. 2007 Prog Polym Sci 32: 991-1007.*
Askarieh et al., "Self-assembly of spider silk proteins is controlled by a pH-sensitive relay," *Nature* 465:236-240, May 13, 2010.
Ayoub et al., "Blueprint for a High-Performance Biomaterial: Full-Length Spider Dragline Silk Genes," *PLoS ONE* 2(6):e514, Jun. 2007, 13 pages.
Dalla Valle et al., "β-Keratins of the Crocodilian Epidermis: Composition, Structure, and Phylogenetic Relationships," *Journal of Experimental Zoology (Mol Dev Evol)* 312B:42-57, 2009.
Edgar, "Search and clustering orders of magnitude faster than BLAST," *Bioinformatics* 26(19):2460-2461, 2010.
Fahnestock et al., "Microbial production of spider silk proteins," *Reviews in Molecular Biotechnology* 74:105-119, 2000.
Fancy et al., "Chemistry for the Analysis of Protein-Protein Interactions: Rapid and Efficient Cross-Linking Triggered by Long Wavelength Light," *Proc. Natl. Acad. Sci. USA* 96(11):6020-6024, May 25, 1999.
Gatesy et al., "Extreme Diversity, Conservation, and Convergence of Spider Silk Fibroin Sequences," *Science* 291:2603-2606, Mar. 30, 1999.
GenBank Accession No. BAM18105 (2012).
GenBank Accession No. EDY68088 (2005).
GenBank Accession No. FO179121 (2012).
Gosline et al., "The mechanical design of spider silks: from fibroin sequence to mechanical function," *The Journal of Experimental Biology* 202:3295-3303, 1999.
Grabherr et al., "Full-length transcriptome assembly from RNA-Seq data without a reference genome," *Nature Biotechnology* 29(7):644-655, Jul. 2011.
Guan et al., "Two Mechanisms for Supercontraction in *Nephila* Spider Dragline Silk," *BioMacromolecules* 12:4030-4035, 2011.
Guerette et al., "Accelerating the design of biometric materials by integrating RNA-seq with proteomics and materials science," *Nature Biotechnology* 31(10):908-919, Oct. 2013.

(Continued)

*Primary Examiner* — Marsha Tsay
(74) *Attorney, Agent, or Firm* — Seed IP Law Group LLP

(57) ABSTRACT

Sucker ring tooth (SRT) proteins called Suckerins were identified from the sucker tissue of three distantly related Decapodiformes species. These proteins assemble into silk-like beta-sheet reinforced materials. The use of suckerin proteins to produce fibres, films and tissue scaffolds is also described.

24 Claims, 17 Drawing Sheets

Specification includes a Sequence Listing.

(56) References Cited

OTHER PUBLICATIONS

Guerette et al., "Silk Properties Determined by Gland-Specific Expression of a Spider Fibroin Gene Family," *Science* 272(5258):112-115, Apr. 5, 1996.
Hagn et al., "A conserved spider silk domain acts as a molecular switch that controls fibre assembly," *Nature* 465:239-245, May 13, 2010.
Hagn et al., "pH-Dependent Dimerization and Salt-Dependent Stabilization of the N-terminal Domain of Spider Dragline Silk—Implications for Fiber Formation," *Agnew. Chem. Int. Ed.* 50:310-313, 2011.
Hayashi et al., "Evidence from Flagelliform Silk cDNA for the Structural Basis of Elasticity and Modular Nature of Spider Silks," *J. Mol. Biol.* 275:773-784, 1998.
Hayashi et al., "Molecular Architecture and Evolution of a Modular Spider Silk Protein Gene," *Science* 287(5457):1477-1479, Feb. 25, 2000.
Holland et al., "Silk and Synthetic Polymers: Reconciling 100 Degrees of Separation," *Adv. Mater.* 24:105-109, 2012.
Kerkam et al., "Liquid crystallinity of natural silk secretions," *Nature* 349:596-598, Feb. 14, 1991.
Keten et al., "Nanoconfinement controls stiffness, strength and mechanical toughness of β-sheet crystals in silk," *Nature Materials* 9:359-367, Apr. 2010.
Knight et al., "Hexagonal columnar liquid crystal in the cells secreting spider silk," *Tissue & Cell* 31(6):617-620, 1999.
Lazaris et al, "Spider Silk Fibers Spun from Soluble Recombinant Silk Produced in Mammalian Cells," *Science* 295:472-477, Jan. 18, 2002.
Lee et al., "Mussel-Inspired Adhesives and Coatings," *Annu. Rev. Mater. Res.* 41:99-132, 2011.
Li et al., "RSEM: accurate transcript quantification from RNA-Seq data with or without a reference genome," *BMC Bioinformatics* 12:323, 2011, 17 pages.
Lichtenegger et al., "High Abrasion Resistance with Sparse Mineralization: Copper Biomineral in Worm Jaws," *Science* 298:389-393, Oct. 11, 2002.
Lindgren et al., "A multi-gene phylogeny of Cephalopoda supports convergent morphological evolution in association with multiple habitat shifts in the marine environment," *BMC Evolutionary Biology* 12:129, 2012, 16 pages.
Menassa et al., "Spider dragline silk proteins in transgenic tobacco leaves: accumulation and field production," *Plant Biotechnology Journal* 2:431-438, 2004.
Miserez et al., "Microstructural and Biochemical Characterization of the Nanoporous Sucker Rings from *Dosidicus gigas*," *Adv. Mater.* 21:401-406, 2009.
Miserez et al., "Sucker Rings from the Humboldt Squid *Dosidicus gigas*: The Role of Nanotubule Architecture on the Mechanical Properties," *Mater. Res. Soc. Symp. Proc.* 1187, 2009, 6 pages.
NCBI Reference Sequence: XP_002133922.1 (2012).
Omenetto et al., "New Opportunities for an Ancient Material," *Science* 329:528-532, Jul. 30, 2010.
Rammensee et al., "Assembly Mechanism of Recombinant Spider Silk Proteins," *Proc. Natl. Acad. USA* 105(18):6590-6595, May 6, 2008.
Rousseau et al., "Study of Protein Conformation and Orientation in Silkworm and Spider Silk Fibers Using Raman Microspectroscopy," *Biomacromolecules* 5:2247-2257, 2004.
Scheller et al., "Production of spider silk proteins in tobacco and potato," *Nature Biotechnology* 19:573-579, Jun. 2001.
Strugnell et al., "Divergence time estimates for major cephalopod groups: evidence form multiple genes," *Cladistics* 22:89-96, 2006.
Suzuki et al., "Characterization of Prismalin-14, a novel matrix protein from the prismatic layer of the Japanese pearl oyster (*Pinctada fucata*)," *Biochem J.* 382:205-213, 2004.
Tao et al., "Silk Materials—A Road to Sustainable High Technology," *Adv. Mater.* 24:2824-2837, 2012.
Teulé et al., "Silkworms transformed with chimeric silkworm/spider silk genes spin composite silk fibers with improved mechanical properties," *Proc. Natl. Acad. Sci. USA* 109(3):923-928, Jan. 17, 2012.
Van Beek et al,. "Supercontracted spider dragline silk: a solid-state NMR study of the local structure," *International Journal of Biological Macromolecules* 24:173-178, 1999.
Vollrath et al., "Liquid crystalline spinning of spider silk," *Nature* 410:541-548, Mar. 29, 2001.
Vollrath et al., "The effect of spinning conditions on the mechanics of a spider's dragline silk," *Proc. R. Soc. Lond. B* 268:2339-2346, 2001.
Willcox et al., "Evidence of a Cholesteric Liquid Crystalline Phase in Natural Silk Spinning Processes," *Macromolecules* 29:5106-5110, 1996.
Xia et al., "Native-sized recombinant spider silk protein produced in metabolically engineered *Escherichia coli* results in a strong fiber," *Proc. Natl. Acad. USA* 107(32):14059-14063, Aug. 10, 2010.
Yamao et al., "Gene targeting in the silkworm by use of a baculovirus," *Genes & Development* 13:511-516, 1999.
Yang et al., "High yield recombinant silk-like protein production in transgenic plants through protein targeting," *Transgenic Research* 14:313-324, 2005.
Yano et al., "Shematrin: A family of glycine-rich structural proteins in the shell of the pearl oyster *Pinctada fucata*," *Comparative Biochemistry and Physiology, Part B* 144:254-262, 2006.
Zhou et al., "Fine organization of *Bombyx mori* fibroin heavy chain gene," *Nucleic Acids Research* 28(12):2413-2419, 2000.
Database ID No. Q1MW93_PINFU, "*Pinctada fucata* (Akoya pearl oyster) (*Pinctada imbricate fucata*)," May 30, 2006, 1 page.
Database ID No. B1Q4V4_PINMA, "*Pinctada maxima* (Silver-lipped pearl oyster) (White-lipped pearl oyster)," May 20, 2008, 1 page.
Database ID No. B6CHA9_PINFU, "*Pinctada fucata* (Akoya pearl oyster) (*Pinctada imbricata fucata*)," Nov. 25, 2008, 1 page.
Ding et al., "Biomimetic Production of Silk-Like Recombinant Squid Sucker Ring Teeth Proteins," *Biomacromolecules* 15: 3278-3289, 2014.
Extended European Search Report, dated May 9, 2016, for European Application No. 13846625.5-1410 / 2909231, 11 pages.
Guerette et al., "Nanoconfined β-Sheets Mechanically Reinforce the Supra-Biomolecular Network of Robust Squid Sucker Ring Teeth," *ACSNANO* 8(7): 7170-7179, 2014.
Studart, "Towards High-Performance Bioinspired Composites," *Advanced Materials* 24: 5024-5044, 2012.

\* cited by examiner

A

B

(e)

COMPOUNDS AND METHODS FOR THE PRODUCTION OF SUCKERIN AND USES THEREOF

CROSS-REFERENCE TO RELATED APPLICATION

This application claims the benefit of priority of U.S. Provisional Patent Application No. 61/715,068 filed Oct. 17, 2012, the contents of which being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_482USPC_SEQUENCE_LISTING.txt. The text file is 283KB, was created on Sep. 8, 2020, and is being submitted electronically via EFS-Web.

FIELD

The invention relates to new robust proteins and polymers, their chemical designs and methods of production and use thereof.

BACKGROUND

The plastics industry alone accounts for about 7% of all petroleum used per annum, amounting to billions of dollars spent on non-renewable resources that clearly have a negative impact on the environment. Therefore there is a need to develop industrially useful materials including textiles, biocompatible materials and "smart" materials with tailored mechanical properties and innumerable additional functionalities that manifest at the atomic, molecular, supra-molecular, meso and macroscopic scales.

There are many groups and companies around the world uniquely devoted to engineering high-value materials based on proteins. An excellent case study comes from the high-performance adhesive proteins used by marine mussels to adhere to their substrates'. These proteins exhibit unrivalled adhesion in an aqueous milieu, dramatically outperforming the other best known glues. Protein based materials are also gaining significant traction in the field of biomedical engineering where they are being used for controlled drug release and as substrates for tissue engineering and repair. Key advantages of proteins include 1) biocompatibility; 2) ability to assemble proteins, often through multiple scales of structural hierarchy, to achieve desired nano and microstructures and 3) diversity in material states and shapes—for example films, fibers, hydrogels, foams, nano-scale templates, nano-spheres and microspheres etc. can all be engineered into materials with tailored structure and mechanical properties. In the push towards these advanced "green techno-materials" silkworm and spider silk protein-based materials have gained significant headway[2,3]. The list of applications and high-profile publications and patents on the subject is ever growing and far reaching. As part of the effort to understand and manipulate silk into useful materials, groups from around the world have studied the primary amino acid sequence, structure, processing mechanisms and mechanical properties of natural silk spinning animals including silkworms and spiders[4-11]. The strong industrial push towards the production of artificial silk is best demonstrated by the efforts of several groups focusing on the genes and proteins[12-18] and the methods for processing and spinning reconstituted or recombinantly derived silk fibroins[19-23]. Each of these report spun artificial spider dragline silk fibers from recombinant fibroins, but unfortunately, the mechanical properties of these fibers generally remain inferior to those observed in nature, for example[24]. One of the main reasons for this shortcoming is that the spinning mechanism employed by the spider has yet to be adequately mimicked. Therefore, there are several obstacles that that must be overcome before the production of artificial silk on an industrial scale becomes reality.

First, the production of artificial spider silk on an industrial scale will require a cost effective recombinant silk fibroin protein source. Native silk genes are extremely large and repetitive and, as a result; they can be unstable in bacteria or yeast because of the occurrence of undesired recombination events. Excessively large transcripts may also misfold in expression hosts, a process that can result in translational pausing and the truncation of recombinant products[25]. In addition, native spider silk genes contain heavy codon usage biases that render them incompatible with many expression systems[25]. Mammalian expression systems appear to have less trouble with spider silk genes, but these systems are more costly than microbial expression systems. More recently, the drive toward the production of large quantities of recombinant fibroins has focused on the use of transgenic organisms such as plants[26-30], silkworms[31,32], and goats[24,33]. Xia et. al.[34] recently demonstrated that by modifying the tRNA pool in $E.\ coli$ it was possible to express a large spider silk protein of 285 KDa that was close to the molecular weight of native spider silk proteins. The authors were able to spin their proteins into fibers with mechanical properties rivaling those of native silks. The data clearly demonstrates that silk properties depend directly on molecular weight and that silks spun from proteins of lower molecular weight were inferior. While this recent work offers significant potential, it also highlights a second major problem with the creation of biomimetic silk, the fact that fibroins have a tendency to aggregate into unwanted precipitates during processing. In fact efficient spinning was only achieved using the extremely harsh (and expensive) hexafluoroisopropanol that would be impractical to scale up. Nexia Biotechnologies Inc., have demonstrated the ability to spin a fragment of recombinant dragline silk fibroin from the aqueous phase[24]. However the basis of this achievement remains unclear. While these results suggest that a method for the production of artificial silk from the aqueous phase may be at hand, the mechanical properties of these materials remain inferior to those measured from native dragline silk. The main reason for this shortcoming appears to be that a precise level of control over fibroin folding and chain alignment is not yet attainable. In the spider, the fibroins self-assemble through several scales of structural hierarchy, involving the sequential development of at least three liquid-crystalline mesophases within the silk-gland[11,35-37]. Control over fibroin folding, self-assembly and the global molecular orientation of fibroin dopes within the silk gland involves very precise micro-environments and elongational flow forces along the length of the glandular lumen that facilitate polymer chain alignment and the spinning of the fibroin dope into a solid state beta-sheet re-enforced fiber. During spinning, silk proteins are folded and packed into colloidal and/or liquid crystal assemblies and their conversion into solid state fibers requires a combination of draw elongation[38,39], pH and salt gradients along the spinning gland[38] and very precise molecular designs of the N- and C-terminal domains that are sensitive to shear and micro-environment and that are believed to facilitate processing and polymerization into a beta-sheet re-enforced polymer network[40-43]. Clearly, the mimetics of such a mechanism will require a combination of significant advances in the field in order to translate these concepts into industrial processes.

Finally, as desirable as the mechanical properties of spider silk are in the dry state, dragline undergoes a process known as "supercontraction" when it is hydrated, where it shrinks to about 50% of its original length and becomes rubbery, where glassy structure becomes mobile and some of the beta-sheet structure that re-enforces the fiber melts and re-arranges[9,44,45]. Clearly supercontraction must be avoided if artificial spider silks are to be used for industrial applications. Despite these potential caveats, it is important to consider that the mechanical properties of native silk fibers are truly exceptional and in many cases may not be required for many applications. In fact the silk field has witnessed a dramatic expansion in the development of silk-based materials where extreme strength and toughness are not absolutely required. Currently the major challenges in the silk field for many applications are 1) industrial scale-up and production of large quantities of pure recombinant protein in a cost effective manner, a topic whose challenges have been addressed thoroughly by[25]; 2) preventing aggregation and/or solubilizing the protein for processing using inexpensive and/or environmentally friendly conditions; 3) controlling/tailoring the supra-molecular organization of the materials in order to tailor properties.

Efforts to engineer other new materials inspired by biological structures are limited by the lack of genomic data from many model organisms. Although knowledge of the primary sequence is key, several challenges remain with identifying target protein sequences. In particular, the genomes of most model organisms studied in biomimetics research have not been sequenced, and the proteins that constitute these materials are notoriously difficult to solubilize and characterize. A comprehensive analysis through traditional cDNA cloning approaches can take years, substantially limiting the scope and depth of information that can be extracted. Therefore, a comprehensive view of molecular design and natural manufacturing processes that ranges from genotype to mechanical phenotype is usually not directly accessible.

The Decapodiformes are a superorder of the class cephalopoda that include over 300 species of squid and cuttlefish. The tentacles and arms of all Decapodiformes species are lined with hooks, spines and crown shaped "teeth" that are used in predation, grappling and object manipulation (FIG. 1A). Squid and Cuttlefish exhibit impressive predatory prowess that involves a rapid tenticular strike. Their attack efficiency depends intimately on their ability to ensnare prey using their strong suckers which are lined with crowns of sharp, teeth-like structures. While initially thought to be comprised entirely of chitin, more recent work by Miserez[46, 47] indicates that these robust structures are assembled almost entirely from protein. These structures are unique to Decapodiformes and are collectively referred to as Sucker Ring Teeth (SRT).

SUMMARY

A first aspect of the invention includes an isolated polypeptide comprising; or consisting of:

a. the amino acid sequence set forth in any one of SEQ ID NOS. 2, 21, 23, 24 or 25; or
b. a variant of the amino acid sequence of (a) that shares at least 40%, preferably at least 50%, more preferably at least 60%, 80% or 90% sequence identity with any one of the amino acid sequences of (a) over its entire length
c. a fragment of the amino acid sequence of (a) or (b), the fragment having a length of at least 50, preferably at least 100, more preferably at least 150, most preferably at least 200, 400, or 600 amino acids;

wherein the polypeptide is at least partially in beta sheet conformation.

Another aspect of the invention includes an isolated nucleic acid molecule comprising a nucleic acid sequence encoding the polypeptide as described herein.

Another aspect of the invention includes a host cell comprising the expression construct as described herein able to express the polypeptide of the invention. The host cell may be any suitable host cell for recombinant production. The cell may be a prokariotic cell or a eukariotic cell. There are many cell based systems known in the art. Alternatively the polypeptide may be expressed by cell free translation.

Another aspect of the invention includes a material comprising the polypeptide as described herein. Preferably the material maintains the beta sheet structure. In various embodiments the material is selected from the group: a fibre, filament, a film, a foam, a nano fibre, a nano sphere, a nano particle, a liquid crystal mesogen, a colloid, a copolymer, or a block copolymer.

Another aspect of the invention includes a method of making the material comprising the polypeptide as described herein comprising the steps of: (a) crushing the polypeptide; (b) heating and/or using a solvent to dissolve the crushed polypeptide into a liquid; and (c) forming the material from the liquid. In various embodiments forming the material comprises spinning the liquid into a fibre. In various other embodiments forming the material comprises placing the liquid into a mold; and removing the mold after the liquid solidifies.

Another aspect of the invention includes a tissue scaffold comprising the polypeptide as described herein.

Another aspect of the invention includes a multimer of the polypeptides as described herein.

Other aspects of the invention would be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following exemplary drawings.

Figure 1:
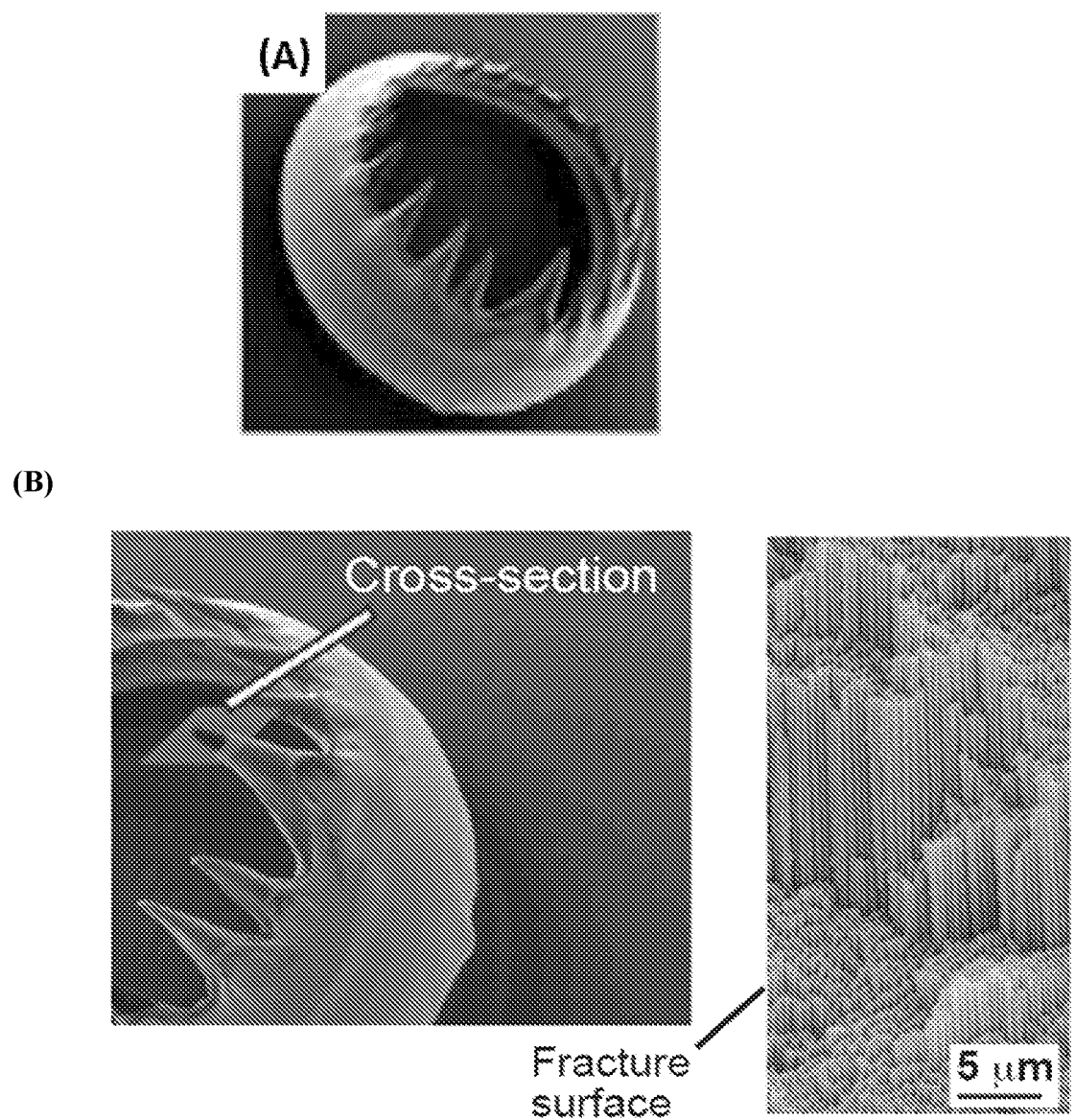
FIG. 1: (A) Low-magnification SEM micrograph image of a single Squid Sucker Ring Tooth (SRT) from *Dosidicus gigas*. (B) high-magnification SEM image of fracture surface (right image) showing the nanotubular architecture of SRT cross section through (A) as indicated in left image.

| Suckerin peptide sequence module | SEQ ID NO: |
|---|---|
| VSHTT | 616 |
| SHTTH | 617 |
| TAVSH | 618 |
| ATAVS | 619 |
| AATAV | 620 |
| ATSVS | 621 |
| TVTHT | 622 |
| SSVTH | 623 |
| HTTHG | 624 |
| AATSV | 625 |
| VSTVS | 626 |
| TVSHG | 627 |
| STVSH | 628 |
| ATTVS | 629 |
| VSHGV | 630 |
| VHTVH | 631 |
| TTVSH | 632 |
| TSVSH | 633 |
| TSVKT | 634 |
| SVSTV | 635 |
| YGGYG | 520 |
| GGLYG | 116 |
| GLYGG | 118 |
| GGYGL | 521 |
| LYGGY | 522 |
| GYGLG | 523 |
| GGYGG | 524 |
| LGGYG | 525 |
| YGGLY | 529 |
| GYGGY | 527 |
| YGLGG | 528 |
| GFGGL | 539 |
| GYGLH | 534 |
| LGFGG | 572 |
| LGYGL | 555 |
| GGLGG | 551 |
| GGYGF | 561 |
| GLGYG | 556 |
| HGGYG | 580 |
| THHA | 636 |
| TTHH | 637 |
| HTTH | 638 |
| SHTT | 639 |
| VSHT | 640 |
| AVSH | 641 |
| TVSH | 642 |
| ATVS | 643 |
| AATV | 655 |
| TAVS | 645 |
| ATAV | 646 |
| GAVS | 647 |
| VTHH | 648 |
| AATA | 649 |
| AAVS | 650 |
| TSVS | 651 |
| TVTH | 652 |
| AAAV | 653 |
| SRTT | 654 |

| Suckerin peptide sequence module | SEQ ID NO: |
|---|---|
| VSRT | 655 |
| VSHG | 656 |
| VSTV | 657 |
| SVST | 658 |
| STVS | 659 |
| SHGV | 660 |
| TTHG | 661 |
| STSV | 662 |
| QTVS | 663 |
| VSHV | 664 |
| VTHT | 665 |
| VKTV | 666 |
| SVHH | 667 |
| SVSH | 668 |
| HGAH | 669 |
| TVSQ | 670 |
| AAST | 671 |
| TTVS | 672 |
| VSHH | 673 |
| AATS | 674 |
| ASHG | 675 |
| TTSV | 676 |
| ATSV | 678 |
| HMTH | 679 |
| SHGS | 680 |
| GGYG | 117 |
| YGGY | 450 |
| GYGL | 451 |
| GGLY | 449 |
| GLYG | 453 |
| LYGG | 454 |
| GYGG | 452 |
| YGGL | 456 |
| YGLG | 455 |
| LGGY | 458 |
| HGGL | 459 |
| GLGG | 457 |
| YGYG | 461 |
| YGFG | 460 |
| GLGA | 463 |
| GFGG | 462 |
| GAYG | 466 |
| LHGG | 470 |
| LGYG | 464 |
| GFGY | 468 |
| GLGG | 457 |
| GGLG | 465 |
| LGGL | 477 |
| GLGY | 469 |
| GGVY | 518 |
| GVYG | 498 |
| YGGW | 496 |
| YGHG | 681 |
| GLGL | 491 |
| YGGF | 682 |
| FGGL | 471 |
| GWGF | 683 |
| WGFG | 684 |
| HYGG | 685 |
| GGFG | 686 |
| GGWG | 519 |
| VSHTTHHA | 612 |
| AVSHTTHH | 687 |
| ATVSHTTH | 688 |
| TVSHTTHH | 689 |
| AATVSHTT | 690 |
| TAVSHTTH | 691 |
| ATAVSHTT | 692 |
| GAVSHTTH | 693 |
| AATAVSHT | 694 |
| GLGAVSHT | 695 |
| LGVASHTT | 696 |
| AAVSHTTH | 697 |
| TSVSRTTH | 698 |
| AAVSHTT | 699 |
| ATSVSRTT | 700 |
| AAATVSHT | 701 |

| Suckerin peptide sequence module | SEQ ID NO: |
|---|---|
| VSRTTHHA | 702 |
| GAATVSHT | 703 |
| VSHVTHHA | 704 |
| AATSVSRT | 705 |
| SVSTVSHG | 706 |
| TSVSHTTH | 707 |
| STVSMGVH | 708 |
| RSVSTVSH | 709 |
| VSTVSHGI | 710 |
| TVSHGVHS | 711 |
| SVSHTTHG | 712 |
| STSVKTVT | 713 |
| GHTVSHVS | 714 |
| SSSVHTVH | 715 |
| VNHVSHRY | 716 |
| SSSISRVS | 717 |
| SVKSVHHS | 718 |
| AVATYRVL | 719 |
| GTTHTSIH | 720 |
| SSISTVSH | 721 |
| SINTVSHG | 722 |
| VKSVMHSV | 723 |
| VYGSTHAY | 724 |
| AVSSSSVH | 725 |
| ATSVSHTT | 726 |
| TSVSHAIH | 727 |
| SSSAVHTV | 728 |
| THTVSHTS | 729 |
| LSASTTKY | 730 |
| KSTSQTSS | 731 |
| VLVLISSS | 732 |
| ATATLLVL | 733 |
| SAVTTHEQ | 734 |
| ATSVSHAI | 735 |
| FATALVLV | 736 |
| VAHTVHSI | 737 |
| TIESVSHH | 738 |
| SLSTVSQG | 739 |
| TTVSHMTH | 740 |
| SVSHTTQR | 741 |
| LAAALAAI | 742 |
| TVSHGFGH | 743 |
| AVSSSAVH | 744 |
| GGLYGGYG | 745 |
| GLVGGYGL | 746 |
| HGGLYGGY | 747 |
| LYGGYGLG | 748 |
| GYGGLYGG | 749 |
| GYGLGGYG | 750 |
| YGGYGLGA | 751 |
| YGGLYGGY | 752 |
| GGYGLGAY | 753 |
| GYGLGAYG | 754 |
| LHGGLYGG | 755 |
| GGYGLGGY | 756 |
| YGLGAYGF | 757 |
| GLGAYGFG | 758 |
| GLLHGGLY | 759 |
| LGAYGFGY | 760 |
| LLHGGLYG | 761 |
| GGYGGYGG | 762 |
| GFGGLYGG | 763 |
| LYGGYGLA | 764 |
| VGGYGLGG | 765 |
| GLGGLYGG | 766 |
| GGYGLGGL | 767 |
| GYGLGGLV | 768 |
| YGLGGLVG | 769 |
| GYGGLGYG | 770 |
| GLGGLVGG | 771 |
| GGLGLGGL | 772 |
| GLGGVGLG | 773 |
| LGGVYGHG | 774 |
| HYGGYGLG | 775 |
| GGLYGGVY | 776 |
| LGGLVGGY | 777 |
| GGYGLGGV | 778 |

-continued

| Suckerin peptide sequence module | SEQ ID NO: |
|---|---|
| LYGGVYGL | 779 |
| YGHVHHYG | 780 |
| GVGGYGLG | 781 |
| GLGLGGLY | 782 |
| GHYGGYGL | 783 |
| RGYGLGGQ | 784 |
| SGHYGGYG | 785 |
| ISGHYGGY | 786 |
| YSHGGLYG | 787 |
| GFGGLVGS | 788 |
| VGLGGISG | 789 |
| SWGYSHGG | 790 |
| WGYSHGGL | 791 |
| GYGLGGLQV | 792 |
| SHGGLYGG | 793 |
| GWGFGGLY | 794 |
| GISGHYGG | 794 |
| GLYGGYGF | 796 |
| GGYGGYGL | 797 |

Figure 11:
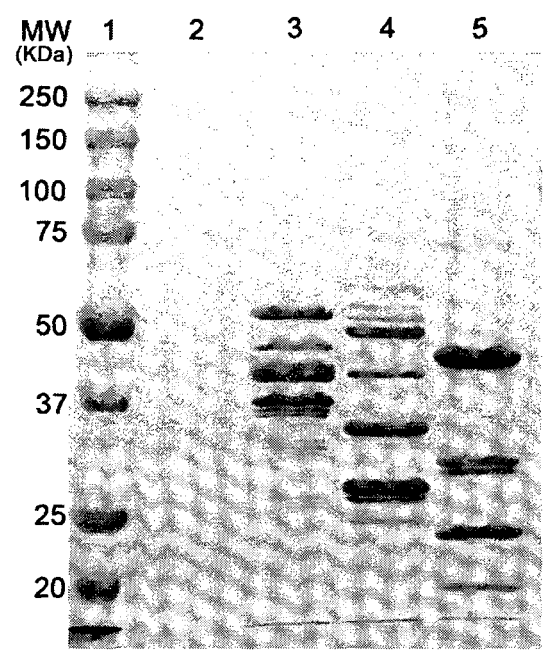
Figure 11:
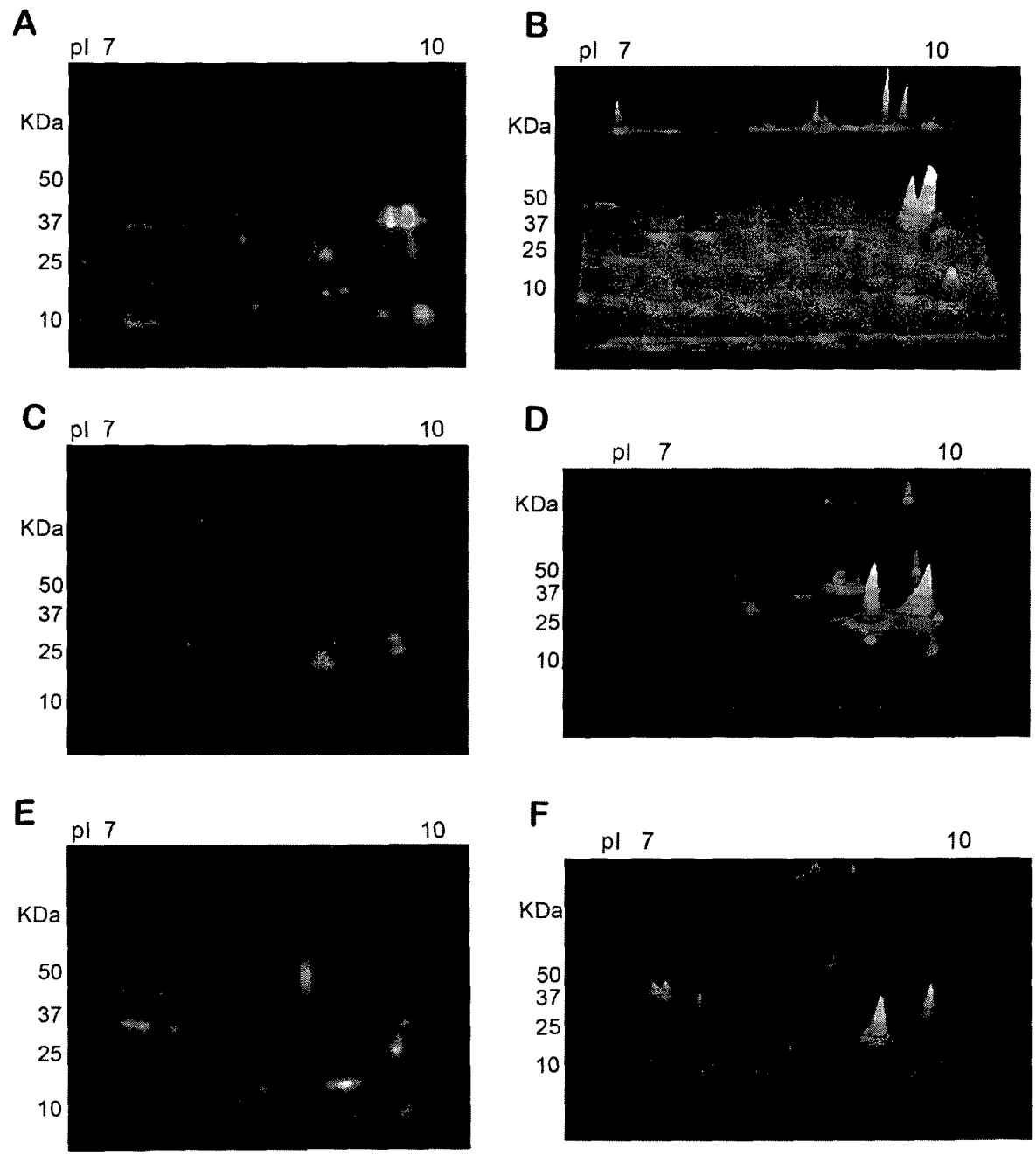

FIG. 11. (A) SDS PAGE of SRT proteins from 3 distantly related Decapodiformes. Lane 1: Molecular weight marker. Lane 3, 4 and 5 are, *D. gigas, S. lessoniana* and *S. esculenta* total SRT protein extracts respectively. (B) 2D isoelectric focusing gel of *D. gigas* (A and B); *S. lessoniana* (C and D) and *S. esculenta* (E and F) SRT proteins with pH 7-10 focusing strips.

Figure 12:
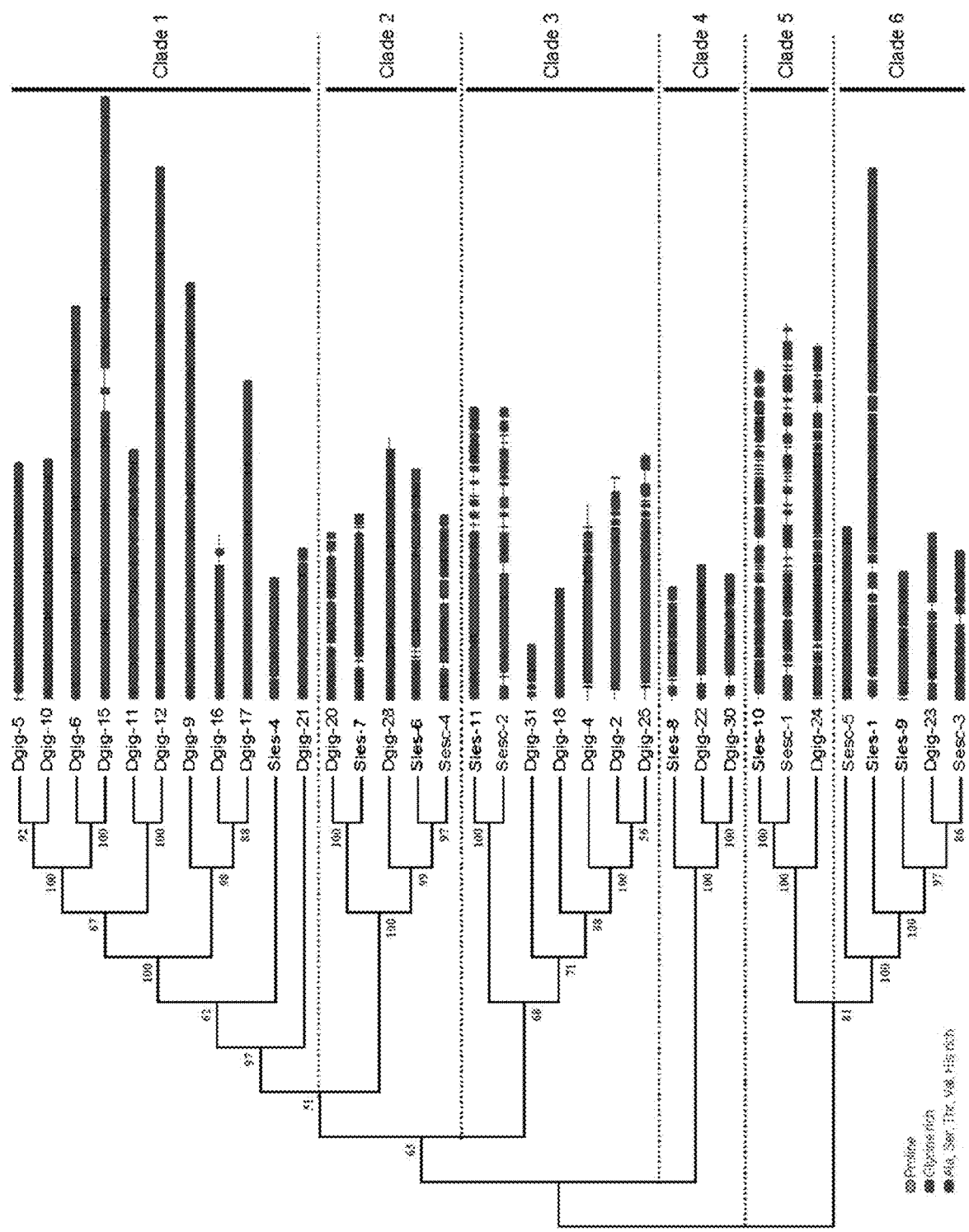

FIG. 12. Phylogenetic relationships of all known Suckerin proteins. Left: Neighbor Joining model based phylogenetic relationships of all known Suckerin proteins from *D. gigas* (Dgig), *S. lessoniana* (Sless), and *S. esculenta* (Sesc) and bootstrap scores listed at branch nodes. Right: Large scale modular architecture of Suckerin proteins from the sequences. (SEQ ID NO:2=Dgig-9 in CLADE 1); (SEQ ID NO:3=Dgig-25 in CLADE 3); (SEQ ID NO: 21=Dgig-20 CLADE 2); (SEQ ID NO:23=Dgig-22 in CLADE 4); (SEQ ID NO:24=Dgig-23 CLADE 6); (SEQ ID NO:25=Dgig-24 CLADE 5).

Figure 13:
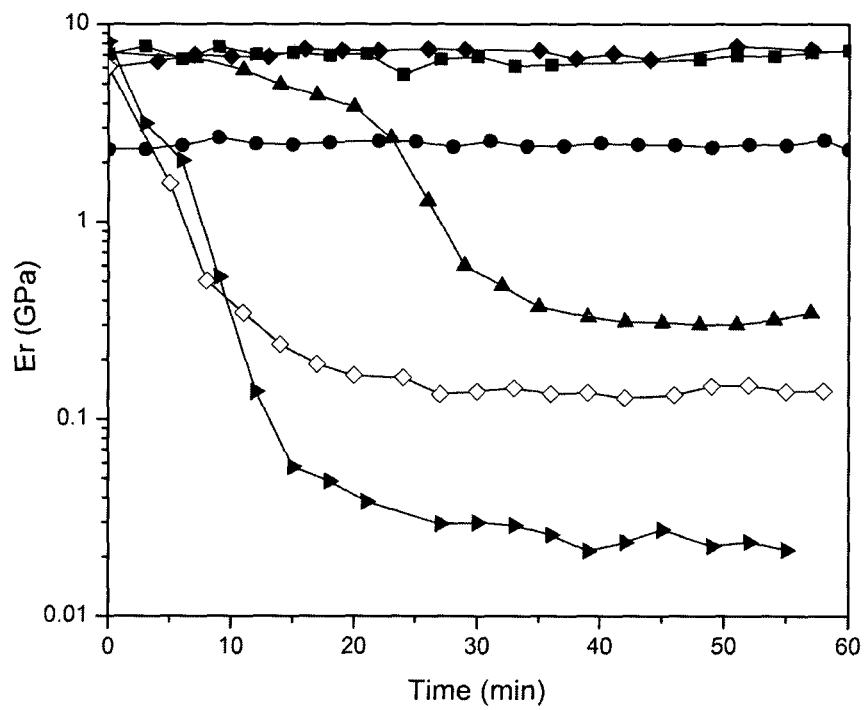
Figure 13:
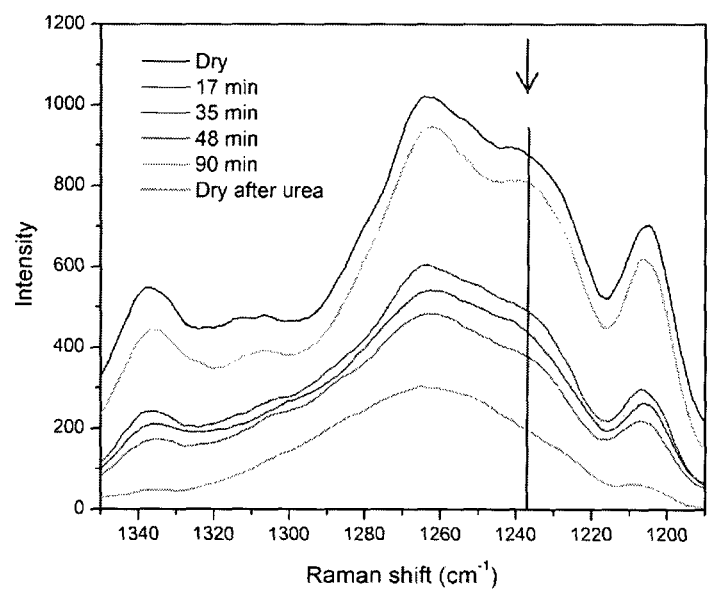

FIG. 13. Mechanical Properties and structural arrangement of SRT tip cross-section under various micro-environments (A) Nanomechanics of *D. gigas* SRT tip cross sections in air (■); water (●); 100% ethanol (◆); 0.02 M Urea (▲:); 0.2 M Urea (◇); 2M Urea (►) (B) Corresponding Micro-raman spectroscopy of *D. gigas* sucker SRT section subjected to the same micro-environments described in (C). Arrow and dotted lines indicate 1236 $cm^{-1}$ peaks that correspond to beta-sheet structure. 1236 $cm^{-1}$ peaks that correspond to beta-sheet structure. Curves from top to bottom: Curve 1 Dry; Curve 2 Dry after Urea; Curve 3, 17 minutes; 4, 35 minutes; 5, 48 minutes and 6, 90 minutes exposure to 0.2 M Urea respectively.

DETAILED DESCRIPTION

Here we describe entirely novel proteins that assemble into silk-like beta-sheet re-enforced materials and that offer multiple advantages for circumventing the major pitfalls of silk engineering. The novel SRT proteins (Suckerins) were identified from RNA-seq databases that were generated from the Sucker tissue of three distantly related Decapodiformes species. Similarity in amino acid composition, primary amino acid sequence and modular sequence designs and phylogenetic analysis suggested that these proteins are encoded by a gene family. This description relates to new robust polymers produced by all Decapodiformes species, their chemical designs and methods of production and use thereof.

The Sucker ring teeth (SRT) exhibit a distinct nanotubular architecture (FIG. 1B) and function under multiple loading regimes including bending, torsion and compression. The actual proteins of SRT and the nucleic acids that encode them have never been reported before the priority date.

Using Next Generation Sequencing combined with proteomics tools, we have identified an entirely novel family of genes that encode a new family of modular SRT proteins unique to Decapodiformes. The proteins have been named Suckerins.

Accordingly, a first aspect of the invention includes an isolated polypeptide comprising; or consisting of:
  a. the amino acid sequence set forth in any one of SEQ ID NOS: 2, 21, 23, 24 or 25; or
  b. a variant of the amino acid sequence of (a) that shares at least 40%, preferably at least 50%, more preferably at least 60%, 80% or 90% sequence identity with any one of the amino acid sequences of (a) over its entire length
  c. a fragment of the amino acid sequence of (a) or (b), the fragment having a length of at least 50, preferably at least 100, more preferably at least 150, most preferably at least 200, 400, or 600 amino acids;
  wherein the polypeptide is at least partially in beta sheet conformation.

The term "isolated polypeptide" refers to a polymer of amino acids and its equivalent and does not refer to a specific length of the product; thus, peptides, oligopeptides and proteins are included within the definition of a polypeptide. Isolated polypeptides are separated from other cellular components with which it may naturally occur including cellular debris or are synthesized using known methods such as liquid or solid phase synthesis preferably by SPPS using either Fmoc or Boc. The resulting polypeptides are preferably 70, 80 or 90% pure, preferably at least 95 or 98% pure polypeptide containing less than 30% contaminants, preferably less than 20 or 10% and most preferably less than 5 or 2% contaminants that cannot be identified as the polypeptide. In various embodiments the polypeptides may be linked together to form multimers. This term also does not refer to, or exclude modifications of the polypeptide, for example, glycosylates, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring. Polypeptides of the present invention are isolated, synthesized or engineered peptides and may have between about 70 and about 600 amino acids that form a structural protein. In various embodiments the poly peptides may have between about 50 to 500, preferably between about 100 to 400, more preferably between about 150 to 300, most preferably between about 200 to 280 amino acids.

The term "at least partially in beta sheet conformation" refers to a protein at least capable of forming an architecture whereby at least two backbones of 3 or more amino acids are connected laterally via hydrogen bonds. The protein may include other structural architecture provided at least part of the polypeptide is able have at least two backbones of 3 or more amino acids are connected laterally via hydrogen bonds. Preferably, at least 20% or at least 40, 50, 60, 70, 80 or 90% of the polypeptide is able to form into a beta sheet. Beta strands may be formed of typically 3 to 10 amino acids connected laterally by at least two or three backbones via hydrogen bonds, generally forming a pleated sheet. The hydrogen bonds need not be perfect and may exhibit localized disruptions. Generally the hydrogen bonds lie roughly in the plane of the beta sheet. The bonding pattern may be parallel, antiparallel or a mixture of both parallel and antiparallel bonding. The pleats may form in an isotropic formation or an anisotropic formation and may be anywhere in the range of 5 to 8 angstroms apart. In preferred embodiments the beta sheet structure may be isotropic pleats of 5 to 6 angstroms. In preferred embodiments the polypeptides conform into beta sheets under dry or hydrated treatments via localized hydrogen bonds that play a role in the mechanical properties of the suckerin polypeptides.

The term "percent sequence identity" is taken to include an amino acid sequence which is at least 40, 50, 60, 70, 80 or 90% identical, preferably at least 95 or 98% identical at the amino acid level over at least 10, 20, 50, 100, 200 or 300 amino acids with the amino acid sequences within each alternative sequence. In particular, percent sequence identity should typically be considered with respect to those regions of the sequence known to be essential for the structure of the protein rather than non-essential neighboring sequences. Preferred polypeptides of the invention comprise a contiguous sequence having greater than 40, 60 or 70% identity, more preferably greater than 80 or 90% identity, to one or more of amino acids set forth in any one of SEQ ID NOS:2 to 53 within each alternative sequence.

The term "percent Sequence homology" as used herein in relation to amino acid sequences, means that a residue of a given molecule is identical or homologous or similar to that at the corresponding position of a reference molecule. Similarity or homology means that the residue has similar characteristics as the one in the corresponding position of the reference molecule but is not identical. One example for such similarity is a "conservative amino acid replacement", where one amino acid is replaced by another with similar properties. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. In some embodiments, the term "percent sequence homology" is taken to have the same meaning as above in relationship to polypeptides that are isolated from the sucker ring teeth of organisms that share descent from a common decipodiforme ancestor.

Calculation of the % sequence identity or % sequence homology preferably firstly requires the production of an optimal alignment, taking into consideration gap penalties. A suitable computer program for carrying out such an alignment is the GCG Wisconsin Bestfit package and others known in the art. Examples of other software that can perform sequence comparisons include, but are not limited to, the BLAST package and the GENEWORKS suite of comparison tools. Both BLAST and FASTA are available for offline and online searching.

Although the final % sequence identity or % sequence homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

The term "fragment" includes a length of at least 20 amino acids; a length of at least 50, preferably at least 100, more preferably at least 150, most preferably at least 200 amino acids sequences set forth in any one of SEQ ID NOS: 2, 21, 23 24 or 25; or the variant having at least 70, at least 80, at least 90, at least 95, at least 96, at least 97, at least 98 or at least 99% sequence identity with the amino acid sequence set forth in any one of SEQ ID NOS: 2, 21, 23 24 or 25; or the variant over the stretch of at least 20 amino acids. In preferred embodiments the fragments occur over domains, particularly over consensus domains or peptides whereby the fragment of the amino acid sequence of (a) that shares at least 90%, preferably at least 95%, more preferably at least 99% sequence identity or sequence homology with any one of the amino acid consensus domains or peptides described herein.

The polypeptide sequences SEQ ID NOS: 2, 21, 23 24 or 25 represent clades 1-6. A clade is a subgroup of polypeptides within the suckerin polypeptides that is closely related to polypeptides within the same clade. Preferably the polypeptides of Clades 1 to 6 are represented by a specific sequence whereby any amino acid sequence of that shares at least 40%, preferably at least 50%, more preferably at least 60% sequence identity or sequence homology with the representative amino acid sequences over its entire length, falls within the same clade, wherein the representative amino acid sequence of clade 1 comprises the sequence set forth in SEQ ID NO: 2, the representative amino acid sequence of clade 2 comprises the sequence set forth in SEQ ID NO: 21, the representative amino acid sequence of clade 3 comprises the sequence set forth in SEQ ID NO: 3, the representative amino acid sequence of clade 4 comprises the sequence set forth in SEQ ID NO: 23, the representative amino acid sequence of clade 5 comprises the sequence set forth in SEQ ID NO: 25, the representative amino acid sequence of clade 6 comprises the sequence set forth in SEQ ID NO:. 24.

Preferably the polypeptide remains soluble in water and/or under mildly acidic conditions. Preferably mildly acidic conditions have a pH in the range of about 4 to 7, or 4 to 6 or 4 to 5. Alternatively, mildly acidic conditions include any acid having a pKa of above 4. The solubility under non-toxic conditions has the advantage that the polypeptides can be processed in large volumes without producing toxic waste.

In various embodiments the polypeptide comprises at least one domain 1 comprising or consisting of an amino acid sequence selected from the group consisting of HH, TT, SS, AV, TTH, THH, IAAL (SEQ ID NO: 111), SY, VTHHAP (SEQ ID NO: 112), VVLLAAF (SEQ ID NO: 113), HTTHHA (SEQ ID NO: 114), AATVSHTTHHA (SEQ ID NO: 115), FPY, THT, HVT, HHP, VSH and TVS. Preferably the at least one domain 1 comprising amino acid sequences having one or more Alanine, Valine, Threonine, Serine or Histidine.

In various embodiments the polypeptide comprises at least one glycine rich domain 2.

In various enbodiments the glycine rich domain 2 comprises at least one peptide sequence selected from GGLYG (SEQ ID NO: 116), GGYG (SEQ ID NO: 117) GLYGG (SEQ ID NO: 118), YGIG (SEQ ID NO: 119), GIG and GYG.

In preferred embodiments the glycine rich domain may also have a high number of Tyrosine and Leucine amino acids. Domain 2 is a glycine rich [M2] module that may be ~3-90 residues long or 10-100 residues long and is itself often assembled from smaller tripeptides tetrapeptides and pentapeptides modules or referred to herein as sub-domains with consensus sequences. In various embodiments at least one glycine rich domain 2 comprises at least one sub-domain 3 comprising amino acid sequence $GGX_1X_2X_3Y$ (SEQ ID NO:1) wherein $X_1$ is nothing, L, F or V; wherein $X_2$ is nothing, G, or F; and wherein $X_3$ is nothing, G or A. In various preferred embodiments the $X_1$ of the sub-domain 3 is Leucine. In various preferred embodiments the sub-domain 3 has the amino acid sequence GGLY. In various preferred embodiments the at least one glycine rich domain 2 may further comprise at least one sub-domain 4 comprising amino acid sequence GGY. The sub-domains may only occur once within the domain 2 or the sub-domains may be repeated several times within domain 2.

In various embodiments the amino acid sequence comprises, at least one consensus sequence selected from sequences set forth in SEQ ID NOS. 105, 106, 107, 108, 109, 110.

In various embodiments the polypeptides of clade 1 comprises a group of sequences comprising at least one domain 1 including the peptide THH and at least one domain 2 including the peptide GGLYG (SEQ ID NO: 116), These polypeptides may include any one of amino acid sequence set forth in SEQ ID NOS: 2, 7, 8, 10, 12, 13, 15, 17, 22 and 38 having a consensus sequence set forth in SEQ ID NO: 105 ($XGX_1XXGGYGX_2X$ wherein X is any amino acid, $X_1$ is W or G and $X_2$ is L or A). The polypeptides of clade 2 comprises a group of sequences comprising at least one domain 1 including the peptide IAAL (SEQ ID NO: 111) and at least one domain 2 including the peptide GGLYG (SEQ ID NO: 116), These polypeptides may include any one of amino acid sequence set forth in SEQ ID NOS: 21, 30, 42, 43 and 52, having a consensus sequence set forth in SEQ ID NO: 106 ($AALXCQXX_1AX_2X_3XnPXX_4XGXX_5X_6X_7GXYG$ wherein X is any amino acid, $X_1$ is A or E, $X_2$ is A or I, $X_3$ is L or I, $X_4$ is G or V, $X_5$ is P or G, $X_6$ is F or L, $X_7$ is G or N and n is 90-200). The polypeptides of clade 3 comprises a group of sequences comprising at least one domain 1 including the peptide SY and at least one domain 2 including the peptide GGYG SEQ NO: 117), These polypeptides may include any one of amino acid sequence set forth in SEQ ID NOS. 3, 5, 19, 26, 35, 47 and 50, having a consensus sequence set forth in SEQ ID NO: 107 ($X_1XGGX_2GXnX_3G$ wherein X is any amino acid, $X_1$ is G or L, $X_2$ is Y or G, $X_3$ is G or V, and n is 2-15). The polypeptides of clade 4 comprises a group of sequences comprising at least one domain 1 including the peptide VTHHAP (SEQ ID NO: 112), or VVLLAAF (SEQ ID NO: 113) and at least one domain 2 including the peptide GLYGG (SEQ ID NO: 118). These polypeptides may include any one of amino acid sequence set forth in SEQ ID NOS: 23, 32 and 44 having a consensus sequence set forth in SEQ ID NO: 108 ($LIFVVLLAAFGX_1AX_2X_3EXn-VTHHAPYX_4XGXnGLYGG$ wherein X is any amino acid, $X_1$ is L or F, $X_2$ is C or Y, $X_3$ is G or S, $X_4$ is T or G and n is 2-100). The polypeptide of clade 5 comprises a group of sequences comprising at least one domain 1 including the peptide FPY, THT, HVT, HHP and at least one domain 2 including the peptide YGIG (SEQ ID NO: 119) or GIG, These polypeptides may include any one of amino acid sequence set forth in SEQ ID NOS: 25, 46 and 49 having a consensus sequence set forth in SEQ ID NO: 109 ($GX_1VSX_2QXPFXX_3X_4PXYGIGXnGAX_5XHGF$ wherein X is any amino acid, $X_1$ is L or I, $X_2$ is A or G, $X_3$ is A or P, $X_4$ is G or F, $X_5$ is F or Y and n is 10-15). The polypeptides of clade 6 comprises a group of sequences comprising at least one domain 1 including the peptide TVS and at least one domain 2 including the peptide GYG, These polypeptides may include any one of amino acid sequence set forth in SEQ ID NOS: 24, 37, 45, 51 and 53, having a consensus sequence set forth in SEQ ID NO: 110 ($XGXX_1XnSX_2XTVSH$ wherein X is any amino acid, $X_1$ is Y or F, $X_2$ is V or I, and n is 2-10).

In various embodiments the polypeptide comprises an amino acid sequence set forth in any one of SEQ ID NOS: 2 to 53; or (b) a variant of the amino acid sequence of (a) that shares at least 40%, preferably at least 50%, more preferably at least 60% sequence identity or sequence homology with the amino acid sequence of the amino acid sequence set forth in any one of SEQ ID Nos. 2 to 53 over its entire length.

Preferably the percent sequence identity should typically be considered with respect to those domains or regions of the sequence known to be essential for the structure of the protein rather than non-essential neighboring sequences. Preferably the polypeptide comprises at least one domain 1 comprising amino acid sequences having one or more Alanine, Valine, Threonine, Serine or Histidine and forms the beta-sheet domains that are occupied by A, V, T S, and H rich sequences. This domain is designated as the [M1] module. In various embodiments domain 1 comprises amino acid sequence HH, or TT, or SS or AV. or AA, or, TV. In various embodiments domain 1 is flanked by prolines at either side of the domain or at least at one side of the domain. Without being limited by any theories it is postulated that in various embodiments the prolines form the edges of the beta-sheet. In various preferred embodiments the domain 1 has the amino acid sequence THE or TTH. or VSH. In various embodiments the domain 1 has the amino acid sequence HTTHHA (SEQ ID NO: 114 In various embodiments the domain 1 has the amino acid sequence AATVSHTTHHA (SEQ ID NO: 115).

Fragments and derivatives of full length polypeptides, particularly include fragments or derivatives having substantially the same biological structure and mechanics involved with the formation of the beta sheet. A particularly preferred polypeptide consists of amino acids with domain 1 and 2 mentioned herein. There may be repeats, substitutions and deletions within the domains meaning the domains can greatly vary in length.

In various preferred embodiments the polypeptide may further comprise at least one proline residue. The proline residues may form at the edges of the beta sheets, as such they are often either before and/or after domain 1. In various embodiments the proline residues flank either side of the domain 1.

In various embodiments the polypeptide comprises a peptide unit from N- to C-terminus: Proline-Domain 1-Domain 2.

In various embodiments the polypeptide comprises a peptide unit from N to C terminus, Proline-Domain 1-Proline-Domain 2.

In various embodiments the domain 2 comprises from N to C terminus, (sub-Domain 3-sub-Domain 4) n, wherein n is independently 1 to 4. In various embodiments the domain 2 comprises from N to C terminus, (sub-Domain 3-sub-Domain 4-sub-Domain 3)n, wherein n is independently 1 to 3.

In various embodiments any of the described peptide units may be repeated from 2 to 13 times. There may be other amino acid residues between each of the domains or each of the peptide units mentioned herein provided the polypeptide is able to form a beta sheet structure.

The polypeptide may be isolated and purified from a species in the Decapodiformes super order. Decapodiforme is a superorder of cephalopoda having 10 limbs and sucker ring teeth within the suckers on there limbs. The identified orders are Bathyteuthoidea, Spirulidea, idiosepidea, Sepolidea, Oegeopsidea and Myopsidea. There are about 95 identified genera and about 450 species. The polypeptide may be isolated and purified from any of these 450 species.

Another aspect of the invention includes an isolated nucleic acid molecule comprising a nucleic acid sequence encoding the polypeptide as described herein.

The term "isolated nucleic acid" as used herein refers to any nucleic acid molecule in any possible configuration, such as single stranded, double stranded or a combination thereof. Isolated nucleic acids include for instance DNA molecules, RNA molecules, analogues of the DNA or RNA generated using nucleotide analogues or using nucleic acid chemistry, locked nucleic acid molecules (LNA), peptide nucleic acid molecules (PNA) and tecto-RNA molecules. DNA or RNA may be of genomic or synthetic origin and may be single or double stranded: Such nucleic acid can be e.g. mRNA, cRNA, synthetic RNA, genomic DNA, cDNA, synthetic DNA, a copolymer of DNA and RNA, oligonucleotides, etc. Any nucleic acid capable of expressing the polypeptides of the invention including the domains in a host cell would be suitable. Isolated nucleic acid are separated from other cellular components with which it may naturally occur including cellular debris or are synthesized using known methods The resulting nucleic acids are preferably 70, 80 or 90% pure, preferably at least 95 or 98% pure nucleic acid containing less than 30% contaminants, preferably less than 20 or 10% and most preferably less than 5 or 2% contaminants that cannot be identified as the nucleic acid as described herein.

Many nucleotide analogues are known and can be used in the isolated nucleic acid of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

In a preferred embodiment the isolated nucleic acid molecule comprises any one of the sequences set forth in SEQ ID NOS: 54 to 100. Preferably the isolated nucleic acid molecule is optomised for expression in a given host.

The term "optomised for expression" as used herein, refers to the addition of regulatory elements. This could include promoter or enhancer sequences as known in the art. promoter or enhancer sequences vary from organism to organism, but are well known to persons skilled in the art for different organisms. The promoter selected is preferably a strong promoter capable of high levels of transcription to drive rapid polypeptide expression. Generally viral promoters have these criteria as these are required for efficient viral propagation, and they frequently induce much higher levels of transcription than eukaryotic promoters by using mechanisms to control and recruit host transcription machinery. Moreover, viral promoters tend to be far more compact and hence easier to manipulate and accommodate into gene vectors. Human cytomegalovirus major immediate early gene promoter (hCMV) would by suitable. Other suitable viral promoters include the simian virus 40 (SV40), Rous sarcoma virus long terminal repeat (RSV-LTR), Moloney murine leukaemia virus (MoMLV) LTR, and other retroviral LTR promoters. Any other suitable promoter known in the art capable of high levels of transcription would be suitable. The isolated nucleic acid of the invention is operably linked to the promoter, and preferably lies 3' to the promoter sequence, more preferably lies directly adjacent to the promoter sequence.

In a preferred embodiment the nucleic acid sequence is comprised in an expression construct preferably a vector as is known in the art. The term "vector" relates to a single or double-stranded circular nucleic acid molecule that can be transfected into cells and replicated within or independently of a cell genome. A circular double-stranded nucleic acid molecule can be cut and thereby linearized upon treatment with restriction enzymes. An assortment of nucleic acid vectors, restriction enzymes, and the knowledge of the nucleotide sequences cut by restriction enzymes are readily available to those skilled in the art. A nucleic acid molecule encoding a polypeptide can be inserted into a vector by cutting the vector with restriction enzymes and ligating the pieces together. Preferably the vector is a plasmid.

Another aspect of the invention includes a host cell comprising the expression construct as described herein able to express the polypeptide of the invention. The host cell may be any suitable host cell for recombinant production. The cell may be a prokariotic cell or a eukariotic cell. There are many cell based systems known in the art. Alternatively the polypeptide may be expressed by cell free translation. The host cell may include a multicellular host system of a plant or an animal. Transgenic models are known in the art.

Another aspect of the invention includes a material comprising the polypeptide as described herein. Preferably the material maintains the beta sheet structure. In various embodiments the material is selected from the group: a fibre, filament, a film, a foam, a nano fibre, a nano sphere, a nano particle, a liquid crystal mesogen, a colloid, a copolymer, or a block copolymer.

Another aspect of the invention includes a method of making the material comprising the polypeptide as described herein comprising the steps of: (a) crushing the polypeptide; (b) heating and/or using a solvent to dissolve the crushed polypeptide into a liquid; and (c) forming the material from the liquid. In various embodiments forming the material comprises spinning the liquid into a fibre. In various other embodiments forming the material comprises placing the liquid into a mold; and removing the mold after the liquid solidifies.

Another aspect of the invention includes a tissue scaffold comprising the polypeptide as described herein.

Another aspect of the invention includes a multimer of the polypeptides as described herein.

The present invention is further illustrated by the following examples. However, it should be understood, that the invention is not limited to the exemplified embodiments.

Examples of Preferred Embodiments

Tissue Collection

Jumbo squid were caught off the east coast of the Baja Peninsula La Paz, Mexico. *Sepioteuthis lessoniana* squid, were caught off the east coast of Singapore, Changi. *Sepia esculenta* were bought in a pet shop in Singapore. These represent three distantly related Decapodiformes species 1) jumbo squid (*Dosidicus gigas*, Order Oegeopsida); 2) green eyed reef squid (*Sepioteuthis lessoniana*, Order Myopsida) and 3) the golden cuttle fish (*Sepia esculenta*: Order Sepiidae). Live animals were sacrificed, dissected and materials and SRT and sucker tissues harvested immediately. Tissues were stored in RNA-later (Qiagen).

Macro Structure of Sucker Ring Teeth

Figure 3:
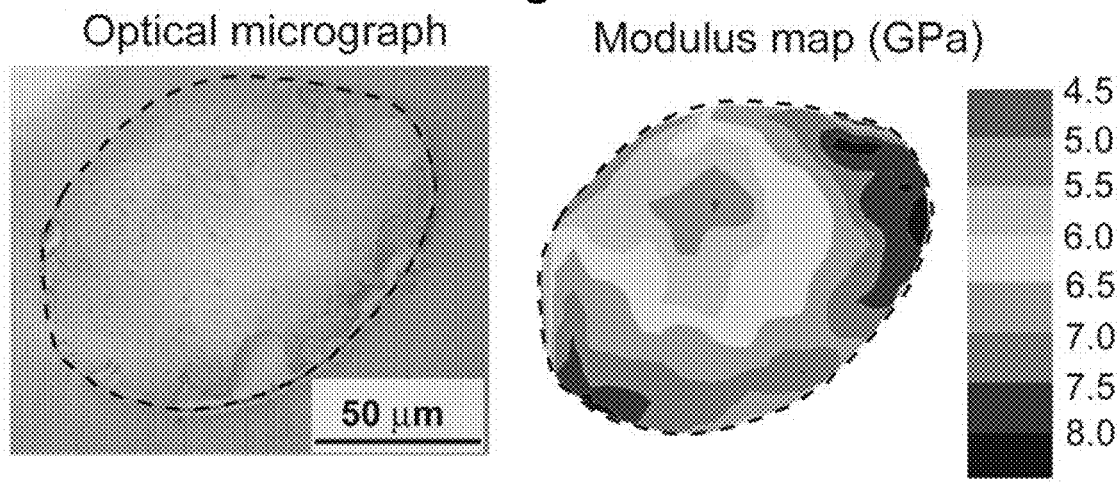
FIG. 3: Optical micrograph of a microtomed cross-section surface of a SRT and elastic modulus mapping of the sections obtained by nanoindentation.

The protein-based SRTs exhibit a precise nanotubular architecture (FIG. 1*b*) and feature micro-mechanical properties matching those of strong synthetic polymers[47], with elastic moduli in the range of 6-8 GPa in the dry state (FIG. 3) and 2-4 GPa when hydrated Notably, these robust properties are achieved in the absence of covalent bonds between the constituent proteins, which are soluble in 2M urea/weak acidic conditions implying that the cooperation of weak interactions are responsible for holding the entire structure together into a robust supramolecular network.

Raman Spectroscopy

Microtomed SRT cross-sections were probed with a confocal Raman CRM200 microscope (WITec) equipped with a diode-pumped 785 nm near infrared laser (Toptica Photonics), a water immersion objective (Nikon, ×60, numerical aperture of 1) and a P-500 piezo-scanner (Physik Instrumente). ScanCtrlSpectroscopyPlus software (WITec) was used for measurement and image processing. Protein amide I chemical images (with 500 nm steps and 0.4 s integration time) were obtained using a sum filter and integrating the 1600-1700 $cm^{-1}$ spectral range.

Isolation and Purification of a New Class of Proteins

RNA-seq uses deep sequencing to survey the transcriptome in an unbiased and comprehensive manner. Full-length transcripts can be assembled de novo from short sequence reads generated from massively parallel sequencing, and this approach has had a profound impact in a number of areas of research. However, to our knowledge its broad integrative potential for biomimetic engineering has not yet been demonstrated. Transcriptomic data sets were integrated with proteomics data in three ways to identify relevant transcripts. First, where Edman protein sequence was available, we identified assembled transcript sequences by sequence alignment. Second, if only amino acid composition was available, we calculated amino acid profiles for each transcript, and identified the transcript using the most similar profiles in terms of molecular weight, amino acid composition and isoelectric point values. Third, we used the translated transcriptome database as a reference protein database for mass spectrometry analysis.

Using Next Generation Sequencing combined with proteomics tools, we have identified an entirely novel family of genes that encode a family of modular SRT proteins unique to decapodiformes of the cephalopods. The proteins have been named Suckerins. The complete genes (Gene SEQ ID NOS: 53-100) and protein (Protein SEQ ID NOS: 2-52) sequences (in corresponding order) for Suckerins identified from the Jumbo Squid *Dosidicus gigas*; Green Eyed Reef squid *Sepioteuthis lessoniana*; and the Golden Cuttle fish *Sepia esculenta*. are provided.

Figure 2:
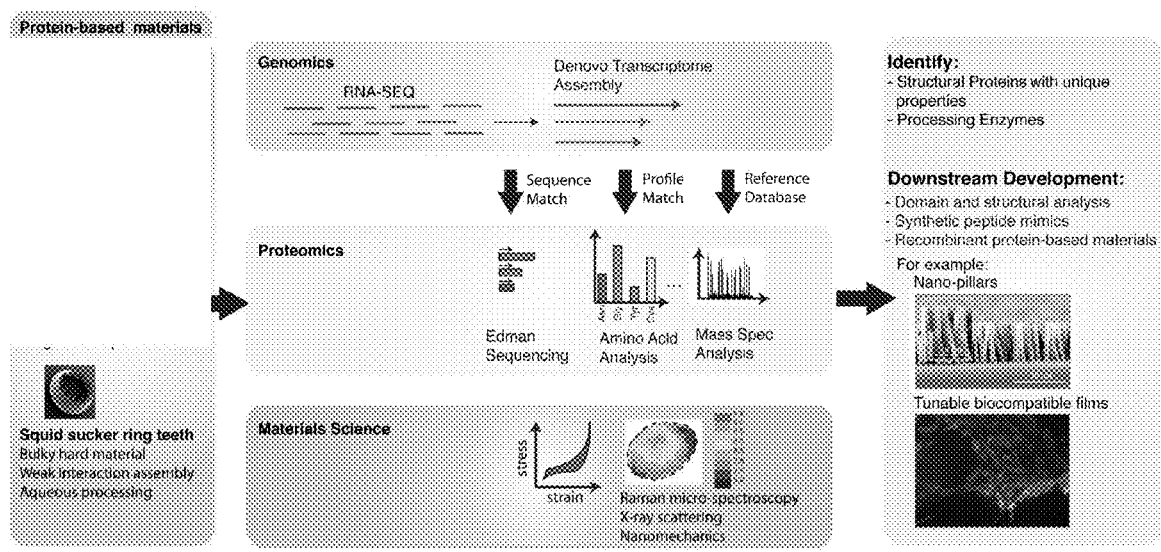
FIG. 2: Integrating RNA-seq, proteomics and material science. RNA-seq of the tissue of interest is performed and the transcriptome is assembled de novo. In parallel, comprehensive proteomics of the protein building blocks is conducted, as well as materials and biophysical characterization. Transcriptome data are integrated with one or a combination of different proteomic techniques (Edman sequencing, amino acid analysis and mass spectrometry analysis) to identify the relevant transcripts. The integrated approach allows for the rapid generation of genomic to mechanical phenotype maps, eventually providing key information for subsequent structural analysis and biotechnological applications that mimic the properties of the starting materials, using for instance recombinant protein expression or synthetic peptide mimics.

Integrating the primary protein sequence with Raman micro-spectroscopy, x-ray scattering and mechanical data at various length scales allowed us to rapidly generate genotype to mechanical phenotype maps for each of these model biological materials (FIG. 2).

RNA-Seq Transcriptome Library Preparation

Total RNA was extracted with a Qiagen RNeasy mini kit. 2-10 μg Total RNA per tissue was used in the construction of three separate RNA-Seq libraries. DEPC water was added to total RNA to a final 50 μl volume and incubated at 65° C. for 5 min. Poly-A mRNA was enriched with oligo dT beads (Invitrogen) and used for constructing strand-specific paired-end libraries (ScriptSeq™ mRNA-Seq library kit v1, Epicenter, Illumine). Phusion PCR polymerase (Thermo Scientific) was used for the final library amplification (12 cycles). PCR cleanup was performed with the MinElute PCR purification kit (Qiagen). Library quantity and quality was assessed with an Agilent 21000 Bioanalyzer.

Library Sequencing

Each library was diluted to 8 pM and clusters were generated on paired-end-read flow cells on an Illumine cBot. Each library was sequenced on a separate lane and 2×76 by paired-end-reads were collected.

Transcriptome Assembly

Raw reads were converted to fastq format using the Illumina's Offline Base Caller (v1.6). De novo transcript assembly was performed with the Trinity software suite using standard parameters on a computational cluster. The final butterfly output predicted transcript files were used for subsequent analysis.

Protein Annotation

Open reading frames were predicted using custom Perl scripts. Predicted transcripts were quantified by RSEM software. Predicted protein sequences were first searched using USEARCH against NR (Genbank) and Pfam protein databases to identify homologous sequences. Custom Pen scripts were written to match predicted proteins against proteomic data including: (i) De novo LC MS/MS peptides, (ii) MW, Edman sequences, and (iv) amino acid composition.

LC MS/MS

5 μl of digested peptides were separated with a Nano C18 HPLC column (Agilent 1200) and data were collected with a QTOF 6520 (Agilent). The m/z range for the parent ion was 350 to 1200 Da, and 100-800 Da for the fragment ions. Data were acquired with MassHunter Acquisition B.040 and processed with MassHunter Qualitative Analysis 8.040 (Agilent). PEAKS Studio 5.3 was used for DeNovo sequence tag creation, and searches against our created transcriptome libraries were conducted using Spider and Peaks search routines.

X-RAY Diffraction

Wide-Angle X-Ray Scattering (WAXS) and Small angle scattering (SAX) were collected using a synchrotron source.

2D Electrophoresis.

SRT from the tentacles of *D. gigas, S. Lessoniana* and *S. esculenta* were pulverized separately in liquid nitrogen and re-suspended in Bio-Rad rehydration buffer with the appropriate ampholytes at 2 mg/ml concentration. 125 ul of each sample was incubated overnight with BioRad 3-10 and 7-10 Ready strips in preparation for isoelectric focussing. Samples were focused using a 0-4000V ramp. The strips were then subjected to reduction and alkylation steps according to manufacturers' instructions and then the second dimension was run with a low initial voltage of 10V/cm followed by 200V for 30 minutes. Mini-Gels were stained with Sypro Ruby stain according to manufacturers' instructions SRT from the tentacles were pulverized in liquid nitrogen, homogenized in 5% acetic acid/2M Urea, and subjected to SDS-PAGE. Bands were transferred to a PVDF membrane, stained with Commassie blue and subjected to Edman sequencing (Iowa State Protein Facility). Suckerin was also isolated by Size-Exclusion (SE) HPLC (Agilent 1260 Infinity LC) and subjected to chymotrypsin digestion and LC-MS/MS. De novo peptides determined using PEAKS software were screened against our transcriptome database.

Figure 4:
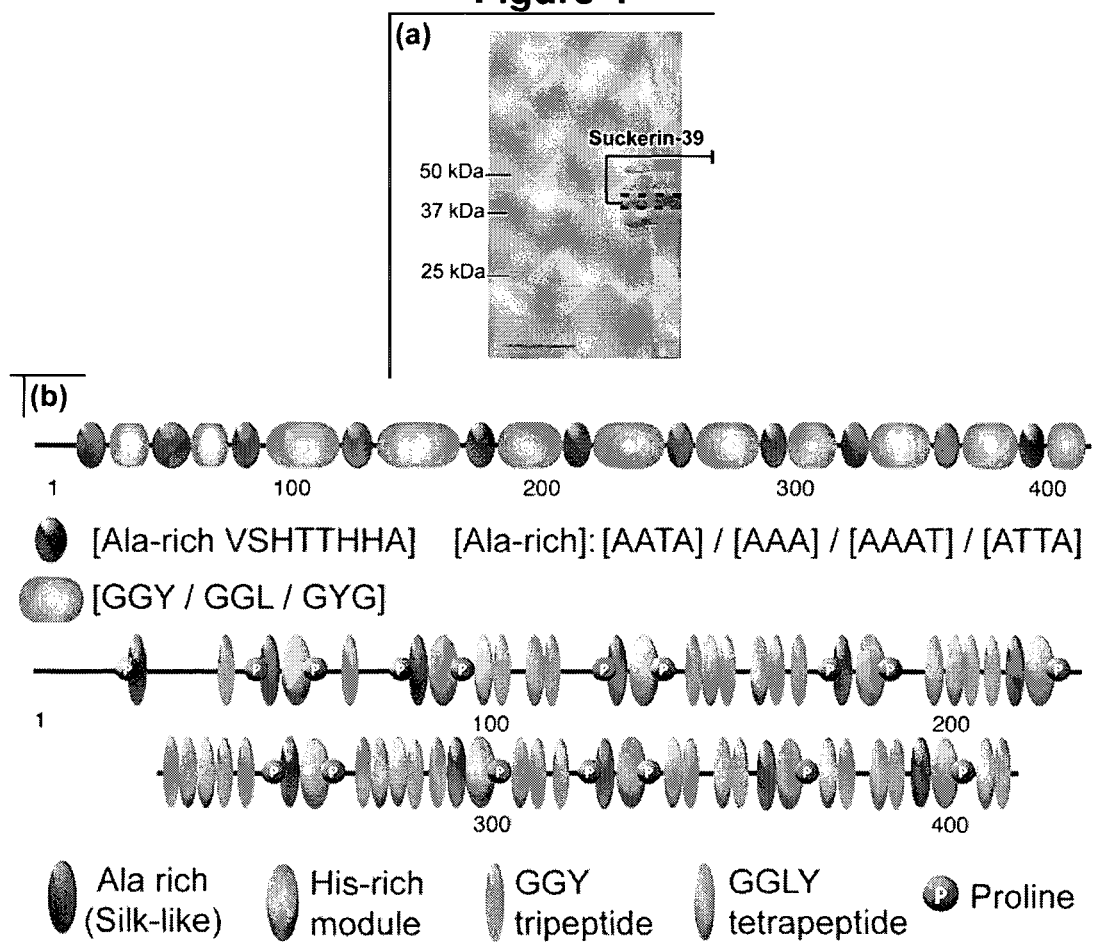
FIG. 4: Isolation and characterisation of Suckerin protein (a) SDS Page of the crude SRT extract. The most abundant protein at ~39 kDa was targeted for this study. (b) Primary sequence modularity of Suckerin, illustrating extreme modularity, with alternating Ala/His and Gly/Tyr rich domains. These domains are composed of smaller repeats with some homology to dragline silks. (VSHTTHHA (SEQ ID NO:612); AATA (SEQ ID NO:613); AAAT (SEQ ID NO:614); AATA (SEQ ID NO:615)).

A list of candidate transcripts was generated by matching the overall amino acid composition of the SRT against the translated predicted transcripts. We initially focused our attention on the most abundant protein present in the sucker crown (FIG. 4a). An N-terminal Edman sequence of the isolated protein was mapped to one candidate sequence, which was also among the most highly expressed transcripts in our transcriptome library (Table 1). The gene contained highly repetitive sequences resulting in fragmentation of the transcript assembly. Therefore we used RACE-PCR to identify the full-length transcript. Total RNA was subjected to RACE-PCR using Invitrogen's Generacer Kit. PCR primers were designed based on Trinity assembled transcripts and KOD extreme Taq-polymerase was used for PCR (Merck Milipore). Products were sub-cloned into pCR2.1 by TA cloning, subjected to Sanger sequencing and alignments performed with ClustalW.

The identified gene/protein was a highly modular, glycine-, histidine- and tyrosine-rich 39 kDa protein with partial homology to silk[4,5] and oyster shell matrix proteins[55]. However, the protein is clearly distinct from these or any other proteins, supporting the view that we have identified a structural protein, named Suckerin that had previously not been described. The identity of Suckerin was corroborated by LC-MS/MS with 80% sequence coverage (data not shown). Here, the repetitive nature of the protein sequence informed our decision to use the more promiscuous chymotrypsin protease for protein digestion for subsequent LC-MS/MS analysis that provided ~80% coverage of the protein sequence confirming the identity and sequence design of this protein rator with methanol (SpeedVac), and amino acid composition was analyzed on a post-column derivatization, Ninydrin-based S433 Sykam analyzer.

Evolutionary Relationships of the Suckerin Gene/Protein Family Members.

The Suckerins are clearly an entirely novel class of proteins and blast searches of each of the known members provides low homology with all other known proteins, with values ranging from 20-39% for the closest matching unrelated structural proteins. All of the Suckerins we have identified to date exhibit variable degrees of identity and divergence. However, they are clearly members of the same or related family of proteins based on the fact that 1) they are rich in Glycine, Alanine, Histidine and/or Tyrosine 2) they are usually highly modular at multiple scales of hierarchy. Suckerins in general are assembled from large modules (defined as [L]) ~20-40 amino acids long that are reiterated ~1-13 times within the entire full length native protein. [L] modules often contain at least 1 and often all three types of smaller modules defined as [M1], [M2] and [M3] where [M1] is usually A, V, T, H or S Rich, [M2] and [M3] which are G rich; 3) the proteins are present in the SRT structure but are not observed in any other known tissue characterized to date. By way of example, which is in no way intended to limit the scope of the current invention, the conserved modular nature of two Suckerins from the 3 diverse decapodiformes when compared and contrasted have similar domains but still have a level of variation. Sequence alignments of selected Suckerins from the three species show some conservation of both N-terminal signal peptides and extensive conservation of repetitive sequences. Taken together, this provides strong evidence that all of the known Suckerins reported herein are members of a gene family.

Our sequence data on the Suckerins was obtained from three distantly related squid species. In fact, according to

TABLE 1

Transcript expression levels determined by RSEM. Transcript abundance estimation from RNA-SEQ reads mapped to Trinity assembled transcripts.
*Dosidicus gigas* Sucker (149,005 predicted transcripts)

| Transcript ID | Expected Read Counts | Tau (Estimated fraction of transcripts) | Transcripts per million (Tau × 10⁶) | Abundance Rank | Annotation |
| --- | --- | --- | --- | --- | --- |
| comp3_c1 | 1,888,587 | 0.028133893 | 28133.89 | 2 | Myosin Regulatory Light Chain |
| comp14_c0 | 152,983 | 0.02743 | 27432.24 | 3 | Suckerin-39 |
| comp15_c0 | 292,197 | 0.01860 | 18597.67 | 5 | Suckerin-39 |
| comp4_c0 | 1,918,297 | 0.016067085 | 16067.09 | 7 | Tropomyosin |
| comp0_c0 | 9,655,271 | 0.015045237 | 15045.24 | 9 | Myosin Heavy Chain |

Expected Count: the estimated number of reads that are derived from the transcript. Tau: the estimated fraction of transcripts made up by this transcript. Transcripts per million: estimated number of transcripts per million transcript molecules. Abundance Rank: the relative rank of the transcript in the entire transcriptome sorted by Tau.

The combined use of proteomic tools with RNA-seq-generated transcriptome databases, the sequence identification, structure function analysis and biomimetic/protein engineering was rapidly sped up. One of the main advantages of the approach is that it provides a permanent database of all expressed genes in the target tissue that can be rapidly used for further searches. This approach facilitates the rapid characterization of novel structural proteins and provides insights into natural processing mechanisms of uncharacterized biological materials within a matter of weeks, providing a strong foundation for the elucidation of complex structural and functional dynamics.

Amino Acid Analysis

Tissues and purified proteins were hydrolyzed in vacuo in 6M HCl/5% phenol overnight, washed on a vacuum evapocurrent squid cladistics and systematic efforts by others, these species diverged very early on in the history of decapodiformes evolution, having shared a common ancestor dating back as far as 350 million years ago[48,49] and references therein. This common ancestor is believed to have given rise to all known extant squid species. This information provides strong support for the view that, while they have yet to be sequenced, SRT from all decapodiformes are assembled from related proteins expressed from members of the Suckerin gene family described herein. Therefore similar domain structures are considered to describe all members of the Suckerins identified and those yet to be identified that are clearly related evolutionarily and uses thereof.

Similarity at the genetic level, in amino acid composition, signal peptide sequence, primary protein sequence and modular design at multiple amino sequence length scales support the view that the Suckerins are encoded by members of a gene family. Using the Maximum Joining (NJ) model a statistically reasonable unrooted tree was generated (FIG. 12). Based on potential caveats involved in the use of NJ methods for the phylogenetic analysis of protein families, we make only the most conservative observations based on this tree. First, the NJ tree is statistically well supported, indicating that all of the Suckerin proteins we have identified are evolutionarily related. Second, the genes appear to have diverged by both gene duplication and speciation events. Third, the proteins cluster into 6 distinct clades suggesting that the Suckerin genes comprise a multigene superfamily. Fourth, five of the six clades contain proteins from all three of the species studied. These species shared a common ancestor ~354 MYa suggesting that the Suckerin gene family is ancient, with Suckerin gene(s) likely arising at least in the Devonian period. Understanding the molecular mechanisms that underlie the evolution of modular proteins remains a major challenge and an elucidation of these mechanisms as they relate to the Suckerin protein family will likely provide unique insights into the biomechanical and ecological roles of these proteins. Based on the observed variations in size and the presence or absence of small and large modules across the Suckerin proteins it appears likely that genetic divergence has involved gene duplication, segmental expansion/deletion, and slippage of DNA polymerase, non-reciprocal homologous crossing-over and/or gene conversion events observed in genes encoding highly modular proteins. As is the case with spider silk proteins, Suckerins are encoded by guanine:cytosine rich sequences that are known recombination hot-spots. The occurrence of these regions, combined with high degree of homologous modular sequences may have influenced the divergence in the Suckerin gene family. Finally, in addition to molecular drive mechanisms, it will, in the future, be key to unravel the relative contribution the selective pressures acting at the level of the mechanical properties of the SRT.

Phylocientic Analysis.

Full-length Suckerin protein sequences were aligned using ClustalW as implemented in BioEdit sequence alignment editor. We used three different methods of phylogenetic estimation—Neighbor Joining (NJ), Maximum Parsimony (MP) and Maximum Likelihood (ML). Since bootstrap support values were generally low for most clades in the MP and ML trees, we have presented only the NJ tree for the present analysis (FIG. 12). Homology searches against the NCBI non-redundant database were unable to pick up sequences related to Suckerins for use as an outgroup. Thus, the tree presented here is an unrooted tree. The NJ tree was generated using MEGA5 using the p-distance method, pairwise-deletion of gaps and 100 bootstrap replicates for node support. Most of the nodes in the NJ tree showed a high bootstrap support value. Based on the topology of the NJ tree, the Suckerin sequences could be assigned to six distinct phylogenetic clades. This suggests that the common ancestor of *D. gigas*, *S. Lessoniana* and *S. esculenta* possessed at least six suckerin genes.

The protein modular architectures of the suckerin sequences are shown juxtaposed with the NJ tree to clarify the evolutionary history of this protein family.

Structure of Native SRT

Our current data indicates that the Suckerin proteins are encoded by a large gene family that is of ancient origin. The large scale modular architecture of the Suckerins likely facilitates their intra and inter-molecular assembly into polymer networks consisting of amorphous and/or semi-amorphous structure stabilized by optimally small, nano-confined beta-sheets. The observed distinctions in molecular weights and large scale modular architectures of the Suckerins may offer the potential for the modulation of network properties including cross-link density and intervening amorphous chain lengths, which would directly influence the mechanical properties of the SRT. It is interesting to speculate that these factors may play a role in the creation of the observed gradients in SRT mechanical properties that likely-prevent modulus mismatch failure at the tissue-SRT interface. The hierarchical design and mechanical behavior of native SRT provides a unique model system for the development of biomimetic engineering strategies and the Suckerin gene family provides an expanded tool-box for the engineering of a range of tailored high-performance biomimetic materials.

We conducted SDS-PAGE and 2D electrophoresis on three distantly related Decapodiformes species 1) jumbo squid (*Dosidicus gigas*, Order Oegeopsida); 2) green eyed reef squid (*Sepioteuthis lessoniana*, Order Myopsida) and 3) the golden cuttle fish (*Sepia esculenta*: Order Sepiidae). FIGS. 11A & B show that, for all three species examined, SRT are assembled from mixture proteins whose molecular weights range from ~8 KDa to ~60 KDa and whose pIs fall in a relatively confined window between 7 and 10. The data also indicated that *D. gigas* SRT contain a larger repertoire of proteins than those of *S. lessoniana* and *S. esculenta*. Interestingly, the amino acid composition of Suckerin-39 closely matched the global amino acid composition of the entire *D. gigas* SRT suggesting possible similarities between proteins, at least within *D. gigas*.

To understand the molecular bases for the mechanical properties of native SRT we first examined the protein conformations of SRT slices using micro-RAMAN spectroscopy. Interestingly the SRT exhibits the presence of beta-sheet-structure that is also observed in silks (FIG. 7*d* & *e*). Polarized micro-raman spectroscopy supports the view that the distribution of beta-sheets is isotropic, an arrangement that would be useful for a material that is subject to a range of loading regimes. In silico predictions using JPRED suggest that the beta-sheet domains are occupied by A, V, T S, rich sequences in the [M1] module. The data indicates that the SRT maintains silk-like supra-molecular organization while being assembled from an entirely novel set of proteins, the Suckerins. The SRT beta sheets likely stabilize and re-enforce the network and may offer superior strength based on nanoconfinement principles[50].

An exhaustive search of all protein databases such as swissprot failed to provide statistically significant hits, supporting the view that the Suckerins represent a novel class of structural proteins. The Suckerins generally have a ~20-24 amino acid signal peptide with ~40%-90% similarity between all of the proteins identified. The full length Suckerin proteins exhibit similarity in amino acid composition, with a heavy biases Glycine, Tyrosine, Leucine, Alanine, Threonine, Histidine, Serine and Valine (FIG. 4*b*). The complete primary amino acid sequences are listed in SEQ ID NOS: 2-52 and color coded modular designs of the Suckerins are shown in FIG. 4*b*. Most of the Suckerins identified contain sets of commonly occurring small peptide modules, including GGY and GGLY. GGY peptides are also present other structural proteins including the spider silk protein family (4, 5), silk worm fibroins (58), the shell matrix proteins Shematrins (55) and Prismalin-14 (59), and crocodile skin β-keratins (60) suggesting convergent evolution of this peptide design.

The current invention relates to the novelty of nucleic acids encoding the Suckerin proteins and the novelty in amino acid primary sequence and modular designs observed in all known Suckerins, natural and synthetic variants thereof and evolutionary related Suckerin genes and proteins. Here, the molecular design of the proteins is described in detail.

In general the Suckerins range in molecular weight form ~5 KDa to 60 KDa. The [L] modules are reiterated consecutively (~between 3 and 13 times) depending on the size of the [L] and [M] modules and the overall size of the protein. [L] modules usually occur throughout majority of the protein, with the exception of the peptide signal sequence. As mentioned above, the large-scale [L] modules themselves comprise smaller [M] modules. In the clearest cases [L] modules are assembled from clustered domains and/or sequential organization of [M1], [M2]. FIG. 4b provides a clear example of the modular architecture of selected Suckerin from *D. gigas, S. lessoniana* and *S. esculenta*. [M1] and [M2] modules often appear in sequence and can be preceded and/or proceeded by proline residues. Clearly defined hexapeptides that occur within [M1] and [M2] and/or that span [M1] and [M2] are listed in Table 2. The glycine rich [M2] module can be ~0-90 residues long and is itself often assembled from smaller sub-domains of tripeptides tetrapeptides and pentapeptides also shown in Table 2 Tri, tetra and pentapeptides can also sometimes be rearranged within the glycine rich [M2] domain. In some of the Suckerin proteins the strict use of the small glycine rich peptides listed in Table 2 is not adhered to and the sequence, while biased in glycine residues contains few if any clearly definable tri, tetra and pentapeptides. Deviations from the bipartite [M1][M2] design of the [L] modules can also be observed. However all the proteins examined so far have at least one sub-domain within the [M2] domain 2 comprising amino acid sequence GGXX'Y (SEQ ID NO:1), wherein X is L, F or V; and wherein X' is missing, G, GG, FG, or GA; for example Suckerin (SEQ ID NOS: 2-52). Nevertheless, some proteins identified to be present in the SRT represent a protein that has diverged significantly from the common ancestor of the original Suckerin, or another related Suckerin gene/protein family of similar design and function and there is less consensus in domain 1 however at least one domain 1 amino acid sequence HH, TT, SS, or AV is present in all known suckerin sequences.

The proteins are encoded by genes (SEQ ID NOS: 53-100) producing modular proteins can also be emphasized by examination of SEQ ID NOS: 1-52 where the use and arrangement of large and small scale modules is unique and not observed in any other known proteins. A clear example, which is not intended to limit the scope of design and/or use of Suckerin based materials, is the occurrence of domain organization of the large module with precise placement of prolines, where [L]=P[M1]P[M2] which is observed on many occasions throughout the known Suckerins (SEQ ID NOS: 2-53). Note that Proline can be present or absent depending on the module and/or Suckerin protein considered. Only amino acid sequence set forth in SEQ ID NO: 20 has no proline in the protein sequence. These modular designs are not observed in any other protein and may play a significant role in the structure and function of the material as will be described below. The current invention relates to peptides, protein modules, full length proteins and copolymers based on the novel amino acid motifs of Suckerins large and small, as defined above, including point mutations and insertion or deletion of [L] or [M] modules.

Figure 10A:
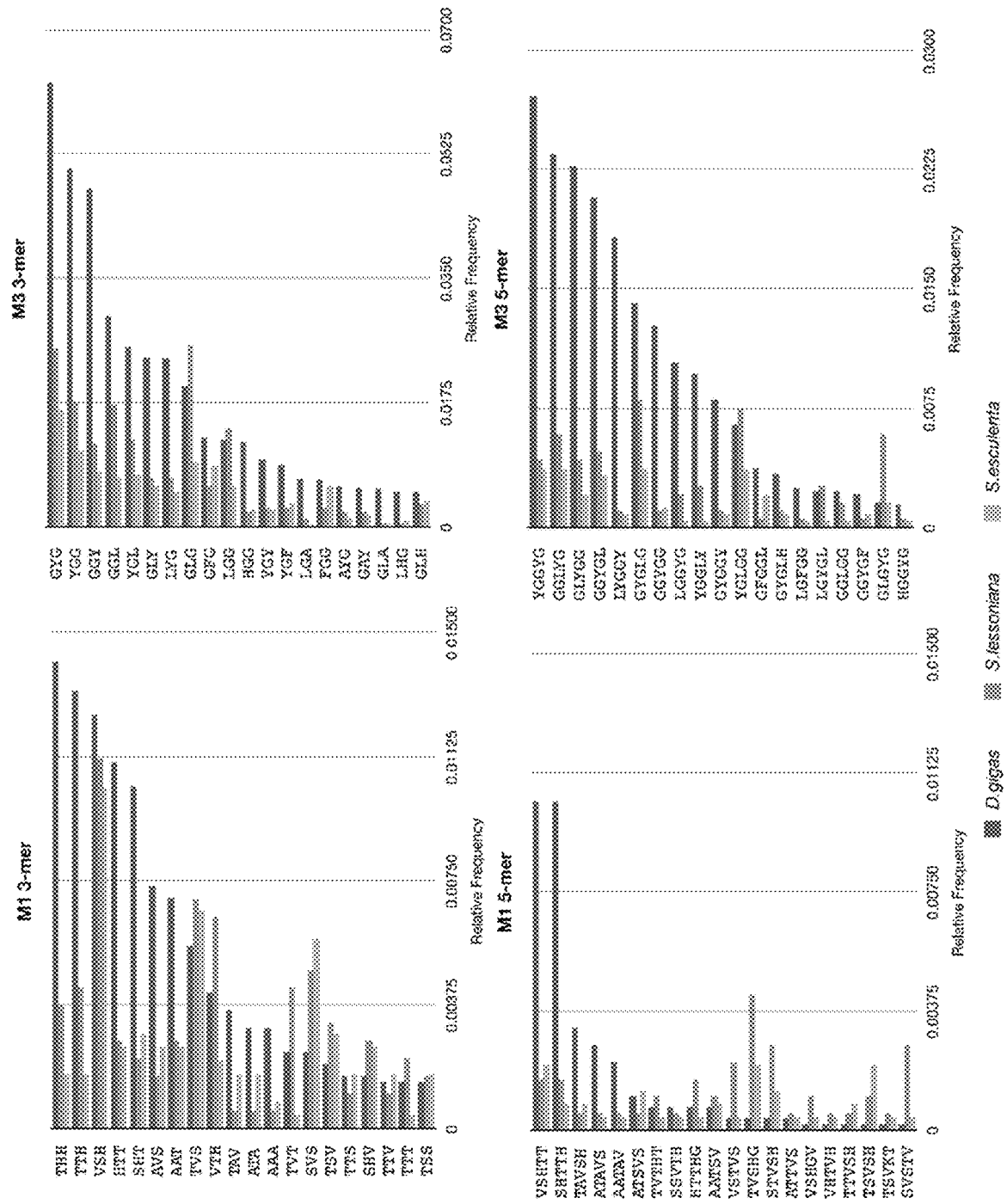
FIG. 10. depiction of the top 20 common peptide domains observed in known Suckerins. Counts of each module are normalized to total lengths of all Suckerins within each species. (A) The top 20 D. gigas modules sorted based on 3-mer and 5-mer frequency. For comparisons, the frequency for S. lessoniana and S. esculenta are shown. (B) The top 20 modules for all 3 species sorted based on 4-mer frequency. (C) The top 20 modules for all 3 species sorted based on 8-mer frequency.
Figure 10B:
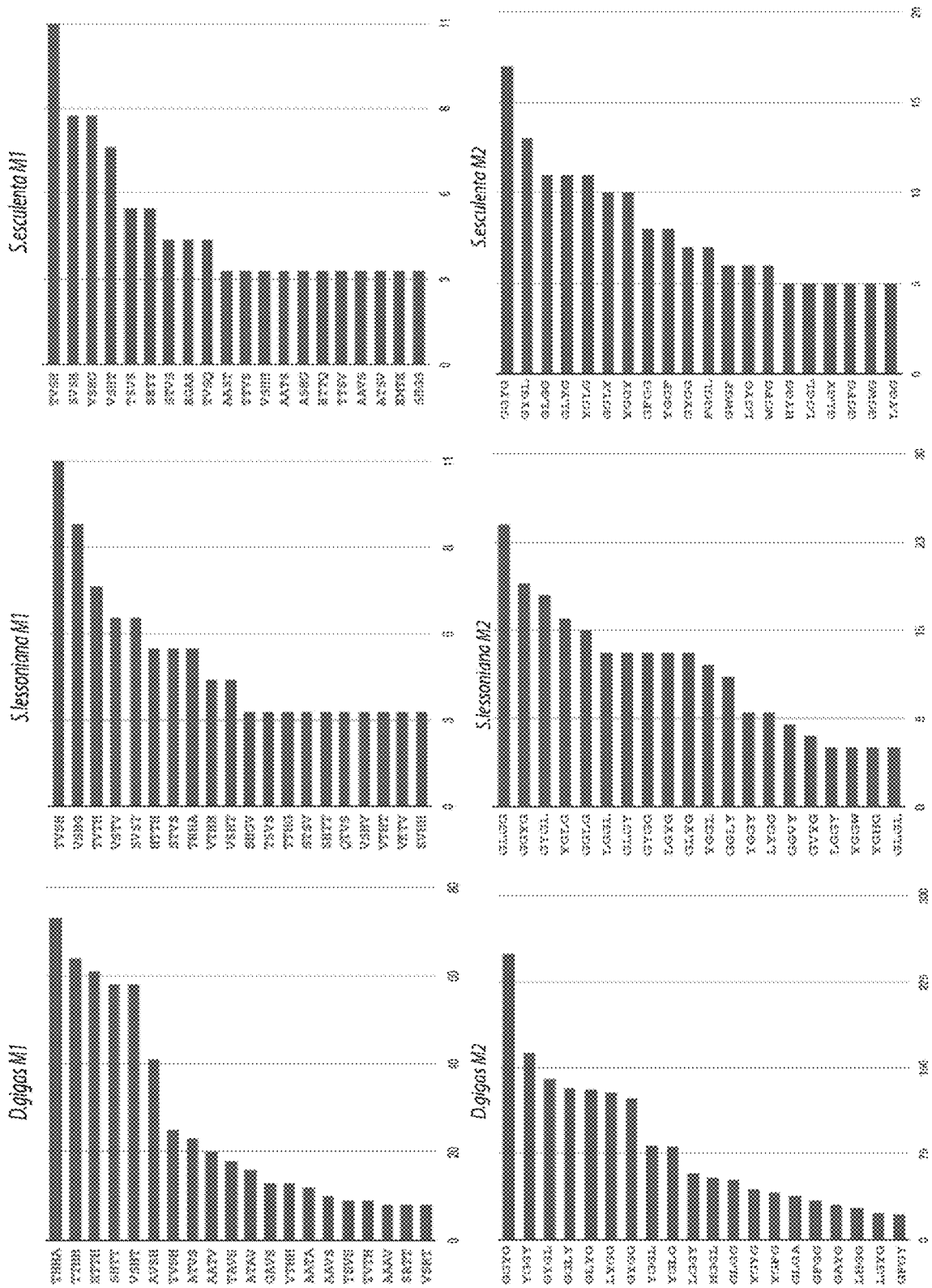
Figure 10C:
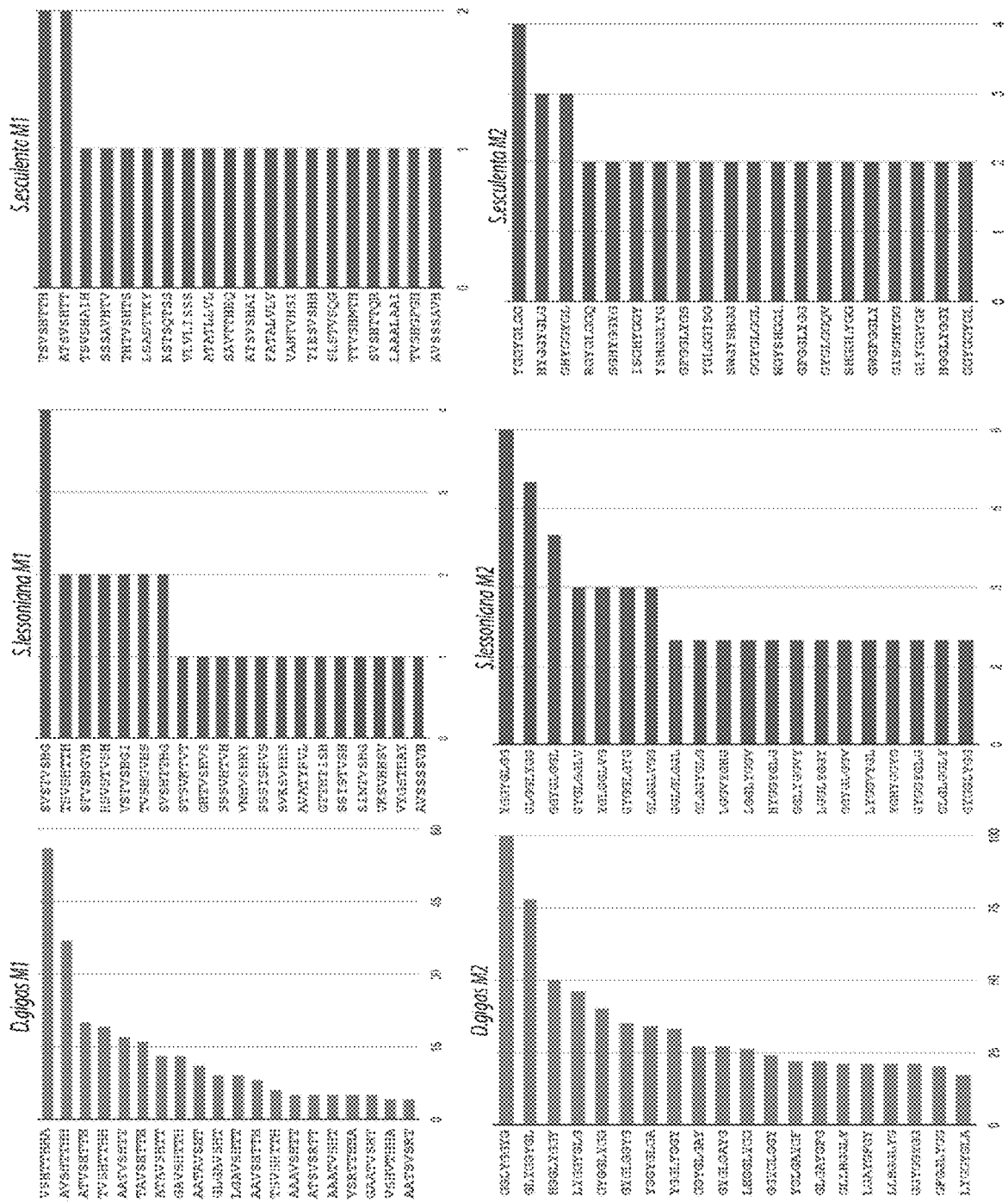

A summary of commonly occurring small domain peptide modules is presented in Table 2 and depicted in FIG. 10. Medium sized modules are also evident in the Suckerins, where we use [M1] to denote a ~6-15 amino acid long A, V, T, S, H rich domain modules and [M2] to denote the ensemble of repetitive and non-repetitive Glycine rich domain sequences. [M1] and [M2] modules often occur in tandem are often flanked by proline residues. The combined Pro[M1]Pro[M2] unit (which is an example large module [L]) ranges in length from ~10 to 80 amino acids is re-iterated 3-15 times in the different proteins. Similarities and distinctions between Suckerins are also observed upon examination of their remarkable large scale modular architectures (FIGS. 4b and 12). The large scale modularity of suckerin highlights the fact that some of these proteins exhibit extreme conservation of large scale module design, while others only marginally do. It is also notable that different Suckerins exhibit differences in glycine-rich module length, a feature that may have a direct impact on SRT mechanics.

Without being bound by any theory proline is unique among the 20 protein-forming amino acids in that the amine nitrogen is bound to not one but two alkyl groups, thus making it a secondary amine this coupled with the distinctive cyclic structure of proline's side chain locking its φ backbone at a dihedral angle at approximately −60°, giving proline an exceptional conformational rigidity compared to other amino acids. Thus, when proline is bound as an amide in a peptide bond, its nitrogen is not bound to any hydrogen, meaning it cannot act as a hydrogen bond donor, but can be a hydrogen bond acceptor. The distinct side chain/amine group interactions allow proline to aid in the formation of beta turns and minimizes aggregation of proteins.

TABLE 2

Summary of peptides found in [L] modules of Suckerin proteins.
Hexapeptides that appear more than twice in all known Suckerin
are listed. Hexapeptides can appear in domain 1[M1], domain 2 [M2] and/or
domain 3 that can span M2. Domain 2 and 3 [M2] peptides include tri, tetra and
pentapeptides that occur more than 10 times in all known Suckerins are listed.

| Hexapeptides |
| --- |
| M1 VSHTTH(SEQ ID NO: 120), AVSHTT (SEQ ID NO: 121), TVSHTT (SEQ ID NO: 122), ATVSHT (SEQ ID NO: 123), AATVSH (SEQ ID NO: 124), TAVSHT (SEQ ID NO: 125), ATAVSH (SEQ ID NO: 126), AATAVS (SEQ ID NO: 127), GAVSHT (SEQ ID NO: 128), STVSHG (SEQ ID NO: 129), VSTVSH (SEQ ID NO: 130), AVIALS (SEQ ID NO: 131), AAVSHT (SEQ ID NO: 132), VSRTTH (SEQ ID NO: 133), SVSTVS (SEQ ID NO: 134), AAAVSH (SEQ ID NO: 135), AAATVS(SEQ ID NO: 136), TSVSRT (SEQ ID NO: 137), SVSRTT (SEQ ID |

TABLE 2-continued

Summary of peptides found in [L] modules of Suckerin proteins. Hexapeptides that appear more than twice in all known Suckerin are listed. Hexapeptides can appear in domain 1[M1], domain 2 [M2] and/or domain 3 that can span M2. Domain 2 and 3 [M2] peptides include tri, tetra and pentapeptides that occur more than 10 times in all known Suckerins are listed.

NO: 138), VSHVTH (SEQ ID NO: 139), SSSGFV (SEQ ID NO: 140), GAATVS (SEQ ID NO: 141), TSSGSY (SEQ ID NO: 142), HTSSGS (SEQ ID NO: 413), SSSSGF (SEQ ID NO: 144), VIALSS (SEQ ID NO: 145), ISSSSG (SEQ ID NO: 146), ATSVSR (SEQ ID NO: 147), SNYASA (SEQ ID NO: 148), AATSVS (SEQ ID NO: 149), SVTHHA (SEQ ID NO: 150), LVSLAV (SEQ ID NO: 151), TATSTT (SEQ ID NO: 152), SSVTHH (SEQ ID NO: 153), ALVSLA (SEQ ID NO: 1564), SLAVVL (SEQ ID NO: 155), FSALVS (SEQ ID NO: 156), TSNSNS (SEQ ID NO: 157), TSAYHA (SEQ ID NO: 158), SALVSL(SEQ ID NO: 159), VSLAVV (SEQ ID NO: 160), AVVLGV (SEQ ID NO: 161), TVSHGV (SEQ ID NO: 162), TTMFSA (SEQ ID NO: 163), AATTVS (SEQ ID NO: 164), TSTTST (SEQ ID NO: 165), LSYTSA (SEQ ID NO: 166), TSTSNS (SEQ ID NO: 167), SYTSAY (SEQ ID NO: 168), AVSHVT (SEQ ID NO: 169), VLSYTS (SEQ ID NO: 170), TTSTSN (SEQ ID NO: 171), YGAAVS (SEQ ID NO: 172), GAAAVS (SEQ ID NO: 173), GAAVSH (SEQ ID NO: 174) YGAAAV (SEQ ID NO: 175), STSNSN (SEQ ID NO: 176), ATSTTS (SEQ ID NO: 177), STTSTS (SEQ ID NO: 178), ALSSCT (SEQ ID NO: 179), VVLLAA (SEQ ID NO: 180), VSQTTH (SEQ ID NO: 181), GATVSH (SEQ ID NO: 182), ASVSTV SEQ ID NO: 183), TSVSQT (SEQ ID NO: 184), ATTVSR (SEQ ID NO: 185), VTHTTH (SEQ ID NO: 186), CTLAVV (SEQ ID NO: 187), AASILT (SEQ ID NO: 188), TVSRTT (SEQ ID NO: 189), TTAVSH (SEQ ID NO: 190), RSVSTV (SEQ ID NO: 191), SCTLAV (SEQ ID NO: 192), ATTAVS (SEQ ID NO: 193), AVLAIS (SEQ ID NO: 194), SSCTLA (SEQ ID NO: 195), TSSVTH (SEQ ID NO: 196), VSHVSH (SEQ ID NO: 197), TTVSRT (SEQ ID NO: 198), AATTYR (SEQ ID NO: 199), HTVTHT (SEQ ID NO: 200), THTVTH (SEQ ID NO: 201), AATVGY (SEQ ID NO: 202), HSVSTV (SEQ ID NO: 203), TVSHVS (SEQ ID NO: 204), ATVGYS (SEQ ID NO: 205), TAVSHV (SEQ ID NO: 206), TVTHTT (SEQ ID NO: 207), ATTSVS (SEQ ID NO: 208), VTSSVT (SEQ ID NO: 209), GHSVST (SEQ ID NO: 210), SVSTLS (SEQ ID NO: 211), TVSTVS (SEQ ID NO: 212), TTTKTV (SEQ ID NO: 213), SSISRV (SEQ ID NO: 214), ISTVSH (SEQ ID NO: 215), SISRVS (SEQ ID NO: 216), VSTVHR (SEQ ID NO: 217), VTVTHH (SEQ ID NO: 218), TVHTVS (SEQ ID NO: 219), VKTVTH (SEQ ID NO: 220), TVTGLV (SEQ ID NO: 221), HTVSHV (SEQ ID NO: 222), KTTSSV (SEQ ID NO: 223), VSHTAH (SEQ ID NO: 224), TVSQTT (SEQ ID NO: 225), STTTKT (SEQ ID NO: 226), SISTVS (SEQ ID NO: 227), TSVKTT (SEQ ID NO: 228), VSIIAA (SEQ ID NO: 229), SSVSHV (SEQ ID NO: 230), QRSVST (SEQ ID NO: 231), ISSSAK (SEQ ID NO: 232), AAASVT (SEQ ID NO: 233), SVRHTV (SEQ ID NO: 234), AAVSHV (SEQ ID NO: 235), VKTVVH (SEQ ID NO: 236), VRHTVS (SEQ ID NO: 237), TSSVHH (SEQ ID NO: 238), TKTVTV (SEQ ID NO: 239), KTVTVT (SEQ ID NO: 240), RVSHTA (SEQ ID NO: 241), SHVTHS (SEQ ID NO: 242), TTSVHH (SEQ ID NO: 243), VTSSSV (SEQ ID NO: 244), GATVHT (SEQ ID NO: 245), STVTHT (SEQ ID NO: 246), AASVST (SEQ ID NO: 247), AVTSSS (SEQ ID NO: 248), TTHGVA (SEQ ID NO: 249), GISSSA (SEQ ID NO: 250), MAAAVL (SEQ ID NO: 251), VVSHVT (SEQ ID NO: 252), QVTSSV (SEQ ID NO: 253), VATAVS (SEQ ID NO: 254), SINTVS (SEQ ID NO: 255), TSVSHT (SEQ ID NO: 256), YGATAV (SEQ ID NO: 257), VSTLSH (SEQ ID NO: 258), DSSSYS (SEQ ID NO: 259), AVMALS (SEQ ID NO: 260), SSSAKG (SEQ ID NO: 261), SRVSHT (SEQ ID NO: 262), ALDSSS (SEQ ID NO: 263), TGSSVS (SEQ ID NO: 264), AASSVS (SEQ ID NO: 265), AVATYR (SEQ ID NO: 266), HTVSTV (SEQ ID NO: 267), TVTHHA (SEQ ID NO: 268), TSVHHT (SEQ ID NO: 269), SSSYSH (SEQ ID NO: 270), RHTVST (SEQ ID NO: 271), VATYRV (SEQ ID NO: 272), ASINTV (SEQ ID NO: 273), TTSVSQ (SEQ ID NO: 274), ATTVSH (SEQ ID NO: 275), TVTVTH (SEQ ID NO: 276), TTKTVT (SEQ ID NO: 277), AAAVLF (SEQ ID NO: 278), VSHAGA (SEQ ID NO: 279), QTSHSV (SEQ ID NO: 280), AALDSS (SEQ ID NO: 281), SVSHTT (SEQ ID NO: 282), AISTVG (SEQ ID NO: 283), AASTVT (SEQ ID NO: 284), TGLVSA (SEQ ID NO: 285), SHTAHS (SEQ ID NO: 286), GSSVST (SEQ ID NO: 287), TSSSVT (SEQ ID NO: 288), AHVSQS (SEQ ID NO: 289), SSVSTL (SEQ ID NO: 290), VHTVSH (SEQ ID NO: 291), AAAAVS (SEQ ID NO: 292), SSSVTH (SEQ ID NO: 293), STSVSQ (SEQ ID NO: 294), GSTTTK (SEQ ID NO: 295), TVTHSN (SEQ ID NO: 296), GASVST (SEQ ID NO: 297), TVSHGS (SEQ ID NO: 298), TRSVST (SEQ ID NO: 299), VSRTAL (SEQ ID NO: 300), SVKTTS (SEQ ID NO: 301), ATTIFA (SEQ ID NO: 302), AATVSQ (SEQ ID NO: 303), AAASVS (SEQ ID NO: 304), SSSISR (SEQ ID NO: 305), LTTTSV (SEQ ID NO: 306),VGASVS (SEQ ID NO: 307), VSQTSH (SEQ ID NO: 308), GQSVST (SEQ ID NO: 309), SVHHTT (SEQ ID NO: 310), GATAVS (SEQ ID NO: 311), GTSVKT (SEQ ID NO: 312), YVSRTA (SEQ ID NO: 313), SVQTVS (SEQ ID NO: 314), YASAIA (SEQ ID NO: 315), TSSSIS (SEQ ID NO: 316), ATVSQT (SEQ ID NO: 317), SVSTVH (SEQ ID NO: 318), TTTSVH (SEQ ID NO: 319), ASVTHG (SEQ ID NO: 320), QAISTV (SEQ ID NO: 321), ASTVTH (SEQ ID NO: 322), SVSQTS (SEQ ID NO: 323), GSSIST (SEQ ID NO:324), QSVSTV (SEQ ID NO: 325), SSISTV (SEQ ID NO: 326), VKTTSS (SEQ ID NO: 327), TVSHAG (SEQ ID NO: 328), ASTSVS (SEQ ID NO: 329), VTGLVS (SEQ ID NO: 332), VGQSVS (SEQ ID NO: 331), TTVSHT (SEQ ID

TABLE 2-continued

Summary of peptides found in [L] modules of Suckerin proteins. Hexapeptides that appear more than twice in all known Suckerin are listed. Hexapeptides can appear in domain 1[M1], domain 2 [M2] and/or domain 3 that can span M2. Domain 2 and 3 [M2] peptides include tri, tetra and pentapeptides that occur more than 10 times in all known Suckerins are listed.

NO: 332), AASVTH (SEQ ID NO: 333), TTSSVH (SEQ ID NO: 334), ATVHTV (SEQ ID NO: 335), SVSQTT (SEQ ID NO: 336), STVSHA (SEQ ID NO: 337), SQTSHS (SEQ ID NO: 338)
TTHHAP (SEQ ID NO: 339),VSHTTH (SEQ ID NO: 120), HTTHHA (SEQ ID NO: 114), SHTTHH (SEQ ID NO: 340), THHAPY (SEQ ID NO: 341), HHAPYG (SEQ ID NO: 342), HHAPLG (SEQ ID NO: 343), THHAPL (SEQ ID NO: 344), GYGLHH (SEQ ID NO: 345), GLHHGG (SEQ ID NO: 346), YGLHHG (SEQ ID NO: 347), LHHGGL (SEQ ID NO: 348), HHGGLY (SEQ ID NO: 349), VTHHAP (SEQ ID NO: 112), HGLLHG (SEQ ID NO: 350), GHGLLH (SEQ ID NO: 351), RTTHHA (SEQ ID NO: 352), VSHVTH (SEQ ID NO: 139), SRTTHH (SEQ ID NO: 353), TGGHGH (SEQ ID NO: 354), SVTHHA (SEQ ID NO: 150), GHGHGG (SEQ ID NO 355), VSHGVH (SEQ ID NO: 356), SSVTHH (SEQ ID NO: 153), GGHGHG (SEQ ID NO: 357), HANHVG (SEQ ID NO: 358), HGHGGY (SEQ ID NO: 359), YHANHV (SEQ ID NO: 360), AYHANH (SEQ ID NO: 361), SHVTHH (SEQ ID NO: 362), HVTHHA (SEQ ID NO: 363), HTTHGV (SEQ ID NO: 364), SHTTHG (SEQ ID NO: 365), THHAPA (SEQ ID NO: 366), HHAPAA (SEQ ID NO: 367), VTHTTH (SEQ ID NO: 186), SHVSHG (SEQ ID NO: 368), VSHVSH (SEQ ID NO: 197), THTTHG (SEQ ID NO: 369), HTVTHT (SEQ ID NO: 200), TVTVTH (SEQ ID NO: 201), TTHGVH (SEQ ID NO: 370), THGVHH (SEQ ID NO: 371), HGVHSP (SEQ ID NO: 372), SHGIGH (SEQ ID NO: 373), THHAPV (SEQ ID NO: 374), SHGVHS (SEQ ID NO: 375), HHGPYG (SEQ ID NO: 376), TTHHAG (SEQ ID NO: 377), SVHHHV (SEQ ID NO: 378), SHGSHY SEQ ID NO: 379), HGVSHP (SEQ ID NO: 380), THHAGY (SEQ ID NO: 381), HHLPAA (SEQ ID NO: 382), HAGAHP (SEQ ID NO: 383), SSVHHH (SEQ ID NO: 384), HGVHHP (SEQ ID NO: 385), VSHGLH (SEQ ID NO: 386), HHAPVY (SEQ ID NO: 387), SHGVHP (SEQ ID NO: 388), VTVTHH (SEQ ID NO: 218), SQTTHH (SEQ ID NO: 389), HVSHGP (SEQ ID NO: 390), SHTAHS (SEQ ID NO: 286), HGVHHL (SEQ ID NO: 391), HGIHAP (SEQ ID NO: 392), VSHGIH (SEQ ID NO: 393), HTVSHV (SEQ ID NO: 222), HTAHSP (SEQ ID NO: 394), QTTHHA (SEQ ID NO: 395), VGHGIH (SEQ ID NO: 395), SHDVHQ (SEQ ID NO: 397), VSHTAH (SEQ ID NO: 224), GHGIHP (SEQ ID NO: 398), VHTVSH (SEQ ID NO: 291), HHHVVP (SEQ ID NO: 399), HSVPHI (SEQ ID NO: 400), HTTHGI (SEQ ID NO: 401), HTVSHG (SEQ ID NO: 402), GHHGPY (SEQ ID NO: 403), HHTTHG (SEQ ID NO: 404), HHAPTY (SEQ ID NO: 405), HDVHQP (SEQ ID NO: 406), TVHHPA (SEQ ID NO: 407), THHAPT (SEQ ID NO: 408), HGVAHP (SEQ ID NO: 409), RGHGAH (SEQ ID NO: 410), GVHHLP (SEQ ID NO: 411), THGFHP (SEQ ID NO: 412), TSSVHH (SEQ ID NO: 238), VTHGFH (SEQ ID NO: 413), SHAGAH (SEQ ID NO: 414), THGIHH (SEQ ID NO: 415), HGFHPA (SEQ ID NO: 415), SHGISH (SEQ ID NO: 417), SVHHTT (SEQ ID NO: 310), SHVTHS (SEQ ID NO: 242), TTSVHH (SEQ ID NO: 243), GGHHGP (SEQ ID NO: 418), VSHGSH (SEQ ID NO: 419), VHHTTH (SEQ ID NO: 420), HHAGYG (SEQ ID NO: 421), HGIHPT (SEQ ID NO: 422), HAVHRV (SEQ ID NO: 423), HGVHPS (SEQ ID NO: 424), VHHLPA (SEQ ID NO: 425), SGGHHG (SEQ ID NO: 426), HHVVPS (SEQ ID NO: 427), GHAVHR (SEQ ID NO: 428), VHTVHH (SEQ ID NO: 429), SHGVSH (SEQ ID NO: 430), GSGGHH (SEQ ID NO: 431), GHTVSH (SEQ ID NO: 432), VSHDVH (SEQ ID NO: 433), HAPVAH (SEQ ID NO: 434), VHHHVV (SEQ ID NO: 435), HGIGHP (SEQ ID NO: 435), SHSVPH (SEQ ID NO: 437), IGHAVH (SEQ ID NO: 438), HYPMGH (SEQ ID NO: 439), HGSHYP (SEQ ID NO: 440), TVTHHA (SEQ ID NO: 268), TSVHHT (SEQ ID NO: 269), HGAHVS (SEQ ID NO: 441), HTTHGG (SEQ ID NO: 442), SHGIHA (SEQ ID NO: 443), GHGAHV (SEQ ID NO: 444), THGVAH (SEQ ID NO: 445), HVTHSI (SEQ ID NO: 446), HGISHA (SEQ ID NO: 447), TVTHHP (SEQ ID NO: 448).

| | Tri-peptide | Tetra-peptide | Penta-peptide |
|---|---|---|---|
| M2 | GYG, GGY, YGG, GGL, YGL, GLG, GLY, LYG, LGG, GFG, HGG, YGF, YGY, PYG, FGG, GYP, LGY, LGA, GLH, AYG, GAY, GLA, PLG, QGG, GQG, GHG, GLL, FGY, GGV, AGY, LHG, YGV, YGA, YGQ, PVG, GAG, VGG, GVG, AHG, GGH, SHG, SYG, GAV, HHG, LAG, PGA, LGL, YGS, LGF, GGF, GGS, GSY, FPF, GGF, GGS, GSY, FPG, HGL, GAA, VYG, YGH, GYL, GVS, YPG, | GGLY (SEQ ID NO: 449), GGYG (SEQ ID NO: 117), YGGY (SEQ ID NO: 450), GYGL (SEQ ID NO: 451), GYGG (SEQ ID NO: 452), GLYG (SEQ ID NO: 453), LYGG (SEQ ID NO: 454), YGLG (SEQ ID NO: 455), YGGL (SEQ ID NO: 456), GLGG (SEQ ID NO: 457), LGGY (SEQ ID NO: 458), HGGL (SEQ ID NO: 459), YGFG (SEQ ID NO: 460), YGYG (SEQ ID NO: 461), GFGG (SEQ ID NO: 462), GLGA (SEQ ID NO: 463), | YGGYG (SEQ ID NO: 520), GGLYG (SEQ ID NO: 116), GLYGG (SEQ ID NO: 118), GGYGL (SEQ ID NO: 521), LYGGY (SEQ ID NO: 522), GYGLG (SEQ ID NO: 523), GGYGG (SEQ ID NO: 524), LGGYG (SEQ ID NO: 525), GYGGL (SEQ ID NO: 526), GYGGY (SEQ ID NO: 527), YGLGG (SEQ ID NO: 528), YGGLY (SEQ ID NO: 529), GLGGY (SEQ ID NO: 530), HGGLY (SEQ ID NO: 531), YGLGA (SEQ ID NO: 532), GYGLA (SEQ ID NO: 533), |

TABLE 2-continued

Summary of peptides found in [L] modules of Suckerin proteins. Hexapeptides that appear more than twice in all known Suckerin are listed. Hexapeptides can appear in domain 1[M1], domain 2 [M2] and/or domain 3 that can span M2. Domain 2 and 3 [M2] peptides include tri, tetra and pentapeptides that occur more than 10 times in all known Suckerins are listed.

| | | |
|---|---|---|
| VGY, GGA, THG, SSG, | LGYG (SEQ ID NO: 464), | GYGLH (SEQ ID NO: 534), |
| GWG, GVY, GYS, GVH, | GGLG (SEQ ID NO: 465), | LGAYG (SEQ ID NO: 535), |
| HGV, GGW, GSG, SGY, | GAYG (SEQ ID NO: 466), | GLGAY (SEQ ID NO: 536), |
| GGG, LGV, SGG, GIG, | GQGG (SEQ ID NO: 467), | PYGYG (SEQ ID NO: 537), |
| GGI, YLG, TYG, NQG, | GFGY (SEQ ID NO: 468), | YGYGG (SEQ ID NO: 538), |
| TGG, LLG, VSG, GAP, | GLGY (SEQ ID NO: 469), | GFGGL (SEQ ID NO: 539), |
| VLG, GVL, HGI, GYH, | LHGG (SEQ ID NO: 470), | GFGYP (SEQ ID NO: 540), |
| GLS, FGL, GST, PGY, | FGGL (SEQ ID NO: 471), | GYGQG (SEQ ID NO: 541), |
| GLV, GVF, GAT, GSS, | AGYG (SEQ ID NO: 472), | LHGGL (SEQ ID NO: 542), |
| PAG, GAH, PGV, GYY, | GYGY (SEQ ID NO: 473), | GQGGY (SEQ ID NO: 543), |
| VGA, GHY | YGQG (SEQ ID NO: 474), | YGFGG (SEQ ID NO: 544), |
| | QGGY (SEQ ID NO: 475), | YGQGG (SEQ ID NO: 545), |
| | GYGQ (SEQ ID NO: 476), | GGYGQ (SEQ ID NO: 546), |
| | LGGL (SEQ ID NO: 477), | YGGLG (SEQ ID NO: 547), |
| | GYGA (SEQ ID NO: 478), | GAYGF (SEQ ID NO: 548), |
| | GYGF (SEQ ID NO: 479), | FGGLY (SEQ ID NO: 549), |
| | AHGG (SEQ ID NO: 480), | AYGFG (SEQ ID NO: 550), |
| | GLAG (SEQ ID NO: 481), | GGLGG (SEQ ID NO: 551), |
| | GYGV (SEQ ID NO: 482), | YGFGY (SEQ ID NO: 502), |
| | FGGY (SEQ ID NO: 483), | GLLHG (SEQ ID NO: 553), |
| | GGHG (SEQ ID NO: 484), | LYGGL (SEQ ID NO: 554), |
| | LGFG (SEQ ID NO: 485), | LGYGL (SEQ ID NO: 555), |
| | SYGG (SEQ ID NO: 486), | GLGYG (SEQ ID NO: 556), |
| | GYGS (SEQ ID NO: 487), | QGGYG (SEQ ID NO: 557), |
| | VGGY (SEQ ID NO: 488), | LLHGG (SEQ ID NO: 558), |
| | HGGY (SEQ ID NO: 489), | AHGGL (SEQ ID NO: 559), |
| | HHGG (SEQ ID NO: 490), | AGYGG (SEQ ID NO: 560), |
| | GLGL (SEQ ID NO: 491), | GGYGF (SEQ ID NO: 561), |
| | YGGH (SEQ ID NO: 492), | GLGGL (SEQ ID NO: 562), |
| | LGLG (SEQ ID NO: 493), | PLGYG (SEQ ID NO: 563), |
| | GHGL (SEQ ID NO: 494), | LAGTG (SEQ ID NO: 564), |
| | GGYL (SEQ ID NO: 495), | LAHGG (SEQ ID NO: 565), |
| | YGGW (SEQ ID NO: 496), | GLAGY (SEQ ID NO: 566), |
| | GGLL (SEQ ID NO: 497), | GLAHG (SEQ ID NO: 567), |
| | GVYG (SEQ ID NO: 498), | YGLAG (SEQ ID NO: 568), |
| | YGGV (SEQ ID NO: 499), | GYGFG (SEQ ID NO: 569), |
| | GYLG (SEQ ID NO: 500), | PLGFG (SEQ ID NO: 570), |
| | GVGG (SEQ ID NO: 501), | GYGYG (SEQ ID NO: 571), |
| | PYGG (SEQ ID NO: 502), | LGFGG (SEQ ID NO: 572), |
| | GSYG (SEQ ID NO: 503), | GGYGV (SEQ ID NO: 573), |
| | GYGH (SEQ ID NO: 504), | PYGFG (SEQ ID NO: 574), |
| | YGVG (SEQ ID NO: 505), | GGYGA (SEQ ID NO: 575), |
| | GHGG (SEQ ID NO: 506), | GLHHG (SEQ ID NO: 576), |
| | GVSG (SEQ ID NO: 507), | VGGYG (SEQ ID NO: 577), |
| | SGYG (SEQ ID NO: 508), | FGGYG (SEQ ID NO: 578), |
| | TYGG (SEQ ID NO: 509), | LHHGG (SEQ ID NO: 579), |
| | VSGG (SEQ ID NO: 510), | HGGYG (SEQ ID NO: 580), |
| | GAGY (SEQ ID NO: 511), | HHGGL (SEQ ID NO: 581), |
| | LLGG (SEQ ID NO: 512), | YGGHG (SEQ ID NO: 582), |
| | YLGG (SEQ ID NO: 513), | GFGGY (SEQ ID NO: 583), |
| | GYPG (SEQ ID NO: 514), | LGYGG (SEQ ID NO: 584), |
| | VYGG (SEQ ID NO: 515), | GLGLG (SEQ ID NO: 585), |
| | VGYG (SEQ ID NO: 516), | GYGLL (SEQ ID NO: 586), |
| | GSGY (SEQ ID NO: 517), | YGGYL (SEQ ID NO: 587), |
| | GGVY (SEQ ID NO: 518), | GGYGY (SEQ ID NO: 588), |
| | GGWG (SEQ ID NO: 519) | YGYGL (SEQ ID NO: 589), |
| | | GYGYP (SEQ ID NO: 590), |
| | | LGGLY (SEQ ID NO: 591), |
| | | YGGLL (SEQ ID NO: 592), |
| | | GGHGL (SEQ ID NO: 593), |
| | | GSYGG (SEQ ID NO: 594), |
| | | GVSGG (SEQ ID NO: 595), |
| | | GGYGH (SEQ ID NO: 596), |
| | | GHGGY (SEQ ID NO: 597), |
| | | GLGAV (SEQ ID NO: 598), |
| | | GYLGG (SEQ ID NO: 599), |
| | | GGYLG (SEQ ID NO: 600), |
| | | YGYGY (SEQ ID NO: 601), |
| | | GHGLL (SEQ ID NO: 602), |

TABLE 2-continued

Summary of peptides found in [L] modules of Suckerin proteins.
Hexapeptides that appear more than twice in all known Suckerin
are listed. Hexapeptides can appear in domain 1[M1], domain 2 [M2] and/or
domain 3 that can span M2. Domain 2 and 3 [M2] peptides include tri, tetra and
pentapeptides that occur more than 10 times in all known Suckerins are listed.

```
LYGGH (SEQ ID NO: 603),
GVYGG (SEQ ID NO: 604),
GGLGY (SEQ ID NO: 605),
SYGGY (SEQ ID NO: 606),
GGYGS (SEQ ID NO: 607),
GYGAA (SEQ ID NO: 608),
LLGGY (SEQ ID NO: 609),
GYPGA (SEQ ID NO: 610),
YGGWG (SEQ ID NO: 611)
```

Figure 5:
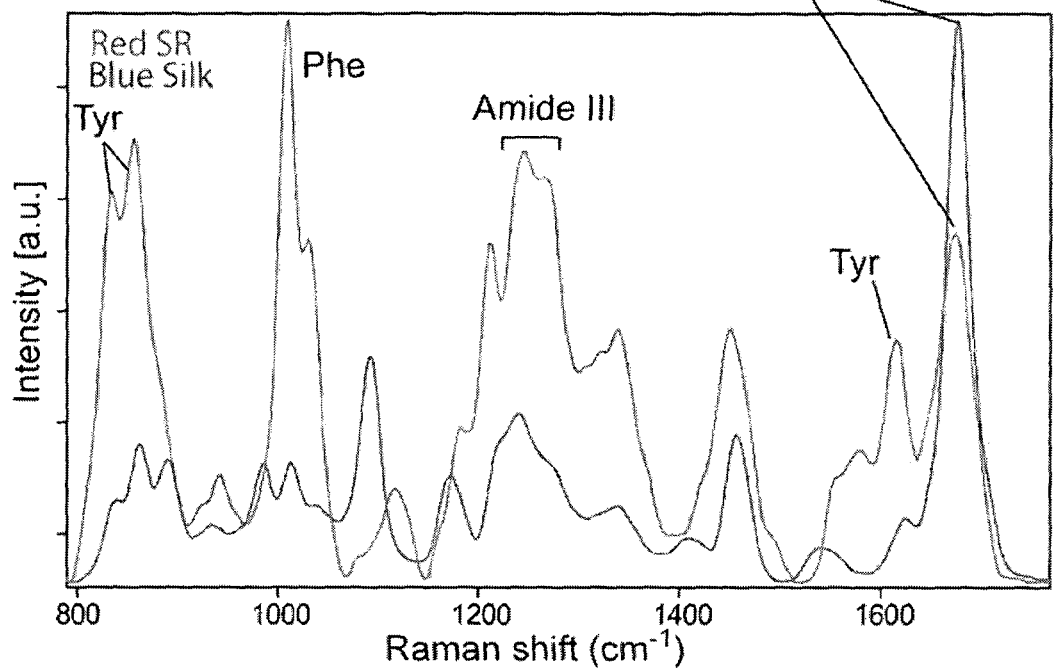
FIG. 5: (A) Raman spectrum of a microtomed section compared against a Bombyx mori silk standard, showing matching of the Amide I band centered at 1666 cm-1, which is attributed to β-sheet conformation. The lower intensity suggests that the β-sheets are less oriented than in silk fibers. (B) Raman spectra in cross-polarized modes confirm that the β-sheet domains in SRT are randomly oriented in the cross-sectional plane.
Figure 5B:
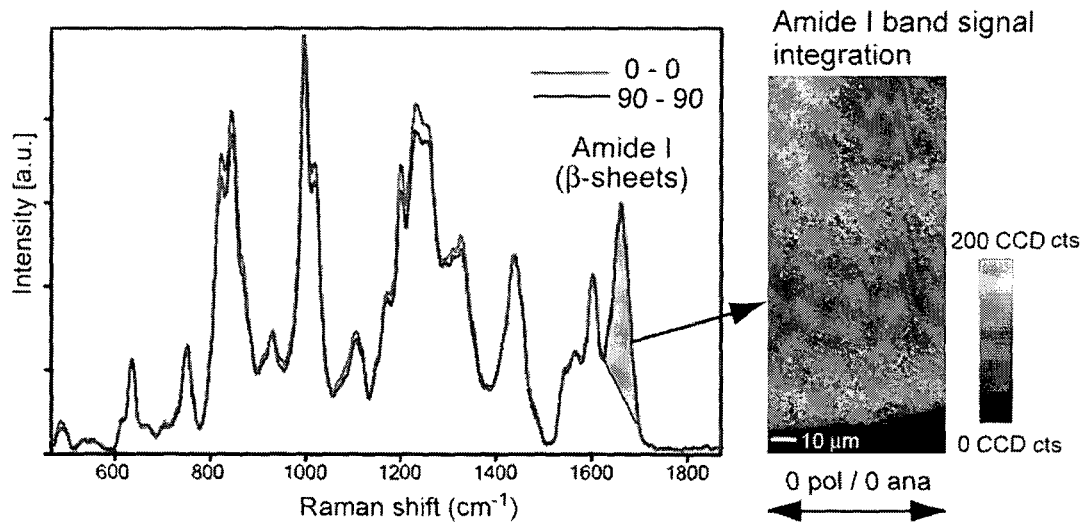

The large-scale modular architecture of Suckerin (FIG. 4b) exhibits two alternating domains containing: (i) Ala/His rich motifs ~13 residues long often flanked by proline residues, and (ii) Gly/Tyr rich sequences ~2-70 residues long comprised of silk-like GGY repeats, suggesting convergent evolution of these motifs. The Ala-His rich motifs are reminiscent of poly-Ala motifs known to assemble into the reinforcing β-sheet based nano-crystals in spider dragline silk[50]. Micro-Raman spectroscopy (FIG. 5a) on ultra-microtomed SRT cross-sections confirmed a clear β-sheet band across the entire ring with the position of the Amide I band matching that of *Bombyx mori* silk[56]. Polarized Raman spectra (FIG. 5b) showed that, in contrast to spider dragline and silkworm silks, the β-sheet domains are randomly oriented. This isotropic distribution (FIG. 6A), is consistent with the predatory function of SRT that must resist complex compressive, shear and torsional load regimes, with β-sheet domains providing the load-bearing function.

In view of the extreme potential for robust tailorable materials and protein-based materials re-enforced by beta-sheets, the identification and characterization of the chemical and physical properties described above provide evidence that the Suckerin genes and proteins are useful new reagents having utility in a range material forms and applications. Suckerin-based films, fibers, foams, scaffolds, micro-spheres, nanoparticles and other forms can be engineered from synthetic, recombinant or naturally derived Suckerin peptides, proteins and homologues thereof.

Here we further summarize the proteins encoded by the Suckerins and related variants thereof. The equations are not intended to summarize all Suckerin proteins and potential mimetic variants thereof but rather to facilitate use and are in no way designed to limit the scope of the use of Suckerin-based proteins motifs, modules, fragments and mimetic versions thereof.

In one simplified version [L]=Large Suckerin module 10-40 residues long comprising Proline and Domains [M] modules. An exemplary, but non limiting list of small peptides is observed in Suckerins and provided in Table 2. [M1]=A, V, T S H rich modules 1-15 residues long; [M2]=a glycine rich module containing the following: A tripeptide module found in any Suckerin protein or any close variant thereof with >66% identity to natural Suckerin tripeptide, named [sM3] or [sM4]. Sub-Domain 3 [sM3] and sub-Domain 4 [sM4] sits within the [M2] domain. Tetrapeptide module or variant thereof with >75% identity to natural observed Suckerin and a pentapeptide or mimetic variant thereof with >60% identity to natural observed Suckerin. A summary of the sequences found in known Suckerins can be found in Table 2.

Example 1

Suckerin (SEQ ID NO: 2) Large Module 4

[L]=P[M1] P [M2]

Each of the Suckerin Large modules can be summarized in a similar manner. Use of individual [L] modules, reiterated [L] (for example but not limited to $[L]_{1\text{-}100}$) or [M] modules (for example, but not limited to $[M1]_{1\text{-}100}$, $[M2]_{1\text{-}100}$) and variable arrangement of modules and peptides (listed in Table 2) are available for Suckerin-based materials engineering. Mimetic proteins based on these modules are also considered part of the current invention. It is emphasized that Suckerin proteins are continuous molecules and the description of the genes and proteins in terms of modular designs is by no way intended to limit the use of the proteins and modules in tandem and/or in overlapping sequences and/or that omit or insert individual amino acids, modules or non-repetitive sequence. They are merely provided as a generalized framework for the construction of Suckerin based materials. The simplified representation of an [L] module in Example 1 is presented to facilitate the design and use of the current invention for the scope of potential engineered nucleic acids and proteins based on the essential components that define the Suckerin gene and protein family and/or evolutionarily related gene and protein families and mimetic genes and proteins based on these.

Mechanical Properties

The SRT in bulk exhibits exceptional mechanical properties. Furthermore, as is the case with silk, SRT proteins have the potential to be sculpted into a wide variety of materials with an extreme range of mechanical properties. Properties can be tailored by 1) designing Suckerin based proteins with chosen amount of large and small scale modules, to tailor the proportion of beta sheets and other secondary and tertiary structures; 2) Processing micro-environment can be used to modulate chain alignment, structure and mechanical properties; 3) Physical processing, including but not limited to shear, draw and elongational flow can be used to modify chain alignment, beta-sheet crystallization and mechanical properties. The native SRT also exhibits unique nano-tubular architecture. This fact supports the view that it is feasible to assemble Suckerins into a range of useful meso-scale structures.

Based, on these observations and on the similarities in sequence design of Suckerins with Spidroins and silkworm fibroins we asked whether the SRT also contained 3-dimensional silk-like nano-crystals where inter-digitation of residues in the 200 crystal plane can contribute to mechanical properties of the nano-structures and thus the material. We therefore deployed synchrotron-based wide angle x-ray diffraction (WAX) on SRT cross-section sections which revealed a diffuse pattern with line scan analysis providing the signature 4.7 Å inter-strand spacing characteristic of beta-sheets. However, the pattern exhibits significant peak broadening and clear equatorial reflections are absent, indicating that SRT do not contain silk-like 3D nano-crystals and suggesting that SRT beta-sheet strands are likely smaller that 5 nm. While the absence of inter-chain packing is predicted to result in a decrease in local rupture forces, small beta-sheet domains have been shown by simulation to exhibit superior properties, where hydrogen bonds exhibit co-operatively under mechanical deformation. Moreover, confined beta-sheets can exhibit stick-slip behavior, enhancing toughness and enabling self-healing behavior where hydrogen bonds are recovered following deformation. Based on this information it will be of interest to determine how primary Suckerin sequence design at once enables beta-sheet formation while placing limits on the dimensions and packing of the beta-sheets. Sequences in the [M1] region bear similarity with the beta-sheet forming poly-Alanine sequences of dragline silks and VT motifs recently shown to adopt beta-sheet structure in orb-spider viscid silk. However, the [M1] motifs are not as repetitive as Spidroin and silk worm sequences, suggesting that irregularity in side chain chemistry in the Suckerins may reduce the potential for inter-sheet crystal packing. Examination of the majority of the Suckerin proteins clearly shows the rigorous positional conservation of prolines in many cases. Proline is a know beta-sheet disrupter that may also place limits on beta-sheet size and directly influence the mechanical properties of the SRT. At this stage we can also not rule out the possibility that the [M2] domains contain order. For example the glycine rich regions of dragline spidroins occupy amorphous domains that, in some cases contain local structure. In addition, glycine rich sequences can have the capacity to adopt amyloid like conformations.

Solubility of Suckerin-Based Proteins

The large scale modular architecture we observe across many of the Suckerins appears well suited for intra and inter-molecular assembly into beta-sheet cross-linked 3-dimensional polymer networks. To further dissect the role Suckerin structure plays in determining the mechanical properties of the SRT, we developed complementary nano-indentation and micro-raman spectroscopy experiments using a set of micro-environmental conditions designed to target and disrupt hydrophobic interactions and hydrogen bonds. FIG. 13A is a plot of Modulus vs. Time obtained by nano-indentation of a section of D. gigas SRT tip under dry, hydrated, ethanol and Urea treatments. In the dry and hydrated states the moduli remain linear. Ethanol treatment results in a modest decay in modulus, which is contrary to the behavior of silkworm and spider silk fibers whose moduli increase in the presence of polar solvents.

Urea treatments were used to target and disrupt hydrogen bonds in SRT sections. In this case, the samples exhibit significant loss in modulus with decay plateaus that correlate with Urea concentration (FIG. 13A). At the highest concentration of Urea used (2M) the final modulus of the SRT was 20 MPa which is dramatically lower than both dry and hydrated conditions. These data provide the first direct evidence of the key role for hydrogen bonds in SRT mechanics and function. We then used micro-raman spectroscopy under a parallel set of micro-environmental conditions to evaluate the changes in secondary structures that occur during these treatments (FIG. 13B). While ethanol treatment yielded no significant peak shifts, Urea treatment leads to a distinct in shift in the Amide III 1236 peak that corresponds directly to a loss of beta-sheet structure and to the decrease in modulus observed by nano-indentation. Together, these data indicate that the hydrogen bonds localized to beta-sheets play a key role in the mechanical properties of the SRT.

In contrast to silk proteins, Suckerins can be purified and remain soluble under mild acid conditions, while the solubilization of silkworm cocoons and spider threads often requires high salt concentrations and solvents such as Hexafluoroisoproponal that are hazardous to handle even in small volumes. We have also determined that high concentrations of Suckerin protein remain soluble in low concentrations of Urea (1-2M) and/or under mildly acidic conditions. Facile control of solubility offers unrivalled ability to concentrate and process this material into an extreme range of materials.

Urea treatments were used to target and disrupt hydrogen bonds in SRT sections. In this case, the samples exhibit significant loss in modulus with decay plateaus that correlate with Urea concentration (FIG. 13A). At the highest concentration of Urea used (2M) the final modulus of the SRT was 20 MPa which is dramatically lower than both dry and hydrated conditions. These data provide the first direct evidence of the key role for hydrogen bonds in SRT mechanics and function. We then used micro-raman spectroscopy under a parallel set of micro-environmental conditions to evaluate the changes in secondary structures that occur during these treatments (FIG. 13B). While ethanol treatment yielded no significant peak shifts, Urea treatment leads to a distinct shift in the Amide III 1236 peak that corresponds directly to a loss of beta-sheet structure and to the decrease in modulus observed by nano-indentation. Together, these data indicate that the hydrogen bonds localized to beta-sheets play a key role in the mechanical properties of the SRT.

Designing Synthetic Suckerin Proteins and Uses Thereof.

The following methods for designing synthetic variants of proteins based on Suckerins are described. This section emphasizes that natural Suckerin proteins from any Decapodiformes, natural protein variants thereof, synthesized or engineered suckerins can be use in making sukerin based materials. In general Suckerins can be comprised of a series of repeats with or without local amino acid residue differences that still maintain the essence of the overall large and/or small scale design of the natural proteins observed in Decapodiformes. Genetic engineering or other methods can be used to create chimeras of known Suckerin modules or chimeric genes/proteins that contain non-repetitive sequences while retaining the essence of the large and/or small scale molecular design of Suckerin. Modifications can be done to tune mechanical properties and/or to confer new functionality or processing ability. Novel mechanical properties can include but are not limited to decrease or increase extensibility, failure strength, toughness, compressibility among others.

Engineering Suckerin-Based Proteins to Include Different Functionality

Functionalization of Suckerin-based materials in any and all material forms into materials with desired functionalities is anticipated. Functionalization by the incorporation of the amino acids described herein using genetic engineering or synthetic chemistry is one way in which the Suckerin based material can be endowed with additional functionality. The modules may reduce or confer structure by the introduction of for example, but not limited to, random coils, alpha helices, coiled coils, beta-turns and/or additional beta-sheet forming domains/sequences to the Suckerin. In another embodiment, modules are included that confer cell binding, adhesive domains for example fibronectin domains. In another embodiment the additional modules enhance solubility, improve spinability, and/or improve the ability to assemble and process the material. Incorporated peptide sequences can be used to provide enzymatic cleavage cites to tailor the biodegradability of the material. Peptides released by cleavage or any other means may be biologically active or cytotoxic depending on design and intended use. In one embodiment cell signaling properties are conferred to the Suckerin-based material.

Amino acid side chain modification offers extreme potential for the functionalization of Suckerin based proteins and materials described in the Claims. Suckerins contain amino acids that can be converted, by chemical, enzymatic and any other chosen mode(s) of processing into side chains that confer new functions. The Suckerin-based materials may be any material that incorporates the amino acids described herein with individual, multiple and/or combinations of amino acid side chain modifications that confer functionality. These modifications may find use in areas including, but not limited to 1) industrial processing; 2) the incorporation and/or cross linking of additional atoms, molecules, peptides and polymers; 3) materials with novel biophysical functions, including but not limited to tailored materials with adhesive and/or anti-adhesive properties; materials that provide specific cell signaling cues.

There exist a wide variety of known amino acid side chain modification that occur in biology and these are generally referred to as post-translational modifications. Examples of potential amino acid side-chain modification to the Suckerin-based materials include but are not limited to the following: 1) acetylation/deacetylation; 2) alkylation; 3) amidation; 4) biotinylation; 6) citrullination; 7) formylation; 8) gamma carboxylation; 9) glutamylation of glutamic acid; 10) glycosylation; 11) glycation; 12) glycylation; 13) heme moiety may be covalently attached; 14) hydroxylation; 15) iodination; 16) isoprenylation; 17) lipoylation including: prenylation, and GPI anchor formation such as myristoylation farnesylation and geranylgeranylation; 18) methylation/demythalation of arginine or lysine; 19) nucleotide addition or derivatives thereof may be covalently attached (ADP, ribosylation, Flavin); 20) nitrosylation; 21) oxidation; 22) palmitoylation; 23) pegylation; 24) phosphatidylinositol may be covalently attached; 25) phospopentetheinylation; phosphorylation, the addition of a phosphate group to serine, threonine, tyrosine and/or histidine; 26) polysialylation (addition of polysialylic acid to NCAM); 27) pyroglutamte formation; 28) tRNA mediated addition of amino acids such agenylation; 29) sulfation, for example the addition of a sulphate group to tyrosine; 30) selenoylation; 31) Tyrosine hydroxylation into adhesive Dihydroxyphenylalanine side chains.

Expression of Recombinant Suckerin Proteins.

Expression of recombinant engineered Suckerin genes can be inserted into vectors for subcloning, clone propagation, protein expression and other manipulations common to those skilled in the art of molecular biology and its related techniques.

Figure 7:
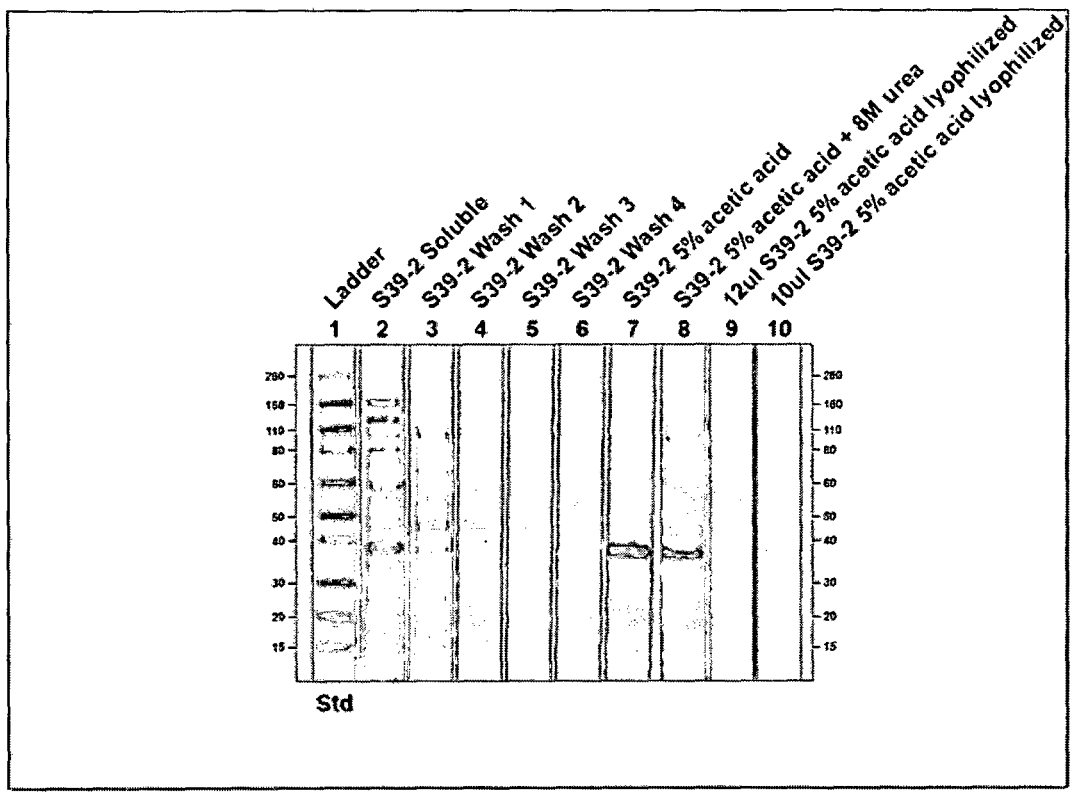
FIG. 7: Recombinant suckerin-39 protein expression. Lanes 7 and 8 show recombinant suckerin at ~39 kDa.

While there are many challenges and subtleties involved in the generation of recombinant silk proteins, we have successfully expressed full length 39 Kilo Dalton Suckerin (SEQ ID NO: 2) and purified it using standard IMAC chromatography under denaturing conditions (FIG. 7). These results demonstrate the feasibility of expressing and purifying the Suckerins in a straightforward manner.

Suckerins and variants thereof can be produced using in vitro translation systems, by recombinant protein expression using any from a range of prokaryotic or eukaryotic hosts/cell lines. These host cells include but are not limited to bacterial cells, fungal cells, insect cells, mammalian cells and algal and other plant cells. The proteins can also be produced in transgenic organisms for example in plants, silkworms, mammals or any other suitable host. Depending on the application the product may be Suckerin protein or variants and/or fragments thereof according to the Claims. These proteins may be synthesized in the same or different hosts as desired. Host cells and organisms expressing and/or over expressing desired Suckerin proteins, protein modules and/or variants and combinations thereof provide valuable reagents for many applications including but not limited to the production of nano-fibers, filaments, fibers, films, foams, bulk material and other materials listed but not limited to those presented in the Claims Section of this document.

To translate the SRT molecular design into engineering applications, we expressed SEQ ID NO: 61 and purified recombinant protein based on SEQ ID NO: 2 named (rec) Suckerin-39 and processed the purified proteins into structural and functional materials. Full-length Suckerin-39 were readily expressed without the issues commonly faced with the expression of large silk proteins in bacteria (such as gene instability and translational pausing), and (rec)Suckerin protein-based materials could be processed from mildly acidic aqueous solutions. Dry (rec)Suckerin-39 exhibited a β-sheet enriched content by ATR-FTIR (estimated to more than 50%, FIG. 8a), suggesting that we have engineered a supramolecular network that mimics the native SRT. In the dry state, (rec)Suckerin-39 films exhibited moduli comparable to the native SRT (~7.5 GPa, FIG. 8c), whereas under hydrated conditions the modulus decreased to 5-8 MPa (FIG. 8c), which is considerably lower than the native hydrated material (4 GPa) but similar to hydrated spider dragline silk (10 MPa)[9].

Figure 8:
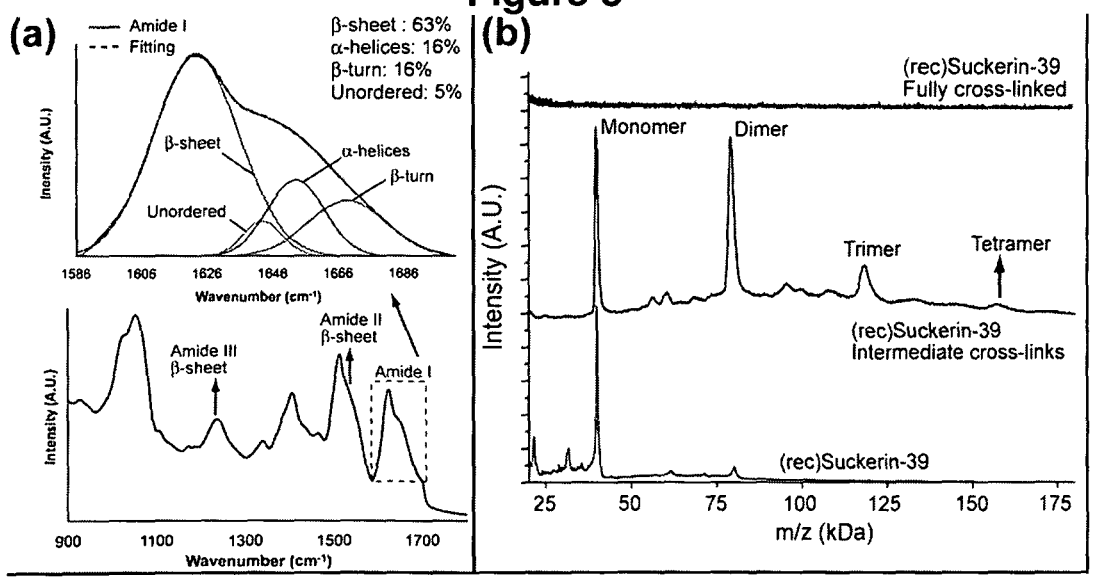
FIG. 8: Engineering of recombinant Suckerin-39. (a) FTIR of (rec)Suckerin-39 films illustrating the β-sheet dominated content. (b) MALDI-TOF analysis of photo cross-linked (rec)Suckerin-39. Oligomers are observed under intermediate cross-linking conditions (middle spectrum). In the fully cross-linked state, all peaks disappear (top). (c) Elastic modulus of (rec)Suckerin-39 films before and after cross-linking under dry and wet conditions; moduli of dragline silk are shown for comparison. (d) H vs. E Ashby plot of engineering materials and comparison with cross-linked (rec)Suckerin-39 (wet). Wear resistance is predicted to scale with H3/E2, which can be represented by guidelines with slope 2/3 on the chart. In this representation, best-performing materials against wear lie along the upper-most guidelines. (e) (rec)Suckerin-39 as a matrix for cell culture, showing hMSCs viability after 2 weeks by live/dead staining and variation in cell morphology as a function of protein concentration.
Figure 8:
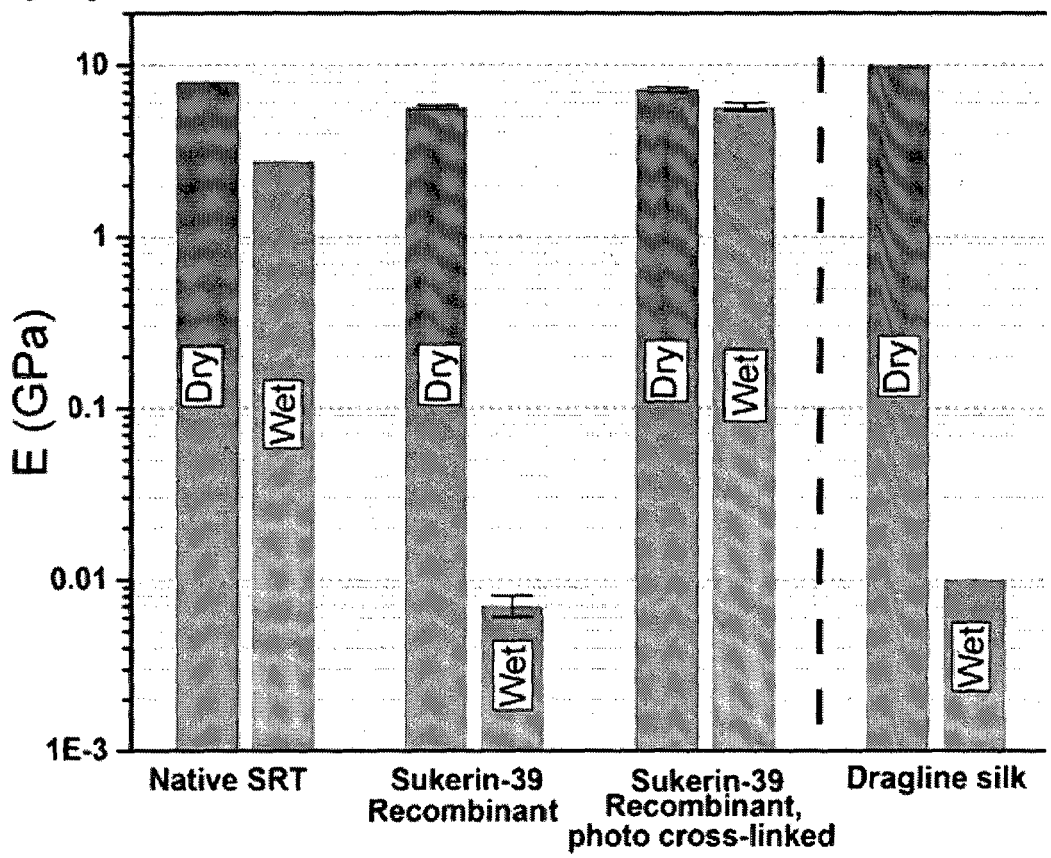
Figure 8:
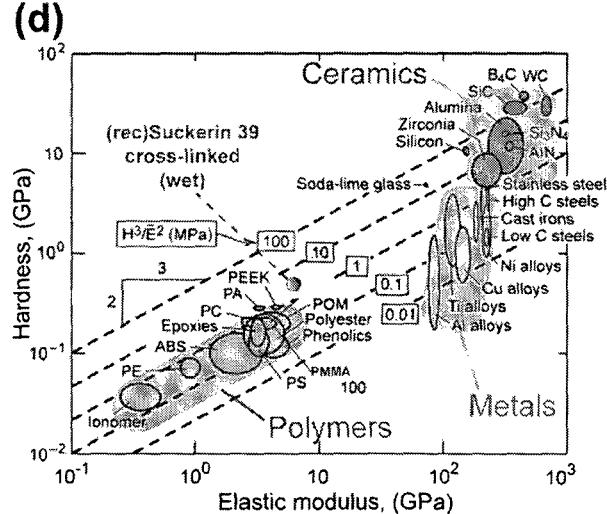
Figure 8:
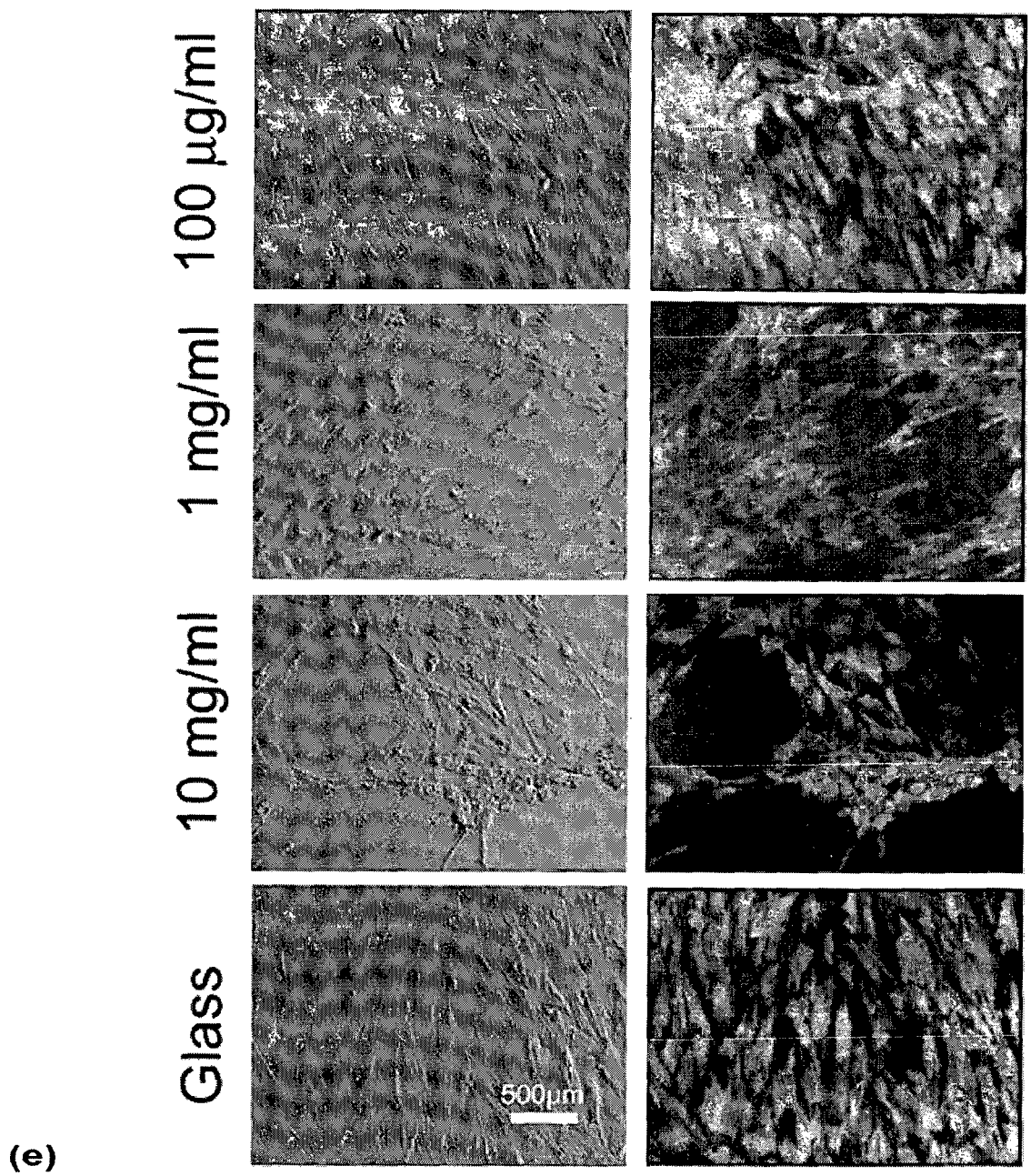
Figure 9:
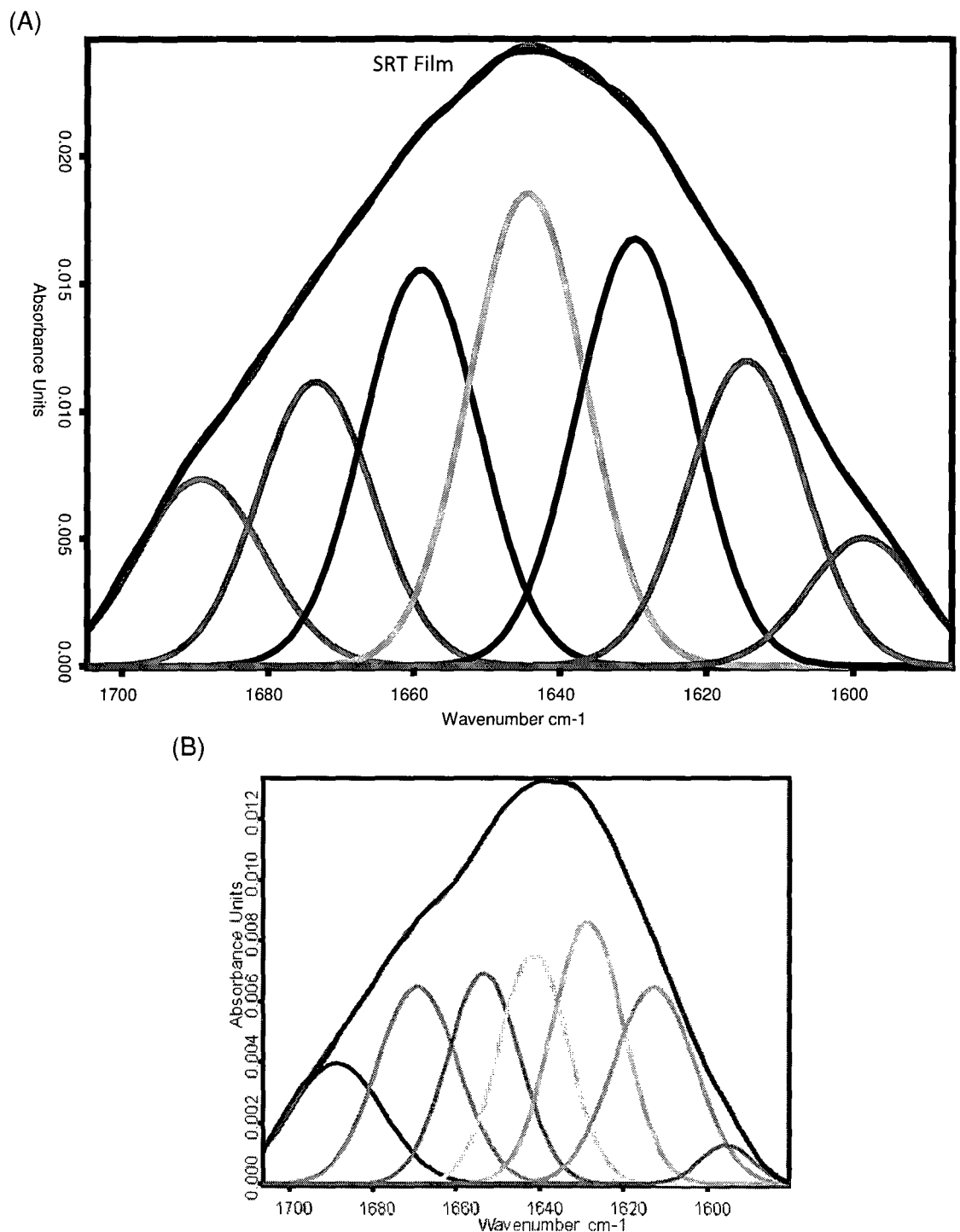
FIG. 9. Fourier Transform infrared Spectroscopy of (A) Suckerin-based film and (B) Suckerin based fiber. The data show that the transformed Suckerin-based material contains a significant percentage of beta-sheet structure. Fiber/Film wavenumber; Side Chain 1598/1595; Beta-Sheet 1614/1613; Beta-Sheet 1629/1629; Random coil Film 1644; alpha helix 1644/1653; turn 1673/1669; beta-sheet 1689/1689.

This low wet modulus suggested a window of opportunity for tuning the stiffness, which we hypothesized could be modulated by targeting the abundant tyrosine residues via the introduction of di-tyrosine covalent cross-linking. We used a ruthenium-based photo-optical cross-linking approach[61] and established optical cross-linking conditions using SDS-PAGE (FIG. 6B) and MALDI-TOF analysis (FIG. 8b). These conditions were then used to cross-link the (rec)Suckerin-39 films. The elastic modulus of cross-linked recombinant films increased to 8-9 GPa in dry conditions. Notably, the modulus remained similar under hydrated conditions with values ranging from 6-7 GPa (FIG. 8c). This represents one of the the highest elastic modulus of any recombinant protein-based material under hydrated conditions—the modulus is higher than that of hydrated dragline silk by 2 to 3 orders of magnitude. The results also indicate an efficient route for tuning the mechanical properties of Suckerin-based materials over a very broad range.

Comparing the modulus and hardness (H) against engineering materials on a classical Ashby plot (FIG. 8d), the cross-linked films are stiffer and harder than any engineered polymer (including PMMA, PEEK or Polyamides), and are also predicted to exhibit a superior wear resistance than synthetic structural polymers.

Expression and Purification of Recombinant (Rec)Suckerin-39 Protein

The full-length Suckerin-39 open reading frame was amplified by RT-PCR from the 3' RACE library using primers designed based on the 5' sequence of the Suckerin39 gene which was confirmed by Sanger sequencing. The 5' primer was specific to Suckerin-39 (5'-TGAAGGAGTAGAAAGTAGTCTCC-3' SEQ ID NO: 101) while the 3' primer used was the GeneRacer 3' primer (5'-GCTGTCAACGATACGCTACGTAACG-3' SEQ ID NO: 102). The PCR product was cloned into the pCR2.1 vector by TA cloning. The sequence omitting the signal peptide sequence was then amplified by PCR using the following primers:

```
Suckerin-39-FWD primer:
                                    (SEQ ID NO. 103
5'-AAAAAAGCTAGCATTTTGCCAGCGGCAACATCTG-3';

Suckerin-39-REV primer:
                                    (SEQ ID NO. 104)
5'-AAAAAACTCGAGTTAGTGGAGGAGACCATATCCAC-3'.
```

The PCR fragment was then cloned into the NheI/XhoI site of the pET23 vector (Novagen). A stop codon was added at the 3' end of the gene to prevent expression of the c-terminal HIS tag encoded in the expression vector, resulting in a protein that exactly mirrors the native suckerin-39 sequence. The sequence verified construct was transformed into BL21 DE3 cells and maintained with carbenicillin selection.

Test expression revealed that SRT-39 was expressed as inclusion bodies and we used this method to generate relatively pure protein fractions. A single colony was inoculated and grown overnight in 20 ml of LB with carbenicillin (100 μg/ml). The next day, the overnight culture was inoculated into a 1 L shake flask culture with carbenicillin (100 μg/ml) at a 1:100 dilution. The culture was grown at 37° C. until an $OD_{600}$ of 0.4-0.6. IPTG was added to a final concentration of 0.5 mM and protein induction was performed at 37° C. for 4 hours. The cells were pelleted at 10,000 rpm for 15 minutes and washed twice with 10 mL of 20 mM Tris pH8 and stored at −20° C.

The cell pellet was resuspended in 50 ml of Lysis buffer (50 mM Tris pH 7.4, 200 mM NaCl, 1 mM PMSF) and lysed using a high pressure homogenizer (Microfluidics Corp). Inclusion bodies and cellular debris were pelleted at 19,000 rpm for 1 hour at 4° C. The pellet was washed twice with urea wash buffer (100 mM Tris pH7.4, 5 mM EDTA, 2M urea, 2% (v/v) Triton X-100, 5 mM DTT) and twice with wash buffer (100 mM Tris pH7.4, 5 mM EDTA, 5 mM DTT). Inclusion bodies were pelleted by centrifugation at 5,000 g for 15 min at 4° C. in between washes. The inclusion body pellet was re-solubilized in 5% or 20% acetic acid, snap frozen with liquid nitrogen and lyophilized overnight. Recombinant proteins of ~90-95% purity were obtained in this manner and yields were estimated at 10 mg/L.

MALDI-TOF

Proteins mixed with sinapinic acid dissolved in a mixture of 50/50 Q-water/ACN with 0.1% TFA and dried prior to irradiation. Experiments were conducted on a Kratos Axima TOF² (Kratos-Shimadzu Biotech) equipped with an $N_2$ laser (337 nm, 4 ns pulse width). An accelerating voltage of 20 kV was used, spectra were recorded in linear mode by averaging at least 100 laser shots at a power of 120 system units.

Peptide Synthesis

Suckerins and variants thereof can be assembled by peptide synthesis either manually or for example, with the aid of commonly available peptide synthesizers.

Naturally occurring Suckerin proteins exhibit some imperfectly repetitive structure. In some cases imperfections are likely a consequence of the process by which the Suckerin protein genes evolved rather than a requirement for the local and supra-molecular organization of the SRT. Therefore local imperfections will not dramatically effect properties, nucleic acid sequences are engineered which encode clean Suckerin proteins, each of which encodes a polypeptide having direct repeats of naturally occurring and/or engineered variants of [L], [M1], [M2] and [M3] and/or sequences bearing at least 60% similarity to these. Alternatively, nucleic acid sequences may include sequences from different Suckerins, [L], [M1], [M2] and [M3] peptides to form a "copolymer" Suckerin protein.

Formation of Suckerin-Based Material

Suckerin proteins exhibit solubility in mild acetic conditions and can also be heated and deformed to process them into any complex shape. Suckerin-based solutions, gels, fibers, melts, liquid-crystals and any other chosen state of matter are processed further by manipulation by methods including but not limited to micro-environment, addition of water, salts, elements of the periodic table, solvent, heating, cooling, magnetism, mechanical stress, mechanical strain, pressure, compression, torsion and/or shear for example.

Suckerin proteins, peptides, copolymers and variants and combinations thereof are folded into structures containing beta-sheet secondary structure.

Suckerin-based solutions, gels, fibers, melts, liquid-crystals and any other chosen state of matter are processed further by manipulation by methods including but not limited to microenvironment, addition or removal of water, solvent, addition of elements from the period table, mechanical stress, magnetism, mechanical strain, pressure, compression, torsion and/or shear.

We envisage a broad range of applications for SRT-based materials, which could rival natural and engineered silks in fields such as photonics and sensing devices, or as tissue scaffolds with tailored properties. They could also be exploited as biocompatible films for food and drug packaging, and as cost-effective encapsulants that shield drugs against thermal degradation during transportation and storage. Their tandem repeat design with high Tyr content is also deemed ideal to direct gold nanoparticles growth[61] through the reducing activity of Tyr residues, which are useful in sensing and diagnostic applications.

Suckerin Powder

SRT were pulverized into a powder in liquid nitrogen using a mortar and pestle. A dry powder containing the protein resulted. The powder can be used for further processing to make any of the products listed, herein.

Fabrication, Visualization, and Characterization of SRT

Hydrated and/or Heated SRT powder can be formed into many different patterns

Spun Fiber Material

As another illustration of their processability, melted SRT-proteins were readily spun into fibers. After drawing the liquid SRT proteins into fibers, we observed slight shifts and changes in relative FTIR peak intensities, indicating in this case significant re-arrangement of SRT protein secondary structure. However, a clear β-sheet signature was still observed for the fibers, supporting the view that they maintain a silk-like supramolecular organization. Silks have proven to be suitable for an extreme range of both textile and high-technology applications[2,3]. However, a large majority of these materials require harsh processing conditions to solubilize and process the fibroin or spidroin proteins. Our data clearly demonstrate that these silk-like materials can be sculpted and spun by facile aqueous-based processing.

Heat-Drawn Spinning of SRT Proteins into Fibers

Natural, recombinant and synthetic Suckerin-based materials, including fibers are of utility in which other natural fibers are considered and used. For example Suckerin-based materials and/or fibers can be mixed with various plastics, resins and any other compound to prepare reinforced plastic, resin and/or composite products. Given that the natural and synthetic Suckerins can be effectively melted, they can be processed together or in parallel with thermal plastics and other materials at temperatures up to the degradation temperature of the peptide backbone ~280 degrees.

Fabrication of Recombinant (Rec)Suckerin-39 Films and Nano-Surfaces (Rec)Suckerin-39 was found to be soluble in 5% acetic acid at 20 mg/ml. These conditions were considered suitable as they represented mild, eco-friendly aqueous-based conditions for the assembly of solid-state Suckerin based films from solution. Films were generated by the addition of 10 µl of the protein solution into custom 3D printed mini-wells (2 mm diameter, 2 mm height) secured to a glass microscope slide base. The samples were allowed to dry for 12 hours resulting in ~5 µm thick films. A second layer was then introduced on top of the first layer in the same manner to create a film that was thick enough to eliminate surface effects in subsequent nano-indentation experiments. Tested films were approximately ~7-10 µm thick. The test chamber humidity was ~55% RH.

Figure 6:
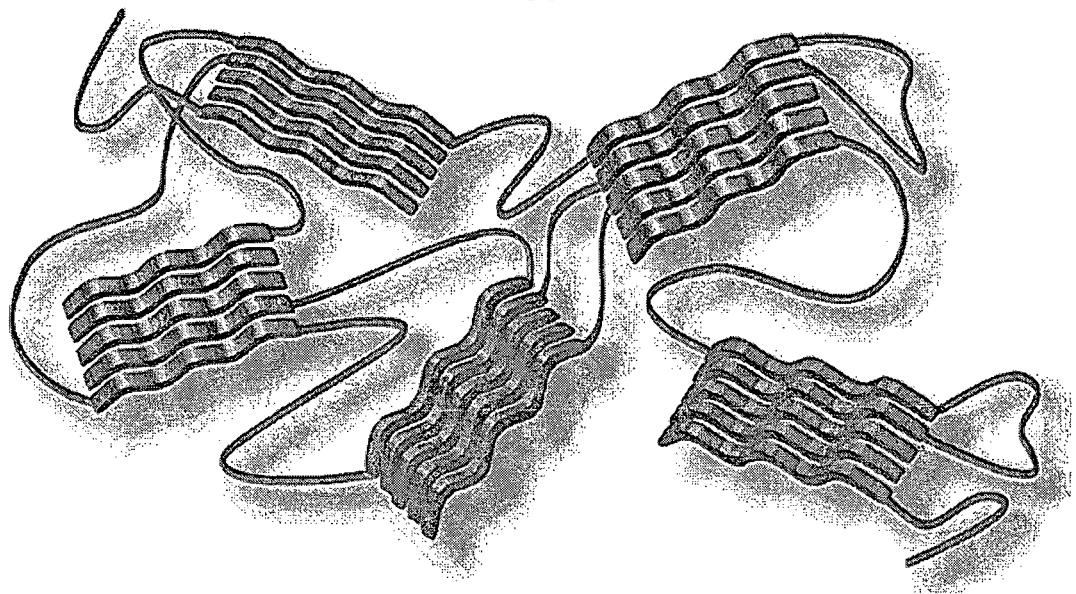
FIG. 6: (A) stylized drawing of the random orientation of β-sheets in SRT. (B) Evaluation of photo-cross-linking efficiency with recombinant protein (rec)Suckerin-39. (a) Effect of APS concentration on cross-linking: SDS-PAGE of 1 mg/ml (rec)Suckerin-39 with Ru salt at various APS concentrations. Lanes 1 and 2 demonstrate little to no protein migration indicating effective cross-linking. Cross-linked intermediates are visible in Lanes 3-6. At lower APS only monomers were observed. (b) SDS-PAGE of 1 mg/ml (rec)Suckerin-39 at various light exposure times. (c) MALDI-TOF analysis of cross-linking at various light exposure times. Bottom spectrum: (rec)Suckerin-39 control sample. At 5 sec (middle spectrum), oligomeric intermediates are detected; at 2 min (top spectrum) no signal is observed indicative of effective cross-linking. (C) the mean distances between prolines for all three species, reflecting the mean length of the [M1] domains.
Figure 6:
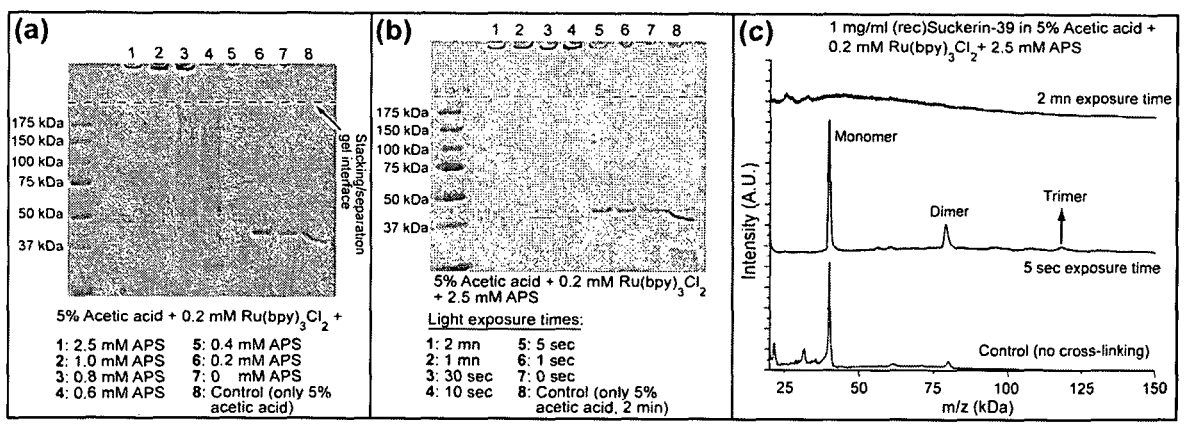
Figure 6C:
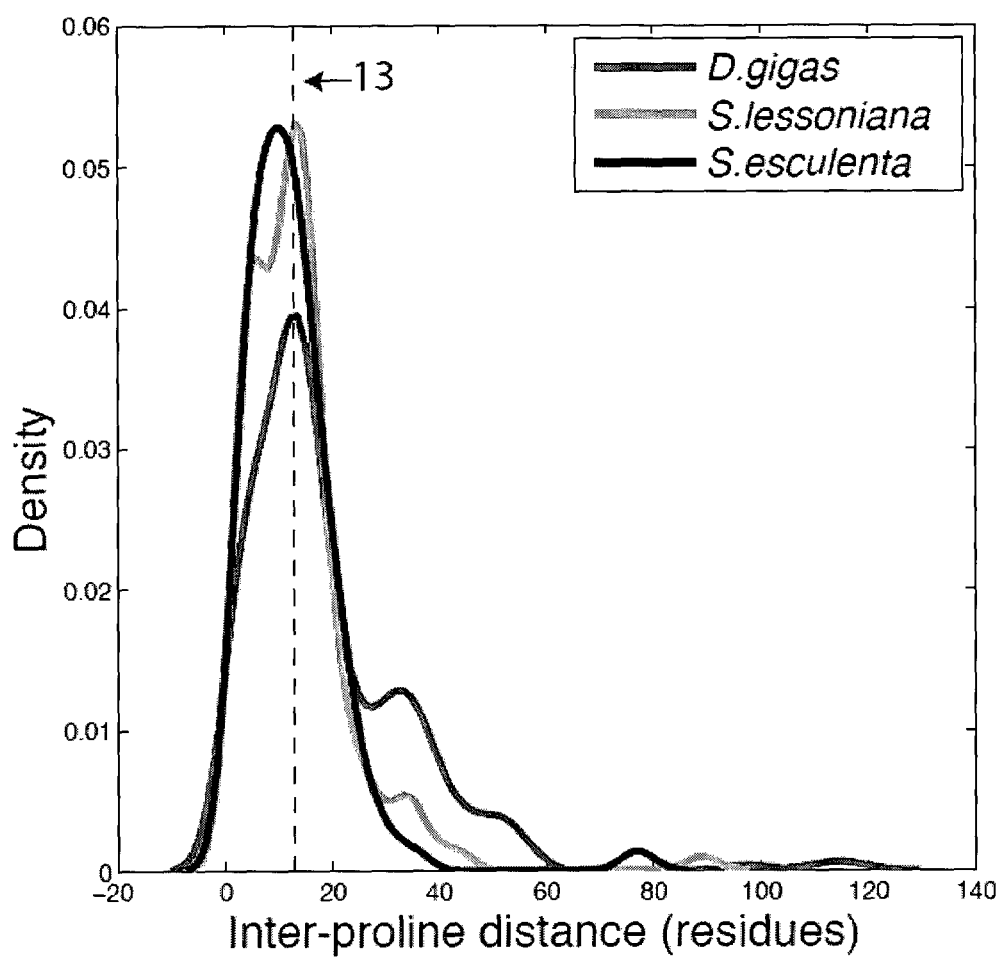

Photo-Cross Linking of (Rec)Suckerin-39 Proteins (Rec)Suckerin-39 protein cross-linking conditions were first established using 1 mg/ml preparations of rec-Suckerin-39 in 5% acetic acid with 0.2 mM $Ru(bpy)_3Cl_2$ (Sigma Aldrich) and a range of Ammonium persulfate (APS) concentrations (2.5 mM to 0 mM) in 20 µl reaction volumes. Following the introduction of the reactants, the samples were immediately exposed to white light from a 500 W halogen lamp for 2 minutes. Samples were then mixed with Laemmli loading buffer, boiled for 10 minutes and subjected to SDS-PAGE. Heavily cross-linked samples (2.5 and 1.0 mM APS samples) displayed little to no mobility on SDS-PAGE gels compared to samples tested with lower concentrations of APS (FIG. 6Ba). By titrating APS concentration we identified conditions where the proteins were cross-linked into lower molecular weight oligomers (FIG. 6Ba). We used MALDI-TOF to confirm the presence of these cross-linking intermediates where dimers, trimers and tetramers were observed using 0.6 mM APS, 0.2 mM $Ru(bpy)_3Cl_2$ and 2 minutes light exposure (FIG. 8b). At higher APS concentrations (rec)Suckerin-39 is not observed by MALDI supporting the view that the protein is cross-linked into very high molecular weight assemblies. We also performed parallel experiments to evaluate the effect of light exposure time on cross-linking using 1 mg/ml protein in 5% acetic acid with 2.5 mM APS and 0.2 mM $Ru(bpy)_3Cl_2$. Here, intermediates are observed after a light exposure duration of 5 seconds. Beyond exposure durations greater than 10 seconds, SDS PAGE and MALDI indicate that (rec) Suckerin-39 is cross-linked into very high molecular weight oligomers (FIG. 6Bb-c). Together the data support the view that the Di-Tyrosine cross-linking method is highly efficient for our Tyrosine rich proteins and suggests that reaction conditions can be used to tune the cross-link density and mechanical properties of Suckerin based materials.

Photo-Cross-Linking of Rec-Suckerin Films

Cross-linked (rec)Suckerin-39 films were generated by the following method. 20 mg/ml (rec)Suckerin-39 in 5% acetic acid with 2.5 mM APS and 0.2 mM $Ru(bpy)_3Cl_2$ in 20 µl reaction volumes were used. 10 µl of the sample was introduced into the custom 3D printed test platform described above and allowed to dry in the dark for 2 hours. Partially dried films were then exposed to light from a 500 W halogen lamp for 3 minutes and allowed to dry for another 2 hours, followed by another round of 3 minutes exposure to light. A second layer was then introduced in the same manner to ensure that the film was thick enough to eliminate potential substrate effects during nano-indentation. The final processed films were approximately 5-10 µm thick.

Nanoindentation of Native and Recombinant Suckerin-Based Materials

Ultra-microtomed cross sections of Sucker Ring Teeth (SRT) were probed by Nanoindentation using a TriboScan 950 (Hysitron), following previously described procedures. The engineered films were probed in various locations using a cube corner fluid cell tip at maximum loads of 50 µN, chosen such as to eliminate stiffness substrate effects. A total of 50 indents were carried out at a loading rate of 5 µN/sec using 5 s holding time before unloading. Water droplets were then introduced within the mini-well and the film was hydrated for 30 minutes prior to indentation. The films were tested under fully hydrated conditions in three separate regions of the sample at maximum loads of 10 µN, for a total of 50 indents. Between each set of indents in one region, water was re-introduced within the mini-well in order ensure fully hydrated conditions. Identical experimental set-up was employed for cross-linked films. Because of the stiffer nature of the films even in hydrated conditions, maximum loads of 50 µN were kept identical for both dry and the wet measurements. All indentation curves were analyzed using the classic Oliver-Pharr analysis.

Suckerin-based materials engineered in any shape and/or physical state, as described above can be designed to provide an extreme range of desired functions by way of modification of the materials themselves and/or the addition/incorporation of additional functional atoms, molecules and/or materials. Modifications may include 1) amino acid side chain modifications; 2) the addition of metals, peptides, proteins and/or any pharmacological agent including the addition (via embedding, adsorption, cross-linking etc) of low molecular weight, biological and/or synthetic compounds, RNA, DNA, molecules, carbohydrates inorganic compounds etc.; 3) the addition of cells (at any stage of differentiation, including stem cells, predifferentitated stem cells and/or induced pleuripotent stem cells), and/or combinations of cell types; Below, we provide several examples of the potential design and utility of functionalized Suckerin-based materials.

Addition/Binding/Inclusion of Elements of the Periodic Table:

The combination of elements of the periodic table with Suckerin-based materials offers enormous potential in a wide range of industrial and biomedical applications. For example, the incorporation of copper into other biological proteins is already known to result in the creation of light weight, wear resistant materials, such as those observed in blood worm's teeth[51]. The incorporation of metals may also enable electron transport and/or conductivity and/or influence oxidation/reduction pathways in the aqueous milieu are also considered. The Suckerin-based materials may also be combined with radio-active materials that may find use in for the targeting, for example, of wide range of cancer cells. In all cases the physico-chemical properties of the Suckerin-based material can be use to enable binding/release of the elements and to provide mechanical stability for the bound elements in a wide range of industrial and/or biomedical niches.

Suckerin-Based Materials for Controlled Drug Release:

The primary sequence design, secondary, tertiary, quaternary structure and/or nano, meso, micro and macro scale structures imparted from the physical and/or chemical processing of these Suckerin-based materials, in the novel embodiments described below can be used to provide functional control over the incorporation and/or physical adsorption of pharmacologically active entities (hereafter referred to as "agents") and the subsequent specio-temporal control of their release. Agents can be coated, attached and/or incorporated on or into materials for drug delivery, alone or in combination include but are not limited to the following: 1) Growth factors; 2) Single and/or double stranded DNA and/or oligonucleotides; 3). RNA; 4) Sugars; 5) Lipids; 6) Proteolipids; 7) any class of prescription or over the counter drug; 8) Peptides; 9) Cytokines; 10) Chemokines; 11) Glycoproteins; 12) Organic and/or inorganic atoms (nano, meso, micro and macro scale metallic materials; 13) Ions; 14) Salts, 15) Metals; 16) Radioactive Isotopes; 17) Antibodies; 18) Viruses; 19) Vulnerary agents; 20) Hemostatic agents; 21) Antibiotics; 22) Antithelmintics; 23) anti-fungal agents; 24) hormones; 25) anti-inflammatory agents; 26) ATP; 27) enzymes; 28) protein domain module(s) and combinations thereof; 29) Neurotransmitter(s); 30) ion channel and porin related proteins and molecules.

It is well documented that beta-structure can dictate the diffusion and release kinetics of an extreme range of agents from beta-sheet containing silk proteins. These materials are being designed to test the release kinetics and biological activity of model compounds/molecules with diverse functions, with the eventual goal of using a chosen agent (by way of illustration a drug or protein etc.), or combination of agents to effect cellular homeostasis, cell signaling, differentiation and/or the physiological status of targeted cells or tissues. The fact that Suckerin beta-sheet content can be tailored indicates that these materials will find utility in sustained and controlled drug delivery. These materials will provide not only tailored release kinetics but they can also be engineered to maintain specific mechanical properties and offer biocompatibility.

Suckerin-based materials may be any size scale, thickness, physical state and morphology. These may included gels, electrogels, liquid crystals, hydrogels, thin films, films, nano-fibers, fibrils, fibers, (including tissue scaffolds), nano-spheres and other nano-scale shapes, micro-spheres and all macroscopic materials. The agent loaded materials may be used alone, or in combination with any other agent(s) without limitation.

Suckerin Based Materials as Sensors/Switches and/or Actuators.

The field of nano-technology offers huge potential for the engineering of molecular scale switches, sensors and actuators etc. that could be used to assess local micro-environments, measure cellular status and perform mechanical functions and/or electrical functions at the nano-scale. However, the materials currently in use, namely carbon-based nano-tubes, nano-crystalline materials and synthetic materials have their own limitations in terms of engineering flexibility and biocompatibility. Given that Suckerins can be sculpted into a wide range of materials, they clearly have enormous potential as substrates and structures that will form the basis for the addition of switching, sensing functions for example. By way of example, the beta-sheet content of material can be monitored, (using antibodies, congo-red binding, thioflavin-T binding, raman spectroscopy and/or any other technique) which can provide direct read-outs of the stability of the material, it's bioresorption rates and, by mathematical inference with polymer network theory, it's mechanical status. In another embodiment the Suckerin material is modified to include sensing structures, compounds, chemicals and materials.

Suckerin Based Materials with Cells and Tissues:

When processed into the appropriate physical states and structures many synthetic materials offer the potential to act as scaffolds/adhesion substrates for cell and tissue growth and in vivo tissue repair. While these materials offer significant potential they exhibit limitations in engineering flexibility, biocompatibility and biodegradability that proteins may not. Therefore there has been a recent surge in interest of creating engineered biomimetic scaffold that offer greater control of these key aspects. For example there is an extensive body of literature on the use of collagens and fibronectin in tissue repair. Each of these materials has advantages and disadvantages, depending on the cell/tissues used and the repair strategy being used. Suckerin-based materials and mimetics thereof represent a novel class of potential cellular substrates/tissue scaffolds that could offer engineering flexibility, biocompatibility, direct control over the biomechanical properties of the substrate and tailored biodegradability to provide substrates that are 1) robust 2) have precisely tailored physical properties 3) provide finely tuned surfaces that influence cell cellular homeostasis and cell signaling 4) have tailored degradation kinetics. Examples of cell types that can be combined with Suckerin-based materials include but are not limited to 1) Neurons 2) Glia 3) any class of stem cells and stem cell lineages 4) muscle cells 5) bone cells 6) pancreas 7) hematopoetic cells 8) liver cells 9) cardiac myocytes 10) cartilaginous cells; 11) bone 12) tendon 13) cells derived from or comprising artery or venous tissue 14) skin cells 15) reproductive cells 16) cells conferring immunity 17) genetically engineered cells 18) plant cells 19) bacterial cells 20) yeast cells 21) algal cells 22) oligodendrocytes etc.

Evaluation of Cell Culture Compatibility of (Rec)Suckerin-39 Films

As an additional proof-of-concept of the versatility of (rec)Suckerin-39, we examined the viability and proliferation of human mesenchymal stem cells (hMSC) grown on (rec)Suckerin-39 films.

Human mesenchymal stem cells (hMSCs, Lonza PT-2501) were cultured in Minimum Essential Medium (MEM)-(Invitrogen 12571-063) with 10% fetal bovine serum (FBS) and 100 U/mL penicillin and 100 µg/mL streptomycin at 37° C. in a 5% $CO_2$ humidified atmosphere. Lyophilized (rec)Suckerin39 was dissolved in 50% acetic acid to 10 mg/ml and diluted where needed in 50% acetic acid. 50 µl of each protein solution was deposited onto a 14 mm glass coverslip and dried under air flow in a fume hood. The protein film was then crosslinked with a 1% glutaraldehyde solution, rinsed thrice with distilled water and air dried. The film-covered cover slip was then placed in a 24-well tissue culture plate and UV sterilized. $3.75 \times 10^4$ hMSCs per well were seeded on the prepared (rec)Suckerin-39 films and cultured for 16 days with frequent media change. For live/dead staining, the cells were treated with 2 µM fluorescein diacetate and 2.5 µg/mL propidium iodide for 0.5 h at 37° C. Thereafter, the hMSCs were imaged using a Nikon fluorescence microscope (TE2000-U).

The hMSCs were cultured for more than 2 weeks and displayed high cell viability for all conditions demonstrating that (rec)Suckerin-39 is biocompatible and can support cell growth (FIG. 8f). Notably, we observed that hMSCs grown on films generated from higher concentrations of (rec) Suckerin-39 displayed increasingly branched and spindle-shaped cell morphologies, which may be related to celllineage specification of hMSCs as a result of variations in matrix elasticity at different protein concentrations.

Uses of Suckerin Based Materials

Mechanically and functionally useful nano-fibers; meso and macro-scale fibers, films, thin films nano-meso and micro and macro-scale fibrous mats, materials with tailored porosity, liquid-crystals, gels, nano-spheres, microspheres, foams, hydrogels, electrogels. Fibers, woven fabrics, high-tech clothing, rope, sails, fishing line parachute, wings on arial devices, flexible tie downs for electrical components, sutures biomedical implants, tissue scaffold. Biomedical applications include but are not limited to, tissue repair scaffold, tissue engineering scaffold, reconstructive eye surgery ear surgery implant. Sutures used in surgical procedures including eye surgery, reconstructive nerve surgery, tympanic membrane surgery, vascular closure, bowel surgery, cosmetic surgery, and central nervous system surgery. Natural and synthetic Suckerin-based fibers may also be of utility in the generation of antibiotic impregnated sutures and implant material and matrix material for bone, connective tissue and soft tissue. Implants and matrix material for reconstruction may be impregnated with growth factors, differentiation factors, and/or cell attractants to facilitate incorporation of exogenous material and optimize repair. Sensors, switches actuators insulators and above mentioned devices in this category. Drug delivery devices including nano-particle, microspheres, membranes gels foams Cosmetic components and fillers, composite materials. The materials of the current invention may also be incorporated into bandages, surgical and dental wound packing material, diapers and catamenial devices, and the like By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

References

1 Lee, P. L., Messersmith, P. B., Israelachvili, J. N. & Waite, J. H. Mussel-Inspired Adhesives and Coatings. *Annual Reviews of Materials Research* 41, 99-132 (2011).

2 Omenetto, F. G. & Kaplan, D. New Opportunities for an Ancient Material. *Science* 329, 528-531 (2010).

3 Tao, H., Kaplan, D. L. & Omenetto, F. G. Silk materials—a road to sustainable high technology. *Adv Mater* 24, 2824-2837, doi:10.1002/adma.201104477 (2012).

4 Guerette, P., Gizinger, D., Weber, B. & Gosline, J. M. Silk Properties Determined by Gland-Specific Expression of a Spider Fibroin Gene Family. *Science* 272, 112-115 (1996).

5 Gatesy, J., Hayashi, C. Y., Motriuk, D., Woods, J. & Lewis, R. Extreme Diversity, Conservation, and Convergence of Spider Silk Fibroin Sequences. *Science* 291, 2603-2605 (2001).

6 Hayashi, C. Y. & Lewis, R. V. Molecular architecture and evolution of a modular spider silk protein gene. *Science* 287, 1477-1479 (2000).

7 Hayashi, C. Y. & Lewis, R. V. Evidence from flagelliform silk cDNA for the structural basis of elasticity and modular nature of spider silks. *J Mol Biol* 275, 773-784, doi:10.1006/jmbi.1997.1478 (1998).

8 Ayoub, N. A., Garb, J. E., Tinghitella, R. M., Collin, M. A. & Hayashi, C. Y. Blueprint for a high-performance biomaterial: full-length spider dragline silk genes. *PLoS One* 2, e514, doi:10.1371/journal.pone.0000514 (2007).

9 Gosline, J. M., Guerette, P. A., Ortlepp, C. S. & Savage, K. N. The Mechanical Design of Spider Silks: From Fibroins Sequence to Mechanical Function. *Journal of Experimental Biology* 202, 3295-3303 (1999).

10 Holland, C., Vollrath, F., Ryan, A. J. & Mykhaylyk, O. O. Silk and synthetic polymers: reconciling 100 degrees of separation. *Adv Mater* 24, 105-109, 104, doi:10.1002/adma.201103664 (2012).

11 Vollrath, F. & Knight, D. P. Liquid Crystalline Spinning of Spider Silk. *Nature* 410, 541-548 (2001).

12 Lewis, R. V. & Hayashi, C. Y. Extremely elastic spider silk protein and DNA coding thereof. U.S. Pat. No. 5,994,099 (1999).

13 Lewis, R. V., Hayashi, C. Y., Gatesy, J. E. & Motriuk, D. Spider silk protein encoding nucleic acids, polypeptides, antibodies and methods of use thereof. U.S. Pat. No. 7,521,228 (2009).

14 Scheibel, T. & Huemmerich, D. Proteins of natural origin and materials made therefrom. 8097583 (2012).

15 Scheibel, T., Huemmerich, D. & Ackerschott, C. Recombinant spider silk proteins. U.S. Pat. No. 8,034,897 (2011).

16 Scheibel, T., Huemmerich, D. & C., A. Recombinant spider silk proteins. U.S. Pat. No. 7,951,908 (2011).

17 Fahnestock, S. R. Recombinantly produced spider silk. U.S. Pat. No. 6,268,169 (2001).

18 Johansson, J., Hjalm, G., Stark, M., Engstrom, W. & Hedhammar, M. Spider silk proteins and methods for producing silk proteins. U.S. Pat. No. 8,173,772 (2012).

19 Kaplan, D. L., Jin, H. J., Rutledge, G. & Fridrikh, S. Silk biomaterials and methods of use thereof. U.S. Pat. No. 7,674,882 (2010).

20 Kaplan, D. L., Kim, U.-J., Park, J. H. & Jin, H. J. Concentrated aqueous silk fibroin solution and use thereof. (2009).

21 Lock, R. L. Process for making silk fibroin fibers. U.S. Pat. No. 5,252,285 (1993).

22 Mello, C., Arcidiacono, S. & Butler, M. M. Methods for the purification and aqueous fiber spinning of spider silks and other structural proteins. U.S. Pat. No. 7,335,739 (2008).

23 Islam, S. et al. Methods and apparatus for spinning spider silk protein. U.S. Pat. No. 7,057,023 (2006).

24 Lazaris, A. et al. Spider silk fibers spun from soluble recombinant silk produced in mammalian cells. *Science* 295, 472-476, doi:10.1126/science.1065780 (2002).

25 Fahnestock, S. R., Yao, Z. & Bedzyk, L. A. Microbial production of spider silk proteins. *J Biotechnol* 74, 105-119 (2000).

26 Scheller, J., Guhrs, K. H., Grosse, F. & Conrad, U. Production of spider silk proteins in tobacco and potato. *Nat Biotechnol* 19, 573-577, doi:10.1038/89335 (2001).

27 Yang, J. Production of silk-like proteins in plants. U.S. Pat. No. 6,965,060 (2005).

28 Yang, J. Production of silk-like proteins in plants. U.S. Pat. No. 6,608,242 (2003).

29 Yang, J., Barr, L. A., Fahnestock, S. R. & Liu, Z. B. High yield recombinant silk-like protein production in transgenic plants through protein targeting. *Transgenic Res* 14, 313-324 (2005).

30 Menassa, R. et al. Spider dragline silk proteins in transgenic tobacco leaves: accumulation and field production. *Plant Biotechnol J* 2, 431-438, doi:10.1111/j.1467-7652.2004.00087.x (2004).

31 Yamao, M. et al. Gene targeting in the silkworm by use of a baculovirus. *Genes Dev* 13, 511-516 (1999).

32 Teule, F. et al. Silkworms transformed with chimeric silkworm/spider silk genes spin composite silk fibers with improved mechanical properties. *Proc Natl Acad Sci USA* 109, 923-928, doi:10.1073/pnas.1109420109 (2012).

33 Karatzas, C. N., Turner, J. D. & Lazaris-Karatzas, A. Production of biofilament in transgenic animals. U.S. Pat. No. 7,157,615 (2007).

34 Xia, X. X. et al. Native-sized recombinant spider silk protein produced in metabolically engineered *Escherichia coli* results in a strong fiber. *Proc Natl Acad Sci USA* 107, 14059-14063, doi:10.1073/pnas.1003366107 (2010).

35 Kerkam, K., Viney, C., Kaplan, D. & Lombardi, S. Liquid crystallinity of natural silk secretions. *Nature* 349, 596-598 (1991).

36 Willcox, J. P., Gido, S. P., Muller, W. & Kaplan, D. Evidence of cholesteric liquid crystalline phase in natural silk spinning process. *Macromolecules* 29, 5106-5110 (1996).

37 Knight, D. & Vollrath, F. Hexagonal columnar liquid crystal in the cells secreting spider silk. *Tissue Cell* 31, 617-620, doi:10.1054/tice.1999.0076 (1999).

38 Vollrath, F., Madsen, B. & Shao, Z. The effect of spinning conditions on the mechanics of a spider's dragline silk. *Proc Biol Sci* 268, 2339-2346, doi:10.1098/rspb.2001.1590 (2001).

39 Vollrath, F. & Knight, D. P. Liquid crystalline spinning of spider silk. *Nature* 410, 541-548, doi:10.1038/35069000 (2001).

40 Hagn, F. et al. A conserved spider silk domain acts as a molecular switch that controls fibre assembly. *Nature* 465, 239-242, doi:10.1038/nature08936 (2010).

41 Hagn, F., Thamm, C., Scheibel, T. & Kessler, H. pH-dependent dimerization and salt-dependent stabilization of the N-terminal domain of spider dragline silk—implications for fiber formation. *Angew Chem Int Ed Engl* 50, 310-313, doi:10.1002/anie.201003795 (2011).

42 Rammensee, S., Slotta, S., Scheibel, T. & Bausch, A. R. Assembly Mechanism of Recombinant Spider Silk Proteins. *Proc Natl Acad Sci USA* 105, 6590-6595 (2008).

43 Askarieh, G. et al. Self-assembly of spider silk proteins is controlled by a pH-sensitive relay. *Nature* 465, 236-238, doi:10.1038/nature08962 (2010).

44 Guan, J., Vollrath, F. & Porter, D. Two mechanisms for supercontraction in Nephila spider dragline silk. *Biomacromolecules* 12, 4030-4035, doi:10.1021/bm201032v (2011).

45 van Beek, J. D., Kummerlen, J., Vollrath, F. & Meier, B. H. Supercontracted spider dragline silk: a solid-state NMR study of the local structure. *Int J Biol Macromol* 24, 173-178 (1999).

46 Miserez, A., Weaver, J. C., Kisailus, D. & Birkedal, H. in *MRS Spring meeting* 2009. (Materials Research Society).

47 Miserez, A. et al. Microstructural and Biochemical Characterization of the Nano-porous Sucker Rings from *Dosidicus gigas*. *Adv Mater* 21, 401-406 (2009).

48 Strugnell, J., Jackson, J., Drummond, A. J. & Cooper, A. Divergence time estimates for major cephalopod groups: evidence from multiple genes. *Cladistics* 22, 89-96 (2006).

49 Lindgren, A. R., Pankey, M. S., Hochberg, F. G. & Oakley, T. H. A multi-gene phylogeny of Cephalopoda supports convergent morphological evolution in association with multiple habitat shifts in the marine environment. *BMC Evol Biol* 12, 129, doi:10.1186/1471-2148-12-129 (2012).

50 Keten, S., Xu, Z., Ihle, & Buehler, M. J. Nanoconfinement Controls Stiffness, Strength and Mechanical Toughness of Beta-Sheet Crystals in Silk. *Nat Mater* vol. 9, 359-367 (2010).

51 Lichtenegger, H. C., Schöberl, T., Bartl, M. H., Waite, H. & Stucky, G. D. High Abrasion Resistance with Sparse Mineralization: Copper Biomineral in Worm Jaws. *Science* 298, 389-392 (2002).

52 Grabherr, M. G. et al. Full-Length Transcriptome Assembly from RNA-Seq Data Without a Reference Genome. *Nat Biotechnol* 29, 644-652 (2011).

53 Li, B. & Dewey, C. N. RSEM: Accurate Transcript Quantification from RNA-Seq Data with or without a Reference Genome. *BMC Bioinformatics* 12, 323, doi: 10.1186/1471-2105-12-323 (2011).

54 Edgar, R. C. Search and Custering Orders of Magnitude Faster than BLAST. *Bioinformatics* (Oxford, England) 26, 2460-2461, doi:10.1093/bioinformatics/btq461 (2010).

55 Yano, M., Nagai, K., Morimoto, K. & Miyamoto, K. Shematrin: A Family of Glycine-Rich Structural Proteins in the Shell of the Pearl Oyster Pinctada fucata. *Comparative Biochemistry and Physiology B-Biochemistry & Molecular Biology* 144, 254-262 (2006).

56. Rousseau, M.-E., Lefevre, T., Beaulieu, L., Asakura, T. & Pezolet, M. Study of Protein Conformation and Orientation in Silkworm and Spider Silk Fibers Using Raman Microspectroscopy. *Biomacromolecules* 5, 2247-2257 (2004).
57. Fancy, D. A. & Kodadek, T. Chemistry for the Analysis of Protein-Protein Interactions: Rapid and Efficient Cross-Linking Triggered by Long Wavelength Light. *Proc. Natl. Acad. Sci. U.S.A.* 96, 6020-6024 (1999).
58. C. Z. Zhou et al., Fine organization of *Bombyx mori* fibroin heavy chain gene. *Nucleic Acids Res* 28, 2413 (Jun. 15, 2000).
59. M. Suzuki et al., Characterization of Prismalin-14, a novel matrix protein from the prismatic layer of the Japanese pearl oyster (Pinctada fucata). *Biochem J* 382, 205 (Aug. 15, 2004).
60. L. Dalla Valle et al., Beta-keratins of the crocodilian epidermis: composition, structure, and phylogenetic relationships. *J Exp Zool B Mol Dev Evol* 312, 42 (Jan. 15, 2009).
61. P. A. Guerette et al., (2013) Accelerating the design of biomimetic materials by integrating RNA-seq with proteomics and materials science. Nat Biotechnol, 31:908-915

The invention claimed is:

1. A composition comprising:
   an isolated recombinant polypeptide comprising or consisting of:
   (a) the amino acid sequence set forth in SEQ ID NO: 2;
   (b) a variant of the amino acid sequence of (a) that shares at least 80% sequence identity with the amino acid sequence of (a) over its entire length; or
   (c) a fragment of the amino acid sequence of (a), the fragment having a length of at least 50 amino acids;
   wherein the recombinant polypeptide is at least partially in beta sheet conformation, and
   one or more materials selected from the group consisting of a foam, a fibre, a filament, a film, a nano fibre, a nano sphere, a nano particle, a liquid crystal mesogen, a tissue scaffold, a colloid, a copolymer, a block copolymer, and combinations thereof,
   wherein the composition comprises, relative to the amount of the isolated recombinant polypeptide, less than 5% contaminants that naturally occur together with the isolated recombinant polypeptide.

2. The composition of claim 1, wherein the recombinant polypeptide is soluble in water and/or under mildly acidic conditions.

3. The composition of claim 1, wherein the recombinant polypeptide comprises at least one domain 1 comprising or consisting of an amino acid sequence selected from the group consisting of HH, TT, SS, AV, TTH, THH, IAAL (SEQ ID NO: 111), SY, VTHHAP (SEQ ID NO: 112), VVLLAAF (SEQ ID NO: 113), HTTHHA (SEQ ID NO: 114), AATVSHTTHHA (SEQ ID NO: 115), FPY, THT, HVT, HHP, VSH and TVS.

4. The composition of claim 1, wherein the recombinant polypeptide comprises at least one glycine rich domain 2 comprising
   (1) an amino acid sequence selected from the group consisting of GGLYG (SEQ ID NO: 116), GGYG (SEQ ID NO: 117), GLYGG (SEQ ID NO: 118), YGIG (SEQ ID NO: 119), GIG and GYG;
   (2) at least one sub-domain 3 comprising the amino acid sequence GGX1X2X3Y (SEQ ID NO: 1)
   wherein $X_1$ is nothing, L, F or V;
   wherein $X_2$ is nothing, G, or F; and
   wherein $X_3$ is nothing, G or A;
   (3) at least one sub-domain 4 comprising the amino acid sequence GGY; or
   (4) a combination of (2) and (3).

5. The composition of claim 4, wherein $X_1$ of sub-domain 3 is L.

6. The composition of claim 4, wherein sub-domain 3 has the amino acid sequence GGLY (SEQ ID NO: 449).

7. The composition of claim 1, wherein the recombinant polypeptide comprises at least one amino acid consensus sequence selected from the sequences set forth in SEQ ID NOS:105, 106, 107, 108, 109 and 110.

8. The composition of claim 4, wherein domain 2 comprises from N to C terminus, (sub-Domain 3-sub-domain 4)$_n$; wherein n is independently 1 to 4.

9. The composition of claim 4 wherein domain 2 comprises from N to C terminus, (sub-Domain 3-sub-Domain 4-sub-Domain 3)$_n$; wherein n is independently 1 to 3 .

10. The composition of claim 1, wherein a peptide unit comprises from N- to C-terminus:
    Proline-Domain 1-Domain 2;
    Proline-Domain 1-Proline-Domain 2; or
    Domain 1-Proline-Domain 2,
    wherein domain 1 comprises or consists of an amino acid sequence selected from the group consisting of HH, TT, SS, AV, TTH, THH, IAAL (SEQ ID NO: 111), SY, VTHHAP (SEQ ID NO: 112), VVLLAAF (SEQ ID NO: 113), HTTHHA (SEQ ID NO: 114), AATVSHTTHHA (SEQ ID NO: 115), FPY, THT, HVT, HHP, VSH and TVS, and
    wherein domain 2 comprises
    (1) an amino acid sequence selected from the group consisting of GGLYG (SEQ ID NO: 116), GGYG (SEQ ID NO: 117), GLYGG (SEQ ID NO: 118), YGIG (SEQ ID NO: 119), GIG and GYG;
    (2) at least one sub-domain 3 comprising the amino acid sequence GGX1X2X3Y (SEQ ID NO: 1)
    wherein $X_1$ is nothing, L, F or V;
    wherein $X_2$ is nothing, G, or F; and
    wherein $X_3$ is nothing, G or A;
    (3) at least one sub-domain 4 comprising the amino acid sequence GGY; or
    (4) a combination of any two or more of (1), (2) and (3);
    is repeated from 2 to 13 times.

11. An isolated nucleic acid molecule comprising a nucleic acid sequence encoding the recombinant polypeptide of claim 1.

12. The nucleic acid molecule of claim 11, wherein the nucleic acid sequence is comprised in an expression construct or a vector.

13. An isolated host cell comprising an expression construct that comprises a nucleic acid sequence encoding the recombinant polypeptide of claim 1, wherein the cell is capable of expressing the recombinant polypeptide.

14. The composition of claim 1, wherein the one or more materials is selected from the group consisting of: a nano sphere, a nano particle, a liquid crystal mesogen, a tissue scaffold, a colloid, a copolymer, and a block copolymer.

15. The composition of claim 1, further comprising plastic, resin or a mixture thereof.

16. The composition of claim 1, wherein the composition has an elastic modulus ranges from 5 MPa to 9 GPa.

17. The composition of claim 1, further comprising adhesive properties.

18. A method of making the composition comprising the recombinant polypeptide and material of claim 1, comprising the steps of:
    crushing the recombinant polypeptide;
    heating the crushed recombinant polypeptide into a liquid comprising the material; and
    forming the composition comprising the recombinant polypeptide and material from the liquid.

19. The method of claim 18, wherein the crushed recombinant polypeptide is mixed with plastic, resin or a mixture of both plastic and resin prior to heating the crushed recombinant polypeptide at temperatures up to 280° C.

20. The method of claim 18, wherein forming the composition comprising the recombinant polypeptide and material comprises spinning the liquid into a fibre.

21. The method of claim 18, wherein forming the composition comprising the recombinant polypeptide and material comprises placing the liquid into a mold; and removing the mold after the liquid solidifies.

22. A tissue scaffold comprising the composition of claim 1.

23. The tissue scaffold of claim 22, wherein the recombinant polypeptide is formed into an adhesion substrate for cell or tissue growth.

24. The composition of claim 1, further comprising a multimer of the recombinant polypeptides.

* * * * *

SEQUENCE LISTING

```
<160> NUMBER OF SEQ ID NOS: 611

<210> SEQ ID NO 1
<211> LENGTH: 6
<212> TYPE: PRT
<213> ORGANISM: Artificial Sequence
<220> FEATURE:
<223> OTHER INFORMATION: Domain 2
<220> FEATURE:
<221> NAME/KEY: NON_CONS
<222> LOCATION: (3)..(3)
<223> OTHER INFORMATION: X1 is L, F or V
<220> FEATURE:
<221> NAME/KEY: NON_CONS
<222> LOCATION: (4)..(4)
<223> OTHER INFORMATION: X2 is nothing, G, or F
<220> FEATURE:
<221> NAME/KEY: NON_CONS
<222> LOCATION: (5)..(5)
<223> OTHER INFORMATION: X3 is nothing, G or A

<400> SEQUENCE: 1

Gly Gly Xaa Xaa Xaa Tyr
1               5

<210> SEQ ID NO 2
<211> LENGTH: 418
<212> TYPE: PRT
<213> ORGANISM: Dosidicus gigas

<400> SEQUENCE: 2

Met Ala Ala Ile Phe Thr Leu Leu Ala Val Leu Ala Ile Ser Asn Tyr
1               5                  10                  15

Ala Ser Ala Ile Leu Pro Ala Ala Thr Ser Val Ser Arg Thr Thr His
            20                  25                  30

Arg Thr Gly Tyr Gly Tyr Gly Gly Leu Leu Gly Gly Tyr Gly Leu His
        35                  40                  45

Tyr Pro Ala Thr Thr Ala Val Ser His Thr Thr His His Ala Pro Ala
    50                  55                  60

Ala Leu Gly Val Tyr Gly Gly Tyr Gly Leu Gly Ala Tyr Gly Phe Gly
65                  70                  75                  80

Tyr Pro Gly Ala Ala Thr Val Ser His Thr Thr His His Ala Pro Tyr
                85                  90                  95

Gly Tyr Gly Gly Leu Tyr Gly Gly Tyr Gly Leu Ala His Gly Gly Leu
            100                 105                 110

Tyr Gly Gly Tyr Gly Leu Gly Ala Tyr Gly Tyr Gly Tyr Pro Ala Ala
            115                 120                 125

Thr Ala Val Ser His Thr Thr His His Ala Pro Tyr Gly Tyr Gly Leu
        130                 135                 140

Gly Gly Tyr Gly Gly Leu Tyr Gly Gly Tyr Gly Leu Ala His Gly Gly
```

```
                145                 150                 155                 160
Leu Tyr Gly Gly Tyr Gly Leu Gly Gly Tyr Gly Leu His Tyr Pro Ala
                    165                 170                 175
Ala Thr Ala Val Ser His Thr Thr His His Ala Pro Leu Gly Tyr Gly
                180                 185                 190
Leu Ala Gly Tyr Gly Gly Leu Tyr Gly Gly Leu Tyr Gly Gly Tyr Gly
                195                 200                 205
Leu Gly Gly Tyr Gly Ala Ala Val Ser His Thr Thr His His Ala
            210                 215                 220
Pro Leu Gly Tyr Gly Leu Gly Gly Tyr Gly Gly Leu Tyr Gly Gly Leu
225                 230                 235                 240
Tyr Gly Gly Tyr Gly Leu Gly Gly Tyr Gly Leu His Tyr Pro Ala Ala
                245                 250                 255
Thr Ala Val Ser His Thr Thr His His Ala Pro Leu Gly Tyr Gly Leu
                260                 265                 270
Gly Gly Tyr Gly Gly Leu Tyr Gly Gly Leu Tyr Gly Gly Tyr Gly Leu
            275                 280                 285
Gly Gly Tyr Gly Ala Ala Val Ser His Thr Thr His His Ala Pro Leu
        290                 295                 300
Gly Phe Gly Gly Leu Tyr Gly Gly Tyr Gly Val Gly Gly Tyr Gly Tyr
305                 310                 315                 320
Gly Tyr Pro Ala Ala Ala Thr Val Ser His Thr Thr His His Ala Pro
                325                 330                 335
Tyr Gly Tyr Gly Gly Leu Tyr Gly Gly Tyr Gly Leu Ala His Gly Gly
                340                 345                 350
Leu Tyr Gly Gly Tyr Gly Phe Gly Ala Val Ser His Thr Thr His His
            355                 360                 365
Ala Pro Leu Gly Phe Gly Gly Leu Tyr Gly Gly Tyr Gly Leu Ala His
        370                 375                 380
Gly Gly Leu Tyr Gly Gly Tyr Gly Leu Gly Ala Val Ser His Thr Thr
385                 390                 395                 400
His His Ala Pro Tyr Gly Phe Gly Gly Leu Tyr Gly Gly Tyr Gly Leu
                405                 410                 415
Leu His

<210> SEQ ID NO 3
<211> LENGTH: 254
<212> TYPE: PRT
<213> ORGANISM: Dosidicus gigas

<400> SEQUENCE: 3

Met Thr Thr Met Phe Ser Ala Leu Val Ser Leu Ala Val Val Leu Gly
1               5                   10                  15
Val Leu Ser Tyr Thr Ser Ala Tyr His Ala Asn His Val Gly Thr Leu
                20                  25                  30
Trp Ala Lys Pro Pro Gln Gln Thr Pro Tyr Gly Gly Tyr Gly Val Ser
            35                  40                  45
Gly Gly Ala Gly Gln Gly Gly Tyr Gly Leu Gly Gly Tyr Gly Gly Tyr
        50                  55                  60
Gly Ser Tyr Gly Gly Leu Gly Gly Tyr Gly Tyr Gly Gly Leu Gly
65                  70                  75                  80
Gly Tyr Gly Gly Tyr Gly Gly Leu Gly Gly Tyr Gly Gly Tyr Gly Gly
                85                  90                  95
Tyr Gly Gln Gly Gly Tyr Ser Thr Gly Gly His Gly His Gly Gly Tyr
```

```
              100                 105                 110
Gly Phe Gly Gly Tyr Gly Gln Gly Tyr Gly Phe Gly Gly Tyr Gly
            115                 120                 125
Gln Gly Gly Tyr Gly Gln Gly Gly Tyr Gly Gln Gly Gly Ser Gly Tyr
        130                 135                 140
Gly Gly Tyr Gly His Tyr Tyr Pro Thr Thr Ser Tyr Gly Gly Tyr Leu
145                 150                 155                 160
Gly Gly Tyr Gly Gly Tyr Gly Gly Tyr Tyr Pro His Thr Ser Ser Gly
                165                 170                 175
Ser Tyr Tyr Pro Thr Thr Tyr Gly Gly Ser Asn Gln Gly Asn Pro Gly
            180                 185                 190
Ala Pro Ile Ser Ser Ser Ser Gly Phe Val Phe Pro Gly Tyr His Phe
            195                 200                 205
Pro Gly Val Phe His Gly Gly Val Asn Gln Gly Ala Gly Arg Thr Ser
            210                 215                 220
Gly Thr Asp Leu Gln Arg Leu Leu Asn Leu Asn Gly Phe Lys Pro Thr
225                 230                 235                 240
Ala Thr Ser Thr Thr Ser Thr Ser Asn Ser Asn Ser Lys Lys
                245                 250

<210> SEQ ID NO 4
<211> LENGTH: 249
<212> TYPE: PRT
<213> ORGANISM: Dosidicus gigas

<400> SEQUENCE: 4

Met Thr Thr Cys Phe Ala Trp Tyr Pro Ser Arg Val Leu Val Cys Ser
1               5                   10                  15
Val His Ile Ser Tyr His Ala Ile Met Ser Val Leu Cys Gly Lys Thr
                20                  25                  30
Pro Pro Thr Thr Pro Tyr Gly Gly Tyr Gly Val Ser Gly Gly Ala Gly
            35                  40                  45
Gln Gly Gly Tyr Gly Leu Gly Gly Tyr Gly Gly Tyr Gly Ser Tyr Gly
        50                  55                  60
Gly Leu Gly Gly Tyr Gly Gly Tyr Gly Gly Leu Gly Gly Tyr Gly Gly
65                  70                  75                  80
Tyr Gly Gly Leu Gly Gly Tyr Gly Gly Tyr Gly Gly Tyr Gly Gln Gly
                85                  90                  95
Gly Tyr Ser Thr Gly Gly His Gly His Gly Gly Tyr Gly Phe Gly Gly
            100                 105                 110
Tyr Gly Gln Gly Gly Tyr Gly Phe Gly Gly Tyr Gly Gln Gly Gly Tyr
            115                 120                 125
Gly Gln Gly Gly Tyr Gly Gln Gly Gly Ser Gly Tyr Gly Gly Tyr Gly
            130                 135                 140
His Tyr Tyr Pro Thr Thr Ser Tyr Gly Gly Tyr Leu Gly Gly Tyr Gly
145                 150                 155                 160
Gly Tyr Gly Gly Tyr Tyr Pro His Thr Ser Gly Ser Tyr Tyr Pro
                165                 170                 175
Thr Thr Tyr Gly Gly Ser Asn Gln Gly Asn Pro Gly Ala Pro Ile Ser
            180                 185                 190
Ser Ser Ser Gly Phe Val Phe Pro Gly Tyr His Phe Pro Gly Val Phe
            195                 200                 205
His Gly Gly Val Asn Gln Gly Ala Gly Arg Thr Gly Thr Asp Leu Gln
            210                 215                 220
```

Arg Leu Leu Asn Leu Asn Gly Phe Lys Pro Thr Ala Thr Ser Thr Thr
225                 230                 235                 240

Leu Thr Ser Asn Ser Asn Ser Lys Lys
                245

<210> SEQ ID NO 5
<211> LENGTH: 254
<212> TYPE: PRT
<213> ORGANISM: Dosidicus gigas

<400> SEQUENCE: 5

Met Thr Thr Met Phe Ser Ala Leu Val Ser Leu Ala Val Val Leu Gly
1               5                   10                  15

Val Leu Ser Ser Thr Ser Ala Tyr His Ala Asn His Val Gly Thr Leu
                20                  25                  30

Trp Ala Lys Pro Pro Gln Gln Thr Pro Tyr Gly Gly Tyr Gly Val Ser
            35                  40                  45

Gly Gly Ala Gly Gln Gly Gly Tyr Gly Leu Gly Gly Tyr Gly Gly Tyr
50                  55                  60

Gly Ser Tyr Gly Gly Leu Gly Gly Tyr Gly Gly Tyr Gly Gly Leu Gly
65                  70                  75                  80

Gly Tyr Gly Gly Tyr Gly Gly Leu Gly Gly Tyr Gly Gly Tyr Gly Gly
                85                  90                  95

Tyr Gly Gln Gly Gly Tyr Ser Thr Gly Gly His Gly His Gly Gly Tyr
            100                 105                 110

Gly Phe Gly Gly Tyr Gly Gln Gly Gly Tyr Gly Phe Gly Gly Tyr Gly
        115                 120                 125

Gln Gly Gly Tyr Gly Gln Gly Gly Tyr Gly Gln Gly Gly Ser Gly Tyr
130                 135                 140

Gly Gly Tyr Gly His Tyr Tyr Pro Thr Thr Ser Tyr Gly Gly Tyr Leu
145                 150                 155                 160

Gly Gly Tyr Gly Gly Tyr Gly Gly Tyr Tyr Pro His Thr Ser Ser Gly
                165                 170                 175

Ser Tyr Tyr Pro Thr Thr Tyr Gly Gly Ser Asn Gln Gly Asn Pro Gly
            180                 185                 190

Ala Pro Ile Ser Ser Ser Gly Phe Val Phe Pro Gly Tyr His Phe
        195                 200                 205

Pro Gly Val Phe His Gly Gly Val Asn Gln Gly Ala Gly Arg Thr Ser
210                 215                 220

Gly Thr Asp Leu Gln Arg Leu Leu Asn Leu Asn Gly Phe Lys Pro Thr
225                 230                 235                 240

Ala Thr Ser Thr Thr Ser Thr Ser Asn Ser Asn Ser Lys Lys
                245                 250

<210> SEQ ID NO 6
<211> LENGTH: 211
<212> TYPE: PRT
<213> ORGANISM: Dosidicus gigas

<400> SEQUENCE: 6

Met Thr Thr Met Phe Ser Ala Leu Val Ser Leu Ala Val Val Leu Gly
1               5                   10                  15

Val Leu Ser Tyr Thr Ser Ala Tyr His Ala Asn His Val Gly Thr Leu
                20                  25                  30

Trp Ala Lys Pro Pro Gln Gln Thr Pro Tyr Gly Gly Tyr Gly Val Ser
            35                  40                  45

```
Gly Gly Ala Gly Gln Gly Tyr Gly Leu Gly Tyr Gly Gly Tyr
    50              55                  60
Gly Ser Tyr Gly Gly Leu Gly Gly Tyr Gly Tyr Gly Gly Leu Gly
65              70                  75                  80
Gly Tyr Gly Gly Tyr Gly Gly Leu Gly Gly Tyr Gly Tyr Gly Gly
                85                  90                  95
Tyr Gly Gln Gly Gly Tyr Ser Thr Gly Gly Tyr Gly Phe Gly Gly Tyr
            100                 105                 110
Gly Gln Gly Gly Tyr Gly Gln Gly Tyr Gly Gln Gly Ser Gly
            115                 120                 125
Tyr Gly Gly Tyr Gly His Tyr Tyr Pro Thr Thr Ser Tyr Gly Gly Tyr
130                 135                 140
Leu Gly Gly Tyr Gly Gly Tyr Gly Gly Tyr Tyr Pro His Thr Ser Ser
145                 150                 155                 160
Gly Ser Tyr Tyr Pro Thr Thr Tyr Gly Ser Asn Gln Gly Asn Pro
                165                 170                 175
Gly Ala Pro Ile Ser Ser Ser Gly Phe Val Phe Pro Gly Ile Phe
            180                 185                 190
Ala Asn Gln Asn Ser Arg Ser Leu Phe Cys Lys His Tyr Glu Ile Lys
            195                 200                 205
Met Val Asn
    210

<210> SEQ ID NO 7
<211> LENGTH: 246
<212> TYPE: PRT
<213> ORGANISM: Dosidicus gigas

<400> SEQUENCE: 7

Met Ala His Ile Ser Leu Thr Ala Val Cys Leu Ser Thr Met His Cys
1               5                   10                  15
Cys Ile Ala Val Pro His Leu Leu Ala Tyr His Ser Ser Cys Ser Ala
            20                  25                  30
Ala Leu Gly Val Tyr Gly Gly Tyr Gly Leu Gly Ala Tyr Gly Phe Gly
            35                  40                  45
Tyr Pro Gly Ala Thr Val Ser His Thr Thr His His Ala Pro Tyr Gly
    50                  55                  60
Phe Gly Gly Leu Tyr Gly Gly Tyr Gly Gly Leu Leu His Gly Gly Leu
65              70                  75                  80
Tyr Gly Gly Tyr Gly Leu Gly Ala Tyr Gly Phe Gly Tyr Pro Ala Ala
                85                  90                  95
Thr Val Ser His Thr Thr His His Ala Pro Tyr Gly Tyr Gly Gly Leu
            100                 105                 110
Tyr Gly Gly Tyr Gly Gly Leu Leu His Gly Gly Leu Tyr Gly Gly Tyr
            115                 120                 125
Gly Leu Gly Ala Tyr Gly Phe Gly Tyr Pro Ala Ala Thr Val Ser Gln
130                 135                 140
Thr Thr His His Ala Pro Tyr Gly Tyr Gly Gly Val Tyr Gly Gly Tyr
145                 150                 155                 160
Gly Leu Leu His Gly Gly Leu Tyr Gly Gly Tyr Gly Leu Gly Gly Tyr
                165                 170                 175
Gly Leu Gly Tyr Pro Ala Ala Thr Ala Val Ser His Thr Thr His His
            180                 185                 190
Ala Pro Leu Gly Tyr Gly Gly Leu Tyr Gly Gly Tyr Gly Gly Leu Leu
            195                 200                 205
```

His Gly Gly Leu Tyr Gly Gly Tyr Gly Ala Thr Ala Val Ser His Thr
    210                 215                 220

Thr His His Ala Pro Leu Gly Tyr Gly Leu Ala Gly Tyr Gly Gly Leu
225                 230                 235                 240

Tyr Gly Gly Phe Leu His
                245

<210> SEQ ID NO 8
<211> LENGTH: 397
<212> TYPE: PRT
<213> ORGANISM: Dosidicus gigas

<400> SEQUENCE: 8

Met Ala Ala Ser Ile Leu Thr Leu Leu Ala Val Ile Ala Leu Ser Ser
1               5                   10                  15

Cys Thr Leu Ala Val Val Pro Ala Ala Thr Thr Val Ser Arg Thr Thr
            20                  25                  30

His His Ala Pro Tyr Gly Tyr Gly Val Leu Gly Gly Tyr Gly Gly
        35                  40                  45

Leu Tyr Gly Gly Tyr Gly Leu Gly Gly Tyr Gly Leu Gly Gly Tyr Gly
    50                  55                  60

Leu Ala Gly Tyr Gly Gly Leu His Gly Gly Leu Tyr Gly Gly Tyr Gly
65                  70                  75                  80

Leu Gly Ala Tyr Gly Phe Gly Tyr Pro Ala Ala Thr Val Ser His Thr
                85                  90                  95

Thr His His Ala Pro Tyr Gly Phe Gly Gly Leu Tyr Gly Gly His Gly
            100                 105                 110

Leu Leu His Gly Gly Leu Tyr Gly Gly Tyr Gly Leu His His Gly Gly
        115                 120                 125

Leu Tyr Gly Gly Tyr Gly Leu Gly Ala Tyr Gly Phe Gly Tyr Pro Val
    130                 135                 140

Ala Thr Ala Val Ser His Val Thr His His Ala Pro Tyr Gly Tyr Gly
145                 150                 155                 160

Leu Ala Gly Tyr Gly Gly Phe His Gly Gly Tyr Gly Leu Leu His Gly
                165                 170                 175

Gly Leu Tyr Gly Gly Tyr Gly Leu His His Gly Gly Leu Tyr Gly Gly
            180                 185                 190

Tyr Gly Leu Gly Ala Tyr Gly Phe Gly Tyr Pro Ala Ala Thr Val Ser
        195                 200                 205

His Thr Thr His His Ala Pro Tyr Gly Phe Gly Gly Leu Tyr Gly Gly
    210                 215                 220

His Gly Leu Leu His Gly Gly Leu Tyr Gly Gly Tyr Gly Leu His His
225                 230                 235                 240

Gly Gly Leu Tyr Gly Gly Tyr Gly Leu Gly Ala Tyr Gly Phe Gly Tyr
                245                 250                 255

Pro Ala Ala Thr Val Ser His Thr Thr His His Ala Pro Tyr Gly Phe
            260                 265                 270

Gly Gly Leu Tyr Gly Gly Tyr Gly Leu His Gly Gly Leu Tyr Gly
        275                 280                 285

Gly Tyr Gly Leu Leu His Gly Gly Leu Tyr Gly Gly Tyr Gly Leu His
    290                 295                 300

His Gly Gly Leu Tyr Gly Gly Tyr Gly Leu Gly Ala Tyr Gly Phe Gly
305                 310                 315                 320

Tyr Pro Gly Ala Ala Thr Val Ser His Thr Thr His His Ala Pro Tyr

```
                    325                 330                 335
Gly Phe Gly Gly Leu Tyr Gly Tyr Gly Leu His His Gly Gly Leu
                340                 345                 350
Tyr Gly Gly Tyr Gly Leu Leu His Gly Gly Leu Tyr Gly Gly Tyr Gly
                355                 360                 365
Leu Gly Ala Val Ser His Thr His His Ala Pro Tyr Gly Tyr Gly
370                 375                 380
Leu Gly Gly Tyr Gly Gly Leu Tyr Gly Gly Trp Leu His
385                 390                 395

<210> SEQ ID NO 9
<211> LENGTH: 321
<212> TYPE: PRT
<213> ORGANISM: Dosidicus gigas

<400> SEQUENCE: 9

Met Ala Ala Ser Ile Leu Thr Leu Leu Ala Val Ile Ala Leu Ser Ser
1               5                   10                  15
Cys Thr Leu Ala Val Val Pro Ala Ala Thr Thr Val Ser Arg Thr Thr
                20                  25                  30
His His Ala Pro Tyr Gly Tyr Gly Gly Val Leu Gly Tyr Gly Gly
            35                  40                  45
Leu Tyr Gly Gly Tyr Gly Leu Gly Gly Tyr Gly Leu Gly Gly Tyr Gly
        50                  55                  60
Leu Ala Gly Tyr Gly Gly Leu His Gly Gly Leu Tyr Gly Gly Tyr Gly
65                  70                  75                  80
Leu Gly Ala Tyr Gly Phe Gly Tyr Pro Ala Ala Thr Val Ser His Thr
                85                  90                  95
Thr His His Ala Pro Tyr Gly Phe Gly Gly Leu Tyr Gly Gly His Gly
            100                 105                 110
Leu Leu His Gly Gly Leu Tyr Gly Gly Tyr Gly Leu His His Gly Gly
        115                 120                 125
Leu Tyr Gly Gly Tyr Gly Leu Gly Ala Tyr Gly Phe Gly Tyr Pro Val
    130                 135                 140
Ala Thr Ala Val Ser His Val Thr His His Ala Pro Tyr Gly Tyr Gly
145                 150                 155                 160
Leu Ala Gly Tyr Gly Gly Phe His Gly Gly Tyr Gly Leu Leu His Gly
                165                 170                 175
Gly Leu Tyr Gly Gly Tyr Gly Leu His His Gly Gly Leu Tyr Gly Gly
            180                 185                 190
Tyr Gly Leu Gly Ala Tyr Gly Phe Gly Tyr Pro Ala Ala Thr Val Ser
        195                 200                 205
His Thr Thr His His Ala Pro Tyr Gly Phe Gly Gly Leu Tyr Gly Gly
    210                 215                 220
His Gly Leu Leu His Gly Gly Leu Tyr Gly Gly Tyr Gly Leu His His
225                 230                 235                 240
Gly Gly Leu Tyr Gly Gly Tyr Gly Leu Gly Ala Tyr Gly Phe Gly Tyr
                245                 250                 255
Pro Ala Ala Thr Val Ser His Thr Thr His His Ala Pro Tyr Gly Phe
            260                 265                 270
Gly Gly Leu Tyr Gly Gly Tyr Gly Leu His His Gly Gly Leu Tyr Gly
        275                 280                 285
Arg Asp Thr Gly Ser Ser Ala Arg Arg Ser Ser Met Gly Arg Asp Met
    290                 295                 300
```

```
Gly Leu Leu His Gly Trp Ser Phe Met Glu Tyr Gly Leu Gly Arg
305                 310                 315                 320

Cys

<210> SEQ ID NO 10
<211> LENGTH: 225
<212> TYPE: PRT
<213> ORGANISM: Dosidicus gigas

<400> SEQUENCE: 10

Met Ala Ala Ile Phe Thr Leu Leu Ala Val Leu Ala Ile Ser Asn Tyr
1               5                   10                  15

Ala Ser Ala Ile Leu Pro Ala Ala Thr Ser Val Ser Arg Thr Thr His
            20                  25                  30

Arg Thr Gly Tyr Gly Tyr Gly Gly Leu Leu Gly Gly Tyr Gly Leu His
        35                  40                  45

Tyr Pro Ala Thr Thr Ala Val Ser His Thr Thr His His Ala Pro Ala
50                  55                  60

Ala Leu Gly Val Tyr Gly Gly Tyr Gly Leu Gly Ala Tyr Gly Phe Gly
65                  70                  75                  80

Tyr Pro Gly Ala Ala Thr Val Ser His Thr Thr His His Ala Pro Tyr
                85                  90                  95

Gly Tyr Gly Gly Leu Tyr Gly Gly Tyr Gly Leu Ala His Gly Gly Leu
            100                 105                 110

Tyr Gly Gly Tyr Gly Leu Gly Ala Tyr Gly Tyr Gly Tyr Pro Ala Ala
        115                 120                 125

Thr Ala Val Ser His Thr Thr His His Ala Pro Tyr Gly Tyr Gly Leu
130                 135                 140

Gly Gly Tyr Gly Gly Leu Tyr Gly Gly Tyr Gly Leu Ala His Gly Gly
145                 150                 155                 160

Leu Tyr Gly Gly Tyr Gly Leu Gly Gly Tyr Gly Leu His Tyr Pro Ala
                165                 170                 175

Ala Thr Ala Val Ser His Thr Thr His His Ala Pro Leu Gly Tyr Gly
            180                 185                 190

Leu Ala Gly Tyr Gly Gly Leu Tyr Gly Gly Leu Tyr Gly Gly Tyr Gly
        195                 200                 205

Leu Val Asp Met Val Pro Gln Leu Ser Ala Thr Pro Pro Ile Met Leu
    210                 215                 220

His
225

<210> SEQ ID NO 11
<211> LENGTH: 251
<212> TYPE: PRT
<213> ORGANISM: Dosidicus gigas

<400> SEQUENCE: 11

Met Ala Ser Thr Ile Phe Ser Leu Leu Ala Val Ile Ala Leu Ser Asn
1               5                   10                  15

Tyr Ala Thr Ala Val Leu Pro Val Ala Thr Ser Val Ser Arg Thr Thr
            20                  25                  30

His His Ala Pro Ala Ala Leu Gly Val Tyr Gly Gly Tyr Gly Leu Gly
        35                  40                  45

Ala Tyr Gly Phe Gly Tyr Pro Gly Ala Thr Val Ser His Thr Thr His
    50                  55                  60

His Ala Pro Tyr Gly Phe Gly Gly Leu Tyr Gly Gly Tyr Gly Gly Leu
```

```
                65                  70                  75                  80
Leu His Gly Gly Leu Tyr Gly Gly Tyr Gly Leu Gly Ala Tyr Gly Phe
                    85                  90                  95
Gly Tyr Pro Ala Ala Thr Val Ser His Thr His His Ala Pro Tyr
            100                 105                 110
Gly Tyr Gly Gly Leu Tyr Gly Gly Tyr Gly Gly Leu Leu His Gly Gly
                115                 120                 125
Leu Tyr Gly Gly Tyr Gly Leu Gly Ala Tyr Gly Phe Gly Tyr Pro Ala
            130                 135                 140
Ala Thr Val Ser Gln Thr Thr His His Ala Pro Tyr Gly Tyr Gly Gly
145                 150                 155                 160
Val Tyr Gly Gly Tyr Gly Leu Leu His Gly Gly Leu Tyr Gly Gly Tyr
                165                 170                 175
Gly Leu Gly Gly Tyr Gly Leu Gly Tyr Pro Ala Ala Thr Ala Val Ser
                180                 185                 190
His Thr Thr His His Ala Pro Leu Gly Tyr Gly Gly Leu Tyr Gly Gly
                195                 200                 205
Tyr Gly Gly Leu Leu His Gly Gly Leu Tyr Gly Gly Tyr Gly Ala Thr
            210                 215                 220
Ala Val Ser His Thr Thr His His Ala Pro Leu Gly Tyr Gly Leu Ala
225                 230                 235                 240
Gly Tyr Gly Gly Leu Tyr Gly Gly Phe Leu His
                245                 250

<210> SEQ ID NO 12
<211> LENGTH: 260
<212> TYPE: PRT
<213> ORGANISM: Dosidicus gigas

<400> SEQUENCE: 12

Met Ala Ser Thr Ile Phe Thr Leu Leu Ala Val Ile Ala Leu Ser Ser
1               5                   10                  15
Tyr Ala Ala Ala Ile Leu Pro Ala Thr Thr Ser Val Ser Arg Thr Thr
                20                  25                  30
His His Ala Pro Val Tyr Gly Gly Tyr Gly Leu Leu His Gly Gly Leu
            35                  40                  45
Tyr Gly Gly Tyr Gly Leu Gly Ala Ala Thr Val Ser His Thr Thr His
        50                  55                  60
His Ala Pro Tyr Gly Tyr Gly Gly Leu Tyr Gly Gly Tyr Gly Leu Ala
65                  70                  75                  80
His Gly Gly Leu Tyr Gly Gly Tyr Gly Leu Gly Ala Tyr Gly Leu Gly
                85                  90                  95
Tyr Pro Ala Ala Ala Val Ser His Thr Thr His His Ala Pro Leu
            100                 105                 110
Gly Phe Gly Gly Leu Tyr Gly Gly Tyr Gly Leu Gly Ala Val Ser His
                115                 120                 125
Thr Thr His His Ala Pro Leu Gly Phe Gly Gly Val Leu Gly Gly Tyr
            130                 135                 140
Gly Leu Gly Ala Val Ser His Thr Thr His Ala Pro Leu Gly Phe
145                 150                 155                 160
Gly Gly Leu Tyr Gly Gly Tyr Gly Leu Gly Ala Val Ser His Thr Thr
                165                 170                 175
His His Ala Pro Leu Gly Phe Gly Gly Val Val Gly Gly Tyr Gly Leu
            180                 185                 190
```

```
Gly Ala Val Ser His Thr Thr His Ala Pro Leu Gly Phe Gly Gly
            195                 200                 205

Leu Tyr Gly Gly Tyr Gly Leu Gly Ala Val Ser His Thr Thr His His
    210                 215                 220

Ala Pro Leu Gly Phe Gly Gly Leu Tyr Gly Gly Tyr Gly Ala Val Ser
225                 230                 235                 240

His Thr Thr His His Ala Pro Leu Gly Tyr Gly Leu Ala Gly Tyr Gly
                245                 250                 255

Ala Trp Leu His
            260

<210> SEQ ID NO 13
<211> LENGTH: 529
<212> TYPE: PRT
<213> ORGANISM: Dosidicus gigas

<400> SEQUENCE: 13

Met Ala Thr Thr Ile Phe Ala Ile Leu Ala Val Ile Ala Leu Ser Asn
1               5                   10                  15

Tyr Ala Ser Ala Ile Ala Pro Ala Ala Thr Ser Val Ser Arg Thr Thr
            20                  25                  30

His His Ala Gly Tyr Gly Tyr Gly Gly Pro Leu Gly Gly Tyr Gly Leu
        35                  40                  45

Gly Ala Tyr Gly Phe Gly Ser Pro Ala Ala Thr Val Ser His Thr Thr
    50                  55                  60

His His Ala Pro Tyr Gly Tyr Gly Gly Leu Tyr Gly Gly Tyr Gly Gly
65                  70                  75                  80

Leu Tyr Gly Gly His Gly Leu Leu His Gly Gly Leu Tyr Gly Gly Tyr
                85                  90                  95

Gly His Leu His Gly Gly Leu Tyr Gly Gly Tyr Gly Leu Gly Ala Tyr
            100                 105                 110

Gly Phe Gly Tyr Pro Ala Ala Ala Val Ser His Thr Thr His His
            115                 120                 125

Ala Pro Leu Gly Phe Gly Leu Ala Gly Tyr Gly Gly Leu Tyr Gly Gly
        130                 135                 140

Tyr Gly Leu Gly Gly Tyr Gly Gly Leu His Gly Gly Leu Tyr Gly Gly
145                 150                 155                 160

Tyr Gly Leu Gly Ala Tyr Gly Phe Gly Tyr Pro Ala Ala Thr Ala Val
                165                 170                 175

Ser His Thr Thr His His Ala Pro Tyr Gly Tyr Gly Leu Gly Gly Tyr
            180                 185                 190

Gly Gly Leu Tyr Gly Gly Leu Tyr Gly Gly Tyr Gly Leu Ala Gly Tyr
        195                 200                 205

Gly Gly Val Tyr Gly Gly His Gly Leu Leu His Gly Gly Leu Tyr Gly
    210                 215                 220

Gly Tyr Gly Leu Gly Ala Tyr Gly Phe Gly Tyr Pro Ala Ala Ala Thr
225                 230                 235                 240

Val Ser His Thr Thr His His Ala Pro Tyr Gly Tyr Gly Gly Leu Tyr
                245                 250                 255

Gly Gly Tyr Gly Leu Ala His Gly Gly Leu Tyr Ala His Gly Gly Leu
            260                 265                 270

Tyr Gly Gly Tyr Gly Leu Gly Gly Tyr Gly Leu His Tyr Pro Ala Ala
        275                 280                 285

Thr Ala Val Ser His Thr Thr His His Ala Pro Leu Gly Tyr Gly Leu
    290                 295                 300
```

Ala Gly Tyr Gly Gly Leu Tyr Gly Gly Leu Tyr Gly Tyr Gly Leu
305                 310                 315                 320

Gly Gly Tyr Gly Ala Ala Val Ser His Thr Thr His His Ala Pro
            325                 330                 335

Leu Gly Tyr Gly Leu Gly Gly Tyr Gly Gly Leu Tyr Gly Gly Leu Tyr
            340                 345                 350

Gly Gly Tyr Gly Leu Gly Gly Tyr Gly Leu His Tyr Pro Ala Ala Thr
            355                 360                 365

Ala Val Ser His Thr Thr His His Ala Pro Leu Gly Tyr Gly Leu Gly
    370                 375                 380

Gly Tyr Gly Gly Leu Tyr Gly Gly Leu Tyr Gly Gly Tyr Gly Leu Gly
385                 390                 395                 400

Gly Tyr Gly Ala Ala Val Ser His Thr Thr His His Ala Pro Leu Gly
            405                 410                 415

Phe Gly Gly Leu Tyr Gly Gly Tyr Gly Val Gly Gly Tyr Gly Tyr Gly
            420                 425                 430

Tyr Pro Ala Ala Ala Thr Val Ser His Thr Thr His His Ala Pro Tyr
            435                 440                 445

Gly Tyr Gly Gly Leu Tyr Gly Gly Tyr Gly Leu Ala His Gly Gly Leu
            450                 455                 460

Tyr Gly Gly Tyr Gly Phe Gly Ala Val Ser His Thr Thr His His Ala
465                 470                 475                 480

Pro Leu Gly Phe Gly Gly Leu Tyr Gly Gly Tyr Gly Leu Ala His Gly
            485                 490                 495

Gly Leu Tyr Gly Gly Tyr Gly Leu Gly Ala Val Ser His Thr Thr His
            500                 505                 510

His Ala Pro Tyr Gly Phe Gly Gly Leu Tyr Gly Gly Tyr Gly Leu Leu
            515                 520                 525

His

<210> SEQ ID NO 14
<211> LENGTH: 408
<212> TYPE: PRT
<213> ORGANISM: Dosidicus gigas

<400> SEQUENCE: 14

Met Ala Thr Thr Ile Phe Ala Ile Leu Ala Val Ile Ala Leu Ser Asn
1               5                   10                  15

Tyr Ala Ser Ala Ile Ala Pro Ala Ala Thr Ser Val Ser Arg Thr Thr
                20                  25                  30

His His Ala Gly Tyr Gly Tyr Gly Gly Leu Tyr Gly Gly Tyr Gly Leu
            35                  40                  45

Gly Ala Tyr Gly Phe Gly Tyr Pro Ala Ala Thr Val Ser His Thr Thr
        50                  55                  60

His His Ala Pro Tyr Gly Phe Gly Gly Leu Tyr Gly Gly Tyr Gly Leu
65                  70                  75                  80

His His Gly Gly Leu Tyr Gly Gly Tyr Gly Leu Leu His Gly Gly Leu
                85                  90                  95

Tyr Gly Gly Tyr Gly Leu His Gly Gly Leu Tyr Gly Gly Tyr Gly
                100                 105                 110

Leu Gly Ala Tyr Gly Phe Gly Tyr Pro Gly Ala Ala Thr Val Ser His
        115                 120                 125

Thr Thr His His Ala Pro Tyr Gly Phe Gly Gly Leu Tyr Gly Gly Tyr
    130                 135                 140

-continued

Gly Leu Ala His Gly Gly Leu Tyr Gly Gly Tyr Gly Leu Gly Tyr
145                 150                 155                 160

Gly Leu His Tyr Pro Ala Ala Thr Ala Val Ser His Thr Thr His
                165                 170                 175

Ala Pro Leu Gly Tyr Gly Leu Ala Gly Tyr Gly Gly Leu Tyr Gly
            180                 185                 190

Leu Tyr Gly Gly Tyr Gly Leu Gly Gly Tyr Gly Ala Ala Val Ser
        195                 200                 205

His Thr Thr His His Ala Pro Leu Gly Tyr Gly Leu Gly Gly Tyr Gly
    210                 215                 220

Gly Leu Tyr Gly Gly Leu Tyr Gly Gly Tyr Gly Leu Gly Gly Tyr Gly
225                 230                 235                 240

Leu His Tyr Pro Ala Ala Thr Ala Val Ser His Thr Thr His His Ala
                245                 250                 255

Pro Leu Gly Tyr Gly Leu Gly Gly Tyr Gly Gly Leu Tyr Gly Gly Leu
            260                 265                 270

Tyr Gly Gly Tyr Gly Leu Gly Gly Tyr Gly Ala Ala Val Ser His Thr
        275                 280                 285

Thr His His Ala Pro Leu Gly Phe Gly Gly Leu Tyr Gly Gly Tyr Gly
    290                 295                 300

Val Gly Gly Tyr Gly Tyr Gly Tyr Pro Ala Ala Thr Val Ser His
305                 310                 315                 320

Thr Thr His His Ala Pro Tyr Gly Tyr Gly Gly Leu Tyr Gly Gly Tyr
                325                 330                 335

Gly Leu Ala His Gly Gly Leu Tyr Gly Gly Tyr Gly Phe Gly Ala Val
            340                 345                 350

Ser His Thr Thr His His Ala Pro Leu Gly Phe Gly Gly Leu Tyr Gly
        355                 360                 365

Gly Tyr Gly Leu Ala His Gly Gly Leu Tyr Gly Gly Tyr Gly Leu Gly
    370                 375                 380

Ala Val Ser His Thr Thr His His Ala Pro Tyr Gly Phe Gly Gly Leu
385                 390                 395                 400

Tyr Gly Gly Tyr Gly Leu Leu His
                405

<210> SEQ ID NO 15
<211> LENGTH: 495
<212> TYPE: PRT
<213> ORGANISM: Dosidicus gigas

<400> SEQUENCE: 15

Met Ala Ala Ser Ile Leu Thr Leu Leu Ala Val Ile Ala Leu Ser Ser
1               5                   10                  15

Cys Thr Leu Ala Val Val Pro Ala Ala Thr Thr Val Ser Arg Thr Thr
            20                  25                  30

His His Ala Pro Tyr Gly Tyr Gly Gly Val Leu Gly Gly Tyr Gly Gly
        35                  40                  45

Leu Tyr Gly Gly Tyr Gly Leu Gly Gly Tyr Gly Leu Gly Gly Tyr Gly
    50                  55                  60

Leu Ala Gly Tyr Gly Gly Leu His Gly Gly Leu Tyr Gly Gly Tyr Gly
65                  70                  75                  80

Leu Gly Ala Tyr Gly Phe Gly Tyr Pro Ala Ala Thr Val Ser His Thr
                85                  90                  95

Thr His His Ala Pro Tyr Gly Phe Gly Gly Leu Tyr Gly Gly His Gly 100                 105                 110
Leu Leu His Gly Gly Leu Tyr Gly Gly Tyr Gly Leu His Gly Gly
            115                 120                 125
Leu Tyr Gly Gly Tyr Gly Leu Gly Ala Tyr Gly Phe Gly Tyr Pro Ala
130                 135                 140
Ala Thr Val Ser His Thr Thr His His Ala Pro Tyr Gly Phe Gly Gly
145                 150                 155                 160
Leu Tyr Gly Gly Tyr Gly Leu His His Gly Gly Leu Tyr Gly Gly Tyr
                    165                 170                 175
Gly Leu Leu His Gly Gly Leu Tyr Gly Gly Tyr Gly Leu His His Gly
                180                 185                 190
Gly Leu Tyr Gly Gly Tyr Gly Leu Gly Ala Tyr Gly Phe Gly Tyr Pro
            195                 200                 205
Ala Ala Ala Thr Val Ser His Thr Thr His His Ala Pro Tyr Gly Tyr
            210                 215                 220
Gly Gly Leu Tyr Gly Gly Tyr Gly Leu Ala His Gly Gly Leu Tyr Gly
225                 230                 235                 240
Gly Tyr Gly Leu Gly Gly Tyr Gly Leu His Tyr Pro Ala Ala Thr Ala
                245                 250                 255
Val Ser His Thr Thr His His Ala Pro Leu Gly Tyr Gly Leu Ala Gly
            260                 265                 270
Tyr Gly Gly Leu Tyr Gly Gly Leu Tyr Gly Gly Tyr Gly Leu Gly Gly
            275                 280                 285
Tyr Gly Ala Ala Ala Val Ser His Thr Thr His His Ala Pro Leu Gly
        290                 295                 300
Tyr Gly Leu Gly Gly Tyr Gly Gly Leu Tyr Gly Gly Leu Tyr Gly Gly
305                 310                 315                 320
Tyr Gly Leu Gly Gly Tyr Gly Leu His Tyr Pro Ala Ala Thr Ala Val
                325                 330                 335
Ser His Thr Thr His His Ala Pro Leu Gly Tyr Gly Leu Gly Gly Tyr
            340                 345                 350
Gly Gly Leu Tyr Gly Gly Leu Tyr Gly Gly Tyr Gly Leu Gly Gly Tyr
            355                 360                 365
Gly Ala Ala Val Ser His Thr Thr His His Ala Pro Leu Gly Phe Gly
        370                 375                 380
Gly Leu Tyr Gly Gly Tyr Gly Val Gly Gly Tyr Gly Tyr Gly Tyr Pro
385                 390                 395                 400
Ala Ala Ala Thr Val Ser His Thr Thr His His Ala Pro Tyr Gly Tyr
            405                 410                 415
Gly Gly Leu Tyr Gly Gly Tyr Gly Leu Ala His Gly Gly Leu Tyr Gly
            420                 425                 430
Gly Tyr Gly Phe Gly Ala Val Ser His Thr Thr His His Ala Pro Leu
        435                 440                 445
Gly Phe Gly Gly Leu Tyr Gly Gly Tyr Gly Leu Ala His Gly Gly Leu
        450                 455                 460
Tyr Gly Gly Tyr Gly Leu Gly Ala Val Ser His Thr Thr His His Ala
465                 470                 475                 480
Pro Tyr Gly Phe Gly Gly Leu Tyr Gly Gly Tyr Gly Leu Leu His
                485                 490                 495

<210> SEQ ID NO 16
<211> LENGTH: 597
<212> TYPE: PRT
<213> ORGANISM: Dosidicus gigas -continued

<400> SEQUENCE: 16

```
Met Ala Ala Ser Ile Leu Thr Leu Leu Ala Val Ile Ala Leu Ser Ser
1               5                   10                  15

Cys Thr Leu Ala Val Val Pro Ala Ala Thr Thr Val Ser Arg Thr Thr
                20                  25                  30

His His Ala Pro Tyr Gly Tyr Gly Gly Leu Leu Gly Gly Tyr Gly Gly
            35                  40                  45

Leu His Gly Gly Tyr Gly Leu Gly Gly Tyr Gly Leu Ala Gly Tyr Gly
        50                  55                  60

Gly Leu His Gly Gly Leu Tyr Gly Gly Tyr Gly Leu Gly Ala Tyr Gly
65                  70                  75                  80

Phe Gly Tyr Pro Ala Ala Thr Val Ser His Thr Thr His His Ala Pro
                85                  90                  95

Tyr Gly Phe Gly Gly Leu Tyr Gly Gly His Gly Leu Leu His Gly Gly
            100                 105                 110

Leu Tyr Gly Gly Tyr Gly Leu His His Gly Gly Leu Tyr Gly Gly Tyr
        115                 120                 125

Gly Leu Gly Ala Tyr Gly Phe Gly Tyr Pro Ala Ala Thr Ala Val Ser
130                 135                 140

His Val Thr His His Ala Pro Tyr Gly Tyr Gly Leu Ala Gly Tyr Gly
145                 150                 155                 160

Gly Leu Tyr Gly Gly Tyr Gly Leu Ala His Gly Gly Leu Tyr Gly Gly
                165                 170                 175

Tyr Gly Leu Ala Gly Tyr Gly Gly Leu Tyr Gly Gly Tyr Gly Leu Gly
            180                 185                 190

Ala Tyr Gly Phe Gly Tyr Pro Ala Ala Thr Ala Val Ser His Thr Thr
        195                 200                 205

His His Ala Pro Tyr Gly Tyr Gly Leu Gly Gly Tyr Gly Gly Leu Tyr
210                 215                 220

Gly Gly Leu Tyr Gly Gly Tyr Gly Leu Ala Gly Tyr Gly Gly Leu Tyr
225                 230                 235                 240

Gly Gly His Gly Leu Leu His Gly Gly Leu Tyr Gly Gly Tyr Gly Leu
                245                 250                 255

Gly Ala Tyr Gly Phe Gly Tyr Pro Ala Ala Ala Thr Val Ser His Thr
            260                 265                 270

Thr His His Ala Pro Tyr Gly Tyr Gly Gly Leu Tyr Gly Gly Tyr Gly
        275                 280                 285

Leu Ala His Gly Gly Leu Tyr Gly Asp Met Asp Leu Ala His Thr Asp
290                 295                 300

Thr Leu Pro Ser Cys Tyr Ser Cys Gln Pro His Thr His Ala Leu
305                 310                 315                 320

Arg Ile Trp Ser Gly Arg Ile Cys Gly Leu Tyr Glu Ile Cys Leu Ala
                325                 330                 335

His Gly Gly Leu Tyr Gly Gly Tyr Gly Leu Gly Gly Tyr Gly Leu His
            340                 345                 350

Tyr Pro Ala Ala Thr Ala Val Ser His Thr Thr His His Ala Pro Leu
        355                 360                 365

Gly Tyr Gly Leu Ala Gly Tyr Gly Gly Leu Tyr Gly Gly Leu Tyr Gly
370                 375                 380

Gly Tyr Gly Leu Gly Gly Tyr Gly Ala Ala Val Ser His Thr Thr
385                 390                 395                 400

His His Ala Pro Leu Gly Tyr Gly Leu Gly Gly Tyr Gly Gly Leu Tyr
```

```
                    405                 410                 415
Gly Gly Leu Tyr Gly Gly Tyr Gly Leu Gly Gly Tyr Gly Leu His Tyr
            420                 425                 430

Pro Ala Ala Thr Ala Val Ser His Thr Thr His His Ala Pro Leu Gly
            435                 440                 445

Tyr Gly Leu Gly Gly Tyr Gly Leu Tyr Gly Gly Leu Tyr Gly Gly
            450                 455                 460

Tyr Gly Leu Gly Gly Tyr Gly Ala Ala Val Ser His Thr Thr His
465                 470                 475                 480

Ala Pro Leu Gly Phe Gly Gly Leu Tyr Gly Gly Tyr Gly Val Gly Gly
                485                 490                 495

Tyr Gly Tyr Gly Tyr Pro Ala Ala Thr Val Ser His Thr Thr His
            500                 505                 510

His Ala Pro Tyr Gly Tyr Gly Gly Leu Tyr Gly Gly Tyr Gly Leu Ala
            515                 520                 525

His Gly Gly Leu Tyr Gly Gly Tyr Gly Phe Gly Ala Val Ser His Thr
            530                 535                 540

Thr His His Ala Pro Leu Gly Phe Gly Gly Leu Tyr Gly Gly Tyr Gly
545                 550                 555                 560

Leu Ala His Gly Gly Leu Tyr Gly Gly Tyr Gly Leu Gly Ala Val Ser
                565                 570                 575

His Thr Thr His His Ala Pro Tyr Gly Phe Gly Gly Leu Tyr Gly Gly
            580                 585                 590

Tyr Gly Leu Leu His
            595

<210> SEQ ID NO 17
<211> LENGTH: 177
<212> TYPE: PRT
<213> ORGANISM: Dosidicus gigas

<400> SEQUENCE: 17

Met Ala Ala Ile Phe Thr Leu Leu Ala Val Leu Ala Ile Ser Asn Tyr
1               5                   10                  15

Ala Ser Ala Ile Leu Pro Ala Ala Thr Ser Val Ser Arg Thr Thr His
            20                  25                  30

Arg Thr Gly Tyr Gly Tyr Gly Gly Leu Leu Gly Gly Tyr Gly Leu His
            35                  40                  45

Tyr Pro Ala Thr Thr Ala Val Ser His Thr Thr His His Ala Pro Ala
50                  55                  60

Ala Leu Gly Val Tyr Gly Gly Tyr Gly Leu Gly Ala Tyr Gly Phe Gly
65                  70                  75                  80

Tyr Pro Gly Ala Ala Thr Val Ser His Thr Thr His His Ala Pro Tyr
                85                  90                  95

Gly Tyr Gly Gly Leu Tyr Gly Gly Tyr Gly Leu Ala His Gly Gly Leu
            100                 105                 110

Tyr Gly Gly Tyr Gly Leu His His Gly Gly Leu Tyr Gly Gly Tyr Gly
            115                 120                 125

Leu Leu His Gly Gly Leu Tyr Gly Gly Tyr Gly Leu His His Gly Gly
130                 135                 140

His Leu Val Pro Leu Ile Gln Met Phe Arg Val Ser Asn Gln Thr Ile
145                 150                 155                 160

Val Asn Ile Leu Trp Lys Ile His Leu Ala Phe Arg Asn Gln Gln Asp
                165                 170                 175
```

Ala

<210> SEQ ID NO 18
<211> LENGTH: 324
<212> TYPE: PRT
<213> ORGANISM: Dosidicus gigas

<400> SEQUENCE: 18

Met Ala Ala Ile Phe Thr Leu Leu Ala Val Leu Ala Ile Ser Asn Tyr
1               5                   10                  15

Ala Ser Ala Ile Leu Pro Ala Ala Thr Ser Val Ser Arg Thr Thr His
            20                  25                  30

Arg Thr Gly Tyr Gly Tyr Gly Gly Leu Leu Gly Gly Tyr Gly Leu His
        35                  40                  45

Tyr Pro Ala Thr Thr Ala Val Ser His Thr Thr His His Ala Pro Ala
    50                  55                  60

Ala Leu Gly Val Tyr Gly Gly Tyr Gly Leu Gly Ala Tyr Gly Phe Gly
65                  70                  75                  80

Tyr Pro Gly Ala Ala Thr Val Ser His Thr Thr His His Ala Pro Tyr
                85                  90                  95

Gly Tyr Gly Gly Leu Tyr Gly Gly Tyr Gly Leu Ala His Gly Gly Leu
            100                 105                 110

Tyr Gly Gly Tyr Gly Leu Gly Ala Tyr Gly Tyr Gly Tyr Pro Ala Ala
        115                 120                 125

Ala Val Ser His Val Thr His His Ala Pro Tyr Gly Tyr Gly Leu Gly
    130                 135                 140

Gly Tyr Gly Gly Leu Tyr Gly Gly Leu Tyr Gly Gly His Gly Leu Leu
145                 150                 155                 160

His Gly Gly Leu Tyr Gly Gly Tyr Gly Leu Gly Ala Tyr Gly Tyr Gly
                165                 170                 175

Tyr Pro Ala Ala Ala Val Ser His Val Thr His His Ala Pro Tyr Gly
            180                 185                 190

Tyr Gly Leu Ala Gly Tyr Gly Gly Leu His Gly Gly Tyr Gly Phe Leu
        195                 200                 205

His Gly Gly Leu Tyr Gly Gly His Gly Leu Leu His Gly Gly Leu Tyr
    210                 215                 220

Gly Gly Tyr Gly Leu Gly Ala Tyr Gly Tyr Gly Tyr Pro Ala Ala Thr
225                 230                 235                 240

Val Ser His Pro Thr His His Ala Pro Tyr Gly Tyr Gly Gly Leu Tyr
                245                 250                 255

Gly Gly Tyr Gly His Pro Gly Tyr Gly Gly Leu Tyr Gly Gly Tyr Gly
            260                 265                 270

Phe Ala His Gly Gly Leu Tyr Gly Gly Tyr Gly Phe Phe His Gly Gly
        275                 280                 285

Leu Tyr Gly Gly Tyr Gly Phe Pro His Gly Gly Leu Tyr Gly Gly Tyr
    290                 295                 300

Gly Leu Gly Gly Tyr Gly Leu Gly Gly Tyr Gly Leu Gly Gly Tyr Gly
305                 310                 315                 320

Gly Trp Phe His

<210> SEQ ID NO 19
<211> LENGTH: 128
<212> TYPE: PRT
<213> ORGANISM: Dosidicus gigas

<400> SEQUENCE: 19

```
Met Ala Val Lys Ile Ile Leu Leu Ala Val Met Ala Leu Ser Asn
1               5                   10                  15

Tyr Ala Tyr Gly His Phe Thr Gly Gly Val Gly Gly Tyr Gly Tyr Gly
            20                  25                  30

Ala Gly Ala Gly Tyr Gly Ala Gly Tyr Gly Gly Leu Gly Gly
            35                  40                  45

Gly Val Gly Ser Tyr Gly Gly Val Ser Gly Gly Tyr Gly Gly Tyr Gly
50                  55                  60

Gly Tyr Gly Gly Tyr Gly Gly Tyr Gly Gly Tyr Gly Gly His Gly Gly
65                  70                  75                  80

Tyr Gly Gly Tyr Gly Gly Tyr Gly Gly Tyr Ala Gly His Gly Gly Tyr
                85                  90                  95

Gly Gly Leu Gly Gly Tyr Gly Gly His Gly Gly Tyr Gly Gly Tyr Gly
            100                 105                 110

Ser Gly Gly His His Gly Pro Tyr Gly Gly Tyr Gly Gly Tyr Leu Gly
        115                 120                 125
```

<210> SEQ ID NO 20
<211> LENGTH: 121
<212> TYPE: PRT
<213> ORGANISM: Dosidicus gigas

<400> SEQUENCE: 20

```
Met Ala Val Lys Ile Ile Leu Leu Ala Val Met Ala Leu Ser Asn
1               5                   10                  15

Tyr Ala Tyr Gly His Leu Thr Gly Gly Val Gly Gly Tyr Gly Tyr Gly
            20                  25                  30

Ala Gly Ala Gly Tyr Gly Ala Gly Tyr Gly Ala Gly Tyr Gly Gly Gly
            35                  40                  45

Val Gly Ser Tyr Gly Gly Val Ser Gly Gly Tyr Gly Gly Tyr Gly Gly
50                  55                  60

Tyr Gly Gly Tyr Gly Gly Tyr Gly Gly His Gly Gly Tyr Gly Gly Tyr
65                  70                  75                  80

Gly Gly Tyr Ala Gly His Gly Gly Tyr Gly Gly Leu Gly Gly Tyr Gly
                85                  90                  95

Gly His Gly Gly Tyr Gly Gly Tyr Gly Ser Gly Gly His His Gly Pro
            100                 105                 110

Tyr Gly Gly Tyr Gly Gly Tyr Leu Gly
        115                 120
```

<210> SEQ ID NO 21
<211> LENGTH: 181
<212> TYPE: PRT
<213> ORGANISM: Dosidicus gigas

<400> SEQUENCE: 21

```
Met Thr Ala Thr Leu Leu Phe Leu Met Ser Met Ile Ala Ala Leu Gly
1               5                   10                  15

Cys Gln Ser Glu Ala Ala Ile Ser His Gly Ser His Val Lys Thr Val
            20                  25                  30

Val His His Gly Asn Gly Val Arg Thr Val Thr His Thr Ile His His
            35                  40                  45

Pro Val Val His His Gly Leu His Arg Thr Ser Ile Val Pro Gly Thr
50                  55                  60

Thr Thr Ile Thr His Thr Thr His Asp Asn Arg His Pro Tyr Gly Gly
65                  70                  75                  80
```

```
Val Thr Thr Val Thr His Ser Asn Gln Gly Ala His His Pro Tyr Ser
                85                  90                  95

Phe Gly Tyr Gly Phe Gly Pro Tyr Gly Gly Gly Gly Gly Leu Tyr
            100                 105                 110

Gly Ala Pro Tyr His Met Gly Thr Thr Val Val Asn His Pro Gly His
            115                 120                 125

Gly Met Pro Tyr Pro Tyr Met Tyr Gly Ser Gln Gly Phe Gly Leu Gly
            130                 135                 140

Gly Leu Ser Gly Leu Asp Tyr Pro Val Gly Ser Thr Val Thr His Ser
145                 150                 155                 160

Asn Tyr Gly Phe His His Pro Leu Gly Phe Gly Glu Pro Phe Asn Gly
                165                 170                 175

Pro Tyr Gly Phe Gln
            180

<210> SEQ ID NO 22
<211> LENGTH: 166
<212> TYPE: PRT
<213> ORGANISM: Dosidicus gigas

<400> SEQUENCE: 22

Met Thr Ser Lys Ile Ile Leu Leu Ala Val Leu Ser Val Ser Asn
1               5                   10                  15

Tyr Ala Ser Ala Ile Leu Pro Ala Thr Thr Ser Val Ser Gln Ala Thr
                20                  25                  30

His Arg Gly Tyr Arg Thr Tyr Ala Gly Ile Leu Lys Gly Phe Gly Leu
            35                  40                  45

Thr Tyr Pro Gly Ser Thr Thr Val Ser Lys Thr Thr Arg Arg Tyr Gly
        50                  55                  60

Gly Leu Leu Gly Gly Tyr Gly Tyr Leu Pro Ser Ala Gly Tyr Gly
65                  70                  75                  80

Tyr Gly Tyr Gly Leu Pro Leu Ala Gly Tyr Gly Gly Leu Tyr Gly Gly
                85                  90                  95

Tyr Gly Gly Leu Tyr Gly Gly Trp Gly Tyr Pro Val Gly Ala Val Gly
            100                 105                 110

Ala Tyr Gly Gly Leu Leu Gly Gly Tyr Gly Tyr Gly Leu Pro Leu Gly
            115                 120                 125

Gly Tyr Gly Gly Phe Phe Gly Gly Tyr Gly Ala Pro Tyr Ala Gly Tyr
            130                 135                 140

Gly Tyr Gly Tyr Val Leu Leu Gly Pro Val Gly Pro Ile Ala Thr Ser Val
145                 150                 155                 160

Ser Gln Thr Thr His His
                165

<210> SEQ ID NO 23
<211> LENGTH: 150
<212> TYPE: PRT
<213> ORGANISM: Dosidicus gigas

<400> SEQUENCE: 23

Met Ala Ser Thr Lys Leu Ile Phe Val Val Leu Leu Ala Ala Phe Gly
1               5                   10                  15

Phe Ala Cys Ser Glu Glu Thr Lys Glu Thr Thr Thr Pro Lys Pro Thr
                20                  25                  30

Pro Ala Ala Ser Asn Leu Leu Gly Ser Ser Trp Tyr Thr Pro Thr Leu
            35                  40                  45
```

Gly Leu Gly Tyr Gly Gly Tyr Gly Leu Gly Leu Gly Tyr Gly Gly Tyr
                50                  55                  60

Gly Met Gly Leu Gly Tyr Gly Gly Tyr Gly Leu Gly Leu Gly Tyr Gly
 65                  70                  75                  80

Gly Tyr Gly Leu Gly Leu Gly Tyr Gly Gly Tyr Gly Gly Leu Gly Gly
                 85                  90                  95

Phe Tyr Pro Gly Tyr His Gly Val Ser Thr Ser Ser Val Thr His
            100                 105                 110

His Ala Pro Val Tyr Ser Val Pro His Val Thr Ser Ser Val Thr His
            115                 120                 125

His Ala Pro Tyr Gly Leu Gly Ala Gly Tyr Leu Gly Leu Tyr Gly
            130                 135                 140

Gly Tyr Leu Gly Leu His
145                 150

<210> SEQ ID NO 24
<211> LENGTH: 179
<212> TYPE: PRT
<213> ORGANISM: Dosidicus gigas

<400> SEQUENCE: 24

Met Thr Thr Thr Ala Thr Leu Leu Ala Leu Met Ser Val Ile Gly Leu
 1               5                  10                  15

Gly Ser Cys Phe Pro Gly Phe Met Gly Gly Tyr Gly Gly Ala Tyr Pro
                20                  25                  30

Ile Gly Ser Ser Tyr Ser Gln Val Thr His His Gly Pro Tyr Gly Met
                35                  40                  45

Ser Gly Ile Gly Gly Phe Gly Gly Leu Gly Tyr Gly Ala Ser Leu Pro
 50                  55                  60

Val Ser Ser Val Ser His Val Ser His Gly Ala His Tyr Gly Trp Gly
 65                  70                  75                  80

Gly Met Tyr Gly Gly Gly Val Gln Val Ser Gln Ser Pro Val Met Tyr
                 85                  90                  95

Gln Gly Tyr Ser Val Gly Ala Pro His Val Gln Ser Met Gly Val His
            100                 105                 110

Tyr Pro Thr Thr Thr Ser Val Ser His Ser His Gly Gly Tyr Leu Gly
            115                 120                 125

Gly Leu Gly Gly Ile Gly Ala Val Gly Gly Tyr Gly Gly Tyr Gly Gly
            130                 135                 140

Tyr Gly Leu Ala Gly Gly Leu Gly His Ser Val Ser Thr Val Ser His
145                 150                 155                 160

Gly Ile Gly His Val Gly Met Gly Met Gly Tyr Gly Tyr Gly Gly Phe
                165                 170                 175

Gly His Tyr

<210> SEQ ID NO 25
<211> LENGTH: 361
<212> TYPE: PRT
<213> ORGANISM: Dosidicus gigas

<400> SEQUENCE: 25

Met Ala Ala Thr Tyr Phe Ile Ile Ala Ala Phe Phe Thr Val Thr Gly
 1               5                  10                  15

Leu Val Ser Ala Gln Glu Pro Phe Gly Pro Gly Pro Gly Tyr Gly Ile
                20                  25                  30

Gly Asp Ile Gly Phe Gly Asn Leu Gly Glu Ala Gly Ala Phe Thr His
         35                  40                  45

Gly Phe Gly Pro Phe Pro Gly Ala Pro Phe Pro Pro Phe Pro Ala
 50                  55                  60

Pro Tyr Pro Gly Ile Thr Pro His Pro Ile Ser Trp Ser Pro His Val
 65                  70                  75                  80

Ser Ile Pro Thr His Thr Val Thr His Thr Ser Gly Val Ser Val Pro
                 85                  90                  95

His His Val Ser Thr His Val Gly Ser Thr Thr Thr Lys Thr Val
            100                 105                 110

Thr Val Thr His His Pro Gly Ser His Val Thr Thr Val His His Pro
            115                 120                 125

Ala Thr Pro Met Ala Thr His Val Gln His Val Asn Tyr Gly Ser Gly
130                 135                 140

Phe Pro Val Gly Ala Pro Leu Leu Pro Met Gly Tyr Gly Pro Gly Pro
145                 150                 155                 160

Tyr Pro Val Glu Pro Tyr Pro Tyr Gly Met Gly His Pro Met Ser Trp
                165                 170                 175

Pro Thr Phe Gly Gly Val Gly Gly Thr Thr His Thr Val Thr His Thr
            180                 185                 190

Pro Val Gly Gly Val Thr His His Val Gly Thr His Gly Ser Thr Thr
            195                 200                 205

Thr Lys Thr Val Thr Val Thr His His Pro Ser Ser Gln Val Thr His
        210                 215                 220

Val Thr His His Pro Ala Pro Met Val Thr Ser His Val Asn Val Gly
225                 230                 235                 240

Ala Gly Phe Pro Gly Gly Phe Gly Tyr Gly His Gly Phe Leu Ala Pro
                245                 250                 255

Pro Gly Ile Thr His Gln Thr Phe Ser His Gly Phe Pro Gly Pro Phe
            260                 265                 270

Pro Gly Gly Met Tyr Asp Gln Phe Pro Gly Val Gly Tyr Gly Phe Asp
            275                 280                 285

Thr Gly Met Pro Phe Pro Tyr Ile His Asp Gly Ser Met Gly Met Gln
290                 295                 300

Asn Val His Thr Val His His His Pro Gly Gly Val Thr Thr His
305                 310                 315                 320

Thr Thr Tyr Pro His Pro Leu Thr Ala Tyr Pro Met Gly Asn Pro Tyr
                325                 330                 335

Pro Tyr Gly Ser Thr Thr Thr Val Thr Lys His Thr Lys Thr Val Thr
            340                 345                 350

His Lys Ala Gly Ser Gly Lys Lys Asn
        355                 360

<210> SEQ ID NO 26
<211> LENGTH: 259
<212> TYPE: PRT
<213> ORGANISM: Dosidicus gigas

<400> SEQUENCE: 26

Met Thr Thr Met Phe Ser Ala Leu Val Ser Leu Ala Val Val Leu Gly
1               5                   10                  15

Val Leu Ser Tyr Thr Ser Ala Tyr His Ala Asn His Val Gly Thr Leu
            20                  25                  30

Trp Ala Lys Pro Pro Gln Gln Thr Pro Tyr Gly Gly Tyr Gly Val Ser
        35                  40                  45

```
Gly Gly Ala Gly Gln Gly Gly Tyr Gly Leu Gly Gly Tyr Gly Gly Tyr
        50                  55                  60

Gly Ser Tyr Gly Gly Leu Gly Gly Tyr Gly Tyr Gly Gly Leu Gly
 65                  70                  75                  80

Gly Tyr Gly Gly Tyr Gly Gly Leu Gly Gly Tyr Gly Gly Tyr Gly Gly
                 85                  90                  95

Tyr Gly Gln Gly Gly Tyr Ser Thr Gly Gly His Gly His Gly Gly Tyr
            100                 105                 110

Gly Phe Gly Gly Tyr Gly Gln Gly Gly Tyr Gly Phe Gly Gly Tyr Gly
            115                 120                 125

Gln Gly Gly Tyr Gly Gln Gly Gly Tyr Gly Gln Gly Gly Tyr Gly Gln
        130                 135                 140

Gly Gly Ser Gly Tyr Gly Gly Tyr Gly His Tyr Tyr Pro Thr Thr Ser
145                 150                 155                 160

Tyr Gly Gly Tyr Leu Gly Gly Tyr Gly Gly Tyr Gly Gly Tyr Tyr Pro
                165                 170                 175

His Thr Ser Ser Gly Ser Tyr Tyr Pro Thr Thr Tyr Gly Gly Ser Asn
            180                 185                 190

Gln Gly Asn Pro Gly Ala Pro Ile Ser Ser Ser Gly Phe Val Phe
        195                 200                 205

Pro Gly Tyr His Phe Pro Gly Val Phe His Gly Gly Val Asn Gln Gly
        210                 215                 220

Ala Gly Gly Thr Ser Gly Thr Asp Leu Gln Arg Leu Leu Asn Leu Asn
225                 230                 235                 240

Gly Phe Lys Pro Thr Ala Thr Ser Thr Thr Ser Thr Ser Asn Ser Asn
                245                 250                 255

Ser Lys Lys

<210> SEQ ID NO 27
<211> LENGTH: 254
<212> TYPE: PRT
<213> ORGANISM: Dosidicus gigas

<400> SEQUENCE: 27

Met Thr Thr Met Phe Ser Ala Leu Val Ser Leu Ala Val Val Leu Gly
 1               5                  10                  15

Val Leu Ser Tyr Thr Ser Ala Tyr His Ala Asn His Val Gly Thr Leu
                20                  25                  30

Trp Ala Lys Pro Pro Gln Gln Thr Pro Tyr Gly Gly Tyr Gly Val Ser
            35                  40                  45

Gly Gly Ala Gly Gln Gly Gly Tyr Gly Leu Gly Gly Tyr Gly Gly Tyr
        50                  55                  60

Gly Ser Tyr Gly Gly Leu Gly Gly Tyr Gly Tyr Gly Gly Leu Gly
 65                  70                  75                  80

Gly Tyr Gly Gly Tyr Gly Gly Leu Gly Gly Tyr Gly Gly Tyr Gly Gly
                 85                  90                  95

Tyr Gly Gln Gly Gly Tyr Ser Thr Gly Gly His Gly His Gly Gly Tyr
            100                 105                 110

Gly Phe Gly Gly Tyr Gly Gln Gly Gly Tyr Gly Phe Gly Gly Tyr Gly
            115                 120                 125

Gln Gly Gly Tyr Gly Gln Gly Gly Tyr Gly Gln Gly Gly Ser Gly Tyr
        130                 135                 140

Gly Gly Tyr Gly His Tyr Tyr Pro Thr Thr Ser Tyr Gly Gly Tyr Leu
145                 150                 155                 160
```

Gly Gly Tyr Gly Gly Tyr Gly Tyr Pro His Thr Ser Ser Gly
            165                 170                 175

Ser Tyr Tyr Pro Thr Thr Tyr Gly Gly Ser Asn Gln Gly Asn Pro Gly
                180                 185                 190

Ala Pro Ile Ser Ser Ser Gly Phe Val Phe Pro Gly Tyr His Phe
            195                 200                 205

Pro Gly Val Phe His Gly Gly Val Asn Gln Gly Ala Gly Gly Thr Ser
            210                 215                 220

Gly Thr Asp Leu Gln Arg Leu Leu Asn Leu Asn Gly Phe Lys Pro Thr
225                 230                 235                 240

Ala Thr Ser Thr Thr Ser Thr Ser Asn Ser Asn Ser Lys Lys
                245                 250

<210> SEQ ID NO 28
<211> LENGTH: 249
<212> TYPE: PRT
<213> ORGANISM: Dosidicus gigas

<400> SEQUENCE: 28

Met Thr Thr Met Phe Ser Ala Leu Val Ser Leu Ala Val Val Leu Gly
1               5                   10                  15

Val Leu Ser Tyr Thr Ser Ala Tyr His Ala Asn His Val Gly Thr Leu
                20                  25                  30

Trp Ala Lys Pro Pro Gln Gln Thr Pro Tyr Gly Gly Tyr Gly Val Ser
            35                  40                  45

Gly Gly Ala Gly Gln Gly Gly Tyr Gly Leu Gly Gly Tyr Gly Gly Tyr
50                  55                  60

Gly Ser Tyr Gly Gly Leu Gly Gly Tyr Gly Gly Tyr Gly Gly Leu Gly
65                  70                  75                  80

Gly Tyr Gly Gly Tyr Gly Gly Leu Gly Gly Tyr Gly Gly Tyr Gly Gly
                85                  90                  95

Tyr Gly Gln Gly Gly Tyr Ser Thr Gly Gly His Gly His Gly Gly Tyr
            100                 105                 110

Gly Phe Gly Gly Tyr Gly Gln Gly Gly Tyr Gly Phe Gly Gly Tyr Gly
        115                 120                 125

Gln Gly Gly Tyr Gly Gln Gly Gly Ser Gly Tyr Gly Gly Tyr Gly His
        130                 135                 140

Tyr Tyr Pro Thr Thr Ser Tyr Gly Gly Tyr Leu Gly Gly Tyr Gly Gly
145                 150                 155                 160

Tyr Gly Gly Tyr Tyr Pro His Thr Ser Ser Gly Ser Tyr Tyr Pro Thr
                165                 170                 175

Thr Tyr Gly Gly Ser Asn Gln Gly Asn Pro Gly Ala Pro Ile Ser Ser
            180                 185                 190

Ser Ser Gly Phe Val Phe Pro Gly Tyr His Phe Pro Gly Val Phe His
        195                 200                 205

Gly Gly Val Asn Gln Gly Ala Gly Gly Thr Ser Gly Thr Asp Leu Gln
    210                 215                 220

Arg Leu Leu Asn Leu Asn Gly Phe Lys Pro Thr Ala Thr Ser Thr Thr
225                 230                 235                 240

Ser Thr Ser Asn Ser Asn Ser Lys Lys
                245

<210> SEQ ID NO 29
<211> LENGTH: 117
<212> TYPE: PRT

<213> ORGANISM: Dosidicus gigas

<400> SEQUENCE: 29

```
Met Ala Gly Ser Leu Ile Val Ser Val Leu Ala Val Ile Ala
1               5                   10                  15

Leu Ser Ser Thr Ala Asn Ala Ile Pro Gly Thr Phe Gly Gly Tyr Phe
            20                  25                  30

Gly Ala Gly His Pro Val Gly His Ser Val Ser Thr Val Ser His Gly
        35                  40                  45

Leu Gly Val Gly Ala Gly Val Gly Val Gly Gly Leu Tyr Gly Gly Tyr
    50                  55                  60

Gly Leu Gly Gly His Ser Val Ser Thr Val Ser His Gly Pro Val Gly
65                  70                  75                  80

Tyr Gly Ser Val Gly Val Gly Gly Leu Tyr Gly Gly Tyr Gly Gly Tyr
                85                  90                  95

Gly Leu Gly Ala Gly Tyr Gly Leu Gly Ala Gly Tyr Gly Leu Gly Ala
            100                 105                 110

Gly Tyr Gly Leu Gly
        115
```

<210> SEQ ID NO 30
<211> LENGTH: 274
<212> TYPE: PRT
<213> ORGANISM: Dosidicus gigas

<400> SEQUENCE: 30

```
Met Ala Ala Val Leu Phe Ile Val Ser Ile Ile Ala Ala Leu Ser
1               5                   10                  15

Cys Gln Thr Glu Ala Ile Leu Pro Gly Thr Ser Val Lys Thr Thr Ser
            20                  25                  30

Ser Val His His His Val Val Pro Ser Val Arg His Thr Val Ser Thr
        35                  40                  45

Val Ser His Ala Gly Ala His Pro Phe Ala Tyr Gly Asn Leu Tyr Gly
    50                  55                  60

Gly Leu Tyr Gly Gly Pro Tyr Gly Val Pro Gly Ala Thr Val His Thr
65                  70                  75                  80

Val Ser His Gly Val His Pro Ser Pro Leu Thr Thr Thr Ser Val His
                85                  90                  95

His Thr Thr His Gly Gly Leu Ile Gly Gly Leu Tyr Gly Ala Gly
            100                 105                 110

Tyr Pro Leu Gly Phe Gly Gly Tyr Gly Leu His Pro Ala Gly Leu Gly
        115                 120                 125

Tyr Gly Leu Gly Gly Leu Tyr Gly Gly Leu Tyr Gly Tyr Pro Ala Ala
    130                 135                 140

Ala Ser Val Thr His Gly Phe His Pro Ala Gly Phe Gly Leu Gly Leu
145                 150                 155                 160

Gly Gly Phe Tyr Gly Gly Ser Tyr Gly Tyr Pro Gly Ala Thr Val Ser
                165                 170                 175

His Thr Thr His Gly Leu His Pro Gly Gly Phe Gly Leu Gly Leu Gly
            180                 185                 190

Gly Phe Tyr Gly Gly Ala Tyr Gly Phe Pro Ala Ala Ser Ser Val Ser
        195                 200                 205

His Val Thr His Gly Val His Pro Ala Gly Leu Gly Phe Gly Gly Val
    210                 215                 220

Tyr Gly Thr Gly Tyr Gly Ile Pro Ala Gly Thr Thr Val Ser His Thr
```

```
                    225                 230                 235                 240

Thr His Gly Val His His Leu Pro Ala Ala Ser Thr Val Thr His Thr
                245                 250                 255

Thr His Gly Val Ala His Pro Met Gly Val Ser Tyr Gly Asn Val Phe
                260                 265                 270

Leu His

<210> SEQ ID NO 31
<211> LENGTH: 212
<212> TYPE: PRT
<213> ORGANISM: Dosidicus gigas

<400> SEQUENCE: 31

Met Ala Ala Ala Val Leu Phe Ile Val Ser Ile Ala Ala Leu Ser
1               5                   10                  15

Cys Gln Thr Glu Ala Ile Leu Pro Gly Thr Ser Val Lys Thr Thr Ser
                20                  25                  30

Ser Val His His His Val Val Pro Ser Val Arg His Thr Val Ser Thr
            35                  40                  45

Val Ser His Ala Gly Ala His Pro Phe Ala Tyr Gly Asn Leu Tyr Gly
50                  55                  60

Gly Leu Tyr Gly Gly Pro Tyr Gly Val Pro Gly Ala Thr Val His Thr
65                  70                  75                  80

Val Ser His Gly Val His Pro Ser Pro Leu Thr Thr Thr Ser Val His
                85                  90                  95

His Thr Thr His Gly Gly Leu Ile Gly Gly Gly Leu Tyr Gly Ala Gly
                100                 105                 110

Tyr Pro Leu Gly Phe Gly Gly Tyr Gly Leu His Pro Ala Gly Leu Gly
            115                 120                 125

Tyr Gly Leu Gly Gly Leu Tyr Gly Gly Leu Tyr Gly Tyr Pro Ala Ala
130                 135                 140

Ala Ser Val Thr His Gly Phe His Pro Ala Gly Phe Gly Leu Gly Leu
145                 150                 155                 160

Gly Gly Phe Tyr Gly Gly Ala Tyr Gly Tyr Pro Gly Ala Thr Val Ser
                165                 170                 175

His Thr Thr His Gly Val His His Leu Pro Ala Ala Ser Thr Val Thr
                180                 185                 190

His Thr Thr His Gly Val Ala His Pro Met Gly Val Ser Tyr Gly Asn
            195                 200                 205

Val Phe Leu His
    210

<210> SEQ ID NO 32
<211> LENGTH: 142
<212> TYPE: PRT
<213> ORGANISM: Dosidicus gigas

<400> SEQUENCE: 32

Met Ala His Thr Gln Leu Ile Phe Val Val Leu Leu Ala Ala Phe Gly
1               5                   10                  15

Phe Ala Cys Ser Glu Asp Glu Lys Gln Ala Pro Thr Ala Lys Pro Ala
                20                  25                  30

Thr Ala Pro Ser Asn Leu Leu Arg Ser Ser Trp Tyr Thr Pro Ser Ser
            35                  40                  45

Ser Tyr Gly Ile Gly Leu Gly Tyr Gly Gly Tyr Gly Leu Gly Leu Gly
50                  55                  60
```

```
Tyr Gly Gly Tyr Gly Ala Tyr Gly Gly Tyr Gly Tyr Gly Gly Tyr
65                  70                  75                  80

Leu Pro Tyr Gly Tyr Gly Gly Ile Leu Pro Gly Tyr Phe Gly Gly Tyr
                85                  90                  95

Pro Ala Val Thr Ser Ser Val Thr His His Ala Pro Thr Tyr Pro
                100                 105                 110

Gln Val Thr Ser Ser Val Thr His His Ala Pro Tyr Gly Val Gly Val
            115                 120                 125

Gly Tyr Leu Gly Gly Leu Tyr Gly Gly Tyr Leu Gly Leu His
        130                 135                 140

<210> SEQ ID NO 33
<211> LENGTH: 142
<212> TYPE: PRT
<213> ORGANISM: Dosidicus gigas

<400> SEQUENCE: 33

Met Ala His Thr Gln Leu Ile Phe Val Val Leu Leu Ala Ala Phe Gly
1               5                   10                  15

Phe Ala Cys Ser Glu Asp Glu Lys Gln Ala Pro Thr Ala Lys Pro Ala
                20                  25                  30

Thr Ala Pro Ser Asn Leu Leu Arg Ser Ser Trp Tyr Thr Pro Ser Ser
            35                  40                  45

Ser Tyr Gly Ile Gly Leu Gly Tyr Gly Gly Tyr Gly Leu Gly Leu Gly
50                  55                  60

Tyr Gly Gly Tyr Gly Ala Tyr Gly Gly Tyr Gly Tyr Gly Gly Tyr
65                  70                  75                  80

Leu Pro Tyr Gly Tyr Gly Gly Ile Leu Pro Gly Tyr Phe Gly Gly Tyr
                85                  90                  95

Pro Ala Val Thr Ser Ser Val Thr His His Ala Pro Thr Tyr Pro
                100                 105                 110

Gln Val Thr Ser Ser Val Thr His His Ala Pro Tyr Gly Val Gly Val
            115                 120                 125

Gly Tyr Leu Gly Gly Leu Tyr Gly Gly Tyr Leu Gly Leu His
        130                 135                 140

<210> SEQ ID NO 34
<211> LENGTH: 315
<212> TYPE: PRT
<213> ORGANISM: Dosidicus gigas

<400> SEQUENCE: 34

Thr Val Ser His Val Ser His Gly Thr Val Gly Tyr Gly Gly His Gly
1               5                   10                  15

Leu Gly Gly Tyr Gly Gly Tyr Gly Leu Gly Gly Ile Ser Gly Gly Tyr
                20                  25                  30

Gly Leu Gly Gly His Thr Val Ser His Val Ser His Gly Pro Val Gly
            35                  40                  45

Tyr Gly Gly Tyr Gly Ile Gly Gly Val Ser Gly Gly Tyr Gly Gly Tyr
50                  55                  60

Gly Leu Gly Gly Val Ser Gly Gly Tyr Gly Met Gly Gly Leu Tyr Gly
65                  70                  75                  80

Gly Tyr Gly Gly Tyr Gly Val Gly Val His Ser Arg Tyr Gly Val Gly
                85                  90                  95

His Arg Thr Val Thr Gln Leu Arg His Arg Ile Gln Pro Leu Gly Tyr
                100                 105                 110
```

Gly Val Val Asn Gln Ile Gly His Ala Val His Arg Val Val Gln Pro
            115                 120                 125

Val Ala His His Gly Val Val Ser Arg Arg Tyr Ala Ile Pro His Thr
    130                 135                 140

Glu Val Arg Tyr Val Gln Tyr Pro Val Val Asn Arg Tyr Ile Gln Tyr
145                 150                 155                 160

Val Thr Val Asn Lys Pro Tyr Val Pro Arg Tyr Glu Trp His Val
                165                 170                 175

Arg Ser Tyr Gln Val Pro Val Pro Arg Tyr Ser Val Arg Met Ala Val
                180                 185                 190

Arg Pro Val Tyr Ile Pro Arg Val His Tyr Ala Glu Ser His Thr Pro
                195                 200                 205

Val Thr His Tyr Ser His Val Ser His Asp Val His Gln Pro Ile Tyr
                210                 215                 220

Gly Val His Tyr Pro Met Gly His Ser Val Glu Ala Val Thr His Gln
225                 230                 235                 240

Gln Pro Phe Val Tyr Gly His His Thr Thr Tyr Gly His Gly Gly Leu
                245                 250                 255

Tyr Gly Gly Tyr Gly Gly Tyr Gly Val Gly Ala Val Gly Gly Tyr
                260                 265                 270

Gly Met Gly Gly Ala Val Gly Gly Tyr Gly Leu Gly Gly Ala Val Gly
                275                 280                 285

Gly Tyr Gly Leu Gly Gly Ala Val Gly Gly Tyr Gly Leu Gly Gly Gly
                290                 295                 300

Tyr Gly Gly Tyr Gly Leu Gly Gly Leu Tyr His
305                 310                 315

<210> SEQ ID NO 35
<211> LENGTH: 73
<212> TYPE: PRT
<213> ORGANISM: Dosidicus gigas

<400> SEQUENCE: 35

Met Ala Ser Thr Leu Phe Val Leu Leu Ala Val Ile Ala Leu Ala Ser
1               5                   10                  15

Tyr Ala Ser Gly Ala Leu Thr Tyr Gly Ala Gly Gly Trp Ala Leu Pro
                20                  25                  30

Val Gly Gly Trp Ala Val Pro Thr Gly Gly Val Gly Gly Tyr Gly Val
            35                  40                  45

Pro Gly Gly Tyr Gly Val Pro Gly Gly Phe Gly Gly Phe Gly Gly Tyr
        50                  55                  60

Gly Gly Gly Phe Gly Phe Gly Gly Tyr
65                  70

<210> SEQ ID NO 36
<211> LENGTH: 354
<212> TYPE: PRT
<213> ORGANISM: Dosidicus gigas

<400> SEQUENCE: 36

Gly Gly Leu Tyr Gly Gly His Tyr Gly Gly Tyr Gly Leu Gly Gly Ser
1               5                   10                  15

Ser Leu Gln Tyr Pro Ala Ala Thr Ala Val Ser Gln Thr Tyr His His
                20                  25                  30

Ala Pro Ser Ser Tyr Gly Leu Ala Gly Tyr Gly Gly Val Ser Gly Gly
            35                  40                  45

```
Arg Tyr Gly Gly Tyr Gly Leu Gly Tyr Gly Leu Gly Tyr Pro Thr
    50                  55                  60

Ala Thr Ser Ser Ser Tyr Thr Thr His His Ala Pro Ser Gly Tyr Gly
65                  70                  75                  80

Ser Leu Gly Gly Ser Gly Phe Gly Gly Ile Val Ser Gly Ser Gln Tyr
                85                  90                  95

Pro Val Gly Ala Val Ser Thr Asn Ser Gln Val Leu Gln Gln Pro Tyr
            100                 105                 110

Arg Leu Ile Leu Gly Gly Ser Ser Tyr His Tyr Pro Ala Ala Thr Thr
        115                 120                 125

Val Ser His Thr Ser Gln Asn Gly Gly Tyr Gly Tyr Gly Asn Leu Leu
    130                 135                 140

Gly Gly Tyr Gly Gly Ser Tyr Gly Gly Leu Gly Leu Ser Lys Gln Met
145                 150                 155                 160

Ile Gly Tyr Pro Ala Thr Thr Ser Val Ser Gln Thr Thr His Gln Leu
                165                 170                 175

Pro Tyr Gly Val Phe Gly Leu Tyr Gly Leu Gly Gly Gln Gly Leu Thr
            180                 185                 190

Ser Asn Thr Tyr Gln Ser Gly Tyr Gly Phe Gly Gly Ser Gln Gly Gly
        195                 200                 205

Leu Gly Tyr Thr Ala Gly Asn Gly Gly Leu Ser Ser Gly Leu Pro Gly
    210                 215                 220

Pro Met Gly Ser Gly Leu Gly Val Tyr Asn Phe His Tyr Pro Ala Ala
225                 230                 235                 240

Thr Thr Val Ser Thr Thr Ala Asn His Met Gly Pro Gly Tyr Gly Ser
                245                 250                 255

Leu Leu Gly Gly Tyr Gly Ala Gln Phe Pro Ser Val Ser Ser Gly Ala
            260                 265                 270

Gln Gly Val Asn Ser Gly Val Phe Gly Gly Tyr Gly Ser Thr Phe Gly
        275                 280                 285

Gly Ile Gly Leu Ser Gly Tyr Gly Ser Gln Asn Ser Ala Gly Pro Val
    290                 295                 300

Val Gly Ser Thr Ala Gln Thr Gly Gly Phe Gly Asn Gly Gly Leu Leu
305                 310                 315                 320

Gly Gly Leu Gly Ser Gln Ser Thr Tyr Ser Tyr Gly Leu His Gln Pro
                325                 330                 335

His Ala Ser Gly Leu Ser Gly Tyr Gly Phe His Ser Pro Thr Ser Thr
            340                 345                 350

Leu Gln

<210> SEQ ID NO 37
<211> LENGTH: 504
<212> TYPE: PRT
<213> ORGANISM: Sepioteuthis lessoniana

<400> SEQUENCE: 37

Met Gly Thr Ile Lys Val Ile Val Ala Leu Leu Ile Val Leu Gly Ile
1               5                   10                  15

Ser Ser Ser Ala Lys Gly Ile Tyr Asn Gly Ser Leu Ala Ala Leu Asp
            20                  25                  30

Ser Ser Ser Tyr Ser His Pro Ser Pro Tyr Leu Gln Arg Ser Val Ser
        35                  40                  45

Thr Val Ser His Gly Ser His Tyr Pro Thr Tyr Gly Gly Trp Gly Tyr
    50                  55                  60
```

```
Asn Leu Gly Thr Trp Gly His Gly Leu Gly Leu Gly Gly Tyr Gly
 65                  70                  75                  80

Phe Arg Tyr Pro Thr Ser Ser Ile Ser Arg Val Ser His Thr Ala
                 85                  90                  95

His Ser Pro Val Gly Tyr Gly Trp Gly Gly Tyr Ala Gln His Ser
            100                 105                 110

Pro Leu Gln Tyr Val Ser Arg Thr Ala Leu Pro Pro Val Gly Trp Thr
        115                 120                 125

Phe Gly Gly Ile Tyr Arg Gly His Gly Ala His Val Ser Gln Ser Pro
    130                 135                 140

Val Arg Tyr Gln Gly Tyr Ser Phe Gly Arg Pro Ala Val Ala Thr Tyr
145                 150                 155                 160

Arg Val Leu Tyr Pro Arg Pro Val Val Ser His Val Thr His Ser Ile
                165                 170                 175

Pro Tyr Gly Gly Trp Ser Val Gly Gly Gln Gly Gly Phe Val Ser Ser
            180                 185                 190

Tyr Pro Thr Gly Ala Ser Ile Asn Thr Val Ser His Gly Ile Ser His
        195                 200                 205

Ala Pro Ile Tyr Gly Gly Trp Gly Phe Gly Tyr Pro Ala Gly Gln Ala
    210                 215                 220

Ile Ser Thr Val Gly His Gly Ile His Pro Thr Val Thr Tyr Gly Gly
225                 230                 235                 240

Leu Gly Leu Gly Gly Leu Tyr Gly Gly Tyr Gly Ala His Tyr Pro Thr
                245                 250                 255

Gly Ser Ser Val Ser Thr Leu Ser His Gly Val Ser His Pro Val Gly
            260                 265                 270

Phe Gly Phe Gly Tyr Ser Ser His Tyr Pro Ala Ser Thr Ser Val Ser
        275                 280                 285

Gln Thr Ser His Ser Val Pro His Ile Ile Gly Leu Gly Leu Gly Ser
    290                 295                 300

Trp Gly Gly Tyr Gly Val Gly Tyr Gly Leu His Thr Pro Val Gly Ala
305                 310                 315                 320

Ser Val Ser Thr Val Ser His Gly Ile Gly His Pro Val Gly Tyr Gly
                325                 330                 335

Thr Trp Gly Leu Gly Tyr Gly Ala His Tyr Pro Val Gly Gln Ser Val
            340                 345                 350

Ser Thr Val Ser His Gly Ile His Ala Pro Val Ala His Gly Gly Leu
        355                 360                 365

Ser Gly Leu Ser Glu Gly Tyr Gly Val Phe His Pro Thr Arg Ser Val
    370                 375                 380

Ser Thr Val Ser His Gly Val His Ser Pro Val Ile Tyr Gly Arg Tyr
385                 390                 395                 400

Gly Leu Gly Gly Leu Gly Gly Asn Gly Gly Tyr Gly Leu Gly Gly Leu
                405                 410                 415

Val Gly Gly Tyr Gly Gly Tyr Gly Leu Gly Gly Leu Val Gly Gly Tyr
            420                 425                 430

Gly Thr Tyr Gln Pro Thr Gly Ser Ser Ile Ser Thr Val Ser His Gly
        435                 440                 445

Val His Ser Pro Val Gly Tyr Gly Tyr Gly Leu Gly Gly Leu Gly
    450                 455                 460

Glu Ser Tyr Gly Gly Tyr Gly Leu Gly Gly Leu Val Gly Ser Tyr Gly
465                 470                 475                 480
```

Gly Tyr Gly Leu Gly Gly Leu Val Gly Ser Tyr Gly Gly Tyr Gly Leu
                    485                 490                 495

Gly Gly Leu Val Gly Ser Tyr Gly
            500

<210> SEQ ID NO 38
<211> LENGTH: 129
<212> TYPE: PRT
<213> ORGANISM: Sepioteuthis lessoniana

<400> SEQUENCE: 38

Met Ala Ala Lys Leu Leu Thr Leu Leu Ala Val Ile Ala Leu Ser Asn
1               5                   10                  15

Tyr Ala Tyr Ala Leu Leu Pro Gly Leu Met Gly Gly Tyr Gly Tyr Pro
                20                  25                  30

Ala Ala Thr Thr Tyr Arg Arg Thr Thr Leu Asn Gly Tyr Gly Gly Leu
            35                  40                  45

Tyr Gly Gly Leu Gly Tyr His Tyr Pro Ala Ala Thr Ala Val Ser His
        50                  55                  60

Thr Thr His His Ala Pro Tyr Gly Tyr Gly Gly Leu Tyr Gly Gly Trp
65                  70                  75                  80

Gly Tyr Pro Ala Ala Ser Ser Val Ser Thr Val Ser His Gly Val His
                85                  90                  95

His Pro Val Gly Trp Gly Leu Gly Tyr Gly Leu His Tyr Pro Ala Ala
                100                 105                 110

Thr Val Gly Tyr Ser Gly Leu Gly Leu Gly Tyr Gly Ser Gly Tyr Val
            115                 120                 125

Leu

<210> SEQ ID NO 39
<211> LENGTH: 133
<212> TYPE: PRT
<213> ORGANISM: Sepioteuthis lessoniana

<400> SEQUENCE: 39

Met Ala Ala Lys Leu Leu Thr Leu Leu Ala Val Ile Ala Leu Ser Asn
1               5                   10                  15

Tyr Ala Tyr Ala Leu Leu Pro Gly Leu Met Gly Gly Tyr Gly Tyr Pro
                20                  25                  30

Ala Ala Thr Thr Tyr Arg Arg Thr Thr Leu Asn Gly Tyr Gly Gly Leu
            35                  40                  45

Tyr Gly Gly Leu Gly Tyr His Tyr Pro Ala Ala Thr Ala Val Ser His
        50                  55                  60

Thr Thr His His Ala Pro Tyr Gly Tyr Gly Gly Leu Tyr Gly Gly Trp
65                  70                  75                  80

Gly Tyr Pro Ala Ala Ala Ser Val Ser Thr Val His Arg Pro Val Gly
                85                  90                  95

Tyr Gly Gly Trp Gly Leu Gly Tyr Gly Leu Gly Tyr Gly Leu His
                100                 105                 110

Tyr Pro Ala Ala Thr Val Gly Tyr Ser Gly Leu Gly Leu Gly Tyr Gly
            115                 120                 125

Ser Gly Tyr Val Leu
        130

<210> SEQ ID NO 40
<211> LENGTH: 138
<212> TYPE: PRT

<213> ORGANISM: Sepioteuthis lessoniana

<400> SEQUENCE: 40

Met Ala Ala Lys Leu Leu Thr Leu Leu Ala Val Ile Ala Leu Ser Asn
1               5                   10                  15

Tyr Ala Tyr Ala Leu Leu Pro Gly Leu Met Gly Gly Tyr Gly Tyr Pro
            20                  25                  30

Ala Ala Thr Thr Tyr Arg Arg Thr Thr Leu Asn Gly Tyr Gly Gly Leu
        35                  40                  45

Tyr Gly Gly Leu Gly Tyr His Tyr Pro Ala Ala Thr Ala Val Ser His
    50                  55                  60

Thr Thr His His Ala Pro Tyr Gly Tyr Gly Gly Leu Tyr Gly Gly Trp
65                  70                  75                  80

Gly Tyr Pro Ala Ala Ala Ser Val Ser Thr Val His Arg Pro Val Gly
                85                  90                  95

Tyr Gly Gly Trp Gly Leu Gly Gly Tyr Gly Leu Gly Gly Tyr Gly Leu
            100                 105                 110

Gly Tyr Gly Leu His Tyr Pro Ala Ala Thr Val Gly Tyr Ser Gly Leu
        115                 120                 125

Gly Leu Gly Tyr Gly Ser Gly Tyr Val Leu
    130                 135

<210> SEQ ID NO 41
<211> LENGTH: 483
<212> TYPE: PRT
<213> ORGANISM: Sepioteuthis lessoniana

<400> SEQUENCE: 41

Met Gly Thr Ile Lys Val Ile Val Ala Leu Leu Ile Val Leu Gly Ile
1               5                   10                  15

Ser Ser Ser Ala Lys Gly Ile Tyr Asn Gly Ser Leu Ala Ala Leu Asp
            20                  25                  30

Ser Ser Ser Tyr Ser His Pro Ser Pro Tyr Leu Gln Arg Ser Val Ser
        35                  40                  45

Thr Val Ser His Gly Ser His Tyr Pro Thr Tyr Gly Gly Trp Gly Tyr
    50                  55                  60

Asn Leu Gly Thr Trp Gly His Gly Leu Gly Gly Leu Gly Gly Tyr Gly
65                  70                  75                  80

Phe Arg Tyr Pro Thr Ser Ser Ile Ser Arg Val Ser His Thr Ala
                85                  90                  95

His Ser Pro Val Gly Tyr Gly Trp Gly Gly Tyr Ala Gln His Ser
            100                 105                 110

Pro Leu Gln Tyr Val Ser Arg Thr Ala Leu Pro Pro Val Gly Trp Thr
        115                 120                 125

Phe Gly Gly Ile Tyr Arg Gly His Gly Ala His Val Ser Gln Ser Pro
    130                 135                 140

Val Arg Tyr Gln Gly Tyr Ser Phe Gly Arg Pro Ala Val Ala Thr Tyr
145                 150                 155                 160

Arg Val Leu Tyr Pro Arg Pro Val Val Ser His Val Thr His Ser Ile
                165                 170                 175

Pro Tyr Gly Gly Trp Ser Val Gly Gly Gln Gly Phe Val Ser Ser
            180                 185                 190

Tyr Pro Thr Gly Ala Ser Ile Asn Thr Val Ser His Gly Ile Ser His
        195                 200                 205

Ala Pro Ile Tyr Gly Gly Trp Gly Phe Gly Tyr Pro Ala Gly Gln Ala

```
              210                 215                 220
Ile Ser Thr Val Gly His Gly Ile His Pro Thr Val Thr Tyr Gly Gly
225                 230                 235                 240

Leu Gly Leu Gly Gly Leu Tyr Gly Tyr Gly Ala His Tyr Pro Thr
                245                 250                 255

Gly Ser Ser Val Ser Thr Leu Ser His Gly Val Ser His Pro Val Gly
                260                 265                 270

Phe Gly Phe Gly Tyr Ser Ser His Tyr Pro Ala Ser Thr Ser Val Ser
                275                 280                 285

Gln Thr Ser His Ser Val Pro His Ile Ile Gly Leu Gly Leu Gly Ser
                290                 295                 300

Trp Gly Gly Tyr Gly Val Gly Tyr Gly Leu His Thr Pro Val Gly Ala
305                 310                 315                 320

Ser Val Ser Thr Val Ser His Gly Ile Gly His Pro Val Gly Tyr Gly
                325                 330                 335

Thr Trp Gly Leu Gly Tyr Gly Ala His Tyr Pro Val Gly Gln Ser Val
                340                 345                 350

Ser Thr Val Ser His Gly Ile His Ala Pro Val Ala His Gly Gly Leu
                355                 360                 365

Ser Gly Leu Ser Glu Gly Tyr Gly Val Phe His Pro Thr Arg Ser Val
                370                 375                 380

Ser Thr Val Ser His Gly Val His Ser Pro Val Ile Tyr Gly Arg Tyr
385                 390                 395                 400

Gly Leu Gly Gly Leu Gly Gly Asn Gly Gly Tyr Gly Leu Gly Gly Leu
                405                 410                 415

Val Gly Gly Tyr Gly Gly Tyr Gly Leu Gly Gly Leu Val Gly Gly Tyr
                420                 425                 430

Gly Thr Tyr His Pro Ala Gly Ser Ser Ile Ser Thr Val Ser His Gly
                435                 440                 445

Leu His Ser Leu Gly Ala Tyr Gly Gly Tyr Gly His Gly Ser Leu Leu
                450                 455                 460

Gly Gly Tyr Gly Val Pro Leu Pro Ile Ser Thr Thr Ser His His Ser
465                 470                 475                 480

Val Thr His

<210> SEQ ID NO 42
<211> LENGTH: 238
<212> TYPE: PRT
<213> ORGANISM: Sepioteuthis lessoniana

<400> SEQUENCE: 42

Met Val Ser Thr Val Leu Ile Ile Met Ser Met Ile Ala Ala Leu Ser
1               5                   10                  15

Cys Gln Ser Glu Ala Ala Leu Ser Val Gly Thr Ser Val Lys Ser Val
                20                  25                  30

His His Ser Val His His Pro Ile Ser Ala Val Gly Gln Thr Val Lys
                35                  40                  45

Thr Val Thr His Ala Val Pro Gln Ile Tyr Pro Phe Gly Gly Leu Pro
                50                  55                  60

Phe Gly Asp Ala Tyr Gly Leu Tyr Gly Ala Leu His Gly Gly Val
65                  70                  75                  80

Tyr Gly Val Pro Ala Ala Thr Ser Val Gln Thr Val Ser His Gly Leu
                85                  90                  95

His Pro Thr Val Pro Val Gly Ser Thr Ser Val Ser His Thr Thr His
```

```
                100             105             110
Gly Ile His His Pro Val Thr Tyr Gly Gly Leu Gly Val Gly Gly Leu
            115             120             125
Gly Phe Gly Gly Leu Gly Tyr Gly Gly Val Gly Gly Leu Gly Leu Gly
            130             135             140
Gly Leu Tyr Gly Gly Val Tyr Gly Leu His Tyr Pro Gly Ala Ala Phe
145             150             155             160
His Tyr Pro Ala Gly Leu Gly Tyr Gly Leu Gly Gly Leu Tyr Gly Gly
            165             170             175
Leu Tyr Gly Leu His Leu Pro Ala Ala Thr Ser Val Ser His Thr Thr
            180             185             190
His Gly Val His His Pro Ala Leu Gly Tyr Gly Leu Gly Leu Tyr Gly
            195             200             205
Ala Ala His Tyr Pro Ala Ala Ser Ser Val Thr His Thr Thr His Ala
            210             215             220
Val Pro His Pro Gly Phe Gly Leu Asn Tyr Gly Val Phe His
225             230             235

<210> SEQ ID NO 43
<211> LENGTH: 201
<212> TYPE: PRT
<213> ORGANISM: Sepioteuthis lessoniana

<400> SEQUENCE: 43

Met Thr Ala Thr Val Leu Phe Leu Leu Phe Gly Ile Ala Ala Leu Thr
1               5               10              15
Cys Gln Thr Glu Ala Ala Ile Thr Gly Thr Ser Ser Val Lys Thr Val
            20              25              30
Val His Pro Pro Thr Val Val His Pro Val His Thr Val Thr His Thr
            35              40              45
Asp His His Pro Leu Val Trp Asn Thr Gly Pro Val Tyr Gly Ile Pro
            50              55              60
Ser Ala Gly Ser Thr Ser Val Lys Thr Val Thr His Gly Ile His His
65              70              75              80
Thr Gly Gly Ile Ser Val Thr Ser Pro Gly Gly Ala Thr Val Thr His
            85              90              95
Thr Thr His Gly Ile Ser His Pro Phe Gly Leu Gly His Gly Leu Gly
            100             105             110
Gly Leu Tyr Gly Gly Val Tyr Gly Leu Pro Met Pro Gly Ala Thr Thr
            115             120             125
Val Ser His Ser Thr His Gly Val Pro Tyr Ser Phe Gly Tyr Gly Gly
            130             135             140
Leu Gly Tyr Gly Gly Ile Gly Tyr Gly Gly Leu Gly Tyr Gly Gly Leu
145             150             155             160
Gly Tyr Gly Leu Gly Gly Ala Tyr Gly Leu Pro Tyr Pro Asn Thr Ala
            165             170             175
Ile Ser His Ser Ser Tyr Gly Phe Gln Ser Pro Ser Val Tyr Gly Phe
            180             185             190
Gly Phe Gly Gly Pro Tyr Gly Phe His
            195             200

<210> SEQ ID NO 44
<211> LENGTH: 129
<212> TYPE: PRT
<213> ORGANISM: Sepioteuthis lessoniana
```

<400> SEQUENCE: 44

Met Ala Ser Tyr Arg Leu Ile Phe Val Val Leu Leu Ala Ala Phe Gly
1               5                   10                  15

Leu Ala Tyr Gly Glu Gln Thr Lys Lys Thr Thr Thr Ser Asn Thr
            20                  25                  30

Gly Ala Gln Asn Tyr Tyr Asn Pro Trp Tyr Pro Thr Tyr Asn Tyr
            35                  40                  45

Gly Trp Gly Asn Pro Trp Gly Leu Gly Tyr Tyr Gly Tyr Gly Met Leu
        50                  55                  60

Pro Asn Tyr Gly Thr His Thr Val Thr His His Ala Pro Gln Tyr Pro
65                  70                  75                  80

Phe Tyr Tyr Gly Phe Pro Gln Val Ser Thr Ser His Val Thr His His
                85                  90                  95

Ala Pro Ile Val Pro His Val Thr Ser Asn Thr Val Thr His His Ala
            100                 105                 110

Pro Tyr Thr Phe Gly Asn Leu Gly Leu Tyr Gly Gly Leu Phe Gly Tyr
            115                 120                 125

His

<210> SEQ ID NO 45
<211> LENGTH: 146
<212> TYPE: PRT
<213> ORGANISM: Sepioteuthis lessoniana

<400> SEQUENCE: 45

Met Thr Thr Thr Ser Ser Leu Leu Ala Leu Met Thr Val Ile Gly Leu
1               5                   10                  15

Val Thr Cys Cys Ala Gly Tyr Pro Ser Trp Gly Ser Thr Tyr Ser Gln
            20                  25                  30

Val Ser Thr His His Ala Pro Val Gly Trp Gly Gly Leu Gly Gly Leu
            35                  40                  45

Tyr Gly Tyr Gly Ser Leu Gly Gly Leu Gly Tyr Gly Gly Val Tyr Gly
        50                  55                  60

Gly Gly Val His Val Ala Gln Ser Pro Val Arg Tyr His Gly Tyr Ser
65                  70                  75                  80

Val Gly Thr Pro His Val Gln Ser Tyr Gly Val Asn Tyr Pro Thr Pro
                85                  90                  95

Thr Val Thr His His His Asn Thr Trp His Gly Gly Tyr Gly Gly Phe
            100                 105                 110

Gly Leu Ala Gly Pro Val Gly His Ser Val Gln Thr Val Ser Gln Gly
            115                 120                 125

Val His Thr Pro Gly Trp Gly Leu Gly Tyr Gly Leu Ser Gly Tyr Gly
        130                 135                 140

Tyr Tyr
145

<210> SEQ ID NO 46
<211> LENGTH: 337
<212> TYPE: PRT
<213> ORGANISM: Sepioteuthis lessoniana

<400> SEQUENCE: 46

Met Ala Ala Thr His Val Ile Val Val Ala Phe Leu Thr Val Thr Gly
1               5                   10                  15

Leu Val Ser Ala Gln Met Pro Phe Tyr Ala Gly Pro Asn Tyr Gly Ile
            20                  25                  30

Gly Gly Ile Gly Gly Ile Gly Phe Gly Tyr Pro Gly Gly Leu Gly Ala
            35                  40                  45

Tyr Ala His Gly Phe Glu Pro Val Thr Gly Gly Ile Phe Pro Tyr Tyr
 50                  55                  60

Gly Ala Ala His Ser Leu Pro Trp Ser Ala Pro Val Gly Gly Thr Thr
 65                  70                  75                  80

His Thr Ile Ser His Val Ala His Gly Thr Leu Pro His Pro Val Gly
                 85                  90                  95

Pro His Val Ser Thr Thr Ser Lys Thr Val Ser Val His His Pro Thr
            100                 105                 110

Thr His Val Thr Val His His Pro Ala Val Thr Thr His Val Gln His
            115                 120                 125

Pro Asp Ile Gly Phe Pro Ala Ala Leu Thr Tyr Pro Tyr Pro Gly Leu
130                 135                 140

Ser Pro Phe Phe Pro Gln Tyr Pro Thr Gly Val Leu Glu His His Ser
145                 150                 155                 160

Pro Val Ile Thr Glu Thr Thr Val Glu Lys Asn Leu Ala Lys Lys Asn
            165                 170                 175

Thr Asp Gln Thr Asn Thr Ile Tyr Thr His His Ser Pro Thr His Thr
            180                 185                 190

Ile Val Thr Lys Ser His His Val Pro Ser Gly Tyr Pro Phe Asn Gln
            195                 200                 205

Pro Gly Val Val Ser Thr Ser His His Gln Thr Val Ser His Val Asn
210                 215                 220

Pro Gly Val Gly Val Thr His Leu Pro Gly Thr Phe Pro Gly Thr Phe
225                 230                 235                 240

Pro Ala Thr Tyr Pro Gly Leu Asp Tyr Pro Tyr His Pro Gly Ser Ser
            245                 250                 255

Ala Phe Gly Ile Gln Phe Pro Tyr Leu Asn Ala Gly Leu Gln Gly Gly
            260                 265                 270

Ala Val Ser Ser Ser Ser Val His Thr Val His His Pro Gly Val Gly
            275                 280                 285

Phe Pro Pro Leu Tyr Pro Gly Thr Phe Gly Gly Tyr His Ile Gly Thr
            290                 295                 300

Tyr Pro Phe Gly Phe Ser Ser Val Thr Ser Ser Thr Thr Thr Thr
305                 310                 315                 320

Glu Lys Asp Thr Lys Ser Ser Gly Lys Ser Asp Ser Ser Ser Lys
            325                 330                 335

Asn

<210> SEQ ID NO 47
<211> LENGTH: 106
<212> TYPE: PRT
<213> ORGANISM: Sepioteuthis lessoniana

<400> SEQUENCE: 47

Met Ala Ala Gly His Leu Ile Val Ser Ala Leu Leu Ala Val Ile Ala
1                5                  10                  15

Leu Ser Ser Ser Val Asn Ala Leu Ile Pro Gly Ala Val Gly Gly Phe
            20                  25                  30

Phe Gly Ala Gly His Pro Ile Gly Thr Ser Tyr Ser Ala Ile Ser His
            35                  40                  45

Gly Gly Pro Val Gly Ala Trp Gly His Gly Phe Gly Tyr Gly Leu Gly
50                  55                  60

```
Gly Leu Tyr Gly Gly Tyr Gly Leu Gly Gly His Thr Val Ser His Val
 65                  70                  75                  80

Ser His Gly Pro Val Gly Leu Gly Tyr Gly Gly Leu Tyr Gly His Tyr
                 85                  90                  95

Gly Gly Tyr Gly Leu Gly Gly Val Tyr Gly
            100                 105

<210> SEQ ID NO 48
<211> LENGTH: 206
<212> TYPE: PRT
<213> ORGANISM: Sepioteuthis lessoniana

<400> SEQUENCE: 48

His Gly Tyr Gly Leu Gly Gly Tyr Gly His Gly Tyr Gly Leu Gly
 1               5                  10                  15

Gly Gly Tyr Gly His Gly Tyr Gly Leu Gly Gly Ile Tyr Gly His Tyr
                 20                  25                  30

Gly Gly Tyr Gly Leu Gly Gly Val Tyr Ser His Tyr Gly Val Gly Ser
             35                  40                  45

Arg Thr Val Asn His Val Ser His Arg Tyr His Pro Leu Gly Tyr Gly
 50                  55                  60

Ile Thr Tyr Pro Ile Gly His Ala Val His Arg Val Thr Gln Pro Ile
 65                  70                  75                  80

Ala His His Gly Thr Ile Ser Arg Arg Tyr Ala Ile Pro His Tyr Glu
                 85                  90                  95

Val Arg Tyr Val Ser Tyr Pro Val Gln Arg Tyr Val Gln Met Val
            100                 105                 110

Thr Val Asn Gln Pro Tyr Ile Val Pro Arg Tyr Glu Thr His Ile Arg
            115                 120                 125

Ser Tyr Gln Val Pro Val Pro Arg Tyr Gln Val His Met Ala Gln Tyr
130                 135                 140

Pro Val Val Ile Pro Arg Leu His Ile Ala Glu Ser His His Pro Val
145                 150                 155                 160

Thr His Tyr Ser Gln Val Ser His Asp Val His Gln Pro Ile Tyr Gly
                165                 170                 175

Val His Tyr Pro Met Gly His Thr Val Gln Ala Val Ser His Gln Val
            180                 185                 190

Pro Tyr Val Tyr Gly Ser Thr His Ala Tyr Gly Gly Phe Met
            195                 200                 205

<210> SEQ ID NO 49
<211> LENGTH: 378
<212> TYPE: PRT
<213> ORGANISM: Sepia. esculenta

<400> SEQUENCE: 49

Met Thr Ala Lys Tyr Val Ile Val Ala Ala Phe Leu Ala Gly Ile Val
 1               5                  10                  15

Ser Gly Gln Leu Pro Phe His Ala Phe Pro Ala Tyr Gly Ile Gly Gly
                 20                  25                  30

Ile Gly Ser Leu Gly Tyr Ala Gly Gly Ala Gly Ala Phe Ser His Gly
             35                  40                  45

Phe Gly Gln Phe Pro Gly Phe Ser Pro Tyr Tyr Gly Ile Ser Tyr Ser
 50                  55                  60

Leu Pro Leu Pro Val Ser Ala Ala Gly Ala Ala Gly Thr Thr His Thr
 65                  70                  75                  80
```

Val Ser His Thr Ser Ala Ala Val Val Pro His Pro Ala Ala Ser His
            85                  90                  95

Val Asn Lys Ala Val Thr Val Ala His His Phe Pro Ser Thr His Val
            100                 105                 110

Thr Thr Val His His Pro Val Ser Ala Val Thr Thr His Glu Gln His
            115                 120                 125

Val Asn His Gly Pro Ala Phe His Glu Val Val Pro Tyr Ser Pro Phe
130                 135                 140

Phe Tyr Gly Pro Thr Leu Ser Gln Phe Gly Pro Gln Tyr Arg Thr Ser
145                 150                 155                 160

Phe Val Lys His Gln Pro Ile Pro Ala Thr Ser His Ser Thr Val Val
            165                 170                 175

Lys Ser Thr Ser Gln Thr Ser Ser Thr Pro Gly Ser Tyr Leu Asp Leu
            180                 185                 190

Val Lys Lys Leu Ser Ser Ser Ala Ala Asn Val Ala Gln Pro Ser Thr
            195                 200                 205

Ile Tyr Ser Tyr Gln Asn Tyr Lys Pro Val Ala Ser Val Val Thr Lys
210                 215                 220

Thr Gln His Leu Pro Val Gly Tyr Pro Tyr Asn Leu Pro Asn Ile Ala
225                 230                 235                 240

Thr Thr Arg His His Gln Thr Val Ser His Val Gly Pro Glu Phe Gly
            245                 250                 255

Val Ala His Leu Pro Ser Leu Phe Pro Gly Thr Leu Ser Ala Ser Thr
            260                 265                 270

Thr Lys Tyr Gln Gln Thr Thr Ala Tyr Pro Gly Leu Gly Tyr Ser Tyr
            275                 280                 285

Gly Pro Leu Pro Gly Thr Phe Asn Ser Pro Phe Gly Ala Phe Gly Thr
290                 295                 300

Pro Phe Pro Tyr Val Asn Ala Gly Phe Pro Gly Gly Ala Val Ser Ser
305                 310                 315                 320

Ser Ala Val His Thr Val His His Pro Gly Ala Phe Thr Pro Ala Leu
            325                 330                 335

Tyr Pro Ser Ala Phe Gln Asn Tyr Pro Val Gly Thr Ser Ser Pro Val
            340                 345                 350

Ser Phe Tyr Ser Val Pro Ser Ser His Leu Lys Ile Thr Lys Thr Lys
            355                 360                 365

Ser Gln Lys Ser Ser Ser Asn Asn Lys Lys
            370                 375

<210> SEQ ID NO 50
<211> LENGTH: 326
<212> TYPE: PRT
<213> ORGANISM: Sepia. esculenta

<400> SEQUENCE: 50

Met Ala Ala Gly His Phe Ile Val Ser Ala Leu Leu Ala Val Ile Ala
1               5                   10                  15

Leu Ser Asn Cys Ala Asn Gly Val Leu Pro Gly Val Ala Gly Gly Tyr
            20                  25                  30

Gly Thr Ser Tyr Gly Thr Phe Ser His Gly Ser Phe Pro Ser Gly
            35                  40                  45

Trp Trp Gly Ser Gly Leu Ser Gly Phe Gly His Gly His Thr Val Ser
        50                  55                  60

Gln Val Ser His Gly Pro Val Gly Tyr Gly Trp Gly Tyr Gly Asn Leu

```
                65                  70                  75                  80
Gly Gly Tyr Gly Gly Tyr Gly Leu Gly Gly Ile Ser Gly His Tyr Gly
                    85                  90                  95

Gly Tyr Gly Leu Gly Gly Ile Ser Gly His Tyr Gly Gly Tyr Gly Leu
                100                 105                 110

Gly Gly Leu Tyr Gly His Tyr Gly Tyr Gly Leu Gly Gly Leu His
                115                 120                 125

Gly His Phe Gly Gly Tyr Gly Leu Gly Gly Tyr Gly Gly Tyr Gly
            130                 135                 140

Leu Pro Gly Met Tyr Gly Ala Tyr Gly Gly Tyr Gly His Gly Gly Val
145                 150                 155                 160

Tyr Ser His Tyr Gly Ile Gly Gly Arg Thr Ile Asn Gln Val Thr Arg
                165                 170                 175

Arg Leu His Pro Leu Gly Tyr Gly Ile Pro Tyr Pro Val Gly His Ala
                180                 185                 190

Val His Arg Val Thr Gln Pro Ile Ala His Tyr Gly Thr Ile Ser Arg
                195                 200                 205

Arg Phe Ala Ile Pro Gln Tyr Glu Val Arg Tyr Val Ser Tyr Pro Val
            210                 215                 220

Thr His Arg Tyr Ile Gln Met Val Thr Val Ser Lys Pro Tyr Val Val
225                 230                 235                 240

Pro Arg Tyr Glu Met His Val Arg Gln Tyr Gln Val Pro Val Pro Arg
                245                 250                 255

Tyr Tyr Val Thr Met Ala Gln Tyr Pro Val Val Ile Pro Arg Val His
                260                 265                 270

Ile Ala Glu Ser His Gln Pro Val Thr His Ile Ser His Val Ser Arg
                275                 280                 285

Asp Tyr His Gln Pro Ile Ile Gly Met His Tyr Pro Met Gly Gln Thr
            290                 295                 300

Ile Glu Ser Val Ser His His Glu Pro Phe Val Tyr Gly Ala Thr His
305                 310                 315                 320

Thr Tyr Gly Gly Gly Tyr
                325

<210> SEQ ID NO 51
<211> LENGTH: 162
<212> TYPE: PRT
<213> ORGANISM: Sepia. esculenta

<400> SEQUENCE: 51

Met Ala Ala Thr Ala Thr Leu Leu Val Leu Met Ser Val Ile Gly Leu
1               5                   10                  15

Thr Ser Cys Tyr Pro Gly Tyr Phe Gly Gly Tyr Gly Gly Ala Leu Pro
                20                  25                  30

Ala Ala Ser Thr Tyr Ser Gln Val Ser His His Gly Trp Gly Gly
            35                  40                  45

Leu Gly Gly Leu Tyr Gly Tyr Gly Val His Leu Pro Val Ser Thr Thr
50                  55                  60

Ser His Val Ser His Gly Ala His Tyr Gly Gly Trp Gly Tyr Pro Gly
65                  70                  75                  80

Leu Tyr Gly Gly Val His Val Ser Gln Ser Pro Val Arg Tyr His Gly
                85                  90                  95

Tyr Ser Val Gly Thr Pro His Val Gln Ser Tyr Gly Val His Tyr Pro
                100                 105                 110
```

```
Thr Thr Ser Val Thr His Ser His Gly Asp Trp Gly Leu Gly Glu Tyr
            115                 120                 125

Gly Tyr Gly Ala Pro Leu Ala His Ser Val Gln Thr Val Ser His Gly
        130                 135                 140

Phe Gly His Asn His Leu Glu Leu Gly Tyr Gly Leu His Ser Phe Gly
145                 150                 155                 160

His Phe

<210> SEQ ID NO 52
<211> LENGTH: 201
<212> TYPE: PRT
<213> ORGANISM: Sepia. esculenta

<400> SEQUENCE: 52

Met Met Ala Asn Val Leu Phe Ile Leu Ser Leu Ile Ala Ala Leu Ser
1               5                   10                  15

Cys Gln Leu Ala Ala Ala Leu Ala Ala Ile Lys Thr Ser Ser Thr Ala
            20                  25                  30

Val His His Ser Pro Pro Thr Val Ala His Thr Val His Ser Ile Ala
        35                  40                  45

His Ala Val Pro His Pro Tyr Thr Phe Gly Val Trp Pro Tyr Gly Asp
50                  55                  60

Phe Tyr Gly Gly Leu Tyr Gly Tyr Pro Pro Thr Thr Ser Val Lys Thr
65                  70                  75                  80

Val Ser His Gly Leu His Pro Ala Val Gly Thr Thr Ser Val Ser His
                85                  90                  95

Thr Ser Gln Gly Ile His Gln Pro Leu Pro Tyr Gly Phe His Gly
            100                 105                 110

Gly Phe Tyr Pro Gly Ala Ala Phe His Tyr Pro Leu Gly Leu Gly Tyr
        115                 120                 125

Gly Phe Gly Gly Leu Tyr Gly Gly Phe Gln Gly Phe His Asn Pro Gly
        130                 135                 140

Ala Thr Thr Val Ser His Thr Thr Gln Gly Val His His Pro Gly Leu
145                 150                 155                 160

Gly Tyr Gly Phe Leu Pro Tyr Gly Ala Ala His Val Pro Thr Ser Thr
                165                 170                 175

Ser Val Ser His Thr Thr Gln Gly Leu Ser His Pro Ala Phe Gly Trp
            180                 185                 190

Asn Tyr Gly Asn Val Phe Gly Leu His
        195                 200

<210> SEQ ID NO 53
<211> LENGTH: 189
<212> TYPE: PRT
<213> ORGANISM: Sepia. esculenta

<400> SEQUENCE: 53

Met Ala Ile Lys Thr Phe Thr Ala Thr Leu Ile Ala Val Leu Gly
1               5                   10                  15

Leu Ile Ala Cys Ser Glu Ala Ile Phe Pro Ala Tyr Tyr Gly Ser Tyr
            20                  25                  30

Tyr Pro Gly Tyr Arg Arg Ser Val Ser Ser Val Thr His Pro Val
        35                  40                  45

Gly Tyr Gly Gly Phe Gly Tyr Gly Ser His Tyr Gly Gly Phe Tyr Gly
        50                  55                  60

Gly Tyr Pro Ala Ala Ser Thr Val Thr His Thr Ala His Gly Val Pro
```

```
                 65                  70                  75                  80
Tyr Ser Gly Val Gly Tyr Gly Trp Gly Leu Ala Gly Leu His Gly Gly
                     85                  90                  95
Tyr Gly Trp His Tyr Pro Ala Gly Tyr Gly Gly Trp Gly Leu Asn Gly
                100                 105                 110
Val Tyr Gly Phe His His Pro Val Gly Ala Ser Val Ser Thr Val Ser
                115                 120                 125
His His Pro Gly Phe Tyr Gly Gly Tyr Gly Leu Gly Phe Gly Tyr Gly
            130                 135                 140
Gly Trp Gly Tyr Pro Ala Ala Thr Tyr Ser His Val Ala His Gln Pro
145                 150                 155                 160
Phe Gly Leu Gly Tyr Gly Tyr Gly Ala Trp Gly Tyr Pro Gly Ala Ser
                165                 170                 175
Tyr Thr Ser His Val Ala His His Pro Phe Gly Phe Tyr
            180                 185
```

<210> SEQ ID NO 54
<211> LENGTH: 765
<212> TYPE: DNA
<213> ORGANISM: Dosidicus gigas

<400> SEQUENCE: 54

```
atgacgacca tgttttccgc tttggtatcc ctcgccgttg tactcggtgt gctcagttac    60
acatcagctt atcacgcaaa ccatgtcggt actttgtggg caaaaccccc acaacaaact   120
ccatatggtg gatatggagt ttctggagga gctggtcagg gaggatacgg cttaggtggt   180
tatggtggct atggtagcta tggtggcctt ggaggctatg gtggctatgg tggccttggc   240
ggctatggcg gctacggtgg ccttggcggc tatggtggat atggcggtta tggacaagga   300
ggatatagca caggaggaca tggacatgga ggatacggtt tggaggata tggacaagga   360
ggctacggct ttggtggata tggacaaggg ggctacggac aaggaggcta cggacaagga   420
ggctctggct atggtggata cggccattac tacccgacaa catcatatgg tggctatctt   480
ggcggatacg gcggatacgg cgggtactac ccacacactt catctggttc ttactacccc   540
acaacttacg gaggatctaa tcagggaaat cccggtgccc caatttcatc agttctggt    600
tttgtatttc cgggttatca ctttcctgga gtgttccatg gtggcgtgaa ccaaggcgct   660
ggtagaacta gtggaaccga cctgcaaagg ctccttaatt taaacggatt taaaccaact   720
gcaacttcaa caacatcgac atcaaacagc aactccaaga agtaa                    765
```

<210> SEQ ID NO 55
<211> LENGTH: 753
<212> TYPE: DNA
<213> ORGANISM: Dosidicus gigas

<400> SEQUENCE: 55

```
atgacgacat gtttcgcttg gtatccctcg cgtgtactcg tgtgctcagt acacatcagc    60
tatcacgcaa tcatgtcggt actttgtggc aaaaccccc caacaactcc atatggtgga   120
tatggagttt ctggaggagc tggtcaggga ggatacggct aggtggtta tggtggctat   180
ggtagctatg gtggccttgg aggctatggt ggctatggtg ccttggcgg ctatggcggc   240
tacggtggcc ttggcggcta tggtggatat ggcggttatg gacaaggagg atatagcaca   300
ggaggacatg gacatggagg atacggtttt ggaggatatg gacaaggagg ctacggcttt   360
ggtggatatg gacaagggg ctacggacaa ggaggctacg gacaaggagg ctctggctat   420
```

```
ggtggatacg gccattacta cccgacaaca tcatatggtg gctatcttgg cggatacggc    480
ggatacggcg gtactaccc acacacttca tctggttctt actacccac aacttacgga     540 ggatctaatc agggaaatcc cggtgcccca atttcatcca gttctggttt tgtatttccg    600
ggttatcact ttcctggagt gttccatggt ggcgtgaacc aaggcgctgg tagaactagt    660
ggaaccgacc tgcaaaggct ccttaattta acggattta aaccaactgc aacttcaaca    720
acattgacat caaacagcaa ctccaagaag taa                                  753

<210> SEQ ID NO 56
<211> LENGTH: 765
<212> TYPE: DNA
<213> ORGANISM: Dosidicus gigas

<400> SEQUENCE: 56
atgacgacca tgttttccgc tttggtatcc ctcgctgttg tactcggtgt gctcagttca     60
acatcagctt atcacgcaaa ccatgtcggt actttgtggg caaaaccccc acaacaaact    120
ccatatggtg gatatggagt ttctggagga gctggtcagg gaggatacgg cttaggtggt    180
tatggtggct atggtagcta tggtggcctt ggaggctatg gtggctatgg tggccttggc    240
ggctatggcg gctacggtgg ccttggcggc tatggtggat atggcggtta tggacaagga    300
ggatatagca caggaggaca tggacatgga ggatacggtt ttggaggata tggacaagga    360
ggctacggct ttgtggata tggacaaggg ggctacggac aaggaggcta cggacaagga    420
ggctctggct atggtggata cggccattac tacccgacaa catcatatgg tggctatctt    480
ggcggatacg gcggatacgg cgggtactac ccacacactt catctggttc ttactacccc    540
acaacttacg gaggatctaa tcagggaaat cccggtgccc caatttcatc cagttctggt    600
tttgtatttc cggttatca ctttcctgga gtgttccatg gtggcgtgaa ccaaggcgct     660
ggtagaacta gtggaaccga cctgcaaagg ctccttaatt taaacggatt taaaccaact    720
gcaacttcaa caacatcgac atcaaacagc aactccaaga agtaa                     765

<210> SEQ ID NO 57
<211> LENGTH: 636
<212> TYPE: DNA
<213> ORGANISM: Dosidicus gigas

<400> SEQUENCE: 57
atgacgacca tgttttccgc tttggtatcc ctcgccgttg tactcggtgt gctcagttac     60
acatcagctt atcacgcaaa ccatgtcggt actttgtggg caaaaccccc acaacaaact    120
ccatatggtg gatatggagt ttctggagga gctggtcagg gaggatacgg cttaggtggt    180
tatggtggct atggtagcta tggtggcctt ggaggctatg gtggctatgg tggccttggc    240
ggctatggcg gctacggtgg ccttggcggc tatggtggat atgcggtta tggacaagga    300 ggatatagca caggaggcta cggctttggt ggatatggac aaggggcta cggacaagga    360 ggctacggac aaggaggctc tggctatggt ggatacggcc attactaccc gacaacatca    420
tatggtggct atcttggcgg atacggcgga tacggcgggt actacccaca cacttcatct    480
ggttcttact accccacaac ttacggagga tctaatcagg gaaatcccgg tgccccaatt    540
tcatccagtt ctggttttgt atttccagga attttcgcaa ccaaaattc acgctcatta    600 ttctgtaaac attatgaaat aaagatggtt aattga                               636

<210> SEQ ID NO 58
<211> LENGTH: 741
```

```
<212> TYPE: DNA
<213> ORGANISM: Dosidicus gigas

<400> SEQUENCE: 58
atggctcaca tttctcttac tgcagtatgc ttgagcacta tgcactgctg tattgcagtg      60
ccacatctgt tagcgtacca ctcatcatgc tcagcagcat taggtgtcta tggcggttat     120
ggacttggcg catacggatt tggctaccca ggagccacag taagccacac cactcatcat     180
gctccatacg gatttggagg tctctatgga ggatatggag gtcttctcca tggtggtctc     240
tatggaggat acggtcttgg tgcatatgga ttcggttacc cagcagctac agtaagccac     300
actacccatc atgctccata cggatatgga ggtctctatg gaggatatgg aggtcttctc     360
cacggtggtc tctatggtgg atacggactt ggcgcctatg gattcggtta cccagcagct     420
acagtgagcc aaactaccca tcatgctcca tacggatatg gaggtgtcta tggaggatat     480
ggtcttcttc atggtggtct ttatggtgga tacggacttg gcggatatgg actgggttac     540
ccagcagcta ctgccgttag ccacaccacc accatgctcc actaggaata tggaggtctg     600
tatggaggat atggaggtct tctccatgga ggtctctatg gtggatatgg agctacagcc     660
gttagccaca ccacccatca tgcccctcta ggatatggcc tggctggata tggaggtctc     720
tacggaggtt ttctccactg a                                              741

<210> SEQ ID NO 59
<211> LENGTH: 1194
<212> TYPE: DNA
<213> ORGANISM: Dosidicus gigas

<400> SEQUENCE: 59
atggcagcaa gcatcctcac attgttggca gttattgcct tgagcagctg tacacttgcc      60
gttgttccag cggccacaac tgtcagtcgc acaacacatc atgctccata cggatacggt     120
ggcgtcttag gtggatatgg tggtctttat ggtggatatg gacttggtgg atatggactt     180
ggtggatatg gtcttgctgg atatggcggt ctccatggag gcctctatgg tggatatgga     240
ctcggcgcat atggattcgg ttatccagcc gctacagtaa gtcacacaac acatcatgct     300
ccatacggat ttggtggtct ctatggtgga catggtcttc tccacggcgg tctctatgga     360
ggatatggtc ttcaccatgg tggtctctac ggaggatacg gacttggcgc atacggattc     420
ggttacccag tagccacagc tgttagccat gtaactcatc atgctccata cggatatggt     480
cttgccggat atggtggttt ccatggtggg tatggtcttc tccacggcgg tctctatgga     540
ggatatggtc ttcaccatgg cggtctctat ggtggatatg gacttggcgc atatggattc     600
ggttacccag cagccacagt aagccatacc actcatcatg ctccatacgg atttggaggt     660
ctctatggtg gacatggtct tctccatggc ggtctctacg gaggatatgg tcttcaccat     720
ggcggtctct atggtggata tggacttggc gcatacggat tcggttaccc agcagctaca     780
gtaagtcaca ccactcatca cgctccatac ggatttggag gtctctatgg aggatacggt     840
cttcaccatg gcggtctcta tggaggatat ggtcttctcc acggtggtct ctacggagga     900
tatggtcttc atcatggcgg tctctatggt ggatatggac ttggtgctta tggattcggc     960
tacccaggag ctgctacagt aagccacaca actcatcatg ctccatacgg atttggaggt    1020
ctctatggag atacggtct tcaccatggc ggtctctatg gaggatatgg tcttctccat    1080
ggtggtcttt atggaggata tggacttggc gctgttagcc acaccaccca tcatgctccc    1140
tacggatatg gtcttggcgg atatggtgga ctctatggtg gatggcttca ctag          1194
```

<210> SEQ ID NO 60
<211> LENGTH: 966
<212> TYPE: DNA
<213> ORGANISM: Dosidicus gigas

<400> SEQUENCE: 60

```
atggcagcaa gcatcctcac attgttggca gttattgcct tgagcagctg tacacttgcc      60
gttgttccag cggccacaac tgtcagtcgc acaacacatc atgctccata cggatacggt     120
ggcgtcttag gtggatatgg tggtctttat ggtggatatg acttggtgg atatggactt      180
ggtggatatg gtcttgctgg atatggcggt ctccatggag gcctctatgg tggatatgga     240
ctcggcgcat atggattcgg ttatccagcc gctacagtaa gtcacacaac acatcatgct     300
ccatacggat ttggtggtct ctatggtgga catggtcttc tccacggcgg tctctatgga     360
ggatatggtc ttcaccatgg tggtctctac ggaggatacg acttggcgc atacggattc      420
ggttacccag tagccacagc tgttagccat gtaactcatc atgctccata cggatatggt     480
cttgccggat atggtggttt ccatggtggg tatggtcttc tccacggcgg tctctatgga     540
ggatatggtc ttcaccatgg cggtctctat ggtggatatg acttggcgc atatggattc      600
ggttacccag cagccacagt aagccatacc actcatcatg ctccatacgg atttggaggt     660
ctctatggtg acatggtct ctccatggc ggtctctacg gaggatatgg tcttcaccat       720
ggcggtctct atggtggata tggacttggc gcatacggat tcggttaccc agcagctaca     780
gtaagtcaca ccactcatca cgctccatac ggatttggag gtctctatgg aggatacggt     840
cttcaccatg gcggtctcta cgggaggat acgggttctt cagcacggcg gtcttctatg      900
ggaagggata tgggtcttct ccatgggtgg tcttttatgg agggatatgg acttgggcgc     960
tgttag                                                                 966
```

<210> SEQ ID NO 61
<211> LENGTH: 678
<212> TYPE: DNA
<213> ORGANISM: Dosidicus gigas

<400> SEQUENCE: 61

```
atggctgcaa ttttcacatt gctggcagtt cttgccatca gcaactatgc ttctgctatt      60
ttgccagcgg caacatctgt tagccgaacc acacatcgta ctggatacgg atatggagga     120
ctccttggtg atacggcct acactaccca gcaactacag ctgtcagtca cacaactcac      180
catgctccag cagcattagg tgtctatggt ggatatggac ttggtgctta tggattcggc     240
tacccaggag ctgctacagt aagccacaca actcatcatg ctccttacgg atatggtggt     300
ctctatggtg gatatggtct tgcccatggt ggtctctatg gtggatatgg acttggcgca     360
tacggatacg gctacccagc tgccacagct gtcagccaca ccacccatca tgctccttac     420
ggatatggtc ttggcggata tgtggtctc tatggaggat atggtcttgc ccatggcggt      480
ctctacggag gatatggact tggcggatac ggactccact acccagctgc cacagccgtt     540
agccacacca cccatcatgc cccactcgga tatggtcttg ctggatacgg tggtctctat     600
ggaggtctct atgaaggata tggactggtg gatatggtgc cgcagctgtc agccacacca     660
cccatcatgc tccactag                                                    678
```

<210> SEQ ID NO 62
<211> LENGTH: 1257
<212> TYPE: DNA
<213> ORGANISM: Dosidicus gigas

<400> SEQUENCE: 62

```
atggctgcaa ttttcacatt gctggcagtt cttgccatca gcaactatgc ttctgctatt      60
ttgccagcgg caacatctgt tagccgaacc acacatcgta ctggatacgg atatggagga     120
ctccttggtg gatacggcct acactaccca gcaactacag ctgtcagtca cacaactcac     180
catgctccag cagcattagg tgtctatggt ggatatggac ttggtgctta tggattcggc     240
tacccaggag ctgctacagt aagccacaca actcatcatg ctccttacgg atatggtggt     300
ctttatggtg gatatggtct tgcccatggt ggtctctatg gtggatatgg acttggcgca     360
tacggatacg gctacccagc tgccacagct gtcagccaca ccacccatca tgctccttac     420
ggatatggtc ttgcggata tggtggtctc tatggaggat atggtcttgc ccatggcggt     480
ctctacggag gatatggact tggcggatac ggactccact acccagctgc cacagccgtt     540
agccacacca cccatcatgc cccactcgga tatggtcttg ctggatacgg tggtctctat     600
ggaggtctct atggaggata tggacttggt ggatatggtg ccgcagctgt cagccacacc     660
acccatcatg ctccactagg atatggtctt ggcggatatg gtggtctcta tggaggtctc     720
tacgaggat atggacttgg cggatacgga ctccactacc cagctgccac agccgttagc     780
cacaccaccc atcatgctcc actcggatat ggtcttggcg gatatggtgg tctctatgga     840
ggtctctatg gaggatatgg acttggagga tatggtccgg ctgtcagcca cactactcac     900
catgcccac ttgggtttgg aggtctttat ggaggatatg gagttggtgg atacggatat     960
ggttacccag cagcagctac agtaagccac accaccatc atgctccata cggatatggt    1020
ggtctttatg gcggatatgg tcttgcccat ggtggtcttt atggtggata tggatttggt    1080
gccgttagcc acactactca tcatgctcca cttggattcg gaggtcttta tggcggatat    1140
ggtcttgccc atggtggtct ctatggaggt tatggactcg gtgccgttag ccacaccacc    1200
catcatgctc catatggatt cggtggtctc tatggtggat atggtctcct ccactaa      1257
```

<210> SEQ ID NO 63
<211> LENGTH: 756
<212> TYPE: DNA
<213> ORGANISM: Dosidicus gigas

<400> SEQUENCE: 63

```
atggcttcaa caattttctc tttactggca gttattgctt tgagcaacta tgccactgct      60
gtattgccag tggccacatc tgttagccgt accactcatc atgctccagc agcattaggt     120
gtctatggcg gttatggact tggcgcatac ggatttggct acccaggagc acagtaagc     180
cacaccactc atcatgctcc atacggattt ggaggtctct atggaggata tggaggtctt     240
ctccatggtg gtctctatgg aggatacggt cttggtgcat atggattcgg ttacccagca     300
gctacagtaa gccacactac ccatcatgct ccatacggat atgaggtct ctatggagga     360
tatggaggtc ttctccacgg tggtctctat ggtggatacg gacttggcgc ctatggattc     420
ggttacccag cagctacagt gagccaaact acccatcatg ctccatacgg atatgaggt     480
gtctatggag gatatggtct tcttcatggt ggtctttatg gtggatacgg acttggcgga     540
tatggactgg gttacccagc agctactgcc gttagccaca ccaccacca tgctccacta     600
ggatatggag gtctgtatgg aggatatgga ggtcttctcc atgaggtct ctatggtgga    660
tatggagcta cagccgttag ccacaccacc catcatgccc ctctaggata tggcctggct    720
ggatatggag gtctctacgg aggttttctc cactga                                756
```

<210> SEQ ID NO 64
<211> LENGTH: 783
<212> TYPE: DNA
<213> ORGANISM: Dosidicus gigas

<400> SEQUENCE: 64

| | | | | | |
|---|---|---|---|---|---|
| atggcttcaa | caattttcac | attgctggca | gttattgctt | tgagcagcta | tgccgccgcc | 60 |
| attttgccag | cgaccacatc | tgttagccgc | accacacatc | atgctccagt | ctatggagga | 120 |
| tatggtcttc | tccatggagg | tctctatggt | ggatatggac | ttggcgcagc | tactgtaagc | 180 |
| catacaactc | atcatgctcc | ctacggatat | ggaggtctct | atggtggata | tggtcttgcc | 240 |
| catggtggtc | tttacggagg | ttatggcctt | ggtgcttatg | gactcggtta | cccagcagcc | 300 |
| gcagccgtta | gccacactac | tcatcatgct | ccactaggat | ttggaggtct | ctacggtgga | 360 |
| tatggactcg | gagccgtcag | ccacaccact | caccatgctc | cactcggatt | cggaggtgtt | 420 |
| cttggtggat | atggacttgg | ggccgtcagc | cacactaccc | accatgctcc | acttggattt | 480 |
| ggaggtcttt | atggaggata | cggacttgga | gccgttagcc | acaccaccca | ccatgctcca | 540 |
| cttggatttg | gaggtgttgt | tggaggatat | ggacttggag | ccgttagcca | cactacccat | 600 |
| catgctcccc | ttggatttgg | ggtctctat | ggtggatatg | gacttggagc | cgtcagccac | 660 |
| accacccacc | atgctccact | tggatttggg | ggtctctatg | gaggatatgg | agccgttagc | 720 |
| cacaccactc | atcatgctcc | attaggatat | ggtcttgccg | gatatggtgc | ttggcttcac | 780 |
| tga | | | | | | 783 |

<210> SEQ ID NO 65
<211> LENGTH: 1590
<212> TYPE: DNA
<213> ORGANISM: Dosidicus gigas

<400> SEQUENCE: 65

| | | | | | |
|---|---|---|---|---|---|
| atggcaacaa | caattttcgc | cattttggca | gttattgctt | tgagcaacta | cgcttctgct | 60 |
| atcgccccag | cggcaacttc | tgtaagccgc | accacacacc | atgctggata | cggatatggc | 120 |
| ggtccccttg | gcggatatgg | actcggtgca | tacggtttcg | gttctccagc | agctacagta | 180 |
| agccatacaa | ctcatcatgc | accatacgga | tatggcggtc | tctatggtgg | atatggaggt | 240 |
| ctctatggtg | gacatggcct | tctccatggt | ggtctttatg | gaggatatgg | ccatctccat | 300 |
| ggtggtctct | atggtggata | tggacttggc | gcatatggat | ttggataccc | agcagccgct | 360 |
| gctgttagcc | acaccactca | tcatgctcca | ttaggatttg | gtcttgcagg | atatggaggt | 420 |
| ctttatggag | gatatggact | tggtggatat | ggtggtctcc | acggcggtct | ctatggtgga | 480 |
| tatggacttg | gtgcatacgg | tttcggttac | ccagctgcta | cagctgttag | ccacaccacc | 540 |
| catcatgctc | catacggata | cggtcttggt | ggatatggtg | gtctttatgg | aggtctctat | 600 |
| ggtggatatg | gacttgctgg | atatggaggt | gtctatggtg | gacatggtct | tctccatggc | 660 |
| ggtctatatg | gcgggtatgg | gcttggtgca | tacggattcg | gctacccagc | agctgctaca | 720 |
| gtaagccaca | caactcatca | tgctccttac | ggatatgggg | gtctctacgg | tggatatggt | 780 |
| cttgcccatg | gcggtctcta | cgcccatggc | ggtctctacg | gaggatatgg | acttggcgga | 840 |
| tacggactcc | actacccagc | tgccacagcc | gttagccaca | ccacccatca | tgccccactc | 900 |
| ggatatggtc | ttgctggata | cggtggtctc | tatggaggtc | tctatggagg | atatggactt | 960 |
| ggtggatatg | gtgccgcagc | tgtcagccac | accacccatc | atgctccact | aggatatggt | 1020 |
| cttggcggat | atggtggtct | ctatggaggt | ctctacggag | gatatggact | tggcggatac | 1080 |

| | | | |
|---|---|---|---|
| ggactccact | acccagctgc | cacagccgtt | agccacacca cccatcatgc tccactcgga | 1140 |
| tatggtcttg | gcggatatgg | tggtctctat | ggaggtctct atggaggata tggacttgga | 1200 |
| ggatatggtg | ccgctgtcag | ccacactact | caccatgccc cacttgggtt tggaggtctt | 1260 |
| tatggaggat | atggagttgg | tggatacgga | tatggttacc cagcagcagc tacagtaagc | 1320 |
| cacaccaccc | atcatgctcc | atacggatat | ggtggtcttt atggcggata tggtcttgcc | 1380 |
| catggtggtc | tctatggtgg | atatggattt | ggtgccgtta gccacactac tcatcatgct | 1440 |
| ccacttggat | tcggaggtct | ctatggcgga | tatggtcttg cccatggtgg tctttatgga | 1500 |
| ggttatggac | tcggtgccgt | tagccacacc | acccatcatg ctccatatgg attcggtggt | 1560 |
| ctttatggtg | gatatggtct | cctccactaa | | 1590 |

<210> SEQ ID NO 66
<211> LENGTH: 1227
<212> TYPE: DNA
<213> ORGANISM: Dosidicus gigas

<400> SEQUENCE: 66

| | | | |
|---|---|---|---|
| atggcaacaa | caattttcgc | cattttggca | gttattgctt tgagcaacta cgcttctgct | 60 |
| atcgccccag | cggcaacctc | tgtaagccgc | accacacacc atgctggata cggatatggc | 120 |
| ggtctctatg | gtggatatgg | acttggcgca | tacggattcg gttacccagc agctacagta | 180 |
| agtcacacca | ctcatcacgc | tccatacgga | tttggaggtc tctatggagg atacggtctt | 240 |
| caccatggcg | gtctctatgg | aggatatggt | cttctccacg gtggtctcta cggaggatat | 300 |
| ggtcttcatc | atggcggtct | ctatggtgga | tatggacttg gtgcttatgg attcggctac | 360 |
| ccaggagctg | ctacagtaag | ccacacaact | catcatgctc catacggatt ggaggtctc | 420 |
| tatggaggat | atggtcttgc | ccatggcggt | ctctacggag gatatggact ggcggatac | 480 |
| ggactccact | acccagctgc | cacagccgtt | agccacacca cccatcatgc cccactcgga | 540 |
| tatggtcttg | ctggatacgg | tggtctctat | ggaggtctct atggaggata tggacttggt | 600 |
| ggatatggtg | ccgcagctgt | cagccacacc | acccatcatg ctccactagg atatggtctt | 660 |
| ggcggatatg | gtggtctcta | tggaggtctc | tacggaggat atggacttgg cggatacgga | 720 |
| ctccactacc | cagctgccac | agccgttagc | cacaccaccc atcatgctcc actcggatat | 780 |
| ggtcttggcg | gatatggtgg | tctctatgga | ggtctctatg gaggatatgg acttggagga | 840 |
| tatggtgccg | ctgtcagcca | cactactcac | catgccccac ttgggtttgg aggtctttat | 900 |
| ggaggatatg | gagttggtgg | atacggatat | ggttacccag cagcagctac agtaagccac | 960 |
| accaccatc | atgctccata | cggatatggt | ggtctttatg gcggatatgg tcttgcccat | 1020 |
| ggtggtctct | atggtggata | tggatttggt | gccgttagcc acactactca tcatgctcca | 1080 |
| cttggattcg | gaggtctcta | tggcggatat | ggtcttgccc atggtggtct ttatggaggt | 1140 |
| tatggactcg | gtgccgttag | ccacaccacc | atcatgctc catatggatt cggtggtctt | 1200 |
| tatggtggat | atggtctcct | ccactaa | | 1227 |

<210> SEQ ID NO 67
<211> LENGTH: 1488
<212> TYPE: DNA
<213> ORGANISM: Dosidicus gigas

<400> SEQUENCE: 67

| | | | |
|---|---|---|---|
| atggcagcaa | gcatcctcac | attgttggca | gttattgcct tgagcagctg tacacttgcc | 60 |

| | |
|---|---|
| gttgttccag cggccacaac tgtcagtcgc acaacacatc atgctccata cggatacggt | 120 |
| ggcgtcttag gtggatatgg tggtctttat ggtggatatg gacttggtgg atatggactt | 180 |
| ggtggatatg gtcttgctgg atatggcggt ctccatggag gcctctatgg tggatatgga | 240 |
| ctcggcgcat atggattcgg ttatccagcc gctacagtaa gtcacacaac acatcatgct | 300 |
| ccatacggat ttggtggtct ctatggtgga catggtcttc tccatggcgg tctctacgga | 360 |
| ggatatggtc ttcaccatgg cggtctctat ggtggatatg gacttggcgc atacggattc | 420 |
| ggttacccag cagctacagt aagtcacacc actcatcacg ctccatacgg atttggaggt | 480 |
| ctctatggag gatacggtct tcaccatggc ggtctctatg gaggatatgg tcttctccac | 540 |
| ggtggtctct acggaggata tggtcttcat catggcggtc tatatggcgg gtatgggctt | 600 |
| ggtgcatacg gattcggcta cccagcagct gctacagtaa gccacacaac tcatcatgct | 660 |
| ccttacggat atggggtct ctacggtgga tatggtcttg cccatggcgg tctctacgga | 720 |
| ggatatggac ttggcggata cggactccac tacccagctg ccacagccgt tagccacacc | 780 |
| acccatcatg ccccactcgg atatggtctt gctggatacg gtggtctcta tggaggtctc | 840 |
| tatggaggat atggacttgg tggatatggt gccgcagctg tcagccacac cacccatcat | 900 |
| gctccactag gatatggtct tggcggatat ggtggtctct atggaggtct ctacggagga | 960 |
| tatggacttg gcggatacgg actccactac ccagctgcca cagccgttag ccacaccacc | 1020 |
| catcatgctc cactcggata tggtcttggc ggatatggtg gtctctatgg aggtctctat | 1080 |
| ggaggatatg gacttggagg atatggtgcc gctgtcagcc acactactca ccatgcccca | 1140 |
| cttgggtttg gaggtcttta tggaggatat ggagttggtg gatacggata tggttaccca | 1200 |
| gcagcagcta cagtaagcca caccacccat catgctccat acggatatgg tggtctttat | 1260 |
| ggcggatatg gtcttgccca tggtggtctc tatggtggat atggatttgg tgccgttagc | 1320 |
| cacactactc atcatgctcc acttggattc ggaggtctct atggcggata tggtcttgcc | 1380 |
| catggtggtc tttatggagg ttatggactc ggtgccgtta gccacaccac ccatcatgct | 1440 |
| ccatatggat tcggtggtct ttatggtgga tatggtctcc tccactaa | 1488 |

<210> SEQ ID NO 68
<211> LENGTH: 1794
<212> TYPE: DNA
<213> ORGANISM: Dosidicus gigas

<400> SEQUENCE: 68

| | |
|---|---|
| atggcagcaa gcatcctcac attgttggca gttattgcct tgagcagctg tacacttgcc | 60 |
| gttgttccag cagccacaac tgtcagtcgc acaacacatc atgctccata cggatacggt | 120 |
| ggcctcttag gtggatatgg tggtcttcat ggtggatatg gacttggtgg atatggtctt | 180 |
| gctggatatg gcggtctcca tggaggcctc tatggtggat atggactcgg cgcatatgga | 240 |
| ttcggttatc cagccgctac agtaagtcac acaacacatc atgctccata cggatttggt | 300 |
| ggtctctatg gtggacatgg tcttctccac ggcggtctct atggaggata tggtcttcac | 360 |
| catggcggtc tctacggagg atacggactt ggcgcatacg gattcggtta cccagcagcc | 420 |
| acagctgtta gccatgttac tcatcatgct ccatacggat atggtcttgc cggatatggt | 480 |
| ggtctctacg gtggatatgg tcttgcccat ggtggtctct atggaggata tggacttgcc | 540 |
| ggatatggtg gtctctatgg tggatatgga cttggtgcat acggattcgg ttacccagct | 600 |
| gctacagctg ttagccacac cacccatcat gctccatacg gatacggtct aggtggatat | 660 |
| ggtggtctct atggaggtct ctatggtgga tatggacttg ctggatatgg aggtctctat | 720 |

```
ggtggacatg gtcttctcca tggcggtcta tatggcgggt atgggcttgg tgcatacgga      780
ttcggctacc cagcagctgc tacagtaagc cacacaactc atcatgctcc ttacggatat      840
ggtggtctct acggtggata tggtcttgcc catggcggtc tctatggtga tatggacttg      900
gcgcatacgg atacgctacc cagctgctac agctgtcagc cacacaccca tcatgctcta      960
cggatatggt ctggccggat atgtggtctc tatgagatat gtcttgccca tggcggtctc     1020
tacggaggat atggacttgg cggatacgga ctccactacc cagctgccac agccgttagc     1080
cacaccaccc atcatgcccc actcggatat ggtcttgctg gatacggtgg tctctatgga     1140
ggtctctatg gaggatatgg acttggtgga tatggtgccg cagctgtcag ccacaccacc     1200
catcatgctc cactaggata tggtcttggc ggatatggtg gtctctatgg aggtctctac     1260
ggaggatatg gacttggcgg atacggactc cactacccag ctgccacagc cgttagccac     1320
accacccatc atgctccact cggatatggt cttggcggat atggtggtct ctatggaggt     1380
ctctatggag atatggact tggaggatat ggtgccgctg tcagccacac tactcaccat      1440
gccccacttg ggtttggagg tctttatgga ggatatggag ttggtggata cggatatggt     1500
tacccagcag cagctacagt aagccacacc acccatcatg ctccatacgg atatggtggt     1560
ctttatggcg gatatggtct tgcccatggt ggtctctatg gtggatatgg atttggtgcc     1620
gttagccaca ctactcatca tgctccactt ggattcggag gtctctatgg cggatatggt     1680
cttgcccatg gtggtcttta tggaggttat ggactcggtg ccgttagcca caccacccat     1740
catgctccat atggattcgg tggtctttat ggtggatatg gtctcctcca ctaa          1794

<210> SEQ ID NO 69
<211> LENGTH: 534
<212> TYPE: DNA
<213> ORGANISM: Dosidicus gigas

<400> SEQUENCE: 69
atggctgcaa ttttcacatt gctggcagtt cttgccatca gcaactatgc ttctgctatt        60
ttgccagcgg caacatctgt tagccgaacc acacatcgta ctggatacgg atatggagga      120
ctccttggtg gatacggcct acactaccca gcaactacag ctgtcagtca cacaactcac      180
catgctccag cagcattagg tgtctatggt ggatatggac ttggtgctta tggattcggc      240
tacccaggag ctgctacagt aagccacaca actcatcatg ctccttacgg atatggtggt     300
ctttatggtg gatatggtct tgcccatggt ggtctctatg gaggatatgg tcttcaccat      360
ggcggtctct atgaggata tggtcttctc catggcggtc tctatggagg atatggtctt       420
caccatggcg gtcacttggt tccattgatc caaatgtttc gagtttccaa tcaaaccatt      480
gtgaacatcc tttggaaaat acatttggcg tttcgaaacc aacaggacgc atga            534

<210> SEQ ID NO 70
<211> LENGTH: 975
<212> TYPE: DNA
<213> ORGANISM: Dosidicus gigas

<400> SEQUENCE: 70
atggctgcaa ttttcacatt gctggcagtt cttgccatca gcaactatgc ttctgctatt        60
ttgccagcgg caacatctgt tagccgaacc acacatcgta ctggatacgg atatggagga      120
ctccttggtg gatacggcct acactaccca gcaactacag ctgtcagtca cacaactcac      180
catgctccag cagcattagg tgtctatggt ggatatggac ttggtgctta tggattcggc      240
```

| | |
|---|---|
| tacccaggag ctgctacagt aagccacaca actcatcatg ctccttacgg atatggtggt | 300 |
| ctttatggtg gatatggtct tgcccatggt ggtctctatg gtggttatgg acttggtgca | 360 |
| tacggatacg gttacccagc agctgctgtt agtcacgtaa ctcatcatgc tccatacgga | 420 |
| tatggtcttg gcggatatgg tggtctctac ggcggtctct atggtggaca tggtctcctc | 480 |
| catggtggtc tctatggtgg atatggactt ggcgcatacg gatacggtta cccagcagct | 540 |
| gctgttagtc acgtaactca tcatgctcca tacggatacg gtcttgctgg atatggtggt | 600 |
| ctccatggtg gtatggtttt ctccacggc ggtctttatg gtggacatgg tcttctccat | 660 |
| ggtggtcttt atgcggata tggtcttgga gcatacggat acggttaccc agcagctaca | 720 |
| gtaagccacc ccactcatca tgctccatac ggatatggtg gtctttatgg aggatatgga | 780 |
| catcccggat atggtggtct ttatggagga tatggttttg cccatggtgg tctttatgga | 840 |
| ggatatggtt ttttccatgg cggtctttat ggaggatatg gttttcccca tggcggtctt | 900 |
| tatggtggat atggacttgg tggatatgga cttggtggat atggacttgg tggatatggt | 960 |
| ggttggttcc attga | 975 |

<210> SEQ ID NO 71
<211> LENGTH: 387
<212> TYPE: DNA
<213> ORGANISM: Dosidicus gigas

<400> SEQUENCE: 71

| | |
|---|---|
| atggctgtga aaattatcat tttgttagca gttatggctt tgagcaacta tgcatatggc | 60 |
| cattttacag gcggcgtggg tggttatggc tatggagctg agctggata cggagctgga | 120 |
| tatggaggtg gactcggtgg aggggtgta ggctcttatg gaggagtctc tggcggatat | 180 |
| ggtggatatg gtggatatgg cggatatggc ggttatggtg gatacggtgg acatggtgga | 240 |
| tacggtggat atggtggata cggtggatat gctggacatg gtggatatgg tggacttggt | 300 |
| ggatatggtg gacatggtgg atatggtgga tacggatccg gtggacatca tggtccatat | 360 |
| ggaggatatg gtggttatct tggataa | 387 |

<210> SEQ ID NO 72
<211> LENGTH: 366
<212> TYPE: DNA
<213> ORGANISM: Dosidicus gigas

<400> SEQUENCE: 72

| | |
|---|---|
| atggctgtga aaatcatcat tttgttagca gttatggctt tgagcaacta tgcatatggc | 60 |
| catttgacag gcggcgtggg tggttatggc tatggagctg agctggata cggagctgga | 120 |
| tacggagctg gatatggagg gggtgtaggc tcttatggag gagtctctgg cggatatggt | 180 |
| ggatatggcg gatatggtgg atatggtgga tatggtggac acggtggata tggtggatac | 240 |
| ggtggatatg ctggacatgg tggatatggt ggacttggtg gatatggtgg acatggtgga | 300 |
| tatggtggat acggatctgg tggacatcat ggtccatatg gaggatatgg tggttatctt | 360 |
| ggataa | 366 |

<210> SEQ ID NO 73
<211> LENGTH: 546
<212> TYPE: DNA
<213> ORGANISM: Dosidicus gigas

<400> SEQUENCE: 73

| | |
|---|---|
| atgactgcca cactattgtt tcttatgtcc atgatagcag cgctgggctg tcagtcagaa | 60 |

```
gctgcaatat cacacggctc acatgtcaaa actgttgtac atcatggaaa tggtgtgcgt      120
actgtaacac acactatcca tcacccagtc gttcaccacg gccttcaccg cacgagtatt      180
gttccaggaa ccacaacaat tacccacacc acccatgata accgccatcc atatggaggc      240
gtcacaactg tcacccacag taaccaaggt gcacatcacc cctatagctt tggatacggt      300
tttggaggtc cttatggtgg tggtggtggt ctttatggcg ctccttatca tatgggtact      360
accgtggtta accaccctgg ccacggtatg ccgtatccat atatgtacgg atctcaaggt      420
ttcggtttgg gaggtttatc tggccttgat tatcctgttg gttcaactgt cactcactct      480
aactatggat ccatcatcc attagggttt ggtgaaccct taacggtcc ctacggcttt       540 caatga                                                                546

<210> SEQ ID NO 74
<211> LENGTH: 501
<212> TYPE: DNA
<213> ORGANISM: Dosidicus gigas

<400> SEQUENCE: 74
atgacatcca aaattatcct cttgttggca gtactttctg tgagcaacta tgcctctgcc       60
atcctgcctg caaccacgtc tgttagccag gcaacccacc gcggttacag aacctatgca      120
ggtatcctga aaggatttgg attgacctac ccagggtcta ctacggttag caagaccacc      180
cgtagatatg ggggtctcct cggtggatac gggtatggac tcccatccgc tgggtacgga      240
tacggatacg gacttccact tgctgggtat ggaggacttt acggtggata tggaggtctc      300
tacggtggat ggggatacc tgttggagct gtaggtgctt atggaggtct ccttggcggg      360
tacggatatg gacttcctct gggtggatat ggaggcttct ttggtggata tggggcaccc      420
tatgctgggt atggatatgg ggttcttctt ggccccgtgg gaccaattgc cacttccgta      480
agccaaacca ctcatcattg a                                                501

<210> SEQ ID NO 75
<211> LENGTH: 453
<212> TYPE: DNA
<213> ORGANISM: Dosidicus gigas

<400> SEQUENCE: 75
atggcatcta ccaaattgat ttttgttgtt ttacttgctg cctttggctt tgcatgcagt       60
gaagaaacaa aagagacaac aacaccaaaa cccacacccg ctgcttcaaa tttgttgggc      120
tcatcgtggt acacacctac cttaggtctt ggttacggtg gttatggatt gggacttggt      180
tatggtggtt atggaatggg actcggatac ggcggttacg gattgggact cggttacggc      240
ggttacggat tgggacttgg ttacggcggt tacggcggtc tcgtggtatt ctaccccggc      300
taccacggtg gagtgtcaac cagctcagtg acacaccatg ctccagtata ttcagtacca      360
catgttacca gctccgtgac ccatcatgca ccctacggcc ttggtgccgg atacctaggt      420
ggtctttatg gaggatatct cggactgcat taa                                   453

<210> SEQ ID NO 76
<211> LENGTH: 540
<212> TYPE: DNA
<213> ORGANISM: Dosidicus gigas

<400> SEQUENCE: 76
atgacaacta ccgccacact tcttgcattg atgtccgtaa ttggacttgg ctcctgtttt       60
```

```
ccaggattca tgggaggata tggtggagcc tacccaatcg gtagctcgta cagtcaagtt    120
acccatcatg gtccttacgg tatgagtggc atcggaggct ttggaggtct cggatatggg    180
gcaagcctac ccgtatcatc agtcagtcat gtatcccatg gtgctcatta tggatggggt    240
ggtatgtatg gcggtggtgt acaagtttca caatcaccag taatgtacca aggatacagt    300
gttggagctc cccatgttca gtcaatgggc gtccactatc ctactactac atctgtttcc    360
catagccatg gaggttatct tggtggattg ggcggtattg gtgccgttgg tggttacggt    420
ggttacggtg gttatggcct cgccggtggt cttggacatt ctgtttcaac tgtgtctcat    480
ggtatcggcc atgttggaat gggaatggga tatggttacg gtggcttcgg tcattactaa    540

<210> SEQ ID NO 77
<211> LENGTH: 1086
<212> TYPE: DNA
<213> ORGANISM: Dosidicus gigas

<400> SEQUENCE: 77
atggcagcta catactttat catagcagcc tttttcactg ttacagggct tgtaagtgct     60
caggagccat tcggtccagg tcctgaatat ggaattggag acattggttt cggtaatctt    120
ggagaagcag gtgctttcac tcacggtttc ggaccattcc caggagcccc tttccctccc    180
cctttccctg ccccttatcc cggcattacc ccccacccaa tttcatggtc tccccatgtt    240
agtatcccta ctcacacagt aacacatact tcaggagttt ctgttcctca tcatgtttct    300
acacatgtcg gcggcagcac caccactaag acagttactg tgacccatca tcccggaagc    360
cacgttacta ctgttcacca ccctgcaacg ccaatggcta cccacgtgca acatgtgaac    420
tatggctctg gatttcccgt aggggcccct ctcttaccaa tgggctacgg tccaggacca    480
tacccagtag aaccataccc ctacggaatg ggtcacccaa tgtcatggcc aactttcggt    540
ggagtaggtg gaacaaccca cacagtaacc catactcctg taggaggtgt cacacatcat    600
gttggcaccc atggcagtac caccactaag actgtgactg tgacccatca tccctcatcg    660
caagttactc atgttactca tcatccagca ccaatggtta cgtctcacgt gaacgtgggc    720
gcgggtttcc ccggtggatt cggctatggt catggatttc ttgctccacc cggcatcact    780
catcagacat tctcacatgg ttttcctggc ccctttcccg ggggcatgta tgatcaattt    840
cctggtgtag gctatggttt cgatacggga atgccttttcc cttacattca cgatggatca    900
atgggtatgc agaatgttca tacagtgcat catcatcatc aggtggtgt tactacacat    960 actacgtacc cgcatccttt aacagcatac ccgatgggaa acccttatcc gtatggatca   1020
acaaccacgg tgactaaaca tacgaagacg gtaacacaca aggcgggatc gggcaagaaa   1080
aactaa                                                              1086

<210> SEQ ID NO 78
<211> LENGTH: 780
<212> TYPE: DNA
<213> ORGANISM: Dosidicus gigas

<400> SEQUENCE: 78
atgacgacca tgttttccgc tttggtatcc ctcgccgttg tactcggtgt gctcagttac     60
acatcagctt atcacgcaaa ccatgtcggt actttgtggg caaaacccccc acaacaaact   120 ccatatggtg gatatggagt ttctggagga gctggtcagg gaggatacgg cttaggtggt   180
tatggtggct atggtagcta tggtggcctt ggaggctatg gtggctatgg tggccttggc   240
ggctatggcg gctacggtgg ccttggcggc tatggtggat atgcggtta tggacaagga   300
```

```
ggatatagca caggaggaca tggacatgga ggatacggtt ttggaggata tggacaagga    360
ggctacggct ttggtggata tggacaagga ggctacggac aaggaggcta cggacaagga    420
ggctacggac aaggaggctc tggctatggt ggatacggcc attactaccc gacaacatca    480
tatggtggct atcttggcgg atacggcgga tacggcgggt actacccaca cacttcatct    540
ggttcttact accccacaac ttacggagga tctaatcagg gaaatcccgg tgccccaatt    600
tcatccagtt ctggttttgt atttccgggt tatcactttc tggagtgtt ccatggtggc     660 gtgaaccaag gcgctggtgg aactagtgga accgacctgc aaaggctcct taatttaaac    720
ggatttaaac caactgcaac ttcaacaaca tcgacatcaa acagcaactc caagaagtaa    780

<210> SEQ ID NO 79
<211> LENGTH: 765
<212> TYPE: DNA
<213> ORGANISM: Dosidicus gigas

<400> SEQUENCE: 79
atgacgacca tgttttccgc tttggtatcc ctcgccgttg tactcggtgt gctcagttac     60
acatcagctt atcacgcaaa ccatgtcggt actttgtggg caaaaccccc acaacaaact    120
ccatatggtg gatatggagt ttctggagga gctggtcagg gaggatacgg cttaggtggt    180
tatggtggct atggtagcta tggtggcctt ggaggctatg gtggctatgg tggccttggc    240
ggctatggcg gctacggtgg ccttggcggc tatggtggat atggcggtta tggacaagga    300
ggatatagca caggaggaca tggacatgga ggatacggtt ttggaggata tggacaagga    360
ggctacggct ttggtggata tggacaagga ggctacggac aaggaggcta cggacaagga    420
ggctctggct atggtggata cggccattac tacccgacaa catcatatgg tggctatctt    480
ggcggatacg gcggatacgg cggtactac ccacacactt catctggttc ttactacccc      540
acaacttacg gaggatctaa tcagggaaat cccggtgccc caatttcatc agttctggt    600 tttgtatttc cgggttatca ctttcctgga gtgttccatg gtggcgtgaa ccaaggcgct    660
ggtggaacta gtggaaccga cctgcaaagg ctccttaatt taaacggatt taaaccaact    720
gcaacttcaa caacatcgac atcaaacagc aactccaaga agtaa                     765

<210> SEQ ID NO 80
<211> LENGTH: 750
<212> TYPE: DNA
<213> ORGANISM: Dosidicus gigas

<400> SEQUENCE: 80
atgacgacca tgttttccgc tttggtatcc ctcgccgttg tactcggtgt gctcagttac     60
acatcagctt atcacgcaaa ccatgtcggt actttgtggg caaaaccccc acaacaaact    120
ccatatggtg gatatggagt ttctggagga gctggtcagg gaggatacgg cttaggtggt    180
tatggtggct atggtagcta tggtggcctt ggaggctatg gtggctatgg tggccttggc    240
ggctatggcg gctacggtgg ccttggcggc tatggtggat atggcggtta tggacaagga    300
ggatatagca caggaggaca tggacatgga ggatacggtt ttggaggata tggacaagga    360
ggctacggct ttggtggata tggacaagga ggctacggac aaggaggctc tggctatggt    420
ggatacggcc attactaccc gacaacatca tatggtggct atcttggcgg atacggcgga    480
tacggcgggt actacccaca cacttcatct ggttcttact accccacaac ttacggagga    540
tctaatcagg gaaatcccgg tgccccaatt tcatccagtt ctggttttgt atttccgggt    600
```

| | |
|---|---:|
| tatcactttc ctggagtgtt ccatggtggc gtgaaccaag gcgctggtgg aactagtgga | 660 |
| accgacctgc aaaggctcct taatttaaac ggatttaaac caactgcaac ttcaacaaca | 720 |
| tcgacatcaa acagcaactc caagaagtaa | 750 |

<210> SEQ ID NO 81
<211> LENGTH: 351
<212> TYPE: DNA
<213> ORGANISM: Dosidicus gigas

<400> SEQUENCE: 81

| | |
|---|---:|
| atggcagccg gttcccttat tgtttcagtc ttgcttgcag ttatcgcact gagcagcaca | 60 |
| gctaatgcca ttccaggtac attcggtggc tatttcggag caggccatcc tgttggacat | 120 |
| tccgtcagta ccgtttcgca tggattagga gttggagctg gtgtcggtgt cggtggatta | 180 |
| tacggtggat acggtcttgg tggtcattcc gtcagcacag tatctcatgg accagtagga | 240 |
| tatggttccg taggtgtcgg tggactttat ggtggttatg gtggttacgg tcttggcgct | 300 |
| ggttacggac tcggagctgg ttacggactc ggagctggtt acggactcgg a | 351 |

<210> SEQ ID NO 82
<211> LENGTH: 825
<212> TYPE: DNA
<213> ORGANISM: Dosidicus gigas

<400> SEQUENCE: 82

| | |
|---|---:|
| atggcggctg ctgttctttt tattgtttcg ataattgcag ctttgagctg tcaaacagaa | 60 |
| gctatcttgc caggtacaag tgtgaaaaca acaagttctg ttcatcacca cgtcgtacca | 120 |
| tcagtcagac atactgtaag caccgtcagc catgctggtg cccacccatt cgcctatgga | 180 |
| aatctctatg gtggtcttta cgggggtccc tatgagttc ccggtgcaac agtacacaca | 240 |
| gtctctcacg gcgttcatcc atctccactg accacaactt cagttcacca cacaacccat | 300 |
| gggggtctta ttggtggagg actctatgga gctggttacc cactaggctt ggaggatat | 360 |
| ggtctccatc ccgcaggcct tggatacggt ttaggaggtc tttatggtgg tctctacgga | 420 |
| taccccgcag ctgcatctgt aacccacggt ttccatcccg caggatttgg acttggtctt | 480 |
| ggaggatttt atggtggttc ctacgggtac ccaggagcaa ctgttagcca tacaacccat | 540 |
| ggtctccacc ccgggggttt tggacttggt ttaggaggtt tttatggtgg tgcctacgga | 600 |
| ttccctgctg cttcatccgt tagccacgtt acccatggtg ttcaccctgc tggtcttggt | 660 |
| tttggaggtg tttacggcac tggctatgga atccctgctg gcacaactgt tagccacaca | 720 |
| acccatggag ttcatcattt gccagctgct agcaccgtca cccacaccac ccacggagtt | 780 |
| gcacatccca tgggagtctc ttacggcaat gttttcctcc attga | 825 |

<210> SEQ ID NO 83
<211> LENGTH: 639
<212> TYPE: DNA
<213> ORGANISM: Dosidicus gigas

<400> SEQUENCE: 83

| | |
|---|---:|
| atggcggctg ctgttctttt tattgtttcg ataattgcag ctttgagctg tcaaacagaa | 60 |
| gctatcttgc caggtacaag tgtgaaaaca acaagttctg ttcatcacca cgtcgtacca | 120 |
| tcagtcagac atactgtaag caccgtcagc catgctggtg cccacccatt cgcctatgga | 180 |
| aatctctatg gtggtcttta cgggggtccc tatgagttc ccggtgcaac agtacacaca | 240 |
| gtctctcacg gcgttcatcc atctccactg accacaactt cagttcacca cacaacccat | 300 |

```
gggggtctta ttggtggagg actctatgga gctggttacc cactaggctt tggaggatat    360
ggtctccatc ccgcaggcct tggatacggt ttaggaggtc tttatggtgg tctctacgga    420
taccccgcag ctgcatctgt aacccacggt ttccatcccg caggatttgg acttggtctt    480
ggagggtttt atggtggtgc ctacggatac ccaggagcaa ctgttagcca cacaacccat    540
ggagttcatc atttgccagc tgctagcacc gtcacccaca ccacccacgg agttgcacat    600
cccatgggag tctcttacgg caatgttttc ctccattga                           639
```

<210> SEQ ID NO 84
<211> LENGTH: 429
<212> TYPE: DNA
<213> ORGANISM: Dosidicus gigas

<400> SEQUENCE: 84

```
atggcacata cacaattgat ctttgttgtt ttgcttgctg cattcggttt tgcctgcagt     60
gaagatgaaa acaagcacc cacagcaaaa cctgccaccg ctccttcgaa tttgttgagg    120
tcgtcgtggt acactccttc ttcgagttat ggaattggac ttggttacgg tggttacgga    180
ttgggactcg gatacggtgg ttacggagcc tacggtggtt atggtggtta tggtggttat    240
ttgccttacg gctatggtgg aatcctccca gggtactttg gtggatatcc tgcagttaca    300
tctagctcag taacacacca tgccccaaca tacccacaag ttaccagttc ggtcactcat    360
catgcaccat acggagtcgg agtcggttac cttggtggtc tgtatggagg atatctcgga    420
ttgcattaa                                                            429
```

<210> SEQ ID NO 85
<211> LENGTH: 945
<212> TYPE: DNA
<213> ORGANISM: Dosidicus gigas

<400> SEQUENCE: 85

```
accgttagtc atgtgtctca tggcactgta ggatatggtg ggcacggact cggcggttac     60
ggtggatacg gactcggtgg tatatccggc ggatatggcc ttggtggaca cactgttagt    120
catgtatctc atggtcccgt aggatatggt ggttatggta tcggaggtgt ctctggtggc    180
tatggcggtt acggtcttgg aggcgtttct ggaggttacg gtatgggagg tctctatggt    240
ggttatggcg gctacggagt tggtgttcac agtcgctatg gcgttggtca tcgtaccgtt    300
acacaattgc gccacagaat tcaacccctc ggctatggcg tcgttaacca aatcggtcat    360
gccgtacata gagttgtcca accagttgcc catcatggcg ttgtttctcg tcgttatgcc    420
attcctcata ccgaagtccg ttacgtccaa tatccagttg taaatcgtta cattcaatat    480
gtcactgtca acaaaccata cgttgtaccc cgatatgaat ggcatgttcg ttcttaccaa    540
gttccagtac cccgttattc agtacgtatg gccgtccgcc ccgtatacat cccacgtgtc    600
cattatgctg aaagccacac cccagtaacc cattacagcc atgtatctca tgatgtccat    660
caaccaatct acggagtgca ttacccaatg ggacatagcg tagaagcagt tacccatcaa    720
caacctttcg tatatggaca tcatactact tatggacatg gaggtctgta cggtggatac    780
ggtggttacg gtgtaggagg tgccgttggt ggttacggta tgggtggtgc cgttggcggt    840
tacggtcttg gtggtgccgt tggcggttac ggtcttggag gtgccgtcgg tggttatggt    900
cttggaggtg gctacggcgg ttacggtctt ggaggtctct accac                    945
```

<210> SEQ ID NO 86

<211> LENGTH: 948
<212> TYPE: DNA
<213> ORGANISM: Dosidicus gigas

<400> SEQUENCE: 86

```
accgttagtc atgtgtctca tggcactgta ggatatggtg ggcacggact cggcggttac      60
ggtggatacg gactcggtgg tatatccggc ggatatggcc ttggtggaca cactgttagt     120
catgtatctc atggtcccgt aggatatggt ggttatggta tcggaggtgt ctctggtggc     180
tatggcggtt acggtcttgg aggcgtttct ggaggttacg gtatgggagg tctctatggt     240
ggttatggcg gctacggagt tggtgttcac agtcgctatg gcgttggtca tcgtaccgtt     300
acacaattgc gccacagaat caacccctc ggctatggcg tcgttaacca aatcggtcat     360
gccgtacata gagttgtcca accgttgcc catcatggcg ttgtttctcg tcgttatgcc     420
attcctcata ccgaagtccg ttacgtccaa tatccagttg taaatcgtta cattcaatat     480
gtcactgtca acaaaccata cgttgtaccc cgatatgaat ggcatgttcg ttcttaccaa     540
gttccagtac cccgttattc agtacgtatg gccgtccgcc ccgtatacat cccacgtgtc     600
cattatgctg aaagccacac ccagtaacc cattacagcc atgtatctca tgatgtccat     660
caaccaatct acggagtgca ttacccaatg ggacatagcg tagaagcagt tacccatcaa     720
caacctttcg tatatggaca tcatactact tatggacatg gaggtctgta cggtggatac     780
ggtggttacg gtgtaggagg tgccgttggt ggttacggta tgggtggtgc cgttggcggt     840
tacggtcttg gtggtgccgt tggcggttac ggtcttggag gtgccgtcgg tggttatggt     900
cttggaggtg gctacggcgg ttacggtctt ggaggtctct accactag                 948
```

<210> SEQ ID NO 87
<211> LENGTH: 222
<212> TYPE: DNA
<213> ORGANISM: Dosidicus gigas

<400> SEQUENCE: 87

```
atggcatcta cactgtttgt tttgctggca gttattgctt tggccagcta tgccagtggc      60
gcgttaacgt acggagcagg tgggtgggct cttccagttg gaggatgggc agttccaact     120
ggaggtgtag gtggctacgg agtccctggc ggctacgggg tccctggcgg atttggagga     180
ttcggaggat atggtggtgg ctttggcttt ggtggatatt ga                        222
```

<210> SEQ ID NO 88
<211> LENGTH: 1131
<212> TYPE: DNA
<213> ORGANISM: Dosidicus gigas

<400> SEQUENCE: 88

```
ggtggtcttt atggaggtca ttatggcgga tatggacttg gcggatctag ccttcaatac      60
ccagcagcta cagctgtcag ccaaacctac catcatgctc catcaagtta tggtcttgct     120
ggatatggag gtgtctctgg aggtcgttat ggggatacg gacttggtgg atacggactc     180
ggctacccaa cagctacatc atctagttac accacacatc acgccccatc aggatatggt     240
tcccttgggg gatctggatt tggaggtatc gttagtggtt ctcaataccc cgttggagca     300
gtaagcacca attcacaagt tttgcaacag ccctacaggt taattttggg gggatccagc     360
taccattacc cagccgctac aactgtcagc catacctctc agaatggtgg atacggatat     420
ggtaatctcc tcggtggata tggaggttca tatggtggat taggattaag caaacaaatg     480
atcggctatc ccgcaactac atcagttagc cagaccactc atcaacttcc atacggtgtt     540
```

```
tttggtttat atggacttgg cggacaagga cttacctcaa acacttatca aagcggatac      600
ggatttggag gttcccaagg tggactagga tatacagctg gaaatggagg cctctcttct      660
ggcttgcccg gtcccatggg atccggtctt ggcgtttaca actttcacta cccagcagct      720
acaactgtca gtaccactgc taaccatatg gggcccggat atggaagtct tcttggcgga      780
tatggtgctc aatttccatc tgttagcagc ggcgcacaag gtgtaaatag tggagtcttt      840
ggtggatatg gaagtacttt cggtggaata ggactttctg gatacggttc acaaaactca      900
gccggtccag ttgttggcag caccgctcaa actggtggat cgggaatggg tggtcttctt      960
ggtggacttg gatctcaaag cacgtattct tatggcttgc accaacccca tgcttccggt     1020
ctcagtggat atggctttca ctccccaacc tccacactcc agtaaatttc atgcaacaga     1080
tttcgatttt accttcactg aatgtcccag gagatcggaa gagcacacgt c              1131

<210> SEQ ID NO 89
<211> LENGTH: 1512
<212> TYPE: DNA
<213> ORGANISM: Sepioteuthis lessoniana

<400> SEQUENCE: 89
atgggaacca tcaaagtaat cgtggccttg cttatagtgc ttggaatcag cagttctgcg       60
aagggaattt ataatggctc cttagctgca cttgacagtt catcttacag tcatccctcc      120
ccttatttac aaagatctgt cagcactgtt tcacatggtt cccattatcc cacatacggt      180
gggtggggct ataatcttgg tacatggggg catggtctag gtggtttagg aggttatggt      240
tttcgctatc caacgtcttc atcaatcagt cgtgtttctc acacagctca ctcccccgtt      300
ggatactatg gatggggagg ctatgctcaa cattccccac ttcaatatgt atcaagaact      360
gctcttcctc cagtgggatg gactttcggt ggaatttaca gaggccatgg ggcacatgta      420
tcccagtctc cagttcgtta tcaaggatat agttttggac gtccagcagt tgcaacatat      480
cgagtcctct atccaagacc agttgttagc catgttaccc atagtatccc ttatggtggt      540
tggagcgtgg gtggacaagg tggatttgtt tcatcctatc caactggtgc ttccattaat      600
actgtgtctc atggaattag ccatgcgcct atttatggcg gctggggttt tggctatcct      660
gctggtcaag caataagcac tgttggccat ggcattcacc ctacagtaac ttatggaggt      720
ttgggtcttg gaggtctcta tggaggatat ggcgcacact acccaactgg gtcttctgta      780
agtactcttt cacatggtgt ctcccatcca gtaggatttg gcttcgggta cagctctcac      840
tacccagcat caacatcggt tagccagaca agccacagtg taccacatat tataggtttg      900
ggtcttggaa gctggggtgg ttatggagtt gggtatggct acacacccc agttggagct      960 tctgttagta ccgtgtctca tggaatcggt caccctgtgg gttatggtac ctggggtctt     1020
ggttatggcg cacactatcc agtcggtcag tcagtaagca ccgtgtcaca tggcattcat     1080
gctcctgtag cgcatggagg attaagtggc ctctctgaag gatacggcgt tttccaccca     1140
actagatctg ttagtaccgt atcacacgga gtccactccc ctgtaatcta tggaagatat     1200
ggccttggag gtcttggagg taatggagga tatggtcttg gggtcttgt cggaggttat      1260 ggaggatatg gccttggggg tcttgtcgga ggatatggta cctatcagcc aaccgggtca     1320
tctatcagta ctgtgtcaca tggagtccac tcgccagtag gttatggagg atatggtctt     1380
ggaggtcttg gagaaagtta tggaggatat ggccttggag gtcttgtcgg aagttatggg     1440
ggatatggcc ttgagggtct tgtcggaagt tatggggggat atggccttgg aggtcttgtc     1500
```
ggaagttatg gg                                                1512

<210> SEQ ID NO 90
<211> LENGTH: 390
<212> TYPE: DNA
<213> ORGANISM: Sepioteuthis lessoniana

<400> SEQUENCE: 90
atggcagcga aacttctcac tttgttggca gtcattgctt tgagcaacta tgcctacgcc    60
ctccttccag gtctgatggg tggttatggc tatccggctg ctacaactta tagacgaaca   120
actctaaatg gatatggagg tctctacggt ggtctcggat accactaccc agcagccaca   180
gccgttagcc acactactca ccacgcccct tacggatacg gaggtctcta tggtggatgg   240
ggataccctg ctgcttcatc tgtaagcact gtttctcatg gtgtgcatca cccagttgga   300
tggggactcg gatacggcct tcactaccca gcagccactg taggatactc tggcttaggt   360
cttggctacg gttctggata tgttctctaa                                    390

<210> SEQ ID NO 91
<211> LENGTH: 402
<212> TYPE: DNA
<213> ORGANISM: Sepioteuthis lessoniana

<400> SEQUENCE: 91
atggcagcga aacttctcac tttgttggca gtcattgctt tgagcaacta tgcctacgcc    60
ctccttccag gtctgatggg tggttatggc tatccggctg ctacaactta tagacgaaca   120
actctaaatg gatatggagg tctctacggt ggtctcggat accactaccc agcagccaca   180
gccgttagcc acactactca ccacgcccct tacggatacg gaggtctcta tggtggatgg   240
ggatacccag cagctgcatc agtaagcaca gttcatcgcc cagtaggata tggaggatgg   300
ggactcggag gttacggtct cggatacggc cttcactacc cagcagccac tgtaggatac   360
tctggcttag gtcttggcta cggttctgga tatgttctct aa                      402

<210> SEQ ID NO 92
<211> LENGTH: 417
<212> TYPE: DNA
<213> ORGANISM: Sepioteuthis lessoniana

<400> SEQUENCE: 92
atggcagcga aacttctcac tttgttggca gtcattgctt tgagcaacta tgcctacgcc    60
ctccttccag gtctgatggg tggttatggc tatccggctg ctacaactta tagacgaaca   120
actctaaatg gatatggagg tctctacggt ggtctcggat accactaccc agcagccaca   180
gccgttagcc acactactca ccacgcccct tacggatacg gaggtctcta tggtggatgg   240
ggatacccag cagctgcatc agtaagcaca gttcatcgcc cagtaggata tggaggatgg   300
ggacttggag gttacggtct cggaggttac ggtctcggat acggccttca ctacccagca   360
gccactgtag gatactctgg cttaggtctt ggctacggtt ctggatatgt tctctaa      417

<210> SEQ ID NO 93
<211> LENGTH: 1452
<212> TYPE: DNA
<213> ORGANISM: Sepioteuthis lessoniana

<400> SEQUENCE: 93
atgggaacca tcaaagtaat cgtggccttg cttatagtgc ttggaatcag cagttctgcg    60
aagggaattt ataatggctc cttagctgca cttgacagtt catcttacag tcatccctcc   120

```
ccttatttac aaagatctgt cagcactgtt tcacatggtt cccattatcc cacatacggt      180
gggtggggct ataatcttgg tacatggggg catggtctag gtggtttagg aggttatggt      240
tttcgctatc caacgtcttc atcaatcagt cgtgtttctc acacagctca ctcccccgtt      300
ggatactatg gatggggagg ctatgctcaa cattccccac ttcaatatgt atcaagaact      360
gctcttcctc cagtgggatg gactttcggt ggaatttaca gaggccatgg ggcacatgta      420
tcccagtctc cagttcgtta tcaaggatat agttttggac gtccagcagt tgcaacatat      480
cgagtcctct atccaagacc agttgttagc catgttaccc atagtatccc ttatggtggt      540
tggagcgtgg gtggacaagg tggatttgtt tcatcctatc caactggtgc ttccattaat      600
actgtgtctc atggaattag ccatgcgcct atttatggcg gctggggttt tggctatcct      660
gctggtcaag caataagcac tgttggccat ggcattcacc ctacagtaac ttatggaggt      720
ttgggtcttg gaggtctcta tggaggatat ggcgcacact acccaactgg gtcttctgta      780
agtactcttt cacatggtgt ctcccatcca gtaggatttg gcttcgggta cagctctcac      840
tacccagcat caacatcggt tagccagaca agccacagtg taccacatat tataggtttg      900
ggtcttggaa gctgggggtgg ttatggagtt gggtatggct tacacacccc agttggagct      960
tctgttagta ccgtgtctca tggaatcggt caccctgtgg gttatggtac ctggggtctt     1020
ggttatggcg cacactatcc agtcggtcag tcagtaagca ccgtgtcaca tggcattcat     1080
gctcctgtag cgcatggagg attaagtggc ctctctgaag atacggcgt tttccaccca     1140 actagatctg ttagtaccgt atcacacgga gtccactccc ctgtaatcta tggaagatat     1200
ggccttggag gtcttggagg taatggagga tatggtcttg ggggtcttgt cggaggttat     1260
ggaggatatg gccttggggg tcttgtcgga ggatatggta cctatcatcc cgctggatca     1320
tccatcagta ctgtctcaca tggactccac tcccttggag catatggagg atatggccat     1380
ggaagtcttc tcggaggata tggtgtacca ttacctatca gcactacatc tcatcattca     1440
gtaacacatt ga                                                         1452

<210> SEQ ID NO 94
<211> LENGTH: 717
<212> TYPE: DNA
<213> ORGANISM: Sepioteuthis lessoniana

<400> SEQUENCE: 94
atggtgtcta ctgtgttgat tattatgtca atgattgcag ccttgagctg tcaatcagaa       60
gctgccctgt cagttggtac aagtgtcaaa tcagtacatc atagtgttca ccacccgata      120
tccgcagtag gacaaactgt aaaaactgtc actcatgcag ttccccaaat atatccatt      180 ggaggattgc cattcggtga tgcttatgga ggtctttacg gagctcttca cggaggtgtt      240
tatggagttc cagcagcaac atcagttcaa acagtctctc acggattaca cccaacagtt      300
ccagtaggat caacttctgt tagccacaca acccacggta ttcatcaccc agtaacttat      360
ggtggtctag gtgttggagg tcttggtttt ggaggtcttg gctatggagg tgttggaggt      420
cttggtcttg gaggtctttta tggtggtgtc tacggactcc actaccctgg agcagcattc      480
cactacccag caggcctcgg atacggtctt ggaggtttgt atggggtct ctatggactt      540 cacctcccag cagccacatc tgttagccac acaacccacg gagtccatca cccagccttg      600
ggatatggtc ttggtctgta cggtgctgct cactatccag cagcaagttc ggtcacccac      660
acaactcacg cagttccaca cccaggcttt ggattgaatt atggtgtctt ccactga        717
```

<210> SEQ ID NO 95
<211> LENGTH: 606
<212> TYPE: DNA
<213> ORGANISM: Sepioteuthis lessoniana

<400> SEQUENCE: 95

```
atgacggcta cagttttgtt tcttttgttc gggattgcag ctttaacctg tcaaacagaa      60
gctgcaatta cagggacctc aagcgtcaag actgttgttc atccaccaac agttgtgcat     120
cctgtacaca ctgtaaccca tactgaccac cacccactgg tttggaatac aggacccgtg     180
tatggcattc cttcagctgg atcaacatct gtaaagaccg ttacccatgg tatccaccac     240
accggaggaa tttcggtaac ttctcctgga ggcgccactg ttacccacac acccacggga     300
atctctcacc cattcggact tggacacggt cttggaggcc tctacggtgg tgtgtatggt     360
cttccaatgc ctggggctac cacagtcagc cacagtaccc acggtgtgcc ttattcattt     420
ggatacggag gtctaggata tgggggtata ggatacggag gtttgggata cggaggtctt     480
ggatacggcc ttggaggtgc ctatgggctc ccatacccaa ataccgcaat cagtcactct     540
agttacggct ttcaatctcc atcagtatac ggattcggct ttggagggcc ctacggcttt     600
cattaa                                                                 606
```

<210> SEQ ID NO 96
<211> LENGTH: 390
<212> TYPE: DNA
<213> ORGANISM: Sepioteuthis lessoniana

<400> SEQUENCE: 96

```
atggcatctt accgattgat ctttgttgtt ttgcttgccg cctttggttt ggcctacggt      60
gaacaaacta aaaaacaac aacaacgtct aatactggag ctcaaaatta ttataaccca     120
tggtactatc cgacttacaa ctacggatgg ggtaacccct ggggacttgg ttactacggc     180
tacggaatgc ttccaaacta tggtacacat acagttaccc atcatgctcc acaatacccc     240
ttctactatg gattcccaca gtttcaacc agtcatgtga cacatcatgc tccaatcgta     300
cctcacgtta ccagcaacac agtaactcat catgcaccat atacctttgg caaccttggc     360
ctttatggag gattattcgg atatcattaa                                       390
```

<210> SEQ ID NO 97
<211> LENGTH: 441
<212> TYPE: DNA
<213> ORGANISM: Sepioteuthis lessoniana

<400> SEQUENCE: 97

```
atgacaacta catcatcctt acttgctttg atgaccgtaa ttggactggt cacatgttgt      60
gcaggatacc cctcatgggg tagcacttat agtcaagtgt ccacacatca tgccccgtt     120
ggctggggcg tcttggagg tctgtacgga tatgggtccc ttggtggttt gggttacgga     180
ggtgtgtacg gaggtggagt tcatgttgca cagtcccctg ttagatacca cggatacagc     240
gttggaacac cacatgttca atcatacggt gtgaactatc cgacaccaac tgttacccac     300
catcacaaca catggcatgg cggatatggt ggatttggct tggctggtcc agtcggtcat     360
tcagttcaaa ctgtgtctca aggtgtgcac actcctggct ggggacttgg atatggtctt     420
tctggttatg gttattacta a                                                441
```

<210> SEQ ID NO 98
<211> LENGTH: 1014

```
<212> TYPE: DNA
<213> ORGANISM: Sepioteuthis lessoniana

<400> SEQUENCE: 98
atggccgcta cacacgtgat cgtagtagcc tttctcacag tcacagggct tgtaagtgct      60
cagatgccat tctatgcagg ccccaattat ggaatcggag gaatcggagg aatcggtttc     120
ggttatccag gaggattggg tgcttacgct catggtttcg aaccagtgac aggaggaatt     180
ttcccttact acggagcggc tcattctttg ccatggtccg cacctgtcgg cggaacaacc     240
cacacgatat cccatgtagc ccatggaact cttccacatc cggttggccc acatgttagc     300
accaccagta aaactgtttc tgttcatcat cccactacgc atgtcaccgt tcaccaccca     360
gcggtcacta cccacgtgca cacccagac attggttttc ctgcagcttt gacatatcct     420
tatcctggac tttcgccctt ttttcctcaa tatccaactg tgttctcga acatcactca     480
ccagtaatca ctgaaacaac tgtcgagaaa atctggcta agaagaatac agaccaaacc     540
aacacaatct atacccatca cagtcctact cacacgatag tgacaaagtc acatcacgtt     600
cccagtggat atcccttcaa ccaacccggg gttgtctcaa caagtcacca tcagacggtc     660
tcacatgtaa atcccggtgt gggagttacc catcttcctg gtacttttcc cggtacattt     720
cctgctacat accccggttt ggattatccc taccatccgg ggtctagcgc atttggaatt     780
caattcccctt acttgaatgc tggacttcaa ggtggggcgg tgagttcgtc gtccgttcat     840
acagttcatc atccaggagt tggtttccca cctctgtatc cgggtacttt cggaggatat     900
cacattggaa cttatccgtt cggttttttct agtgtaacta gctcatctac caccacaacg     960
gaaaaagata ccaagtcatc gtcaggaaag tcagattcaa gcagcaaaaa ttaa          1014

<210> SEQ ID NO 99
<211> LENGTH: 319
<212> TYPE: DNA
<213> ORGANISM: Sepioteuthis lessoniana

<400> SEQUENCE: 99
atggcagccg tcatcttat tgtttcagcc ttgcttgcag ttattgccct gagcagctct      60
gtcaatgctt tgattccagg tgcagttggt ggttttttcg gagctggcca ccccatcgga     120
acatcttata gtgctatttc gcatggtggt cccgttggcg cttggggtca tggttttgga     180
tacggacttg gaggactgta cggtggatat ggacttggtg acatactgt tagccatgta     240
tcgcatggtc cagtaggatt gggatatgga ggtctctacg gtcactatgg tggttatggt     300
cttggaggtg tttatggtc                                                 319

<210> SEQ ID NO 100
<211> LENGTH: 621
<212> TYPE: DNA
<213> ORGANISM: Sepioteuthis lessoniana

<400> SEQUENCE: 100
cacggctatg gtcttggagg tggttatggt cacggctatg gtcttggagg tggttatggt      60
cacggctatg gtcttggagg tatctatggt cactatggcg gatacggtct tggaggagtc     120
tacagtcatt atggcgttgg ttctcgcacc gttaatcacg tctctcacag ataccaccca     180
ctcggctatg gcatcactta cccaattggt catgctgtac acagagttac acaaccaata     240
gcacaccatg gtaccatttc tcgccgttat gcaatccccc actatgaagt ccgttatgta     300
tcctacccag tcgtacaacg ttacgttcag atggtcactg taaaccaacc atacatcgta     360
```

-continued

```
cccagatatg aaacccatat ccgttcatat caagttccag taccccgtta ccaggttcac    420
atggctcaat accctgtagt catcccacga cttcacattg ctgaaagcca ccacccagtc    480
acccattaca gccaagtatc ccatgatgtc caccaaccaa tctacggagt gcattaccca    540
atgggccata ccgtacaagc cgtgtctcat caggtaccat acgtgtatgg ttcaacacat    600
gcatatggcg gtttcatgta a                                              621

<210> SEQ ID NO 101
<211> LENGTH: 23
<212> TYPE: DNA
<213> ORGANISM: Artificial Sequence
<220> FEATURE:
<223> OTHER INFORMATION: Forward primer 1

<400> SEQUENCE: 101
tgaaggagta gaaagtagtc tcc                                            23

<210> SEQ ID NO 102
<211> LENGTH: 25
<212> TYPE: DNA
<213> ORGANISM: Artificial Sequence
<220> FEATURE:
<223> OTHER INFORMATION: reverse primer 1

<400> SEQUENCE: 102
gctgtcaacg atacgctacg taacg                                          25

<210> SEQ ID NO 103
<211> LENGTH: 34
<212> TYPE: DNA
<213> ORGANISM: Artificial Sequence
<220> FEATURE:
<223> OTHER INFORMATION: forward primer

<400> SEQUENCE: 103
aaaaaagcta gcattttgcc agcggcaaca tctg                                34

<210> SEQ ID NO 104
<211> LENGTH: 35
<212> TYPE: DNA
<213> ORGANISM: Artificial Sequence
<220> FEATURE:
<223> OTHER INFORMATION: reverse primer

<400> SEQUENCE: 104
aaaaaactcg agttagtgga ggagaccata tccac                               35

<210> SEQ ID NO 105
<211> LENGTH: 11
<212> TYPE: PRT
<213> ORGANISM: Artificial Sequence
<220> FEATURE:
<223> OTHER INFORMATION: Consensus sequence of clade 1
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is W or G
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
```

```
<222> LOCATION: (10)..(10)
<223> OTHER INFORMATION: Xaa is L or A
<220> FEATURE:
<221> NAME/KEY: MISC_FEATURE
<222> LOCATION: (11)..(11)
<223> OTHER INFORMATION: Xaa is any amino acid

<400> SEQUENCE: 105

Xaa Gly Xaa Xaa Xaa Gly Gly Tyr Gly Xaa Xaa
1               5                   10

<210> SEQ ID NO 106
<211> LENGTH: 224
<212> TYPE: PRT
<213> ORGANISM: Artificial Sequence
<220> FEATURE:
<223> OTHER INFORMATION: Consensus sequence of clade 2
<220

<400> SEQUENCE: 106

Ala Ala Leu Xaa Cys Gln Xaa Xaa Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
    195                 200                 205

Xaa Xaa Xaa Pro Xaa Xaa Xaa Gly Xaa Xaa Xaa Xaa Gly Xaa Tyr Gly
    210                 215                 220

<210> SEQ ID NO 107
<211> LENGTH: 23
<212> TYPE: PRT
<213> ORGANISM: Artificial Sequence
<220> FEATURE:
<223> OTHER INFORMATION: Consensus sequence of clade 3
<220> FEATURE:
<221> NAME/KEY: MISC_FEATURE
<222> LOCATION: (1)..(1)
<223> OTHER INFORMATION: Xaa is G or L
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Y or G
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(21)
<223> OTHER INFORMATION: Xaa is any amino acid or is not present
<220> FEATURE:
<221> NAME/KEY: MISC_FEATURE
<222> LOCATION: (22)..(22)
<223> OTHER INFORMATION: Xaa is G or V

<400> SEQUENCE: 107

Xaa Xaa Gly Gly Xaa Gly Xaa Xaa Xaa Xaa Xaa Xaa Xaa Xaa
1               5                   10                  15

Xaa Xaa Xaa Xaa Xaa Xaa Gly
            20

<210> SEQ ID NO 108
<211> LENGTH: 231
<212> TYPE: PRT
<213> ORGANISM: Artificial Sequence
<220> FEATURE:
<223> OTHER INFORMATION: Consensus sequence of clade 4
<220> FEATURE:
<221> NAME/KEY: MISC_FEATURE
<222> LOCATION: (12)..(12)
<223> OTHER INFORMATION: Xaa is L or F
<220> FEATURE:
<221> NAME/KEY: MISC_FEATURE
<222> LOCATION: (14)..(14)
<223> OTHER INFORMATION: Xaa is C or Y
<220> FEATURE:
<221> NAME/KEY: MISC_FEATURE
<222> LOCATION: (15)..(15)
<223> OTHER INFORMATION: Xaa is G or S
<220> FEATURE:
<221> NAME/KEY: MISC_FEATURE
<222> LOCATION: (17)..(18)
<223> OTHER INFORMATION: Xaa is any amino acid
<220> FEATURE:
<221> NAME/KEY: MISC_FEATURE
<222> LOCATION: (19)..(116)
<223> OTHER INFORMATION: Xaa is any amino acid or not present
<220> FEATURE:
<221> NAME/KEY: MISC_FEATURE
<222> LOCATION: (124)..(124)
<223> OTHER INFORMATION: Xaa is T or G
<220> FEATURE:
<221> NAME/KEY: MISC_FEATURE
<222> LOCATION: (125)..(125)
<223> OTHER INFORMATION: Xaa is any amino acid
<220> FEATURE:
<221> NAME/KEY: MISC_FEATURE
<222> LOCATION: (127)..(128)
<223> OTHER INFORMATION: X is any amino acid
<220> FEATURE:
<221> NAME/KEY: MISC_FEATURE
<222> LOCATION: (129)..(226)
<223> OTHER INFORMATION: Xaa is any amino acid or not present

<400> SEQUENCE: 108

Leu Ile Phe Val Val Leu Leu Ala Ala Phe Gly Xaa Ala Xaa Xaa Glu
1               5                   10                  15

Xaa Xaa Xaa Xaa Xaa Xaa Xaa Xaa Xaa Xaa Xaa Xaa Xaa Xaa
            20                  25                  30

Xaa Xaa Xaa X

```
Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Gly Leu Tyr Gly Gly
225                 230

<210> SEQ ID NO 109
<211> LENGTH: 40
<212> TYPE: PRT
<213> ORGANISM: Artificial Sequence
<220> FEATURE:
<223> OTHER INFORMATION: Consensus sequence of clade 5
<220> FEATURE:
<221> NAME/KEY: MISC_FEATURE
<222> LOCATION: (2)..(2)
<223> OTHER INFORMATION: Xaa is L or I
<220> FEATURE:
<221> NAME/KEY: MISC_FEATURE
<222> LOCATION: (5)..(5)
<223> OTHER INFORMATION: Xaa is A or G
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is A or P
<220> FEATURE:
<221> NAME/KEY: MISC_FEATURE
<222> LOCATION: (12)..(12)
<223> OTHER INFORMATION: Xaa is G or F
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (19)..(28)
<223> OTHER INFORMATION: Xaa is any amino acid
<220> FEATURE:
<221> NAME/KEY: MISC_FEATURE
<222> LOCATION: (29)..(33)
<223> OTHER INFORMATION: Xaa is any amino acid or not present
<220> FEATURE:
<221> NAME/KEY: MISC_FEATURE
<222> LOCATION: (36)..(36)
<223> OTHER INFORMATION: Xaa is F or Y
<220> FEATURE:
<221> NAME/KEY: MISC_FEATURE
<222> LOCATION: (37)..(37)
<223> OTHER INFORMATION: Xaa is any amino acid

<400> SEQUENCE: 109

Gly Xaa Val Ser Xaa Gln Xaa Pro Phe Xaa Xaa Xaa Pro Xaa Tyr Gly
1               5                   10                  15

Ile Gly Xaa Xaa Xaa Xaa Xaa Xaa Xaa Xaa Xaa Xaa Xaa Xaa Xaa Xaa
            20                  25                  30

Xaa Gly Ala Xaa Xaa His Gly Phe
```

<210> SEQ ID NO 110
<211> LENGTH: 21
<212> TYPE: PRT
<213> ORGANISM: Artificial Sequence
<220> FEATURE:
<223> OTHER INFORMATION: Consensus sequence of clade 6
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Y or F
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (7)..(14)
<223> OTHER INFORMATION: Xaa is any amino acid or not present
<220> FEATURE:
<221> NAME/KEY: MISC_FEATURE
<222> LOCATION: (16)..(16)
<223> OTHER INFORMATION: Xaa is V or I
<220> FEATURE:
<221> NAME/KEY: MISC_FEATURE
<222> LOCATION: (17)..(17)
<223> OTHER INFORMATION: Xaa is any amino acid

<400> SEQUENCE: 110

Xaa Gly Xaa Xaa Xaa Xaa Xaa Xaa Xaa Xaa Xaa Xaa Xaa Xaa Ser Xaa
1               5                   10                  15

Xaa Thr Val Ser His
            20

<210> SEQ ID NO 111
<211> LENGTH: 4
<212> TYPE: PRT
<213> ORGANISM: Artificial Sequence
<220> FEATURE:
<223> OTHER INFORMATION: Domain 1 peptide

<400> SEQUENCE: 111

Ile Ala Ala Leu
1

<210> SEQ ID NO 112
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 112

Val Thr His His Ala Pro
1               5

<210> SEQ ID NO 113
<211> LENGTH: 7
<212> TYPE: PRT
<213> ORGANISM: Artificial Sequence
<220> FEATURE:
<223> OTHER INFORMATION: Domain 1 peptide

```
<400> SEQUENCE: 113

Val Val Leu Leu Ala Ala Phe
1               5

<210> SEQ ID NO 114
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 114

His Thr Thr His His Ala
1               5

<210> SEQ ID NO 115
<211> LENGTH: 11
<212> TYPE: PRT
<213> ORGANISM: Artificial Sequence
<220> FEATURE:
<223> OTHER INFORMATION: Domain 1 peptide

<400> SEQUENCE: 115

Ala Ala Thr Val Ser His Thr Thr His His Ala
1               5                   10

<210> SEQ ID NO 116
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 116

Gly Gly Leu Tyr Gly
1               5

<210> SEQ ID NO 117
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 117

Gly Gly Tyr Gly
1

<210> SEQ ID NO 118
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 118

Gly Leu Tyr Gly Gly
1               5

<210> SEQ ID NO 119
<211> LENGTH: 4
<212> TYPE: PRT
<213> ORGANISM: Artificial Sequence
<220> FEATURE:
<223> OTHER INFORMATION: Domain 2 peptide
```

```
<400> SEQUENCE: 119

Tyr Gly Ile Gly
1

<210> SEQ ID NO 120
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 120

Val Ser His Thr Thr His
1               5

<210> SEQ ID NO 121
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 121

Ala Val Ser His Thr Thr
1               5

<210> SEQ ID NO 122
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 122

Thr Val Ser His Thr Thr
1               5

<210> SEQ ID NO 123
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 123

Ala Thr Val Ser His Thr
1               5

<210> SEQ ID NO 124
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 124

Ala Ala Thr Val Ser His
1               5

<210> SEQ ID NO 125
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 125
```

```
Thr Ala Val Ser His Thr
1               5

<210> SEQ ID NO 126
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 126

Ala Thr Ala Val Ser His
1               5

<210> SEQ ID NO 127
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 127

Ala Ala Thr Ala Val Ser
1               5

<210> SEQ ID NO 128
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 128

Gly Ala Val Ser His Thr
1               5

<210> SEQ ID NO 129
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 129

Ser Thr Val Ser His Gly
1               5

<210> SEQ ID NO 130
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 130

Val Ser Thr Val Ser His
1               5

<210> SEQ ID NO 131
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 131
```

Ala Val Ile Ala Leu Ser
1               5

<210> SEQ ID NO 132
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 132

Ala Ala Val Ser His Thr
1               5

<210> SEQ ID NO 133
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 133

Val Ser Arg Thr Thr His
1               5

<210> SEQ ID NO 134
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 134

Ser Val Ser Thr Val Ser
1               5

<210> SEQ ID NO 135
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 135

Ala Ala Ala Val Ser His
1               5

<210> SEQ ID NO 136
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 136

Ala Ala Ala Thr Val Ser
1               5

<210> SEQ ID NO 137
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 137

Thr Ser Val Ser Arg Thr

```
<210> SEQ ID NO 138
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 138

Ser Val Ser Arg Thr Thr
1               5

<210> SEQ ID NO 139
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 139

Val Ser His Val Thr His
1               5

<210> SEQ ID NO 140
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 140

Ser Ser Ser Gly Phe Val
1               5

<210> SEQ ID NO 141
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 141

Gly Ala Ala Thr Val Ser
1               5

<210> SEQ ID NO 142
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 142

Thr Ser Ser Gly Ser Tyr
1               5

<210> SEQ ID NO 143
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 143

His Thr Ser Ser Gly Ser
1               5
```

<210> SEQ ID NO 144
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 144

Ser Ser Ser Ser Gly Phe
1               5

<210> SEQ ID NO 145
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 145

Val Ile Ala Leu Ser Ser
1               5

<210> SEQ ID NO 146
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 146

Ile Ser Ser Ser Ser Gly
1               5

<210> SEQ ID NO 147
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 147

Ala Thr Ser Val Ser Arg
1               5

<210> SEQ ID NO 148
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 148

Ser Asn Tyr Ala Ser Ala
1               5

<210> SEQ ID NO 149
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 149

Ala Ala Thr Ser Val Ser
1               5

```
<210> SEQ ID NO 150
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 150

Ser Val Thr His His Ala
1               5

<210> SEQ ID NO 151
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 151

Leu Val Ser Leu Ala Val
1               5

<210> SEQ ID NO 152
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 152

Thr Ala Thr Ser Thr Thr
1               5

<210> SEQ ID NO 153
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 153

Ser Ser Val Thr His His
1               5

<210> SEQ ID NO 154
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 154

Ala Leu Val Ser Leu Ala
1               5

<210> SEQ ID NO 155
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 155

Ser Leu Ala Val Val Leu
1               5
```

```
<210> SEQ ID NO 156
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 156

Phe Ser Ala Leu Val Ser
1               5

<210> SEQ ID NO 157
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 157

Thr Ser Asn Ser Asn Ser
1               5

<210> SEQ ID NO 158
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 158

Thr Ser Ala Tyr His Ala
1               5

<210> SEQ ID NO 159
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 159

Ser Ala Leu Val Ser Leu
1               5

<210> SEQ ID NO 160
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 160

Val Ser Leu Ala Val Val
1               5

<210> SEQ ID NO 161
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 161

Ala Val Val Leu Gly Val
1               5

<210> SEQ ID NO 162
```

```
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 162

Thr Val Ser His Gly Val
1               5

<210> SEQ ID NO 163
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 163

Thr Thr Met Phe Ser Ala
1               5

<210> SEQ ID NO 164
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 164

Ala Ala Thr Thr Val Ser
1               5

<210> SEQ ID NO 165
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 165

Thr Ser Thr Thr Ser Thr
1               5

<210> SEQ ID NO 166
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 166

Leu Ser Tyr Thr Ser Ala
1               5

<210> SEQ ID NO 167
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 167

Thr Ser Thr Ser Asn Ser
1               5

<210> SEQ ID NO 168
<211> LENGTH: 6
```

```
<212> TYPE: PRT
<213> ORGANISM: Artificial Sequence
<220> FEATURE:
<223> OTHER INFORMATION: Domain 1 peptide

<400> SEQUENCE: 168

Ser Tyr Thr Ser Ala Tyr
1               5

<210> SEQ ID NO 169
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 169

Ala Val Ser His Val Thr
1               5

<210> SEQ ID NO 170
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 170

Val Leu Ser Tyr Thr Ser
1               5

<210> SEQ ID NO 171
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 171

Thr Thr Ser Thr Ser Asn
1               5

<210> SEQ ID NO 172
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 172

Tyr Gly Ala Ala Val Ser
1               5

<210> SEQ ID NO 173
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 173

Gly Ala Ala Ala Val Ser
1               5

<210> SEQ ID NO 174
<211> LENGTH: 6
<212> TYPE: PRT
```

```
<213> ORGANISM: Artificial Sequence
<220> FEATURE:
<223> OTHER INFORMATION: Domain 1 peptide

<400> SEQUENCE: 174

Gly Ala Ala Val Ser His
1               5

<210> SEQ ID NO 175
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 175

Tyr Gly Ala Ala Ala Val
1               5

<210> SEQ ID NO 176
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 176

Ser Thr Ser Asn Ser Asn
1               5

<210> SEQ ID NO 177
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 177

Ala Thr Ser Thr Thr Ser
1               5

<210> SEQ ID NO 178
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 178

Ser Thr Thr Ser Thr Ser
1               5

<210> SEQ ID NO 179
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 179

Ala Leu Ser Ser Cys Thr
1               5

<210> SEQ ID NO 180
<211> LENGTH: 6
<212> TYPE: PRT
<213> ORGANISM: Artificial Sequence
```

```
<220> FEATURE:
<223> OTHER INFORMATION: Domain 1 peptide

<400> SEQUENCE: 180

Val Val Leu Leu Ala Ala
1               5

<210> SEQ ID NO 181
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 181

Val Ser Gln Thr Thr His
1               5

<210> SEQ ID NO 182
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 182

Gly Ala Thr Val Ser His
1               5

<210> SEQ ID NO 183
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 183

Ala Ser Val Ser Thr Val
1               5

<210> SEQ ID NO 184
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 184

Thr Ser Val Ser Gln Thr
1               5

<210> SEQ ID NO 185
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 185

Ala Thr Thr Val Ser Arg
1               5

<210> SEQ ID NO 186
<211> LENGTH: 6
<212> TYPE: PRT
<213> ORGANISM: Artificial Sequence
<220> FEATURE:
```

<223> OTHER INFORMATION: Domain 1 peptide

<400> SEQUENCE: 186

Val Thr His Thr Thr His
1               5

<210> SEQ ID NO 187
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 187

Cys Thr Leu Ala Val Val
1               5

<210> SEQ ID NO 188
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 188

Ala Ala Ser Ile Leu Thr
1               5

<210> SEQ ID NO 189
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 189

Thr Val Ser Arg Thr Thr
1               5

<210> SEQ ID NO 190
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 190

Thr Thr Ala Val Ser His
1               5

<210> SEQ ID NO 191
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 191

Arg Ser Val Ser Thr Val
1               5

<210> SEQ ID NO 192
<211> LENGTH: 6
<212> TYPE: PRT
<213> ORGANISM: Artificial Sequence
<220> FEATURE:
<223> OTHER INFORMATION: Domain 1 peptide

```
<400> SEQUENCE: 192

Ser Cys Thr Leu Ala Val
1               5

<210> SEQ ID NO 193
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 193

Ala Thr Thr Ala Val Ser
1               5

<210> SEQ ID NO 194
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 194

Ala Val Leu Ala Ile Ser
1               5

<210> SEQ ID NO 195
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 195

Ser Ser Cys Thr Leu Ala
1               5

<210> SEQ ID NO 196
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 196

Thr Ser Ser Val Thr His
1               5

<210> SEQ ID NO 197
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 197

Val Ser His Val Ser His
1               5

<210> SEQ ID NO 198
<211> LENGTH: 6
<212> TYPE: PRT
<213> ORGANISM: Artificial Sequence
<220> FEATURE:
<223> OTHER INFORMATION: Domain 1 peptide
```

```
<400> SEQUENCE: 198

Thr Thr Val Ser Arg Thr
1               5

<210> SEQ ID NO 199
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 199

Ala Ala Thr Thr Tyr Arg
1               5

<210> SEQ ID NO 200
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 200

His Thr Val Thr His Thr
1               5

<210> SEQ ID NO 201
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 201

Thr His Thr Val Thr His
1               5

<210> SEQ ID NO 202
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 202

Ala Ala Thr Val Gly Tyr
1               5

<210> SEQ ID NO 203
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 203

His Ser Val Ser Thr Val
1               5

<210> SEQ ID NO 204
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 204
```

Thr Val Ser His Val Ser
1               5

<210> SEQ ID NO 205
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 205

Ala Thr Val Gly Tyr Ser
1               5

<210> SEQ ID NO 206
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 206

Thr Ala Val Ser His Val
1               5

<210> SEQ ID NO 207
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 207

Thr Val Thr His Thr Thr
1               5

<210> SEQ ID NO 208
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 208

Ala Thr Thr Ser Val Ser
1               5

<210> SEQ ID NO 209
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 209

Val Thr Ser Ser Val Thr
1               5

<210> SEQ ID NO 210
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 210

```
Gly His Ser Val Ser Thr
1               5

<210> SEQ ID NO 211
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 211

Ser Val Ser Thr Leu Ser
1               5

<210> SEQ ID NO 212
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 212

Thr Val Ser Thr Val Ser
1               5

<210> SEQ ID NO 213
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 213

Thr Thr Thr Lys Thr Val
1               5

<210> SEQ ID NO 214
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 214

Ser Ser Ile Ser Arg Val
1               5

<210> SEQ ID NO 215
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 215

Ile Ser Thr Val Ser His
1               5

<210> SEQ ID NO 216
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 216

Ser Ile Ser Arg Val Ser
```

1               5

<210> SEQ ID NO 217
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 217

Val Ser Thr Val His Arg
1               5

<210> SEQ ID NO 218
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 218

Val Thr Val Thr His His
1               5

<210> SEQ ID NO 219
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 219

Thr Val His Thr Val Ser
1               5

<210> SEQ ID NO 220
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 220

Val Lys Thr Val Thr His
1               5

<210> SEQ ID NO 221
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 221

Thr Val Thr Gly Leu Val
1               5

<210> SEQ ID NO 222
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 222

His Thr Val Ser His Val
1               5

```
<210> SEQ ID NO 223
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 223

Lys Thr Thr Ser Ser Val
1               5

<210> SEQ ID NO 224
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 224

Val Ser His Thr Ala His
1               5

<210> SEQ ID NO 225
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 225

Thr Val Ser Gln Thr Thr
1               5

<210> SEQ ID NO 226
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 226

Ser Thr Thr Thr Lys Thr
1               5

<210> SEQ ID NO 227
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 227

Ser Ile Ser Thr Val Ser
1               5

<210> SEQ ID NO 228
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 228

Thr Ser Val Lys Thr Thr
1               5
```

<210> SEQ ID NO 229
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 229

Val Ser Ile Ile Ala Ala
1               5

<210> SEQ ID NO 230
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 230

Ser Ser Val Ser His Val
1               5

<210> SEQ ID NO 231
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 231

Gln Arg Ser Val Ser Thr
1               5

<210> SEQ ID NO 232
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 232

Ile Ser Ser Ser Ala Lys
1               5

<210> SEQ ID NO 233
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 233

Ala Ala Ala Ser Val Thr
1               5

<210> SEQ ID NO 234
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 234

Ser Val Arg His Thr Val
1               5

-continued

```
<210> SEQ ID NO 235
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 235

Ala Ala Val Ser His Val
1               5

<210> SEQ ID NO 236
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 236

Val Lys Thr Val Val His
1               5

<210> SEQ ID NO 237
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 237

Val Arg His Thr Val Ser
1               5

<210> SEQ ID NO 238
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 238

Thr Ser Ser Val His His
1               5

<210> SEQ ID NO 239
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 239

Thr Lys Thr Val Thr Val
1               5

<210> SEQ ID NO 240
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 240

Lys Thr Val Thr Val Thr
1               5

<210> SEQ ID NO 241
```

```
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 241

Arg Val Ser His Thr Ala
1               5

<210> SEQ ID NO 242
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 242

Ser His Val Thr His Ser
1               5

<210> SEQ ID NO 243
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 243

Thr Thr Ser Val His His
1               5

<210> SEQ ID NO 244
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 244

Val Thr Ser Ser Ser Val
1               5

<210> SEQ ID NO 245
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 245

Gly Ala Thr Val His Thr
1               5

<210> SEQ ID NO 246
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 246

Ser Thr Val Thr His Thr
1               5

<210> SEQ ID NO 247
<211> LENGTH: 6
```

```
<212> TYPE: PRT
<213> ORGANISM: Artificial Sequence
<220> FEATURE:
<223> OTHER INFORMATION: Domain 1 peptide

<400> SEQUENCE: 247

Ala Ala Ser Val Ser Thr
1               5

<210> SEQ ID NO 248
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 248

Ala Val Thr Ser Ser Ser
1               5

<210> SEQ ID NO 249
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 249

Thr Thr His Gly Val Ala
1               5

<210> SEQ ID NO 250
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 250

Gly Ile Ser Ser Ser Ala
1               5

<210> SEQ ID NO 251
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 251

Met Ala Ala Ala Val Leu
1               5

<210> SEQ ID NO 252
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 252

Val Val Ser His Val Thr
1               5

<210> SEQ ID NO 253
<211> LENGTH: 6
<212> TYPE: PRT
```

```
<213> ORGANISM: Artificial Sequence
<220> FEATURE:
<223> OTHER INFORMATION: Domain 1 peptide

<400> SEQUENCE: 253

Gln Val Thr Ser Ser Val
1               5

<210> SEQ ID NO 254
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 254

Val Ala Thr Ala Val Ser
1               5

<210> SEQ ID NO 255
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 255

Ser Ile Asn Thr Val Ser
1               5

<210> SEQ ID NO 256
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 256

Thr Ser Val Ser His Thr
1               5

<210> SEQ ID NO 257
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 257

Tyr Gly Ala Thr Ala Val
1               5

<210> SEQ ID NO 258
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 258

Val Ser Thr Leu Ser His
1               5

<210> SEQ ID NO 259
<211> LENGTH: 6
<212> TYPE: PRT
<213> ORGANISM: Artificial Sequence
```

```
<220> FEATURE:
<223> OTHER INFORMATION: Domain 1 peptide

<400> SEQUENCE: 259

Asp Ser Ser Tyr Ser
1               5

<210> SEQ ID NO 260
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 260

Ala Val Met Ala Leu Ser
1               5

<210> SEQ ID NO 261
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 261

Ser Ser Ser Ala Lys Gly
1               5

<210> SEQ ID NO 262
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 262

Ser Arg Val Ser His Thr
1               5

<210> SEQ ID NO 263
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 263

Ala Leu Asp Ser Ser Ser
1               5

<210> SEQ ID NO 264
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 264

Thr Gly Ser Ser Val Ser
1               5

<210> SEQ ID NO 265
<211> LENGTH: 6
<212> TYPE: PRT
<213> ORGANISM: Artificial Sequence
<220> FEATURE:
```

```
<223> OTHER INFORMATION: Domain 1 peptide

<400> SEQUENCE: 265

Ala Ala Ser Ser Val Ser
1               5

<210> SEQ ID NO 266
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 266

Ala Val Ala Thr Tyr Arg
1               5

<210> SEQ ID NO 267
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 267

His Thr Val Ser Thr Val
1               5

<210> SEQ ID NO 268
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 268

Thr Val Thr His His Ala
1               5

<210> SEQ ID NO 269
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 269

Thr Ser Val His His Thr
1               5

<210> SEQ ID NO 270
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 270

Ser Ser Ser Tyr Ser His
1               5

<210> SEQ ID NO 271
<211> LENGTH: 6
<212> TYPE: PRT
<213> ORGANISM: Artificial Sequence
<220> FEATURE:
<223> OTHER INFORMATION: Domain 1 peptide
```

<400> SEQUENCE: 271

Arg His Thr Val Ser Thr
1               5

<210> SEQ ID NO 272
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 272

Val Ala Thr Tyr Arg Val
1               5

<210> SEQ ID NO 273
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 273

Ala Ser Ile Asn Thr Val
1               5

<210> SEQ ID NO 274
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 274

Thr Thr Ser Val Ser Gln
1               5

<210> SEQ ID NO 275
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 275

Ala Thr Thr Val Ser His
1               5

<210> SEQ ID NO 276
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 276

Thr Val Thr Val Thr His
1               5

<210> SEQ ID NO 277
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 277

Thr Thr Lys Thr Val Thr
1               5

<210> SEQ ID NO 278
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 278

Ala Ala Ala Val Leu Phe
1               5

<210> SEQ ID NO 279
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 279

Val Ser His Ala Gly Ala
1               5

<210> SEQ ID NO 280
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 280

Gln Thr Ser His Ser Val
1               5

<210> SEQ ID NO 281
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 281

Ala Ala Leu Asp Ser Ser
1               5

<210> SEQ ID NO 282
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 282

Ser Val Ser His Thr Thr
1               5

<210> SEQ ID NO 283
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 283

Ala Ile Ser Thr Val Gly
1               5

<210> SEQ ID NO 284
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 284

Ala Ala Ser Thr Val Thr
1               5

<210> SEQ ID NO 285
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 285

Thr Gly Leu Val Ser Ala
1               5

<210> SEQ ID NO 286
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 286

Ser His Thr Ala His Ser
1               5

<210> SEQ ID NO 287
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 287

Gly Ser Ser Val Ser Thr
1               5

<210> SEQ ID NO 288
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 288

Thr Ser Ser Ser Val Thr
1               5

<210> SEQ ID NO 289
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 289

Ala His Val Ser Gln Ser
1               5

<210> SEQ ID NO 290
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 290

Ser Ser Val Ser Thr Leu
1               5

<210> SEQ ID NO 291
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 291

Val His Thr Val Ser His
1               5

<210> SEQ ID NO 292
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 292

Ala Ala Ala Ala Val Ser
1               5

<210> SEQ ID NO 293
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 293

Ser Ser Ser Val Thr His
1               5

<210> SEQ ID NO 294
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 294

Ser Thr Ser Val Ser Gln
1               5

<210> SEQ ID NO 295
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 295

Gly Ser Thr Thr Thr Lys

```
<210> SEQ ID NO 296
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 296

Thr Val Thr His Ser Asn
1               5

<210> SEQ ID NO 297
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 297

Gly Ala Ser Val Ser Thr
1               5

<210> SEQ ID NO 298
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 298

Thr Val Ser His Gly Ser
1               5

<210> SEQ ID NO 299
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 299

Thr Arg Ser Val Ser Thr
1               5

<210> SEQ ID NO 300
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 300

Val Ser Arg Thr Ala Leu
1               5

<210> SEQ ID NO 301
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 301

Ser Val Lys Thr Thr Ser
1               5
```

```
<210> SEQ ID NO 302
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 302

Ala Thr Thr Ile Phe Ala
1               5

<210> SEQ ID NO 303
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 303

Ala Ala Thr Val Ser Gln
1               5

<210> SEQ ID NO 304
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 304

Ala Ala Ala Ser Val Ser
1               5

<210> SEQ ID NO 305
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 305

Ser Ser Ser Ile Ser Arg
1               5

<210> SEQ ID NO 306
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 306

Leu Thr Thr Thr Ser Val
1               5

<210> SEQ ID NO 307
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 307

Val Gly Ala Ser Val Ser
1               5
```

```
<210> SEQ ID NO 308
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 308

Val Ser Gln Thr Ser His
1               5

<210> SEQ ID NO 309
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 309

Gly Gln Ser Val Ser Thr
1               5

<210> SEQ ID NO 310
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 310

Ser Val His His Thr Thr
1               5

<210> SEQ ID NO 311
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 311

Gly Ala Thr Ala Val Ser
1               5

<210> SEQ ID NO 312
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 312

Gly Thr Ser Val Lys Thr
1               5

<210> SEQ ID NO 313
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 313

Tyr Val Ser Arg Thr Ala
1               5
```

```
<210> SEQ ID NO 314
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 314

Ser Val Gln Thr Val Ser
1               5

<210> SEQ ID NO 315
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 315

Tyr Ala Ser Ala Ile Ala
1               5

<210> SEQ ID NO 316
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 316

Thr Ser Ser Ser Ile Ser
1               5

<210> SEQ ID NO 317
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 317

Ala Thr Val Ser Gln Thr
1               5

<210> SEQ ID NO 318
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 318

Ser Val Ser Thr Val His
1               5

<210> SEQ ID NO 319
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 319

Thr Thr Thr Ser Val His
1               5

<210> SEQ ID NO 320
```

```
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 320

Ala Ser Val Thr His Gly
1               5

<210> SEQ ID NO 321
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 321

Gln Ala Ile Ser Thr Val
1               5

<210> SEQ ID NO 322
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 322

Ala Ser Thr Val Thr His
1               5

<210> SEQ ID NO 323
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 323

Ser Val Ser Gln Thr Ser
1               5

<210> SEQ ID NO 324
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 324

Gly Ser Ser Ile Ser Thr
1               5

<210> SEQ ID NO 325
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 325

Gln Ser Val Ser Thr Val
1               5

<210> SEQ ID NO 326
<211> LENGTH: 6
```

```
<212> TYPE: PRT
<213> ORGANISM: Artificial Sequence
<220> FEATURE:
<223> OTHER INFORMATION: Domain 1 peptide

<400> SEQUENCE: 326

Ser Ser Ile Ser Thr Val
1               5

<210> SEQ ID NO 327
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 327

Val Lys Thr Thr Ser Ser
1               5

<210> SEQ ID NO 328
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 328

Thr Val Ser His Ala Gly
1               5

<210> SEQ ID NO 329
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 329

Ala Ser Thr Ser Val Ser
1               5

<210> SEQ ID NO 330
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 330

Val Thr Gly Leu Val Ser
1               5

<210> SEQ ID NO 331
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 331

Val Gly Gln Ser Val Ser
1               5

<210> SEQ ID NO 332
<211> LENGTH: 6
<212> TYPE: PRT
```

```
<213> ORGANISM: Artificial Sequence
<220> FEATURE:
<223> OTHER INFORMATION: Domain 1 peptide

<400> SEQUENCE: 332

Thr Thr Val Ser His Thr
1               5

<210> SEQ ID NO 333
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 333

Ala Ala Ser Val Thr His
1               5

<210> SEQ ID NO 334
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 334

Thr Thr Ser Ser Val His
1               5

<210> SEQ ID NO 335
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 335

Ala Thr Val His Thr Val
1               5

<210> SEQ ID NO 336
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 336

Ser Val Ser Gln Thr Thr
1               5

<210> SEQ ID NO 337
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 337

Ser Thr Val Ser His Ala
1               5

<210> SEQ ID NO 338
<211> LENGTH: 6
<212> TYPE: PRT
<213> ORGANISM: Artificial Sequence
```

```
<220> FEATURE:
<223> OTHER INFORMATION: Domain 1 peptide

<400> SEQUENCE: 338

Ser Thr Val Ser His Ala
1               5

<210> SEQ ID NO 339
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 339

Thr Thr His His Ala Pro
1               5

<210> SEQ ID NO 340
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 340

Ser His Thr Thr His His
1               5

<210> SEQ ID NO 341
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 341

Thr His His Ala Pro Tyr
1               5

<210> SEQ ID NO 342
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 342

His His Ala Pro Tyr Gly
1               5

<210> SEQ ID NO 343
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 343

His His Ala Pro Leu Gly
1               5

<210> SEQ ID NO 344
<211> LENGTH: 6
<212> TYPE: PRT
<213> ORGANISM: Artificial Sequence
<220> FEATURE:
```

```
<223> OTHER INFORMATION: Domain 1 peptide

<400> SEQUENCE: 344

Thr His His Ala Pro Leu
1               5

<210> SEQ ID NO 345
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 345

Gly Tyr Gly Leu His His
1               5

<210> SEQ ID NO 346
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 346

Gly Leu His His Gly Gly
1               5

<210> SEQ ID NO 347
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 347

Tyr Gly Leu His His Gly
1               5

<210> SEQ ID NO 348
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 348

Leu His His Gly Gly Leu
1               5

<210> SEQ ID NO 349
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 349

His His Gly Gly Leu Tyr
1               5

<210> SEQ ID NO 350
<211> LENGTH: 6
<212> TYPE: PRT
<213> ORGANISM: Artificial Sequence
<220> FEATURE:
<223> OTHER INFORMATION: Domain 1 peptide
```

<400> SEQUENCE: 350

His Gly Leu Leu His Gly
1               5

<210> SEQ ID NO 351
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 351

Gly His Gly Leu Leu His
1               5

<210> SEQ ID NO 352
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 352

Arg Thr Thr His His Ala
1               5

<210> SEQ ID NO 353
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 353

Ser Arg Thr Thr His His
1               5

<210> SEQ ID NO 354
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 354

Thr Gly Gly His Gly His
1               5

<210> SEQ ID NO 355
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 355

Gly His Gly His Gly Gly
1               5

<210> SEQ ID NO 356
<211> LENGTH: 6
<212> TYPE: PRT
<213> ORGANISM: Artificial Sequence
<220> FEATURE:
<223> OTHER INFORMATION: Domain 1 peptide

```
<400> SEQUENCE: 356

Val Ser His Gly Val His
1               5

<210> SEQ ID NO 357
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 357

Gly Gly His Gly His Gly
1               5

<210> SEQ ID NO 358
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 358

His Ala Asn His Val Gly
1               5

<210> SEQ ID NO 359
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 359

His Gly His Gly Gly Tyr
1               5

<210> SEQ ID NO 360
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 360

Tyr His Ala Asn His Val
1               5

<210> SEQ ID NO 361
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 361

Ala Tyr His Ala Asn His
1               5

<210> SEQ ID NO 362
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 362
```

```
Ser His Val Thr His His
1               5

<210> SEQ ID NO 363
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 363

His Val Thr His His Ala
1               5

<210> SEQ ID NO 364
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 364

His Thr Thr His Gly Val
1               5

<210> SEQ ID NO 365
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 365

Ser His Thr Thr His Gly
1               5

<210> SEQ ID NO 366
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 366

Thr His His Ala Pro Ala
1               5

<210> SEQ ID NO 367
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 367

His His Ala Pro Ala Ala
1               5

<210> SEQ ID NO 368
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 368
```

Ser His Val Ser His Gly
1               5

<210> SEQ ID NO 369
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 369

Thr His Thr Thr His Gly
1               5

<210> SEQ ID NO 370
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 370

Thr Thr His Gly Val His
1               5

<210> SEQ ID NO 371
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 371

Thr His Gly Val His His
1               5

<210> SEQ ID NO 372
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 372

His Gly Val His Ser Pro
1               5

<210> SEQ ID NO 373
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 373

Ser His Gly Ile Gly His
1               5

<210> SEQ ID NO 374
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 374

Thr His His Ala Pro Val

```
1               5

<210> SEQ ID NO 375
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 375

Ser His Gly Val His Ser
1               5

<210> SEQ ID NO 376
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 376

His His Gly Pro Tyr Gly
1               5

<210> SEQ ID NO 377
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 377

Thr Thr His His Ala Gly
1               5

<210> SEQ ID NO 378
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 378

Ser Val His His His Val
1               5

<210> SEQ ID NO 379
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 379

Ser His Gly Ser His Tyr
1               5

<210> SEQ ID NO 380
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 380

His Gly Val Ser His Pro
1               5
```

```
<210> SEQ ID NO 381
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 381

Thr His His Ala Gly Tyr
1               5

<210> SEQ ID NO 382
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 382

His His Leu Pro Ala Ala
1               5

<210> SEQ ID NO 383
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 383

His Ala Gly Ala His Pro
1               5

<210> SEQ ID NO 384
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 384

Ser Ser Val His His His
1               5

<210> SEQ ID NO 385
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 385

His Gly Val His His Pro
1               5

<210> SEQ ID NO 386
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 386

Val Ser His Gly Leu His
1               5
```

```
<210> SEQ ID NO 387
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 387

His His Ala Pro Val Tyr
1               5

<210> SEQ ID NO 388
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 388

Ser His Gly Val His Pro
1               5

<210> SEQ ID NO 389
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 389

Ser Gln Thr Thr His His
1               5

<210> SEQ ID NO 390
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 390

His Val Ser His Gly Pro
1               5

<210> SEQ ID NO 391
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 391

His Gly Val His His Leu
1               5

<210> SEQ ID NO 392
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 392

His Gly Ile His Ala Pro
1               5
```

```
<210> SEQ ID NO 393
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 393

Val Ser His Gly Ile His
1               5

<210> SEQ ID NO 394
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 394

His Thr Ala His Ser Pro
1               5

<210> SEQ ID NO 395
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 395

Gln Thr Thr His His Ala
1               5

<210> SEQ ID NO 396
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 396

Val Gly His Gly Ile His
1               5

<210> SEQ ID NO 397
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 397

Ser His Asp Val His Gln
1               5

<210> SEQ ID NO 398
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 398

Gly His Gly Ile His Pro
1               5

<210> SEQ ID NO 399
```

```
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 399

His His His Val Val Pro
1               5

<210> SEQ ID NO 400
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 400

His Ser Val Pro His Ile
1               5

<210> SEQ ID NO 401
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 401

His Thr Thr His Gly Ile
1               5

<210> SEQ ID NO 402
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 402

His Thr Val Ser His Gly
1               5

<210> SEQ ID NO 403
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 403

Gly His His Gly Pro Tyr
1               5

<210> SEQ ID NO 404
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 404

His His Thr Thr His Gly
1               5

<210> SEQ ID NO 405
<211> LENGTH: 6
```

```
<212> TYPE: PRT
<213> ORGANISM: Artificial Sequence
<220> FEATURE:
<223> OTHER INFORMATION: Domain 1 peptide

<400> SEQUENCE: 405

His His Ala Pro Thr Tyr
1               5

<210> SEQ ID NO 406
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 406

His Asp Val His Gln Pro
1               5

<210> SEQ ID NO 407
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 407

Thr Val His His Pro Ala
1               5

<210> SEQ ID NO 408
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 408

Thr His His Ala Pro Thr
1               5

<210> SEQ ID NO 409
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 409

His Gly Val Ala His Pro
1               5

<210> SEQ ID NO 410
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 410

Arg Gly His Gly Ala His
1               5

<210> SEQ ID NO 411
<211> LENGTH: 6
<212> TYPE: PRT
```

```
<213> ORGANISM: Artificial Sequence
<220> FEATURE:
<223> OTHER INFORMATION: Domain 1 peptide

<400> SEQUENCE: 411

Gly Val His His Leu Pro
1               5

<210> SEQ ID NO 412
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 412

Thr His Gly Phe His Pro
1               5

<210> SEQ ID NO 413
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 413

Val Thr His Gly Phe His
1               5

<210> SEQ ID NO 414
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 414

Ser His Ala Gly Ala His
1               5

<210> SEQ ID NO 415
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 415

Thr His Gly Ile His His
1               5

<210> SEQ ID NO 416
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 416

His Gly Phe His Pro Ala
1               5

<210> SEQ ID NO 417
<211> LENGTH: 6
<212> TYPE: PRT
<213> ORGANISM: Artificial Sequence
```

```
<220> FEATURE:
<223> OTHER INFORMATION: Domain 1 peptide

<400> SEQUENCE: 417

Ser His Gly Ile Ser His
1               5

<210> SEQ ID NO 418
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 418

Gly Gly His His Gly Pro
1               5

<210> SEQ ID NO 419
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 419

Val Ser His Gly Ser His
1               5

<210> SEQ ID NO 420
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 420

Val His His Thr Thr His
1               5

<210> SEQ ID NO 421
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 421

His His Ala Gly Tyr Gly
1               5

<210> SEQ ID NO 422
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 422

His Gly Ile His Pro Thr
1               5

<210> SEQ ID NO 423
<211> LENGTH: 6
<212> TYPE: PRT
<213> ORGANISM: Artificial Sequence
<220> FEATURE:
```

<223> OTHER INFORMATION: Domain 1 peptide

<400> SEQUENCE: 423

His Ala Val His Arg Val
1               5

<210> SEQ ID NO 424
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 424

His Gly Val His Pro Ser
1               5

<210> SEQ ID NO 425
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 425

Val His His Leu Pro Ala
1               5

<210> SEQ ID NO 426
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 426

Ser Gly Gly His His Gly
1               5

<210> SEQ ID NO 427
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 427

His His Val Val Pro Ser
1               5

<210> SEQ ID NO 428
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 428

Gly His Ala Val His Arg
1               5

<210> SEQ ID NO 429
<211> LENGTH: 6
<212> TYPE: PRT
<213> ORGANISM: Artificial Sequence
<220> FEATURE:
<223> OTHER INFORMATION: Domain 1 peptide

```
<400> SEQUENCE: 429

Val His Thr Val His His
1               5

<210> SEQ ID NO 430
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 430

Ser His Gly Val Ser His
1               5

<210> SEQ ID NO 431
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 431

Gly Ser Gly Gly His His
1               5

<210> SEQ ID NO 432
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 432

Gly His Thr Val Ser His
1               5

<210> SEQ ID NO 433
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 433

Val Ser His Asp Val His
1               5

<210> SEQ ID NO 434
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 434

His Ala Pro Val Ala His
1               5

<210> SEQ ID NO 435
<211> LENGTH: 6
<212> TYPE: PRT
<213> ORGANISM: Artificial Sequence
<220> FEATURE:
<223> OTHER INFORMATION: Domain 1 peptide
```

```
<400> SEQUENCE: 435

Val His His His Val Val
1               5

<210> SEQ ID NO 436
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 436

His Gly Ile Gly His Pro
1               5

<210> SEQ ID NO 437
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 437

Ser His Ser Val Pro His
1               5

<210> SEQ ID NO 438
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 438

Ile Gly His Ala Val His
1               5

<210> SEQ ID NO 439
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 439

His Tyr Pro Met Gly His
1               5

<210> SEQ ID NO 440
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 440

His Gly Ser His Tyr Pro
1               5

<210> SEQ ID NO 441
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 441
```

His Gly Ala His Val Ser
1               5

<210> SEQ ID NO 442
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 442

His Thr Thr His Gly Gly
1               5

<210> SEQ ID NO 443
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 443

Ser His Gly Ile His Ala
1               5

<210> SEQ ID NO 444
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 444

Gly His Gly Ala His Val
1               5

<210> SEQ ID NO 445
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 445

Thr His Gly Val Ala His
1               5

<210> SEQ ID NO 446
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 446

His Val Thr His Ser Ile
1               5

<210> SEQ ID NO 447
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 447

```
His Gly Ile Ser His Ala
1               5

<210> SEQ ID NO 448
<211> LENGTH: 6
<212> TYPE: PRT
<213> ORGANISM: Artificial Sequence
<220> FEATURE:
<223> OTHER INFORMATION: Domain 1 peptide

<400> SEQUENCE: 448

Thr Val Thr His His Pro
1               5

<210> SEQ ID NO 449
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 449

Gly Gly Leu Tyr
1

<210> SEQ ID NO 450
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 450

Tyr Gly Gly Tyr
1

<210> SEQ ID NO 451
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 451

Gly Tyr Gly Leu
1

<210> SEQ ID NO 452
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 452

Gly Tyr Gly Gly
1

<210> SEQ ID NO 453
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 453

Gly Leu Tyr Gly
```

<210> SEQ ID NO 454
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 454

Leu Tyr Gly Gly
1

<210> SEQ ID NO 455
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 455

Tyr Gly Leu Gly
1

<210> SEQ ID NO 456
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 456

Tyr Gly Gly Leu
1

<210> SEQ ID NO 457
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 457

Gly Leu Gly Gly
1

<210> SEQ ID NO 458
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 458

Leu Gly Gly Tyr
1

<210> SEQ ID NO 459
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 459

His Gly Gly Leu
1

```
<210> SEQ ID NO 460
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 460

Tyr Gly Phe Gly
1

<210> SEQ ID NO 461
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 461

Tyr Gly Tyr Gly
1

<210> SEQ ID NO 462
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 462

Gly Phe Gly Gly
1

<210> SEQ ID NO 463
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 463

Gly Leu Gly Ala
1

<210> SEQ ID NO 464
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 464

Leu Gly Tyr Gly
1

<210> SEQ ID NO 465
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 465

Gly Gly Leu Gly
1
```

```
<210> SEQ ID NO 466
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 466

Gly Ala Tyr Gly
1

<210> SEQ ID NO 467
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 467

Gly Gln Gly Gly
1

<210> SEQ ID NO 468
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 468

Gly Phe Gly Tyr
1

<210> SEQ ID NO 469
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 469

Gly Leu Gly Tyr
1

<210> SEQ ID NO 470
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 470

Leu His Gly Gly
1

<210> SEQ ID NO 471
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 471

Phe Gly Gly Leu
1
```

-continued

```
<210> SEQ ID NO 472
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 472

Ala Gly Tyr Gly
1

<210> SEQ ID NO 473
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 473

Gly Tyr Gly Tyr
1

<210> SEQ ID NO 474
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 474

Tyr Gly Gln Gly
1

<210> SEQ ID NO 475
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 475

Gln Gly Gly Tyr
1

<210> SEQ ID NO 476
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 476

Gly Tyr Gly Gln
1

<210> SEQ ID NO 477
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 477

Leu Gly Gly Leu
1

<210> SEQ ID NO 478
```

```
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 478

Gly Tyr Gly Ala
1

<210> SEQ ID NO 479
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 479

Gly Tyr Gly Phe
1

<210> SEQ ID NO 480
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 480

Ala His Gly Gly
1

<210> SEQ ID NO 481
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 481

Gly Leu Ala Gly
1

<210> SEQ ID NO 482
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 482

Gly Tyr Gly Val
1

<210> SEQ ID NO 483
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 483

Phe Gly Gly Tyr
1

<210> SEQ ID NO 484
<211> LENGTH: 4
```

```
<212> TYPE: PRT
<213> ORGANISM: Artificial Sequence
<220> FEATURE:
<223> OTHER INFORMATION: Domain 2 peptide

<400> SEQUENCE: 484

Gly Gly His Gly
1

<210> SEQ ID NO 485
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 485

Leu Gly Phe Gly
1

<210> SEQ ID NO 486
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 486

Ser Tyr Gly Gly
1

<210> SEQ ID NO 487
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 487

Gly Tyr Gly Ser
1

<210> SEQ ID NO 488
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 488

Val Gly Gly Tyr
1

<210> SEQ ID NO 489
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 489

His Gly Gly Tyr
1

<210> SEQ ID NO 490
<211> LENGTH: 4
<212> TYPE: PRT
```

<213> ORGANISM: Artificial Sequence
<220> FEATURE:
<223> OTHER INFORMATION: Domain 2 peptide

<400> SEQUENCE: 490

His His Gly Gly
1

<210> SEQ ID NO 491
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 491

Gly Leu Gly Leu
1

<210> SEQ ID NO 492
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 492

Tyr Gly Gly His
1

<210> SEQ ID NO 493
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 493

Leu Gly Leu Gly
1

<210> SEQ ID NO 494
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 494

Gly His Gly Leu
1

<210> SEQ ID NO 495
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 495

Gly Gly Tyr Leu
1

<210> SEQ ID NO 496
<211> LENGTH: 4
<212> TYPE: PRT
<213> ORGANISM: Artificial Sequence

```
<220> FEATURE:
<223> OTHER INFORMATION: Domain 2 peptide

<400> SEQUENCE: 496

Tyr Gly Gly Trp
1

<210> SEQ ID NO 497
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 497

Gly Gly Leu Leu
1

<210> SEQ ID NO 498
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 498

Gly Val Tyr Gly
1

<210> SEQ ID NO 499
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 499

Tyr Gly Gly Val
1

<210> SEQ ID NO 500
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 500

Gly Tyr Leu Gly
1

<210> SEQ ID NO 501
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 501

Gly Val Gly Gly
1

<210> SEQ ID NO 502
<211> LENGTH: 4
<212> TYPE: PRT
<213> ORGANISM: Artificial Sequence
<220> FEATURE:
```

```
<223> OTHER INFORMATION: Domain 2 peptide

<400> SEQUENCE: 502

Pro Tyr Gly Gly
1

<210> SEQ ID NO 503
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 503

Gly Ser Tyr Gly
1

<210> SEQ ID NO 504
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 504

Gly Tyr Gly His
1

<210> SEQ ID NO 505
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 505

Tyr Gly Val Gly
1

<210> SEQ ID NO 506
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 506

Gly His Gly Gly
1

<210> SEQ ID NO 507
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 507

Gly Val Ser Gly
1

<210> SEQ ID NO 508
<211> LENGTH: 4
<212> TYPE: PRT
<213> ORGANISM: Artificial Sequence
<220> FEATURE:
<223> OTHER INFORMATION: Domain 2 peptide
```

```
<400> SEQUENCE: 508

Ser Gly Tyr Gly
1

<210> SEQ ID NO 509
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 509

Thr Tyr Gly Gly
1

<210> SEQ ID NO 510
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 510

Val Ser Gly Gly
1

<210> SEQ ID NO 511
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 511

Gly Ala Gly Tyr
1

<210> SEQ ID NO 512
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 512

Leu Leu Gly Gly
1

<210> SEQ ID NO 513
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 513

Tyr Leu Gly Gly
1

<210> SEQ ID NO 514
<211> LENGTH: 4
<212> TYPE: PRT
<213> ORGANISM: Artificial Sequence
<220> FEATURE:
<223> OTHER INFORMATION: Domain 2 peptide
```

```
<400> SEQUENCE: 514

Gly Tyr Pro Gly
1

<210> SEQ ID NO 515
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 515

Val Tyr Gly Gly
1

<210> SEQ ID NO 516
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 516

Val Gly Tyr Gly
1

<210> SEQ ID NO 517
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 517

Gly Ser Gly Tyr
1

<210> SEQ ID NO 518
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 518

Gly Gly Val Tyr
1

<210> SEQ ID NO 519
<211> LENGTH: 4
<212> TYPE: PRT
<213> ORGANISM: Artificial Sequence
<220> FEATURE:
<223> OTHER INFORMATION: Domain 2 peptide

<400> SEQUENCE: 519

Gly Gly Trp Gly
1

<210> SEQ ID NO 520
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 520
```

Tyr Gly Gly Tyr Gly
1               5

<210> SEQ ID NO 521
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 521

Gly Gly Tyr Gly Leu
1               5

<210> SEQ ID NO 522
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 522

Leu Tyr Gly Gly Tyr
1               5

<210> SEQ ID NO 523
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 523

Gly Tyr Gly Leu Gly
1               5

<210> SEQ ID NO 524
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 524

Gly Gly Tyr Gly Gly
1               5

<210> SEQ ID NO 525
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 525

Leu Gly Gly Tyr Gly
1               5

<210> SEQ ID NO 526
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 526

```
Gly Tyr Gly Gly Leu
1               5

<210> SEQ ID NO 527
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 527

Gly Tyr Gly Gly Tyr
1               5

<210> SEQ ID NO 528
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 528

Tyr Gly Leu Gly Gly
1               5

<210> SEQ ID NO 529
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 529

Tyr Gly Gly Leu Tyr
1               5

<210> SEQ ID NO 530
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 530

Gly Leu Gly Gly Tyr
1               5

<210> SEQ ID NO 531
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 531

His Gly Gly Leu Tyr
1               5

<210> SEQ ID NO 532
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 532

Tyr Gly Leu Gly Ala
```

1               5

<210> SEQ ID NO 533
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 533

Gly Tyr Gly Leu Ala
1               5

<210> SEQ ID NO 534
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 534

Gly Tyr Gly Leu His
1               5

<210> SEQ ID NO 535
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 535

Leu Gly Ala Tyr Gly
1               5

<210> SEQ ID NO 536
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 536

Gly Leu Gly Ala Tyr
1               5

<210> SEQ ID NO 537
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 537

Pro Tyr Gly Tyr Gly
1               5

<210> SEQ ID NO 538
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 538

Tyr Gly Tyr Gly Gly
1               5

<210> SEQ ID NO 539
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 539

Gly Phe Gly Gly Leu
1               5

<210> SEQ ID NO 540
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 540

Gly Phe Gly Tyr Pro
1               5

<210> SEQ ID NO 541
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 541

Gly Tyr Gly Gln Gly
1               5

<210> SEQ ID NO 542
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 542

Leu His Gly Gly Leu
1               5

<210> SEQ ID NO 543
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 543

Gly Gln Gly Gly Tyr
1               5

<210> SEQ ID NO 544
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 544

Tyr Gly Phe Gly Gly
1               5

```
<210> SEQ ID NO 545
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 545

Tyr Gly Gln Gly Gly
1               5

<210> SEQ ID NO 546
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 546

Gly Gly Tyr Gly Gln
1               5

<210> SEQ ID NO 547
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 547

Tyr Gly Gly Leu Gly
1               5

<210> SEQ ID NO 548
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 548

Gly Ala Tyr Gly Phe
1               5

<210> SEQ ID NO 549
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 549

Phe Gly Gly Leu Tyr
1               5

<210> SEQ ID NO 550
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 550

Ala Tyr Gly Phe Gly
1               5
```

```
<210> SEQ ID NO 551
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 551

Gly Gly Leu Gly Gly
1               5

<210> SEQ ID NO 552
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 552

Tyr Gly Phe Gly Tyr
1               5

<210> SEQ ID NO 553
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 553

Gly Leu Leu His Gly
1               5

<210> SEQ ID NO 554
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 554

Leu Tyr Gly Gly Leu
1               5

<210> SEQ ID NO 555
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 555

Leu Gly Tyr Gly Leu
1               5

<210> SEQ ID NO 556
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 556

Gly Leu Gly Tyr Gly
1               5

<210> SEQ ID NO 557
```

```
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 557

Gln Gly Gly Tyr Gly
1               5

<210> SEQ ID NO 558
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 558

Leu Leu His Gly Gly
1               5

<210> SEQ ID NO 559
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 559

Ala His Gly Gly Leu
1               5

<210> SEQ ID NO 560
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 560

Ala Gly Tyr Gly Gly
1               5

<210> SEQ ID NO 561
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 561

Gly Gly Tyr Gly Phe
1               5

<210> SEQ ID NO 562
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 562

Gly Leu Gly Gly Leu
1               5

<210> SEQ ID NO 563
<211> LENGTH: 5
```

```
<212> TYPE: PRT
<213> ORGANISM: Artificial Sequence
<220> FEATURE:
<223> OTHER INFORMATION: Domain 2 peptide

<400> SEQUENCE: 563

Pro Leu Gly Tyr Gly
1               5

<210> SEQ ID NO 564
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 564

Leu Ala Gly Tyr Gly
1               5

<210> SEQ ID NO 565
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 565

Leu Ala His Gly Gly
1               5

<210> SEQ ID NO 566
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 566

Gly Leu Ala Gly Tyr
1               5

<210> SEQ ID NO 567
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 567

Gly Leu Ala His Gly
1               5

<210> SEQ ID NO 568
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 568

Tyr Gly Leu Ala Gly
1               5

<210> SEQ ID NO 569
<211> LENGTH: 5
<212> TYPE: PRT
```

<213> ORGANISM: Artificial Sequence
<220> FEATURE:
<223> OTHER INFORMATION: Domain 2 peptide

<400> SEQUENCE: 569

Gly Tyr Gly Phe Gly
1               5

<210> SEQ ID NO 570
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 570

Pro Leu Gly Phe Gly
1               5

<210> SEQ ID NO 571
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 571

Gly Tyr Gly Tyr Gly
1               5

<210> SEQ ID NO 572
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 572

Leu Gly Phe Gly Gly
1               5

<210> SEQ ID NO 573
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 573

Gly Gly Tyr Gly Val
1               5

<210> SEQ ID NO 574
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 574

Pro Tyr Gly Phe Gly
1               5

<210> SEQ ID NO 575
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 575

Gly Gly Tyr Gly Ala
1               5

<210> SEQ ID NO 576
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 576

Gly Leu His His Gly
1               5

<210> SEQ ID NO 577
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 577

Val Gly Gly Tyr Gly
1               5

<210> SEQ ID NO 578
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 578

Phe Gly Gly Tyr Gly
1               5

<210> SEQ ID NO 579
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 579

Leu His His Gly Gly
1               5

<210> SEQ ID NO 580
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 580

His Gly Gly Tyr Gly
1               5

<210> SEQ ID NO 581
<211> LENGTH: 5
<212> TYPE: PRT
<213> ORGANISM: Artificial Sequence
<220> FEATURE:

```
<223> OTHER INFORMATION: Domain 2 peptide

<400> SEQUENCE: 581

His His Gly Gly Leu
1               5

<210> SEQ ID NO 582
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 582

Tyr Gly Gly His Gly
1               5

<210> SEQ ID NO 583
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 583

Gly Phe Gly Gly Tyr
1               5

<210> SEQ ID NO 584
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 584

Leu Gly Tyr Gly Gly
1               5

<210> SEQ ID NO 585
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 585

Gly Leu Gly Leu Gly
1               5

<210> SEQ ID NO 586
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 586

Gly Tyr Gly Leu Leu
1               5

<210> SEQ ID NO 587
<211> LENGTH: 5
<212> TYPE: PRT
<213> ORGANISM: YGGYLArtificial Sequence
<220> FEATURE:
<223> OTHER INFORMATION: Domain 2 peptide
```

<210> SEQ ID NO 587
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 587

Tyr Gly Gly Tyr Leu
1               5

<210> SEQ ID NO 588
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 588

Gly Gly Tyr Gly Tyr
1               5

<210> SEQ ID NO 589
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 589

Tyr Gly Tyr Gly Leu
1               5

<210> SEQ ID NO 590
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 590

Gly Tyr Gly Tyr Pro
1               5

<210> SEQ ID NO 591
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 591

Leu Gly Gly Leu Tyr
1               5

<210> SEQ ID NO 592
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 592

Tyr Gly Gly Leu Leu
1               5

<210> SEQ ID NO 593
<211> LENGTH: 5
<212> TYPE: PRT
<213> ORGANISM: Artificial Sequence
<220> FEATURE:
<223> OTHER INFORMATION: Domain 2 peptide

```
<400> SEQUENCE: 593

Gly Gly His Gly Leu
1               5

<210> SEQ ID NO 594
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 594

Gly Ser Tyr Gly Gly
1               5

<210> SEQ ID NO 595
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 595

Gly Val Ser Gly Gly
1               5

<210> SEQ ID NO 596
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 596

Gly Gly Tyr Gly His
1               5

<210> SEQ ID NO 597
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 597

Gly His Gly Gly Tyr
1               5

<210> SEQ ID NO 598
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 598

Gly Leu Gly Ala Val
1               5

<210> SEQ ID NO 599
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 599
```

```
Gly Tyr Leu Gly Gly
1               5

<210> SEQ ID NO 600
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 600

Gly Gly Tyr Leu Gly
1               5

<210> SEQ ID NO 601
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 601

Tyr Gly Tyr Gly Tyr
1               5

<210> SEQ ID NO 602
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 602

Gly His Gly Leu Leu
1               5

<210> SEQ ID NO 603
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 603

Leu Tyr Gly Gly His
1               5

<210> SEQ ID NO 604
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 604

Gly Val Tyr Gly Gly
1               5

<210> SEQ ID NO 605
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 605
```

```
Gly Gly Leu Gly Tyr
1               5

<210> SEQ ID NO 606
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 606

Ser Tyr Gly Gly Tyr
1               5

<210> SEQ ID NO 607
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 607

Gly Gly Tyr Gly Ser
1               5

<210> SEQ ID NO 608
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 608

Gly Tyr Gly Ala Ala
1               5

<210> SEQ ID NO 609
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 609

Leu Leu Gly Gly Tyr
1               5

<210> SEQ ID NO 610
<211> LENGTH: 5
<212> TYPE: PRT
<213> ORGANISM: Artificial Sequence
<220> FEATURE:
<223> OTHER INFORMATION: Domain 2 peptide

<400> SEQUENCE: 610

Gly Tyr Pro Gly Ala
1               5

<210> SEQ ID NO 611
<211> LENGTH: 5
<212> TYPE: PRT
<213> ORGANISM: Artificial Sequence
<220> FEATURE:
<223> OTHER INFORMATION: Domain 2 peptide
```

```
<400> SEQUENCE: 611

Tyr Gly Gly Trp Gly
1               5
```

UNITED STATES PATENT AND TRADEMARK OFFICE
CERTIFICATE OF CORRECTION

PATENT NO. : 10,899,803 B2  
APPLICATION NO. : 14/436745  
DATED : January 26, 2021  
INVENTOR(S) : Paul Andre Guerette et al.

Page 1 of 1

It is certified that error appears in the above-identified patent and that said Letters Patent is hereby corrected as shown below:

On the Title Page

Page 2, Column 2, item (56), References Cited/Other Publications:
"Studart, "Towards High-Performance Bioinspired Composites," Advanced Materials24: 5024-5044, 2012." should read: --Studart, "Towards High-Performance Bioinspired Composites," Advanced Materials 24: 5024-5044, 2012.--.

In the Claims

Column 341, Claim 1, Lines 20-22:
"wherein the recombinant polypeptide is at least partially in beta sheet conformation, and" should read: --wherein the recombinant polypeptide is at least partially in beta sheet conformation, and wherein the recombinant polypeptide can be engineered into materials with tailored structure and mechanical properties; and--.

Column 341, Claim 4, Line 50:
"sequence GGX1X2X3Y (SEQ ID NO: 1)" should read: --sequence $GGX_1X_2X_3Y$ (SEQ ID NO: 1)--.

Column 342, Claim 10, Line 30:
"sequence GGX1X2X3Y (SEQ ID NO: 1)" should read: --sequence $GGX_1X_2X_3Y$ (SEQ ID NO: 1)--.

Column 342, Claim 16, Line 55:
"has an elastic modulus ranges from 5 MPa to 9 GPa." should read: --has an elastic modulus range from 5 MPa to 9 GPa.--.

Column 343, Claim 24, Line 16:
"multimer of the recombinant polypeptides." should read: --multimer of the recombinant polypeptide.--.

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*